United States Patent
Snyder et al.

(10) Patent No.: US 12,188,938 B2
(45) Date of Patent: *Jan. 7, 2025

(54) ANTI-VISTA ANTIBODIES AND FRAGMENTS

(71) Applicant: JANSSEN PHARMACEUTICA NV, Beerse (BE)

(72) Inventors: Linda A. Snyder, Pottstown, PA (US); Gordon Powers, Malvern, PA (US); Manuel Alejandro Sepulveda, Spring House, PA (US); John D. Alvarez, Spring House, PA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 877 days.

This patent is subject to a terminal disclaimer.

(21) Appl. No.: 17/205,193

(22) Filed: Mar. 18, 2021

(65) Prior Publication Data
US 2021/0318322 A1 Oct. 14, 2021

Related U.S. Application Data

(62) Division of application No. 15/738,013, filed as application No. PCT/IB2016/000886 on Jun. 23, 2016, now Pat. No. 11,009,509.

(60) Provisional application No. 62/187,659, filed on Jul. 1, 2015, provisional application No. 62/184,108, filed on Jun. 24, 2015.

(51) Int. Cl.
| C07K 16/28 | (2006.01) |
| G01N 33/574 | (2006.01) |
| G01N 33/68 | (2006.01) |
| A61K 39/00 | (2006.01) |

(52) U.S. Cl.
CPC ... *G01N 33/57492* (2013.01); *C07K 16/2827* (2013.01); *A61K 2039/505* (2013.01); *C07K 2317/24* (2013.01); *C07K 2317/34* (2013.01); *C07K 2317/55* (2013.01); *C07K 2317/56* (2013.01); *C07K 2317/732* (2013.01); *C07K 2317/74* (2013.01); *C07K 2317/76* (2013.01); *C07K 2317/92* (2013.01); *G01N 2333/70532* (2013.01)

(58) Field of Classification Search
None
See application file for complete search history.

(56) References Cited

U.S. PATENT DOCUMENTS

| 4,366,241 A | 12/1982 | Tom et al. |
| 4,376,110 A | 3/1983 | David et al. |
| 4,439,196 A | 3/1984 | Higuchi |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,517,288 A | 5/1985 | Giegel et al. |
| 4,522,811 A | 6/1985 | Eppstein et al. |
| 4,596,556 A | 6/1986 | Morrow et al. |
| 4,676,980 A | 6/1987 | Segal et al. |
| 4,683,195 A | 7/1987 | Mullis et al. |
| 4,683,202 A | 7/1987 | Mullis |
| 4,699,880 A | 10/1987 | Goldstein |
| 4,736,866 A | 4/1988 | Leder et al. |
| 4,790,824 A | 12/1988 | Morrow et al. |
| 4,816,567 A | 3/1989 | Cabilly et al. |
| 4,837,168 A | 6/1989 | de Jaeger et al. |
| 4,870,009 A | 9/1989 | Evans et al. |
| 4,873,191 A | 10/1989 | Wagner et al. |
| 4,873,316 A | 10/1989 | Meade et al. |
| 4,881,175 A | 11/1989 | Ladner |
| 4,941,880 A | 7/1990 | Burns |
| 4,946,778 A | 8/1990 | Ladner et al. |
| 4,954,617 A | 9/1990 | Fanger et al. |
| 4,987,071 A | 1/1991 | Cech et al. |
| 5,013,653 A | 5/1991 | Huston et al. |
| 5,064,413 A | 11/1991 | McKinnon et al. |
| 5,091,513 A | 2/1992 | Huston et al. |
| 5,116,742 A | 5/1992 | Cech et al. |
| 5,116,964 A | 5/1992 | Capon et al. |
| 5,132,405 A | 7/1992 | Huston et al. |
| 5,139,941 A | 8/1992 | Muzyczka et al. |
| 5,190,878 A | 3/1993 | Wilhelm |
| 5,223,409 A | 6/1993 | Ladner et al. |
| 5,225,539 A | 7/1993 | Winter |
| 5,258,498 A | 11/1993 | Huston et al. |
| 5,260,203 A | 11/1993 | Ladner et al. |
| 5,272,071 A | 12/1993 | Chappel |

(Continued)

FOREIGN PATENT DOCUMENTS

| CA | 2383456 | 3/2001 |
| CN | 1753912 | 3/2006 |

(Continued)

OTHER PUBLICATIONS

Aalberse RC, et al. "IgG4 breaking the rules," Immunology. Jan. 2002;105(1):9-19.

Adriouch S, et al. "Improved Immunological Tolerance Following Combination Therapy with CTLA-4/Ig and AAV-Mediated PD-L1/2 Muscle Gene Transfer," Front Microbiol. Sep. 29, 2011;2:199.

(Continued)

*Primary Examiner* — Ilia I Ouspenski

(74) *Attorney, Agent, or Firm* — Robin L. Teskin; Baker, Donelson, Bearman, Caldwell & Berkowitz PC

(57) ABSTRACT

The present invention relates to novel antibodies and fragments that bind to a V-domain Ig Suppressor of T cell Activation (VISTA), and methods of detecting VISTA.

18 Claims, 48 Drawing Sheets

Specification includes a Sequence Listing.

(56) References Cited

U.S. PATENT DOCUMENTS

| | | |
|---|---|---|
| 5,283,173 A | 2/1994 | Fields et al. |
| 5,283,317 A | 2/1994 | Saifer et al. |
| 5,288,641 A | 2/1994 | Roizman |
| 5,312,335 A | 5/1994 | McKinnon et al. |
| 5,328,470 A | 7/1994 | Nabel et al. |
| 5,374,548 A | 12/1994 | Caras |
| 5,383,851 A | 1/1995 | McKinnon, Jr. et al. |
| 5,399,163 A | 3/1995 | Peterson et al. |
| 5,399,331 A | 3/1995 | Loughrey et al. |
| 5,403,484 A | 4/1995 | Ladner et al. |
| 5,416,016 A | 5/1995 | Low et al. |
| 5,427,908 A | 6/1995 | Dower et al. |
| 5,455,030 A | 10/1995 | Ladner et al. |
| 5,476,786 A | 12/1995 | Huston |
| 5,476,996 A | 12/1995 | Wilson et al. |
| 5,478,925 A | 12/1995 | Wallach et al. |
| 5,482,858 A | 1/1996 | Huston et al. |
| 5,530,101 A | 6/1996 | Queen et al. |
| 5,545,806 A | 8/1996 | Lonberg et al. |
| 5,545,807 A | 8/1996 | Surani et al. |
| 5,547,853 A | 8/1996 | Wallner et al. |
| 5,569,825 A | 10/1996 | Lonberg et al. |
| 5,571,698 A | 11/1996 | Ladner et al. |
| 5,580,717 A | 12/1996 | Dower et al. |
| 5,580,756 A | 12/1996 | Linsley et al. |
| 5,585,089 A | 12/1996 | Queen et al. |
| 5,624,659 A | 4/1997 | Bigner et al. |
| 5,624,821 A | 4/1997 | Winter et al. |
| 5,625,126 A | 4/1997 | Lonberg et al. |
| 5,633,425 A | 5/1997 | Lonberg et al. |
| 5,648,260 A | 7/1997 | Winter et al. |
| 5,661,016 A | 8/1997 | Lonberg et al. |
| 5,677,425 A | 10/1997 | Bodmer et al. |
| 5,693,762 A | 12/1997 | Queen et al. |
| 5,698,767 A | 12/1997 | Wilson et al. |
| 5,714,350 A | 2/1998 | Co et al. |
| 5,723,125 A | 3/1998 | Chang et al. |
| 5,731,168 A | 3/1998 | Carter et al. |
| 5,770,429 A | 6/1998 | Lonberg et al. |
| 5,776,427 A | 7/1998 | Thorpe et al. |
| 5,789,650 A | 8/1998 | Lonberg et al. |
| 5,811,097 A | 9/1998 | Allison et al. |
| 5,814,318 A | 9/1998 | Lonberg et al. |
| 5,821,333 A | 10/1998 | Carter et al. |
| 5,837,243 A | 11/1998 | Deo et al. |
| 5,844,095 A | 12/1998 | Linsley et al. |
| 5,851,795 A | 12/1998 | Linsley et al. |
| 5,869,046 A | 2/1999 | Presta et al. |
| 5,874,299 A | 2/1999 | Lonberg et al. |
| 5,877,397 A | 3/1999 | Lonberg et al. |
| 5,885,793 A | 3/1999 | Griffiths et al. |
| 5,888,807 A | 3/1999 | Palsson et al. |
| 5,922,845 A | 7/1999 | Deo et al. |
| 5,932,448 A | 8/1999 | Tso et al. |
| 5,939,598 A | 8/1999 | Kucherlapati et al. |
| 5,969,108 A | 10/1999 | McCafferty et al. |
| 5,985,653 A | 11/1999 | Armstrong et al. |
| 6,054,297 A | 4/2000 | Carter et al. |
| 6,069,134 A | 5/2000 | Roth et al. |
| 6,075,181 A | 6/2000 | Kucherlapati et al. |
| 6,096,532 A | 8/2000 | Armstrong et al. |
| 6,114,598 A | 9/2000 | Kucherlapati et al. |
| 6,121,022 A | 9/2000 | Presta et al. |
| 6,150,584 A | 11/2000 | Kucherlapati et al. |
| 6,153,737 A | 11/2000 | Manoharan et al. |
| 6,162,963 A | 12/2000 | Kucherlapati et al. |
| 6,165,745 A | 12/2000 | Ward et al. |
| 6,172,197 B1 | 1/2001 | McCafferty et al. |
| 6,172,208 B1 | 1/2001 | Cook |
| 6,180,370 B1 | 1/2001 | Queen et al. |
| 6,187,287 B1 | 2/2001 | Leung et al. |
| 6,194,551 B1 | 2/2001 | Idusogie et al. |
| 6,277,375 B1 | 8/2001 | Ward |
| 6,300,319 B1 | 10/2001 | Manoharan |
| 6,335,434 B1 | 1/2002 | Guzaev et al. |
| 6,335,437 B1 | 1/2002 | Manoharan |
| 6,350,861 B1 | 2/2002 | Co et al. |
| 6,395,437 B1 | 5/2002 | Wollesen |
| 6,407,213 B1 | 6/2002 | Carter et al. |
| 6,444,806 B1 | 9/2002 | Veerapanani et al. |
| 6,486,308 B2 | 11/2002 | Kutyavin et al. |
| 6,492,123 B1 | 12/2002 | Holliger et al. |
| 6,521,404 B1 | 2/2003 | Griffiths et al. |
| 6,525,031 B2 | 2/2003 | Manoharan |
| 6,528,631 B1 | 3/2003 | Cook et al. |
| 6,544,731 B1 | 4/2003 | Griffiths et al. |
| 6,545,170 B2 | 4/2003 | Pitzele et al. |
| 6,548,640 B1 | 4/2003 | Winter |
| 6,555,313 B1 | 4/2003 | Griffiths et al. |
| 6,559,279 B1 | 5/2003 | Manoharan et al. |
| 6,562,576 B2 | 5/2003 | Manfredi |
| 6,582,915 B1 | 6/2003 | Griffiths et al. |
| 6,586,474 B2 | 7/2003 | Webber et al. |
| 6,591,889 B2 | 7/2003 | Bettio et al. |
| 6,593,081 B1 | 7/2003 | Griffiths et al. |
| 6,593,372 B2 | 7/2003 | Enikolopov et al. |
| 6,632,927 B2 | 10/2003 | Adair et al. |
| 6,639,055 B1 | 10/2003 | Carter et al. |
| 6,653,104 B2 | 11/2003 | Goldenberg |
| 6,696,686 B1 | 2/2004 | Wainer et al. |
| 6,790,624 B2 | 9/2004 | Mayer |
| 6,809,117 B2 | 10/2004 | Enikolopov et al. |
| 6,818,418 B1 | 11/2004 | Lipovsek et al. |
| 6,924,355 B2 | 8/2005 | Baker et al. |
| 6,936,436 B2 | 8/2005 | Baker et al. |
| 6,936,697 B2 | 8/2005 | Desnoyers et al. |
| 6,982,323 B1 | 1/2006 | Wang et al. |
| 7,026,448 B2 | 4/2006 | Baker et al. |
| 7,049,058 B2 | 5/2006 | Singh |
| 7,196,118 B2 | 3/2007 | Webber et al. |
| 7,226,759 B2 | 6/2007 | Sun |
| 7,250,297 B1 | 7/2007 | Beste et al. |
| 7,488,802 B2 | 2/2009 | Collins et al. |
| 7,595,048 B2 | 9/2009 | Honjo |
| 7,655,778 B2 | 2/2010 | Yang |
| 7,919,585 B2 | 4/2011 | Chen |
| 8,119,117 B2 | 2/2012 | Deisseroth et al. |
| 8,231,872 B2 | 7/2012 | Noelle et al. |
| 8,236,304 B2 | 8/2012 | Noelle et al. |
| 8,465,740 B2 | 6/2013 | Noelle et al. |
| 8,501,915 B2 | 8/2013 | Noelle et al. |
| 8,652,465 B2 | 2/2014 | Freeman |
| 9,217,035 B2 | 12/2015 | Noelle et al. |
| 9,381,244 B2 | 7/2016 | Noelle et al. |
| 9,631,018 B2 | 4/2017 | Noelle et al. |
| 9,879,092 B2 | 1/2018 | Laury-Kleintop et al. |
| 9,890,215 B2 | 2/2018 | Noelle et al. |
| 10,035,857 B2 | 7/2018 | Noelle et al. |
| 10,273,301 B2 | 4/2019 | Snyder et al. |
| 10,370,455 B2 | 8/2019 | Molloy et al. |
| 11,009,509 B2* | 5/2021 | Snyder ............... C07K 16/2827 |
| 11,014,987 B2* | 5/2021 | Snyder ............... C07K 16/2818 |
| 11,180,557 B2 | 11/2021 | Noelle et al. |
| 2003/0031671 A1 | 2/2003 | Welt et al. |
| 2003/0054406 A1 | 3/2003 | Baker et al. |
| 2004/0110704 A1 | 6/2004 | Yamane et al. |
| 2004/0132028 A1 | 7/2004 | Stumpp et al. |
| 2004/0132101 A1 | 7/2004 | Lazar et al. |
| 2004/0259209 A1 | 12/2004 | Sun et al. |
| 2005/0043519 A1 | 2/2005 | Dooley et al. |
| 2005/0063948 A1 | 3/2005 | Dickerson et al. |
| 2006/0025576 A1 | 2/2006 | Miller et al. |
| 2006/0034852 A1 | 2/2006 | Rixon et al. |
| 2006/0084082 A1 | 4/2006 | Ruben et al. |
| 2007/0092512 A1 | 4/2007 | Daaka et al. |
| 2007/0122378 A1 | 5/2007 | Freeman et al. |
| 2007/0148167 A1 | 6/2007 | Stohl |
| 2007/0224633 A1 | 9/2007 | Skerra et al. |
| 2008/0069820 A1 | 3/2008 | Fuh et al. |
| 2008/0139791 A1 | 6/2008 | Lipovsek et al. |
| 2008/0166353 A1 | 7/2008 | Cherwinski |
| 2008/0248007 A1 | 10/2008 | Chen |
| 2008/0287358 A1 | 11/2008 | Noelle et al. |
| 2009/0215991 A1 | 8/2009 | Lazar et al. |

(56) References Cited

U.S. PATENT DOCUMENTS

| | | |
|---|---|---|
| 2010/0316639 A1 | 12/2010 | Lackner |
| 2010/0317834 A1 | 12/2010 | Lazar et al. |
| 2011/0027278 A1 | 2/2011 | Noelle et al. |
| 2011/0158995 A1 | 6/2011 | Tan et al. |
| 2011/0206699 A1 | 8/2011 | Hossain et al. |
| 2011/0223188 A1 | 9/2011 | Langermann |
| 2011/0243942 A1 | 10/2011 | Wang |
| 2012/0195894 A1 | 8/2012 | Noelle et al. |
| 2013/0177557 A1 | 7/2013 | Noelle et al. |
| 2014/0037634 A1 | 2/2014 | Noelle et al. |
| 2014/0056890 A1 | 2/2014 | Gurney et al. |
| 2014/0056892 A1 | 2/2014 | Noelle et al. |
| 2014/0105912 A1 | 4/2014 | Noelle et al. |
| 2014/0220012 A1 | 8/2014 | Noelle et al. |
| 2014/0227279 A1 | 8/2014 | Laury-Kleintop et al. |
| 2014/0341920 A1 | 11/2014 | Noelle et al. |
| 2015/0231215 A1 | 8/2015 | Noelle et al. |
| 2016/0008316 A1 | 1/2016 | Bacha et al. |
| 2016/0083472 A1 | 3/2016 | Noelle et al. |
| 2016/0096891 A1 | 4/2016 | Chen et al. |
| 2016/0159927 A1 | 6/2016 | Molloy et al. |
| 2016/0168248 A1 | 6/2016 | Noelle et al. |
| 2016/0318999 A9 | 11/2016 | Noelle et al. |
| 2016/0331803 A1 | 11/2016 | Noelle et al. |
| 2017/0051061 A1 | 2/2017 | Snyder et al. |
| 2017/0119877 A1 | 5/2017 | Green et al. |
| 2017/0233479 A1 | 8/2017 | Snyder et al. |
| 2017/0320950 A1 | 11/2017 | Snyder et al. |
| 2017/0334990 A1 | 11/2017 | Noelle et al. |
| 2018/0051070 A1 | 2/2018 | Noelle et al. |
| 2018/0079811 A1 | 3/2018 | Molloy et al. |
| 2018/0215826 A1 | 8/2018 | Noelle et al. |
| 2019/0330349 A1 | 10/2019 | Molloy et al. |
| 2020/0017589 A1 | 1/2020 | Snyder et al. |
| 2021/0017281 A1 | 1/2021 | Molloy et al. |
| 2021/0171640 A1 | 6/2021 | Snyder et al. |
| 2021/0317206 A1 | 10/2021 | Molloy et al. |
| 2021/0317207 A1 | 10/2021 | Noelle et al. |

FOREIGN PATENT DOCUMENTS

| | | |
|---|---|---|
| EP | 0 045 665 | 2/1982 |
| EP | 0 125 023 | 11/1984 |
| EP | 0 154 316 | 9/1985 |
| EP | 0 171 496 | 2/1986 |
| EP | 0 173 494 | 3/1986 |
| EP | 0 184 187 | 6/1986 |
| EP | 0 264 166 | 4/1988 |
| EP | 0 401 384 | 12/1990 |
| EP | 1 176 195 | 1/2002 |
| EP | 1 641 818 | 4/2006 |
| JP | 08-506635 | 3/2008 |
| WO | WO 00/045665 | 2/1982 |
| WO | WO 86/001533 | 3/1986 |
| WO | WO 87/002671 | 5/1987 |
| WO | WO 87/005330 | 9/1987 |
| WO | WO 88/000052 | 1/1988 |
| WO | WO 88/009810 | 12/1988 |
| WO | WO 89/010134 | 11/1989 |
| WO | WO 91/006667 | 5/1991 |
| WO | WO 92/003918 | 3/1992 |
| WO | WO 93/008829 | 5/1993 |
| WO | WO 93/012227 | 6/1993 |
| WO | WO 94/010300 | 5/1994 |
| WO | WO 94/010332 | 5/1994 |
| WO | WO 94/025585 | 11/1994 |
| WO | WO 94/029351 | 12/1994 |
| WO | WO 94/029436 | 12/1994 |
| WO | WO 97/007668 | 3/1997 |
| WO | WO 97/007669 | 3/1997 |
| WO | WO 97/013852 | 4/1997 |
| WO | WO 97/028267 | 8/1997 |
| WO | WO 98/024884 | 6/1998 |
| WO | WO 99/045962 | 9/1999 |
| WO | WO 99/054342 | 10/1999 |
| WO | WO 00/006593 | 2/2000 |
| WO | WO 00/029004 | 5/2000 |
| WO | WO 00/031113 | 6/2000 |
| WO | WO 00/042072 | 7/2000 |
| WO | WO 01/000814 | 1/2001 |
| WO | WO 01/003737 | 1/2001 |
| WO | WO 01/014424 | 3/2001 |
| WO | WO 02/029072 | 4/2002 |
| WO | WO 02/043478 | 6/2002 |
| WO | WO 02/079449 | 10/2002 |
| WO | WO 02/092780 | 11/2002 |
| WO | WO 03/035835 | 5/2003 |
| WO | WO 03/074679 | 9/2003 |
| WO | WO 04/018520 | 3/2004 |
| WO | WO 04/037999 | 5/2004 |
| WO | WO 05/056764 | 6/2005 |
| WO | WO 05/112834 | 12/2005 |
| WO | WO 05/113606 | 12/2005 |
| WO | WO 06/012232 | 2/2006 |
| WO | WO 06/050247 | 5/2006 |
| WO | WO 06/050262 | 5/2006 |
| WO | WO 06/116181 | 11/2006 |
| WO | WO 07/030198 | 3/2007 |
| WO | WO 08/098796 | 8/2008 |
| WO | WO 09/089004 | 7/2009 |
| WO | WO 10/027827 | 3/2010 |
| WO | WO 11/120013 | 9/2011 |
| WO | WO 13/184912 | 12/2013 |
| WO | WO 13/192504 | 12/2013 |
| WO | WO 14/039983 | 3/2014 |
| WO | WO 14/190356 | 11/2014 |
| WO | WO 14/197849 | 12/2014 |
| WO | WO 15/097536 | 7/2015 |
| WO | WO 15/109340 | 7/2015 |
| WO | WO 15/191881 | 12/2015 |
| WO | WO 16/090347 | 6/2016 |
| WO | WO 16/207717 | 12/2016 |
| WO | WO 17/181109 | 10/2017 |
| WO | WO 17/181139 | 10/2017 |
| WO | WO 18/027042 | 2/2018 |

OTHER PUBLICATIONS

Allen, et al., (2009), "Interchain disulfide bonding in human IgG2 antibodies probed by site-directed mutagenesis", Biochemistry, 48(17), 3755-3766.

Allen, T. M. "Ligand-targeted therapeutics in anticancer therapy," Nat Rev Cancer. Oct. 2002;2(10):750-63.

Almquist RG, et al. "Synthesis and biological activity of a ketomethylene analogue of a tripeptide inhibitor of angiotensin converting enzyme," J Med Chem. Dec. 1980;23(12):1392-8.

Al-Obeidi F, et al. "Peptide and peptidomimetic libraries. Molecular diversity and drug design," Mol Biotechnol. Jun. 1998;9(3):205-23.

Altman JD, et al. "Phenotypic analysis of antigen-specific T lymphocytes," Science. Oct. 4, 1996;274(5284):94-6.

Altschul SF, et al. "Basic local alignment search tool," J Mol Biol. Oct. 5, 1990;215(3):403-10.

Altschul SF, et al. "Gapped BLAST and PSI-BLAST: a new generation of protein database search programs," Nucleic Acids Res. Sep. 1, 1997;25(17):3389-402.

Amancha PK, et al. "In vivo blockade of the programmed cell death-1 pathway using soluble recombinant PD-1-Fc enhances CD4+ and CD8+ T cell responses but has limited clinical benefit," J Immunol. Dec. 15, 2013;191(12):6060-70.

Ansari MJ, et al. "The programmed death-1 (PD-1) pathway regulates autoimmune diabetes in nonobese diabetic (NOD) mice," J Exp Med. Jul. 7, 2003;198(1):63-9.

Arkin AP, et al. "An algorithm for protein engineering: simulations of recursive ensemble mutagenesis," Proc Natl Acad Sci U S A. Aug. 15, 1992;89(16):7811-5.

Attia, P., et al., Autoimmunity correlates with tumor regression in patients with metastatic melanoma treated with anti-cytotoxic T-lymphocyte antigen-4. J Clin Oncol, 2005. 23(25): p. 6043-53.

Auffray, C et al. "Blood monocytes: development, heterogeneity, and relationship with dendritic cells," Annu Rev Immunol, 2009. 27: p. 669-92.

(56) References Cited

OTHER PUBLICATIONS

Bagley RG, et al. "sFLT01: a novel fusion protein with antiangiogenic activity," Mol Cancer Ther. Mar. 2011;10(3):404-15.
Bak, S. P., et al., Murine ovarian cancer vascular leukocytes require arginase-1 activity for T cell suppression. Mol Immunol, 2008. 46(2): p. 258-68.
Baldari C, et al. "A novel leader peptide which allows efficient secretion of a fragment of human interleukin 1 beta in *Saccharomyces cerevisiae*," EMBO J. Jan. 1987;6(1):229-34.
Banerji J, et al. "A lymphocyte-specific cellular enhancer is located downstream of the joining region in immunoglobulin heavy chain genes," Cell. Jul. 1983;33(3):729-40.
Barringer KJ, et al. "Blunt-end and single-strand ligations by *Escherichia coli* ligase: influence on an in vitro amplification scheme," Gene. Apr. 30, 1990;89(1):117-22.
Bartel DP, et al. "Isolation of new ribozymes from a large pool of random sequences," Science. Sep. 10, 1993;261(5127):1411-8.
Baskar S, et al. "Constitutive expression of B7 restores immunogenicity of tumor cells expressing truncated major histocompatibility complex class II molecules," Proc Natl Acad Sci U S A. Jun. 15, 1993;90(12):5687-90.
Batzer MA, et al. "Enhanced evolutionary PCR using oligonucleotides with inosine at the 3'-terminus," Nucleic Acids Res. Sep. 25, 1991;19(18):5081.
Bauer S, et al. "Immunotherapy of human tumors with T-cell-activating bispecific antibodies: stimulation of cytotoxic pathways in vivo," Cancer Res. Apr. 15, 1999;59(8):1961-5.
Beidler CB, et al. "Cloning and high level expression of a chimeric antibody with specificity for human carcinoembryonic antigen," J Immunol. Dec. 1, 1988;141(11):4053-60.
Beilharz MW, et al. "Timed ablation of regulatory CD4+ T cells can prevent murine AIDS progression," J Immunol. Apr. 15, 2004;172(8):4917-25.
Belousov ES, et al. "Sequence-specific targeting and covalent modification of human genomic DNA," Nucleic Acids Res. Sep. 1, 1997;25(17):3440-4.
Beranger F, et al. "Getting more from the two-hybrid system: N-terminal fusions to LexA are efficient and sensitive baits for two-hybrid studies," Nucleic Acids Res. May 15, 1997;25(10):2035-6.
Berge SM, et al. "Pharmaceutical salts," J Pharm Sci. Jan. 1977;66(1):1-19.
Berney C, et al. "A member of the dendritic cell family that enters B cell follicles and stimulates primary antibody responses identified by a mannose receptor fusion protein," J Exp Med. Sep. 20, 1999;190(6):851-60.
Better M, et al. "*Escherichia coli* secretion of an active chimeric antibody fragment," Science. May 20, 1988;240(4855):1041-3.
Bird RE, et al. "Single-chain antigen-binding proteins," Science. Oct. 21, 1988;242(4877):423-6.
Blank C, et al. "Interaction of PD-L1 on tumor cells with PD-1 on tumor-specific T cells as a mechanism of immune evasion: implications for tumor immunotherapy," Cancer Immunol Immunother. Apr. 2005;54(4):307-14.
Blank, C., et al., "PD-L1/B7H-1 inhibits the effector phase of tumor rejection by T cell receptor (TCR) transgenic CD8+ T cells," Cancer Res, 2004. 64(3): p. 1140-5.
Blazar et al., "Infusion of anti-B7. 1 (CD80) and anti-B7. 2 (CD86) monoclonal antibodies inhibits murine graft-versus-host disease lethality in part via direct effects on CD4+ and CD8+ T cells." The Journal of Immunology 157.8 (1996): 3250-3259.
Bloemen PG, et al. "Adhesion molecules: a new target for immunoliposome-mediated drug delivery," FEBS Lett. Jan. 3, 1995;357(2):140-4.
Blommers MJ, et al. "Effects of the introduction of L-nucleotides into DNA. Solution structure of the heterochiral duplex d(G-C-G-(L)T-G-C-G).d(C-G-C-A-C-G-C) studied by NMR spectroscopy," Biochemistry. Jun. 28, 1994;33(25):7886-96.
Bluestone JA, et al. "Natural versus adaptive regulatory T cells," Nat Rev Immunol. Mar. 2003;3(3):253-7.

Bogdan C. "Nitric oxide and the immune response," Nat Immunol. Oct. 2001;2(10):907-16.
Bolhassani, A. et al., "Improvement of different vaccine delivery systems for cancer therapy", Molecular Cancer, 2011, vol. 10, No. 1, Article No. 3.
Boon T, et al. "Human T cell responses against melanoma," Annu. Rev. Immunol . . . Apr. 23, 2006;24:175-208.
Borriello F, et al. "B7-1 and B7-2 have overlapping, critical roles in immunoglobulin class switching and germinal center formation," Immunity. Mar. 1997;6(3):303-13.
Borrok MJ, "pH-dependent Binding Engineering Reveals an FcRn Affinity Threshold That Governs IgG Recycling," The Journal of Biological Chemistry. 2015;290(7):4282-90.
Boulianne GL, et al. "Production of functional chimaeric mouse/human antibody," Nature. Dec. 13-19, 1984;312(5995):643-6.
Bowen JL, et al. "Innate immune CD11b+Gr-1+ cells, suppressor cells, affect the immune response during Theiler's virus-induced demyelinating disease," J Immunol. Dec. 1, 2009;183(11):6971-80.
Brahmer, J. R., et al., Phase I study of single-agent anti-programmed death-1 (MDX-1106) in refractory solid tumors: safety, clinical activity, pharmacodynamics, and immunologic correlates. J Clin Oncol, 2010. 28(19): p. 3167-75.
Brandt C, et al. "The B7 family member B7-H6 is a tumor cell ligand for the activating natural killer cell receptor NKp30 in humans," J Exp Med. Jul. 6, 2009;206(7):1495-503.
Brennan M, et al. "Preparation of bispecific antibodies by chemical recombination of monoclonal immunoglobulin G1 fragments," Science. Jul. 5, 1985;229(4708):81-3.
Briscoe P, et al. "Delivery of superoxide dismutase to pulmonary epithelium via pH-sensitive liposomes," Am J Physiol. Mar. 1995;268(3 Pt 1):L374-80.
Brisson, et al. "Expression of a bacterial gene in plants by using a viral vector," Nature vol. 310 Aug. 1984, 511-14.
Broglie R, et al. "Light-regulated expression of a pea ribulose-1,5-bisphosphate carboxylase small subunit gene in transformed plant cells," Science. May 25, 1984;224(4651):838-43.
Brown JP, et al. "Protein antigens of normal and malignant human cells identified by immunoprecipitation with monoclonal antibodies," J Biol Chem. Jun. 10, 1980;255(11):4980-3.
Brown JP, et al. "Structural characterization of human melanoma-associated antigen p97 with monoclonal antibodies," J Immunol. Aug. 1981;127(2):539-46.
Brys L, et al. "Reactive oxygen species and 12/15-lipoxygenase contribute to the antiproliferative capacity of alternatively activated myeloid cells elicited during helminth infection," J Immunol. May 15, 2005;174(10):6095-104.
Burg JL, et al. "Single molecule detection of RNA reporter probes by amplification with Q beta replicase," Mol Cell Probes. Aug. 1996;10(4):257-71.
Butte MJ, et al. "Programmed death-1 ligand 1 interacts specifically with the B7-1 costimulatory molecule to inhibit T cell responses," Immunity. Jul. 2007;27(1):111-22.
Byrne GW, et al. "Multiplex gene regulation: a two-tiered approach to transgene regulation in transgenic mice," Proc Natl Acad Sci U S A. Jul. 1989;86(14):5473-7.
Cabilly S, et al. "Generation of antibody activity from immunoglobulin polypeptide chains produced in *Escherichia coli*," Proc Natl Acad Sci U S A. Jun. 1984;81(11):3273-7.
Cabilly S, et al. "Immunoglobulin transcripts and molecular history of a hybridoma that produces antibody to carcinoembryonic antigen," Gene. 1985;40(1):157-61.
Calabro, L., et al., "Clinical studies with anti-CTLA-4 antibodies in non-melanoma indications," Semin Oncol, 2010. 37(5): p. 460-7.
Calame K, et al. "Transcriptional controlling elements in the immunoglobulin and T cell receptor loci," Adv Immunol. 1988;43:235-75.
Camper SA, et al. "Postnatal repression of the alpha-fetoprotein gene is enhancer independent," Genes Dev. Apr. 1989;3(4):537-46.
Cancer Prevention Overview (PDQ®), PDQ Cancer Information Summaries [Internet].2017, 14 pages.
Carell, et al. "A Solution-Phase Screening Procedure for the Isolation of Active Compounds from a Library of Molecules," Angew. Chem. Int. Ed. Engl. 1994, 33. No. 20, 2061-64.

(56) References Cited

OTHER PUBLICATIONS

Carter L, et al. "PD-1:PD-L inhibitory pathway affects both CD4(+) and CD8(+) T cells and is overcome by IL-2," Eur J Immunol. Mar. 2002;32(3):634-43.
Ceeraz S, et al. "VISTA Deficiency Accelerates the Development of Fatal Murine Lupus Nephritis," Arthritis Rheumatol. Apr. 2017;69(4):814-825.
Chambers CA, et al. "Lymphoproliferation in CTLA-4-deficient mice is mediated by costimulation-dependent activation of CD4+ T cells," Immunity. Dec. 1997;7(6):885-95.
Chan AC, et al. "Therapeutic antibodies for autoimmunity and inflammation," Nat Rev Immunol. May 2010;10(5):301-16.
Chen J, et al. "B cell development in mice that lack one or both immunoglobulin kappa light chain genes," EMBO J. Mar. 1993;12(3):821-30.
Chen J, et al. "Immunoglobulin gene rearrangement in B cell deficient mice generated by targeted deletion of the JH locus," Int Immunol. Jun. 1993;5(6):647-56.
Chen L, et al. "Costimulation of antitumor immunity by the B7 counterreceptor for the T lymphocyte molecules CD28 and CTLA-4," Cell. Dec. 24, 1992;71(7):1093-102.
Chen S, et al. "Immunosuppressive functions of hepatic myeloid-derived suppressor cells of normal mice and in a murine model of chronic hepatitis B virus," Clin Exp Immunol. Oct. 2011;166(1):134-42.
Chen SH, et al. "Gene therapy for brain tumors: regression of experimental gliomas by adenovirus-mediated gene transfer in vivo," Proc Natl Acad Sci U S A. Apr. 12, 1994;91(8):3054-7.
Chen, Y., "Development of a sandwich ELISA for evaluating soluble PD-LI (CD274) in human sera of different ages as well as supernatants of PD-L1(+) cell lines," Cytokine 2011.
Cho CY, et al. "An unnatural biopolymer," Science. Sep. 3, 1993;261(5126):1303-5.
Choi TK, et al. "Transgenic mice containing a human heavy chain immunoglobulin gene fragment cloned in a yeast artificial chromosome," Nat Genet. Jun. 1993;4(2):117-23.
Chothia C, et al. "Canonical structures for the hypervariable regions of immunoglobulins," J Mol Biol. Aug. 20, 1987;196(4):901-17.
Church GM, et al. "Genomic sequencing," Proc Natl Acad Sci U S A. Apr. 1984;81(7):1991-5.
Clark KL, et al. "Association of the Arabidopsis CTR1 Raf-like kinase with the ETR1 and ERS ethylene receptors," Proc Natl Acad Sci U S A. Apr. 28, 1998;95(9):5401-6.
Cohen AA, et al. "Structure design: an artificial intelligence-based method for the design of molecules under geometrical constraints," J Mol Graph. Sep. 1993;11(3):166-73.
Cole SP, et al. "Human monoclonal antibodies," Mol Cell Biochem. Jun. 1984;62(2):109-20.
Colman PM. "Effects of amino acid sequence changes on antibody-antigen interactions," Res Immunol. Jan. 1994;145(1):33-6.
Conejo-Garcia, J. R., et al., "Tumor-infiltrating dendritic cell precursors recruited by a beta-defensin contribute to vasculogenesis under the influence of Vegf-A," Nat Med, 2004. 10(9): p. 950-8.
Copin, R., et al., "MyD88-dependent activation of B220-CD11b+LY-6C+ dendritic cells during *Brucella melitensis* infection," J Immunol, 2007. 178(8): p. 5182-91.
Coruzzi G, et al. "Tissue-specific and light-regulated expression of a pea nuclear gene encoding the small subunit of ribulose-1,5-bisphosphate carboxylase," EMBO J. Aug. 1984;3(8):1671-9.
Corzo, C. A., et al., "HIF-1alpha regulates function and differentiation of myeloid-derived suppressor cells in the tumor microenvironment," J Exp Med, 2010. 207(11): p. 2439-53.
Cote RJ, et al. "Generation of human monoclonal antibodies reactive with cellular antigens," Proc Natl Acad Sci U S A. Apr. 1983;80(7):2026-30.
Cox JP, et al. "A directory of human germ-line V kappa segments reveals a strong bias in their usage," Eur J Immunol. Apr. 1994;24(4):827-36.

Cubillos-Ruiz, J. R., et al., "Polyethylenimine-based siRNA nanocomplexes reprogram tumor-associated dendritic cells via TLR5 to elicit therapeutic antitumor immunity," J Clin Invest, 2009. 119(8): p. 2231-44.
Cull MG, et al. "Screening for receptor ligands using large libraries of peptides linked to the C terminus of the lac repressor," Proc Natl Acad Sci U S A. Mar. 1, 1992;89(5):1865-9.
Cunningham BC, et al. "High-resolution epitope mapping of hGH-receptor interactions by alanine-scanning mutagenesis," Science. Jun. 2, 1989;244(4908):1081-5.
Curiel, T. J., et al., "Blockade of B7-H1 improves myeloid dendritic cell-mediated antitumor immunity," Nat Med, 2003. 9(5): p. 562-7.
Curiel, T. J., et al., "Specific recruitment of regulatory T cells in ovarian carcinoma fosters immune privilege and predicts reduced survival," Nat Med, 2004. 10(9): p. 942-9.
Curis, Inc. "A Study of CA-170 (Oral PD-L1, PD-L2 and VISTA Checkpoint Antagonist) in Patients With Advanced Tumors and Lymphomas," U.S. National Library of Medicine, ClinicalTrials.gov; (https://clinicaltrials.gov) 2018. 8 pages.
Cwirla SE, et al. "Peptides on phage: a vast library of peptides for identifying ligands," Proc Natl Acad Sci U S A. Aug. 1990;87(16):6378-82.
Dal Porto J, et al. "A soluble divalent class I major histocompatibility complex molecule inhibits alloreactive T cells at nanomolar concentrations," Proc Natl Acad Sci U S A. Jul. 15, 1993;90(14):6671-5.
David GS, et al. "Protein iodination with solid state lactoperoxidase," Biochemistry. Feb. 26, 1974;13(5):1014-21.
De Vos AM, et al. "Human growth hormone and extracellular domain of its receptor: crystal structure of the complex," Science. Jan. 17, 1992;255(5042):306-12.
Dean PM. "Recent advances in drug design methods: where will they lead?" Bioessays. Sep. 1994;16(9):683-7.
Delagrave S, et al. "Recursive ensemble mutagenesis," Protein Eng. Apr. 1993;6(3):327-31.
Dellinger et al "International Guidelines for Management of Severe Sepsis and Septic Shock" (2013 Intensive Care Med 39: 165-228).
Deng J, et al. "A New VISTA on combination therapy for negative checkpoint regulator blockade," J Immunother Cancer. Dec. 20, 2016;4:86.
Deshayes S, et al. "Insight into the mechanism of internalization of the cell-penetrating carrier peptide Pep-1 through conformational analysis," Biochemistry. Feb. 17, 2004;43(6):1449-57.
D'Eustachio P, et al. "Somatic cell genetics and gene families," Science. May 27, 1983;220(4600):919-24.
Devlin JJ, et al. "Random peptide libraries: a source of specific protein binding molecules," Science. Jul. 27, 1990;249(4967):404-6.
DeWitt SH, et al. "'Diversomers': an approach to nonpeptide, nonoligomeric chemical diversity," Proc Natl Acad Sci U S A. Aug. 1, 1993;90(15):6909-13.
Di Maro, Antimo, et al. "Isolation and characterization of four type-1 ribosome-inactivating proteins, with polynucleotide: adenosine glycosidase activity, from leaves of *Phytolacca dioica* L." Planta 208.1 (1999): 125-131.
DiLillo DJ, et al. "Fc-Receptor Interactions Regulate Both Cytotoxic and Immunomodulatory Therapeutic Antibody Effector Functions," Cancer Immunology Research. 2015;3(7):704-13.
Dillon et al., "Optimization of a reversed-phase high-performance liquid chromatography/mass spectrometry method for characterizing recombinant antibody heterogeneity and stability," J Chromatogr A. Jul. 7, 2006;1120(1-2):112-20.
Dong C, et al. "ICOS co-stimulatory receptor is essential for T-cell activation and function," Nature. Jan. 4, 2001;409(6816):97-101.
Dong H, et al. "B7-H1 pathway and its role in the evasion of tumor immunity," J Mol Med (Berl). May 2003;81(5):281-7.
Dong H, et al. "Tumor-associated B7-H1 promotes T-cell apoptosis: a potential mechanism of immune evasion," Nat Med. Aug. 2002;8(8):793-800.
Dubey AK, et al. "Belimumab: First targeted biological treatment for systemic lupus erythematosus," J Pharmacol Pharmacother. 2011;2(4):317-9.

(56) References Cited

OTHER PUBLICATIONS

Duttagupta et al., "Costimulation signals for memory CD8+ T cells during viral infections." Critical Reviews™ in Immunology 29.6 (2009).
Edlund T, et al. "Cell-specific expression of the rat insulin gene: evidence for role of two distinct 5' flanking elements," Science. Nov. 22, 1985;230(4728):912-6.
Ehst BD, et al. "Development of a novel transgenic mouse for the study of interactions between CD4 and CD8 T cells during graft rejection," American Journal of Transplantation: 2003;3(11):1355-62.
Elbashir SM, et al. "Duplexes of 21-nucleotide RNAs mediate RNA interference in cultured mammalian cells," Nature. May 24, 2001;411(6836):494-8.
Ellenberger TE, et al. "The GCN4 basic region leucine zipper binds DNA as a dimer of uninterrupted alpha helices: crystal structure of the protein-DNA complex," Cell. Dec. 24, 1992;71(7):1223-37.
Erb E, et al. "Recursive deconvolution of combinatorial chemical libraries," Proc Natl Acad Sci U S A. Nov. 22, 1994;91(24):11422-6.
Evans BE, et al. "Design of nonpeptidal ligands for a peptide receptor: cholecystokinin antagonists," J Med Chem. Jul. 1987;30(7):1229-39.
Fallarino F, et al. "B7-1 engagement of cytotoxic T lymphocyte antigen 4 inhibits T cell activation in the absence of CD28," J Exp Med. Jul. 6, 1998;188(1):205-10.
Fan YS, et al. "Mapping small DNA sequences by fluorescence in situ hybridization directly on banded metaphase chromosomes," Proc Natl Acad Sci U S A. Aug. 1990;87(16):6223-7.
Felici F, et al. "Selection of antibody ligands from a large library of oligopeptides expressed on a multivalent exposition vector," J Mol Biol. Nov. 20, 1991;222(2):301-10.
Finn PJ, et al. "Synthesis and properties of DNA-PNA chimeric oligomers," Nucleic Acids Res. Sep. 1, 1996;24(17):3357-63.
Fishwild DM, et al. "High-avidity human IgG kappa monoclonal antibodies from a novel strain of minilocus transgenic mice," Nat Biotechnol. Jul. 1996;14(7):845-51.
Flicek P, et al. "Ensembl 2008," Nucleic Acids Res. Jan. 2008;36(Database issue):D707-14.
Flies DB, et al. "Coinhibitory receptor PD-1H preferentially suppresses CD4+ T cell-mediated immunity," J Clin Invest. May 2014;124(5):1966-75.
Flies DB, et al. "Cutting edge: A monoclonal antibody specific for the programmed death-1 homolog prevents graft-versus-host disease in mouse models," J Immunol. Aug. 15, 2011;187(4):1537-41.
Flies DB, et al. "Mechanistic Assessment of PD-1H Coinhibitory Receptor-Induced T Cell Tolerance to Allogeneic Antigens," J Immunol. Jun. 1, 2015;194(11):5294-304.
Fodor SP, et al. "Multiplexed biochemical assays with biological chips," Nature. Aug. 5, 1993;364(6437):555-6.
Fontenot JD, et al. "Regulatory T cell lineage specification by the forkhead transcription factor foxp3," Immunity. Mar. 2005;22(3):329-41.
Formstecher E, et al. "Protein interaction mapping: a *Drosophila* case study," Genome Res. Mar. 2005;15(3):376-84.
Franklin, et al. "Immunologic differences between the 19 S and 7 S components of normal human gamma-globulin," J Immunol. Jan. 1957;78(1):11-8.
Freeman GJ, et al. "Engagement of the PD-1 immunoinhibitory receptor by a novel B7 family member leads to negative regulation of lymphocyte activation," J Exp Med. Oct. 2, 2000;192(7):1027-34.
Freeman GJ, et al. "Uncovering of functional alternative CTLA-4 counter-receptor in B7-deficient mice," Science. Nov. 5, 1993;262(5135):907-9.
Freeman GJ. "Structures of PD-1 with its ligands: sideways and dancing cheek to cheek," Proc Natl Acad Sci U S A. Jul. 29, 2008;105(30):10275-6.
Freier SM, et al. "Improved free-energy parameters for predictions of RNA duplex stability," Proc Natl Acad Sci U S A. Dec. 1986;83(24):9373-7.

Frenkel K, et al. "7,12-dimethylbenz[a]anthracene induces oxidative DNA modification in vivo," Free Radic Biol Med. Sep. 1995;19(3):373-80.
Fromont-Racine M, et al. "Toward a functional analysis of the yeast genome through exhaustive two-hybrid screens," Nat Genet. Jul. 1997;16(3):277-82.
Futaki S. "Arginine-rich peptides: potential for intracellular delivery of macromolecules and the mystery of the translocation mechanisms," Int J Pharm. Oct. 1, 2002;245(1-2):1-7.
Gabrilovich D. "Mechanisms and functional significance of tumour-induced dendritic-cell defects," Nat Rev Immunol. Dec. 2004;4(12):941-52.
Gabrilovich DI, et al. "Myeloid-derived suppressor cells as regulators of the immune system," Nat Rev Immunol. Mar. 2009;9(3):162-74.
Galfre, G. et al. "Antibodies to major histocompatibility anitigens produced by hybrid cell lines," Nature, vol. 266, Apr. 1977, 550-52.
Gallop MA, et al. "Applications of combinatorial technologies to drug discovery. 1. Background and peptide combinatorial libraries," J Med Chem. Apr. 29, 1994;37(9):1233-51.
Gao J, et al. "VISTA is an inhibitory immune checkpoint that is increased after ipilimumab therapy in patients with prostate cancer," Nat Med. May 2017;23(5):551-555.
Gao, Q., et al., "Overexpression of PD-L1 significantly associates with tumor aggressiveness and postoperative recurrence in human hepatocellular carcinoma," Clin Cancer Res, 2009. 15(3): p. 971-9.
Garg A, et al. "HIV type 1 gp120-induced expansion of myeloid derived suppressor cells is dependent on interleukin 6 and suppresses immunity," J Infect Dis. Feb. 1, 2014;209(3):441-51.
Gautier C, et al. "Alpha-DNA. IV: Alpha-anomeric and beta-anomeric tetrathymidylates covalently linked to intercalating oxazolopyridocarbazole. Synthesis, physicochemical properties and poly (rA) binding," Nucleic Acids Res. Aug. 25, 1987;15(16):6625-41.
Gavin MA, et al. "Homeostasis and anergy of CD4(+)CD25(+) suppressor T cells in vivo," Nat Immunol. Jan. 2002;3(1):33-41.
Gefter ML, et al. "A simple method for polyethylene glycol-promoted hybridization of mouse myeloma cells," Somatic Cell Genet. Mar. 1977;3(2):231-6.
Geissmann, F., et al. "Blood monocytes consist of two principal subsets with distinct migratory properties," Immunity, 2003. 19(1): p. 71-82.
Geissmann, F., et al., "Blood monocytes: distinct subsets, how they relate to dendritic cells, and their possible roles in the regulation of T-cell responses," Immunol Cell Biol, 2008. 86(5): p. 398-408.
Geissmann, F., et al., "Development of monocytes, macrophages, and dendritic cells," Science, 2010. 327(5966): p. 656-61.
GenBank Accession No. NP.sub.--071436 (Sep. 3, 2009), platelet receptor Gi24 precursor [*Homo spaiens*].
GenBank Accession No. NP.sub.--083008 (Mar. 3, 3010) platelet receptor Gi24 isoform 1 precursor [Mus musculus].
Genbank entry EGW09616.1 (Mar. 14, 2015) [retrieved on Jun. 22, 2015 from http://www.ncbi.nlm.nih.gov/protein/EGW09616.1] 1 page.
Geng H, et al. "HSP70 vaccine in combination with gene therapy with plasmid DNA encoding sPD-1 overcomes immune resistance and suppresses the progression of pulmonary metastatic melanoma," Int J Cancer. Jun. 1, 2006;118(11):2657-64.
Ghiringhelli, F., et al., "Tumor cells convert immature myeloid dendritic cells into TGF-beta-secreting cells inducing CD4+CD25+ regulatory T cell proliferation," J Exp Med, 2005. 202(7): p. 919-29.
Gilliland DG, et al. "Antibody-directed cytotoxic agents: use of monoclonal antibody to direct the action of toxin A chains to colorectal carcinoma cells," Proc Natl Acad Sci U S A. Aug. 1980;77(8):4539-43.
Glennie MJ, et al. "Preparation and performance of bispecific F(ab' gamma)2 antibody containing thioether-linked Fab' gamma fragments," J Immunol. Oct. 1, 1987;139(7):2367-75.
Gluzman Y, et al. "SV40 early mutants that are defective for viral DNA synthesis but competent for transformation of cultured rat and simian cells," Virology. Nov. 1982;123(1):78-92.
Goeddel DV. "Systems for heterologous gene expression," Methods Enzymol. 1990;185:3-7.

(56) References Cited

OTHER PUBLICATIONS

Gorczynski RM, et al. "Checkpoint blockade in solid tumors and B-cell malignancies, with special consideration of the role of CD200," Cancer Manag Res. Nov. 13, 2017;9:601-609.

Grabie N, et al. "Endothelial programmed death-1 ligand 1 (PD-L1) regulates CD8+ T-cell mediated injury in the heart," Circulation. Oct. 30, 2007;116(18):2062-71.

Graziano RF, et al. "Construction and characterization of a humanized anti-gamma-Ig receptor type I (Fc gamma RI) monoclonal antibody," J Immunol. Nov. 15, 1995;155(10):4996-5002.

Green KA, et al. "Antibody to the ligand for CD40 (gp39) inhibits murine AIDS-associated splenomegaly, hypergammaglobulinemia, and immunodeficiency in disease-susceptible C57BL/6 mice," J Virol. Apr. 1996;70(4):2569-75.

Green KA, et al. "Myeloid-derived suppressor cells in murine retrovirus-induced AIDS inhibit T- and B-cell responses in vitro that are used to define the immunodeficiency," J Virol. Feb. 2013;87(4):2058-71.

Greenwald RJ, et al. "The B7 family revisited," Annu Rev Immunol. 2005;23:515-48.

Groux H, et al. "A CD4+ T-cell subset inhibits antigen-specific T-cell responses and prevents colitis," Nature. Oct. 16, 1997;389(6652):737-42.

Gruber M, et al. "Efficient tumor cell lysis mediated by a bispecific single chain antibody expressed in *Escherichia coli*," J Immunol. Jun. 1, 1994;152(11):5368-74.

Guatelli JC, et al. "Isothermal, in vitro amplification of nucleic acids by a multienzyme reaction modeled after retroviral replication," Proc Natl Acad Sci U S A. Mar. 1990;87(5):1874-8.

Guindon S, et al. "A simple, fast, and accurate algorithm to estimate large phylogenies by maximum likelihood," Syst Biol. Oct. 2003;52(5):696-704.

Guleria I, et al. "A critical role for the programmed death ligand 1 in fetomaternal tolerance," J Exp Med. Jul. 18, 2005;202(2):231-7.

Gurley WB, et al. "Upstream sequences required for efficient expression of a soybean heat shock gene," Mol Cell Biol. Feb. 1986;6(2):559-65.

Hamilton AJ, et al. "A species of small antisense RNA in post-transcriptional gene silencing in plants," Science. Oct. 29, 1999;286(5441):950-2.

Hann M "On the Double Bond Isostere of the Peptide Bond: Preparation of an Enkephalin Analogue," Journal of the Chemical Society, Perkin Transactions 1982 (1), 307-14.

Hara M, et al. "IL-10 is required for regulatory T cells to mediate tolerance to alloantigens in vivo," J Immunol. Mar. 15, 2001;166(6):3789-96.

Harding FA, et al. "Class switching in human immunoglobulin transgenic mice," nn N Y Acad Sci. Sep. 29, 1995;764:536-46.

Haseloff J, et al. "Simple RNA enzymes with new and highly specific endoribonuclease activities," Nature. Aug. 18, 1988;334(6183):585-91.

Hashida H, et al. "Fusion of HIV-1 Tat protein transduction domain to poly-lysine as a new DNA delivery tool," Br J Cancer. Mar. 22, 2004;90(6):1252-8.

Haskins K, et al. "The major histocompatibility complex-restricted antigen receptor on T cells. I. Isolation with a monoclonal antibody," The Journal of Experimental Medicine. 1983;157(4):1149-69.

Hauser N, et al. "Interaction of cartilage matrix protein with aggrecan. Increased covalent cross-linking with tissue maturation," J Biol Chem. Dec. 13, 1996;271(50):32247-52.

Hauser N, et al. "Native cartilage matrix protein (CMP). A compact trimer of subunits assembled via a coiled-coil alpha-helix," J Biol Chem. Oct. 14, 1994;269(41):25747-53.

Haynes JR, et al. "Particle-mediated nucleic acid immunization," J Biotechnol. Jan. 26, 1996;44(1-3):37-42.

Hedbom E, et al. "Cartilage matrix proteins. An acidic oligomeric protein (COMP) detected only in cartilage," J Biol Chem. Mar. 25, 1992;267(9):6132-6.

Helene C, et al. "Control of gene expression by triple helix-forming oligonucleotides. The antigene strategy," Ann N Y Acad Sci. Oct. 28, 1992;660:27-36.

Hellstrom I, et al. "CD3-mediated activation of tumor-reactive lymphocytes from patients with advanced cancer," Proc Natl Acad Sci U S A. Jun. 5, 2001;98(12):6783-8.

Hinton PR, et al. "Engineered human IgG antibodies with longer serum half-lives in primates," J Biol Chem. Feb. 20, 2004;279(8):6213-6.

Hirano, F., et al., Blockade of B7-H1 and PD-1 by monoclonal antibodies potentiates cancer therapeutic immunity Cancer Res, 2005. 65(3): p. 1089-96.

Ho SN, et al. "Site-directed mutagenesis by overlap extension using the polymerase chain reaction," Gene. Apr. 15, 1989;77(1):51-9.

Ho VT, et al. "The history and future of T-cell depletion as graft-versus-host disease prophylaxis for allogeneic hematopoietic stem cell transplantation," Blood. Dec. 1, 2001;98(12):3192-204.

Hodi, F. S., Overcoming immunological tolerance to melanoma: Targeting CTLA-4. Asia Pac J Clin Oncol, 2010. 6 Suppl 1: p. S16-23.

Hogg N. "The structure and function of Fc receptors," Immunol Today. Jul.-Aug. 1988;9(7-8):185-7.

Holladay, M. W., et al. (1983). "Synthesis of hydroxyethylene and ketomethylene dipeptide isosteres," Tetrahedron Letters 1983 24(41), 4401-4404.

Hollenbaugh D, et al. "Cleavable CD40Ig fusion proteins and the binding to sgp39," J Immunol Methods. Dec. 15, 1995;188(1):1-7.

Holliger P, et al. ""Diabodies": small bivalent and bispecific antibody fragments," Proc Natl Acad Sci U S A. Jul. 15, 1993;90(14):6444-8.

Holm L, et al. "DaliLite workbench for protein structure comparison," Bioinformatics. Jun. 2000;16(6):566-7.

Hoos, A., et al., "Development of ipilimumab: contribution to a new paradigm for cancer immunotherapy," Semin Oncol, 2010. 37(5): p. 533-46.

Hopp TP, et al. "Prediction of protein antigenic determinants from amino acid sequences," Proc Natl Acad Sci U S A. Jun. 1981;78(6):3824-8.

Horn JR, et al. "The role of protein dynamics in increasing binding affinity for an engineered protein-protein interaction established by H/D exchange mass spectrometry," Biochemistry. Jul. 18, 2006;45(28):8488-98.

Hotchkiss RS, et al. "Immunosuppression in sepsis: a novel understanding of the disorder and a new therapeutic approach," Lancet Infect Dis. Mar. 2013;13(3):260-8.

Houghten RA, et al. "The use of synthetic peptide combinatorial libraries for the identification of bioactive peptides," Bioorganic & Medicianl Chemistry Letters, vol. 3, No. 3, 1993. pp. 405-412.

Hruby VJ, et al. "Conformational and topographical considerations in the design of biologically active peptides," Biopolymers. Jul. 1993;33(7):1073-82.

Hruby VJ, et al. "Synthesis of oligopeptide and peptidomimetic libraries," Curr Opin Chem Biol. Jun. 1997;1(1):114-9.

Hruby VJ. "Conformational restrictions of biologically active peptides via amino acid side chain groups," Life Sci. Jul. 19, 1982;31(3):189-99.

Huarte, E., et al., "Depletion of dendritic cells delays ovarian cancer progression by boosting antitumor immunity," Cancer Res, 2008. 68(18): p. 7684-91.

Hudson D, et al. "Methionine enkephalin and isosteric analogues. I. Synthesis on a phenolic resin support," Int J Pept Protein Res. 1979;14(3):177-85.

Huston JS, et al. "Protein engineering of antibody binding sites: recovery of specific activity in an anti-digoxin single-chain Fv analogue produced in *Escherichia coli*," Proc Natl Acad Sci USA. Aug. 1988;85(16):5879-83.

Hutloff A, et al. "ICOS is an inducible T-cell co-stimulator structurally and functionally related to CD28," Nature. Jan. 21, 1999;397(6716):263-6.

Hyrup B, e al. "Peptide nucleic acids (PNA): synthesis, properties and potential applications," Bioorg Med Chem. Jan. 1996;4(1):5-23.

(56) References Cited

OTHER PUBLICATIONS

Ike Y, et al. "Solid phase synthesis of polynucleotides. VIII. Synthesis of mixed oligodeoxyribonucleotides by the phosphotriester solid phase method," Nucleic Acids Res. Jan. 25, 1983;11(2):477-88.

Iliopoulos D, et al. "The negative costimulatory molecule PD-1 modulates the balance between immunity and tolerance via miR-21," Eur J Immunol. Jun. 2011;41(6):1754-63.

Inoue H, et al. "Sequence-dependent hydrolysis of RNA using modified oligonucleotide splints and RNase H," FEBS Lett. May 11, 1987;215(2):327-30.

Inoue H, et al. "Synthesis and hybridization studies on two complementary nona(2'-O-methyl)ribonucleotides," Nucleic Acids Res. Aug. 11, 1987;15(15):6131-48.

Invitrogen (2002) "Guide to Baculovirus Expression Vector Systems (BEVs) and Insect Culture Techniques" Instruction Manual. 30 pages.

Itakura K, et al. "Expression in *Escherichia coli* of a chemically synthesized gene for the hormone somatostatin," Science. Dec. 9, 1977;198(4321):1056-63.

Itakura K, et al. "Synthesis and use of synthetic oligonucleotides," Annu Rev Biochem. 1984;53:323-56.

Iwai, Y., et al., "Involvement of PD-L1 on tumor cells in the escape from host immune system and tumor immunotherapy by PD-L1 blockade," Proc Natl Acad Sci USA, 2002. 99(19): p. 12293-7.

Janssen Clinical Trials "A Study of Safety, Pharmacokinetics, Pharmacodynamics of JNJ-61610588 in Participants With Advanced Cancer," U.S. National Library of Medicine, ClinicalTrials.gov; (https://clinicaltrials.gov) 2017. 9 pages.

Jarvinen LZ, et al. "CD154 on the surface of CD4+CD25+ regulatory T cells contributes to skin transplant tolerance," Transplantation. Nov. 15, 2003;76(9):1375-9.

Jeisy-Scott V, et al. "Increased MDSC accumulation and Th2 biased response to influenza A virus infection in the absence of TLR7 in mice," PLoS One. 2011;6(9):e25242.

Jennings-White, C. et al. (1982). "Synthesis of ketomethylene analogs of dipeptides," Tetrahedron Letters 1982 23(25), 2533-2534.

Jones E, et al. "Depletion of CD25+ regulatory cells results in suppression of melanoma growth and induction of autoreactivity in mice," Cancer Immun. Feb. 22, 2002;2:1.

Jones PT, et al. "Replacing the complementarity-determining regions in a human antibody with those from a mouse," Nature. May 29-Jun. 4, 1986;321(6069):522-5.

Jones TD, et al. "The development of a modified human IFN-alpha2b linked to the Fc portion of human IgG1 as a novel potential therapeutic for the treatment of hepatitis C virus infection," J Interferon Cytokine Res. Sep. 2004;24(9):560-72.

Kaehler, K. C., et al., "Update on immunologic therapy with anti-CTLA-4 antibodies in melanoma: identification of clinical and biological response patterns, immune-related adverse events, and their management," Semin Oncol, 2010. 37(5): p. 485-98.

Kang SM, et al. "Transactivation by AP-1 is a molecular target of T cell clonal anergy," Science. Aug. 21, 1992;257(5073):1134-8.

Karpovsky B, et al. "Production of target-specific effector cells using hetero-cross-linked aggregates containing anti-target cell and anti-Fc gamma receptor antibodies," J Exp Med. Dec. 1, 1984;160(6):1686-701.

Kashmiri SV, et al. "SDR grafting—a new approach to antibody humanization," Methods. May 2005;36(1):25-34.

Kaufman RJ, et al. "Translational efficiency of polycistronic mRNAs and their utilization to express heterologous genes in mammalian cells," EMBO J. Jan. 1987;6(1):187-93.

Kay MA, et al. "Transient immunomodulation with anti-CD40 ligand antibody and CTLA4Ig enhances persistence and secondary adenovirus-mediated gene transfer into mouse liver," Proc Natl Acad Sci U S A. Apr. 29, 1997;94(9):4686-91.

Keinänen K, et al. "Biosynthetic lipid-tagging of antibodies," FEBS Lett. Jun. 6, 1994;346(1):123-6.

Keir ME, et al. "PD-1 and its ligands in tolerance and immunity," Annu Rev Immunol. 2008;26:677-704.

Keir ME, et al. "PD-1 regulates self-reactive CD8+ T cell responses to antigen in lymph nodes and tissues," mmunol. Oct. 15, 2007;179(8):5064-70.

Kessel M, et al. "Murine developmental control genes," Science. Jul. 27, 1990;249(4967):374-9.

Killion JJ, et al. "Systemic targeting of liposome-encapsulated immunomodulators to macrophages for treatment of cancer metastasis," Immunomethods. Jun. 1994;4(3):273-9.

Kimmel AR, et al. "Preparation of cDNA and the generation of cDNA libraries: overview," Methods Enzymol. 1987;152:307-16.

Kipriyanov SM, et al. "Recombinant single-chain Fv fragments carrying C-terminal cysteine residues: production of bivalent and biotinylated miniantibodies," Mol Immunol. Oct. 1994;31(14):1047-58.

Kipriyanov SM, et al. "Single-chain antibody streptavidin fusions: tetrameric bifunctional scFv-complexes with biotin binding activity and enhanced affinity to antigen," Hum Antibodies Hybridomas. 1995;6(3):93-101.

Kiss I, et al. "Structure of the gene for cartilage matrix protein, a modular protein of the extracellular matrix. Exon/intron organization, unusual splice sites, and relation to alpha chains of beta 2 integrins, von Willebrand factor, complement factors B and C2, and epidermal growth factor," J Biol Chem. May 15, 1989;264(14):8126-34.

Klinken SP, et al. "Evolution of B cell lineage lymphomas in mice with a retrovirus-induced immunodeficiency syndrome, Maids," J Immunol. Feb. 15, 1988;140(4):1123-31.

Kohl S, et al. "Human antibody-dependent cellular cytotoxicity and natural killer cytotoxicity to herpes simplex virus-infected autologous and allogeneic cells," Immunology. Jan. 1983;48(1):187-93.

Köhler G, et al. "Continuous cultures of fused cells secreting antibody of predefined specificity," Nature. Aug. 7, 1975;256(5517):495-7.

Kolaskar AS, et al. "A semi-empirical method for prediction of antigenic determinants on protein antigens," FEBS Lett. Dec. 10, 1990;276(1-2):172-4.

Kostelny SA, et al. "Formation of a bispecific antibody by the use of leucine zippers," J Immunol. Mar. 1, 1992;148(5):1547-53.

Kozbor D, et al. "Specific immunoglobulin production and enhanced tumorigenicity following ascites growth of human hybridomas," J Immunol Methods. Jul. 16, 1985;81(1):31-42.

Kozbor D, et al. "The production of monoclonal antibodies from human lymphocytes," Immunol Today. Mar. 1983;4(3):72-9.

Krishnamurthy S, et al. "Molecular and biologic markers of premalignant lesions of human breast," Adv Anat Pathol. May 2002;9(3):185-97.

Krolick KA, et al. "Selective killing of normal or neoplastic B cells by antibodies coupled to the A chain of ricin," Proc Natl Acad Sci U S A. Sep. 1980;77(9):5419-23.

Kroll DJ, et al. "A multifunctional prokaryotic protein expression system: overproduction, affinity purification, and selective detection," DNA Cell Biol. Jun. 1993;12(5):441-53.

Krutzik, S. R., et al., "TLR activation triggers the rapid differentiation of monocytes into macrophages and dendritic cells," Nat Med, 2005. 11(6): p. 653-60.

Kryczek, I., et al., "B7-H4 expression identifies a novel suppressive macrophage population in human ovarian carcinoma," J Exp Med, 2006. 203(4): p. 871-81.

Kryczek, I., et al., "Cutting edge: induction of B7-H4 on APCs through IL-10: novel suppressive mode for regulatory T cells," J Immunol, 2006. 177(1): p. 40-4.

Kurjan J, et al. "Structure of a yeast pheromone gene (MF alpha): a putative alpha-factor precursor contains four tandem copies of mature alpha-factor," Cell. Oct. 1982;30(3):933-43.

Kuroiwa Y, et al. "Cloned transchromosomic calves producing human immunoglobulin," Nat Biotechnol. Sep. 2002;20(9):889-94.

Kwoh DY, et al. "Transcription-based amplification system and detection of amplified human immunodeficiency virus type 1 with a bead-based sandwich hybridization format," Proc Natl Acad Sci U S A. Feb. 1989;86(4):1173-7.

(56) References Cited

OTHER PUBLICATIONS

Labrijn AF, et al. "Efficient generation of stable bispecific IgG1 by controlled Fab-arm exchange," Proc Natl Acad Sci U S A. Mar. 26, 2013;110(13):5145-50.
LaFace D, et al. "Meeting report: regulatory myeloid cells," Int Immunopharmacol. Jul. 2011;11(7):780-2.
Lakso M, et al. "Targeted oncogene activation by site-specific recombination in transgenic mice," Proc Natl Acad Sci U S A. Jul. 15, 1992;89(14):6232-6.
Lam KS, et al. "A new type of synthetic peptide library for identifying ligand-binding activity," Nature. Nov. 7, 1991;354(6348):82-4.
Lam KS. "Application of combinatorial library methods in cancer research and drug discovery," Anticancer Drug Des. Apr. 1997;12(3):145-67. [Abstract Only].
Landegren U, et al. "A ligase-mediated gene detection technique," Science. Aug. 26, 1988;241(4869):1077-80.
Landt O, et al. "A general method for rapid site-directed mutagenesis using the polymerase chain reaction," Gene. Nov. 30, 1990;96(1):125-8.
Latchman Y, et al. "PD-L2 is a second ligand for PD-1 and inhibits T cell activation," Nat Immunol. Mar. 2001;2(3):261-8.
Latchman YE, et al. "PD-L1-deficient mice show that PD-L1 on T cells, antigen-presenting cells, and host tissues negatively regulates T cells," Proc Natl Acad Sci U S A. Jul. 20, 2004;101(29):10691-6.
Lathe R. "Synthetic oligonucleotide probes deduced from amino acid sequence data. Theoretical and practical considerations," J Mol Biol. May 5, 1985;183(1):1-12.
Laubach VE, et al. "Mice lacking inducible nitric oxide synthase are not resistant to lipopolysaccharide-induced death," Proc Natl Acad Sci U S A. Nov. 7, 1995;92(23):10688-92.
Lázár-Molnár e, et al. "Crystal structure of the complex between programmed death-1 (PD-1) and its ligand PD-L2," Proc Natl Acad Sci U S A. Jul. 29, 2008;105(30):10483-8.
Le Borgne, M., et al., "Dendritic cells rapidly recruited into epithelial tissues via CCR6/CCL20 are responsible for CD8+ T cell crosspriming in vivo," Immunity, 2006. 24(2): p. 191-201.
Le Mercier I, et al. "Beyond CTLA-4 and PD-1, the Generation Z of Negative Checkpoint Regulators," Front Immunol. Aug. 21, 2015;6:418.
Lederman, Seth, et al. "A single amino acid substitution in a common African allele of the CD4 molecule ablates binding of the monoclonal antibody, OKT4." Molecular immunology 28.11 (1991): 1171-1181.
Lee et al., "Increased vaccine-specific T cell frequency after peptide-based vaccination correlates with increased susceptibility to in vitro stimulation but does not lead to tumor regression." The Journal of Immunology 163.11 (1999): 6292-6300.
Lemaitre M, et al. " Specific antiviral activity of a poly(L-lysine)-conjugated oligodeoxyribonucleotide sequence complementary to vesicular stomatitis virus N protein mRNA initiation site," Proc Natl Acad Sci U S A. Feb. 1987;84(3):648-52.
Leng et al., "Potential roles of IL-9 in the pathogenesis of systemic lupus erythematosus", American Journal of Clinical and Experimental Immunology 2012;I(I):28-32.
León B, et al. "Monocyte-derived dendritic cells formed at the infection site control the induction of protective T helper 1 responses against Leishmania," Immunity. Apr. 2007;26(4):519-31.
León B, et al. "Monocyte-derived dendritic cells in innate and adaptive immunity," Immunol Cell Biol. May-Jun. 2008;86(4):320-4.
Lerner EA. "How to make a hybridoma," Yale J Biol Med. Sep.-Oct. 1981;54(5):387-402.
Letsinger RL, et al. "Cholesteryl-conjugated oligonucleotides: synthesis, properties, and activity as inhibitors of replication of human immunodeficiency virus in cell culture," Proc Natl Acad Sci U S A. Sep. 1989;86(17):6553-6.
Li CH, et al. "beta-Endorphin omission analogs: dissociation of immunoreactivity from other biological activities," Proc Natl Acad Sci U S A. Jun. 1980;77(6):3211-4.
Li F, et al. "Inhibitory Fcγ receptor is required for the maintenance of tolerance through distinct mechanisms," J Immunol. Apr. 1, 2014;192(7):3021-8.
Li W, et al. "Immunotherapy of murine retrovirus-induced acquired immunodeficiency by CD4 T regulatory cell depletion and PD-1 blockade," J Virol. Dec. 2011;85(24):13342-53.
Li W, et al. "The role of CD4 T cells in the pathogenesis of murine Aids," J Virol. Jun. 2006;80(12):5777-89.
Lin DY, et al. "The PD-1/PD-L1 complex resembles the antigen-binding Fv domains of antibodies and T cell receptors," Proc Natl Acad Sci U S A. Feb. 26, 2008;105(8):3011-6.
Lines JL, et al. "VISTA is a novel broad-spectrum negative checkpoint regulator for cancer immunotherapy," Cancer Immunol Res. Jun. 2014;2(6):510-7.
Lines JL, et al. "VISTA is an immune checkpoint molecule for human T cells," Cancer Res. Apr. 1, 2014;74(7):1924-32.
Liu AY, et al. "Chimeric mouse-human IgG1 antibody that can mediate lysis of cancer cells," Proc Natl Acad Sci U S A. May 1987;84(10):3439-43.
Liu J, et al. "Immune-checkpoint proteins VISTA and PD-1 nonredundantly regulate murine T-cell responses," Proc Natl Acad Sci U S A. May 26, 2015;112(21):6682-7.
Liu MA, et al. "Heteroantibody duplexes target cells for lysis by cytotoxic T lymphocytes," Proc Natl Acad Sci U S A. Dec. 1985;82(24):8648-52.
Lobley A, et al. "pGenTHREADER and pDomTHREADER: new methods for improved protein fold recognition and superfamily discrimination," Bioinformatics. Jul. 15, 2009;25(14):1761-7.
Lonberg N, et al. "Antigen-specific human antibodies from mice comprising four distinct genetic modifications," Nature. Apr. 28, 1994;368(6474):856-9.
Lonberg N, et al. "Human antibodies from transgenic mice," Int Rev Immunol. 1995;13(1):65-93.
Lopez-Pedrera et al., "Accelerated atherosclerosis in systemic lupus erythematosus: role of proinflammatory cytokines and therapeutic approaches", Journal of Biomedicine & Biotechnology, 2010 Article ID 607084.
Lorain S, et al. "Transient immunomodulation allows repeated injections of AAV1 and correction of muscular dystrophy in multiple muscles," Mol Ther. Mar. 2008;16(3):541-7.
Luckow VA, et al. "High level expression of nonfused foreign genes with Autographa californica nuclear polyhedrosis virus expression vectors," Virology. May 1989;170(1):31-9.
Lutz MB, et al. "An advanced culture method for generating large quantities of highly pure dendritic cells from mouse bone marrow," J Immunol Methods. Feb. 1, 1999;223(1):77-92.
Macatangay BJ, et al. "MDSC: a new player in HIV immunopathogenesis," AIDS. Jul. 31, 2012;26(12):1567-9.
Maher LJ. "DNA triple-helix formation: an approach to artificial gene repressors?" Bioessays. Dec. 1992;14(12):807-15.
Mahnke K, et al. "The dendritic cell receptor for endocytosis, DEC-205, can recycle and enhance antigen presentation via major histocompatibility complex class II-positive lysosomal compartments," J Cell Biol. Oct. 30, 2000;151(3):673-84.
Malashkevich VN, et al. "The crystal structure of a five-stranded coiled coil in COMP: a prototype ion channel?" Science. Nov. 1, 1996;274(5288):761-5.
Marigo, I., et al. "Tumor-induced tolerance and immune suppression by myeloid derived suppressor cells," Immunol Rev, 2008. 222: p. 162-79.
Martinez T, et al. "Disulfide connectivity of human immunoglobulin G2 structural isoforms," Biochemistry. Jul. 15, 2008;47(28):7496-508.
McCafferty J, et al. "Phage antibodies: filamentous phage displaying antibody variable domains," Nature. Dec. 6, 1990;348(6301):552-4.
McConnell HM, et al. "The cytosensor microphysiometer: biological applications of silicon technology," Science. Sep. 25, 1992;257(5078):1906-12.
McHugh RS, et al. "CD4(+)CD25(+) immunoregulatory T cells: gene expression analysis reveals a functional role for the glucocorticoid-induced TNF receptor," Immunity. Feb. 2002;16(2):311-23.

(56) References Cited

OTHER PUBLICATIONS

McIvor RS, et al. "Isolation and characterization of a variant dihydrofolate reductase cDNA from methotrexate-resistant murine L5178Y cells," Nucleic Acids Res. Dec. 11, 1990;18(23):7025-32.
Medina D. "The preneoplastic phenotype in murine mammary tumorigenesis," J Mammary Gland Biol Neoplasia. Oct. 2000;5(4):393-407.
Melief CJ. "Cancer immunotherapy by dendritic cells," Immunity. Sep. 19, 2008;29(3):372-83.
Mencacci A, et al. "CD80+Gr-1+ myeloid cells inhibit development of antifungal Th1 immunity in mice with candidiasis," J Immunol. Sep. 15, 2002;169(6):3180-90.
Merrifield B. "Concept and early development of solid-phase peptide synthesis," Methods Enzymol. 1997;289:3-13.
Mezo AR, et al. "Atrial natriuretic peptide-Fc, ANP-Fc, fusion proteins: semisynthesis, in vitro activity and pharmacokinetics in rats," Bioconjug Chem. Mar. 21, 2012;23(3):518-26.
Milstein C, et al. "Hybrid hybridomas and their use in immunohistochemistry," Nature. Oct. 6-12, 1983;305(5934):537-40.
Mingozzi F, et al. "Immune responses to AAV vectors: overcoming barriers to successful gene therapy," Blood. Jul. 4, 2013;122(1):23-36.
Monteiro RC, et al. "Molecular heterogeneity of Fc alpha receptors detected by receptor-specific monoclonal antibodies," J Immunol. Mar. 15, 1992;148(6):1764-70.
Moore GJ. "Designing peptide mimetics," Trends Pharmacol Sci. Apr. 1994;15(4):124-9.
Morrison SL, et al. "Chimeric human antibody molecules: mouse antigen-binding domains with human constant region domains," Proc Natl Acad Sci U S A. Nov. 1984;81(21):6851-5.
Morrison SL. "Transfectomas provide novel chimeric antibodies," Science. Sep. 20, 1985;229(4719):1202-7.
Muller PY, et al. "Safety assessment and dose selection for first-in-human clinical trials with immunomodulatory monoclonal antibodies," Clin Pharmacol Ther. Mar. 2009;85(3):247-58.
Nakano H, et al. "Blood-derived inflammatory dendritic cells in lymph nodes stimulate acute T helper type 1 immune responses," Nat Immunol. Apr. 2009;10(4):394-402.
Nalbandian A, et al. "Interleukin-17 and systemic lupus erythematosus: current concepts," Clin Exp Immunol. Aug. 2009;157(2):209-15.
Nathwani AC, et al. "Adenovirus-associated virus vector-mediated gene transfer in hemophilia B," N Engl J Med. Dec. 22, 2011;365(25):2357-65.
NCBI Accession No. AAH89443 [gi:59807841] with Revision History—Feb. 16, 2005-Jun. 6, 2006.
NCBI Accession No. AK004116 [gi:12835174] with Revision History—Feb. 8, 2001-Sep. 2, 2005.
NCBI Accession No. BC089443 [gi:59807840] with Revision History—Feb. 15, 2005-Jun. 6, 2006.
NCBI Accession No. NM.sub.--022153 [gi:62339431] with Revision History—Apr. 7, 2005-Jun. 26, 2007.
NCBI Accession No. NM.sub.--026125 [gi:13385631] with Revision History—Mar. 20, 2001-May 7, 2006. 142365660 which replaced 13385631 is provided. cited by other.
NCBI Accession No. NM.sub.--028732 [gi:31980769] with Revision History—Mar. 20, 2001-May 7, 2006. 143249860 which replaced 31980769 is provided.
NCBI Accession No. NM.sub.--138530 [gi:51491892] with Revision History—Apr. 4, 2002-Nov. 18, 2006.
NCBI Accession No. NP.sub.--071436 [gi:62339432] with Revision History—Apr. 7, 2005-Aug. 13, 2006.
NCBI Accession No. NP.sub.--080401 [gi:13385632] with Revision History—Mar. 20, 2001-May 7, 2006.
NCBI Accession No. XM.sub.--233720 [gi:109475938] with Revision History—Jan. 13, 2003-Jun. 22, 2006.
Nesbeth YC, et al. "CD4+ T cells elicit host immune responses to MHC class II-negative ovarian cancer through CCL5 secretion and CD40-mediated licensing of dendritic cells," J Immunol. May 15, 2010;184(10):5654-62.
Neuberger MS, et al. "A hapten-specific chimaeric IgE antibody with human physiological effector function," Nature. Mar. 21-27, 1985;314(6008):268-70.
Neuberger MS, et al. "Recombinant antibodies possessing novel effector functions," Nature. Dec. 13-19, 1984;312(5995):604-8.
Nielsen MB, et al. "Melanoma vaccines: the paradox of T cell activation without clinical response," Cancer Chemother Pharmacol. 2000;46 Suppl:S62-6.
Niklinski J, et al. "Molecular genetic abnormalities in premalignant lung lesions: biological and clinical implications," Eur J Cancer Prev. Jun. 2001;10(3):213-26.
Nishikawa H, et al. "Regulatory T cells in tumor immunity," Int J Cancer. Aug. 15, 2010;127(4):759-67.
Nishimura H, et al. "Autoimmune dilated cardiomyopathy in PD-1 receptor-deficient mice," Science. Jan. 12, 2001;291(5502):319-22.
Nishimura H, et al. "Development of lupus-like autoimmune diseases by disruption of the PD-1 gene encoding an ITIM motif-carrying immunoreceptor," Immunity. Aug. 1999;11(2):141-51.
Nomi, T. et al., Clinical significance and therapeutic potential of the programmed death-1 ligand/programmed death-1 pathway in human pancreatic cancer. Clin. Cancer Res. 2007, vol. 13, pp. 2152-2157.
Norde, W.J. et al., "Coinhibitory molecules in hematologic malignancies: targets for therapeutic intervention", Blood, Jul. 2012, vol. 120, No. 4, pp. 728-736.
Nowak EC, et al. "Immunoregulatory functions of VISTA," Immunol Rev. Mar. 2017;276(1):66-79.
Nygren H. "Conjugation of horseradish peroxidase to Fab fragments with different homobifunctional and heterobifunctional cross-linking reagents. A comparative study," J Histochem Cytochem. May 1982;30(5):407-12.
O'Gorman S, et al. "Recombinase-mediated gene activation and site-specific integration in mammalian cells," Science. Mar. 15, 1991;251(4999):1351-5.
Ohtsuka E, et al. "An alternative approach to deoxyoligonucleotides as hybridization probes by insertion of deoxyinosine at ambiguous codon positions," J Biol Chem. Mar. 10, 1985;260(5):2605-8.
Okazaki T, et al. "The PD-1-PD-L pathway in immunological tolerance," Trends Immunol. Apr. 2006;27(4):195-201.
Orlandi R, et al. "Cloning immunoglobulin variable domains for expression by the polymerase chain reaction," Proc Natl Acad Sci U S A. May 1989;86(10):3833-7.
Ortler S, et al. "B7-H1 restricts neuroantigen-specific T cell responses and confines inflammatory CNS damage: implications for the lesion pathogenesis of multiple sclerosis," Eur J Immunol. Jun. 2008;38(6):1734-44.
Ostergaard S, et al. "Peptomers: a versatile approach for the preparation of diverse combinatorial peptidomimetic bead libraries," Mol Divers. 1997;3(1):17-27.
Ostrand-Rosenberg S, et al. "Myeloid-derived suppressor cells: linking inflammation and cancer," J Immunol. Apr. 15, 2009;182(8):4499-506.
Ostrand-Rosenberg S. "Myeloid-derived suppressor cells: more mechanisms for inhibiting antitumor immunity," Cancer Immunol Immunother. Oct. 2010;59(10):1593-600.
Ostresh JM, et al. "Generation and use of nonsupport-bound peptide and peptidomimetic combinatorial libraries," Methods Enzymol. 1996;267:220-34.
Ottavi A, et al. "An improved method to obtain a single recombinant vasoactive intestinal peptide (VIP) analog," Biochimie. Apr. 1998;80(4):289-93.
Owais M, et al. "Chloroquine encapsulated in malaria-infected erythrocyte-specific antibody-bearing liposomes effectively controls chloroquine-resistant Plasmodium berghei infections in mice," Antimicrob Agents Chemother. Jan. 1995;39(1):180-4.
Oyarzun P, et al. "A bioinformatics tool for epitope-based vaccine design that accounts for human ethnic diversity: Application to emerging infectious diseases," Vaccine. 2015;33(10):1267-73.
Ozkaynak, E., et al. "Programmed death-1 targeting can promote al lograft survival," J Immunol 2002. 169: 6546-6553.

(56) References Cited

OTHER PUBLICATIONS

Pain D, et al. "Preparation of protein A-peroxidase monoconjugate using a heterobifunctional reagent, and its use in enzyme immunoassays," J Immunol Methods. 1981;40(2):219-30.
Parisi, S., et al. "A regulatory loop involving Dies1 and miR-125a controls BMP4 signaling in mouse embryonic stem cells," FASEB J 2012. 26: 3957-3968.
Paulsson M, et al. "Purification and structural characterization of a cartilage matrix protein," Biochem J. Aug. 1, 1981;197(2):367-75.
Payne G. "Progress in immunoconjugate cancer therapeutics," Cancer Cell. Mar. 2003;3(3):207-12.
Peranzoni E, et al. "Myeloid-derived suppressor cell heterogeneity and subset definition," Curr Opin Immunol. Apr. 2010;22(2):238-44.
Perry-O'Keefe H, et al. "Peptide nucleic acid pre-gel hybridization: an alternative to southern hybridization," Proc Natl Acad Sci U S A. Dec. 10, 1996;93(25):14670-5.
Piccirillo CA, et al. "Naturally-occurring CD4+CD25+ immunoregulatory T cells: central players in the arena of peripheral tolerance," Semin Immunol. Apr. 2004;16(2):81-8.
Piccotti JR, et al. "T-cell-dependent antibody response: assay development in cynomolgus monkeys," J Immunotoxicol. Oct. 1, 2005;2(4):191-6.
Picha, Kristen M. et al., "Protein Engineering Strategies for Sustained Glucagon-Like Peptide-1 Receptor-Dependent Control of Glucose Homeostasis", Diabetes, 2008. vol. 57, pp. 1926-1934.
Pilat N, et al. "Costimulatory pathways in transplantation," Semin Immunol. Aug. 2011;23(4):293-303.
Pinkert CA, et al. "An albumin enhancer located 10 kb upstream functions along with its promoter to direct efficient, liver-specific expression in transgenic mice," Genes Dev. May 1987;1(3):268-76.
Platt et al., "Gene hunting in the genomic era: approaches to diagnostic dilemmas in patients with primary immunodeficiencies," J Allergy Clin Immunol 2014, 134: 262-268.
Podojil JR, et al. "B7-H4Ig inhibits mouse and human T-cell function and treats EAE via IL-10/Treg-dependent mechanisms," J Autoimmun. Aug. 2013;44:71-81.
Polyak SW, et al. "Introduction of spacer peptides N-terminal to a cleavage recognition motif in recombinant fusion proteins can improve site-specific cleavage," Protein Eng. Jun. 1997;10(6):615-9.
Pontén J. "Cell biology of precancer," Eur J Cancer. Oct. 2001;37 Suppl 8:S97-113.
Powell et al. "Peptide stability in drug development. II. Effect of single amino acid substitution and glycosylation on peptide reactivity in human serum," Pharm Res. Sep. 1993;10(9):1268-73.
Prasad, D. V., et al. "B7S1, a novel B7 family member that negatively regulates T cell activation," Immunity, 2003. 18(6): p. 863-73.
Prokunina, L., A regulatory polymorphism in PDCD1 is associated with susceptibility to systemic lupus erythematosus in humans. Nat Genet 2002. 32: 666-669.
Qin A, et al. "Expansion of monocytic myeloid-derived suppressor cells dampens T cell function in HIV-1-seropositive individuals," J Virol. Feb. 2013;87(3):1477-90.
Qin W, et al. "Fusion protein of CDR mimetic peptide with Fc inhibit TNF-alpha induced cytotoxicity," Mol Immunol. Feb. 2006;43(6):660-6.
Qu, C., et al., Role of CCR8 and other chemokine pathways in the migration of monocyte-derived dendritic cells to lymph nodes. J Exp Med, 2004. 200(10): p. 1231-41.
Queen C, et al. "Immunoglobulin gene transcription is activated by downstream sequence elements," Cell. Jul. 1983;33(3):741-8.
Queen, et al. "A humanized antibody that binds to the interleukin 2 receptor," Proc Natl Acad Sci U S A. Dec. 1989;86(24):10029-33.
Rabinovich, G. A., D. Gabrilovich, and E. M. Sotomayor, Immunosuppressive strategies that are mediated by tumor cells. Annu Rev Immunol, 2007. 25: p. 267-96.
Rai BK, et al. "MMM: a sequence-to-structure alignment protocol," Bioinformatics. Nov. 1, 2006;22(21):2691-2.
Rain J.C. et al. (2001) The protein-protein interaction map of Helicobacter pylori. Nature 409: 211-15.
Ranade VV. "Drug delivery systems. 1. site-specific drug delivery using liposomes as carriers," J Clin Pharmacol. Aug. 1989;29(8):685-94.
Randolph, G. J., et al. "Differentiation of phagocytic monocytes into lymph node dendritic cells in vivo," Immunity, 1999. 11(6): p. 753-61.
Rathore R, et al. "Current State of Tolerance: The Holy Grail," Arch Clin Nephrol 3(2): 057-063.
Rattan SI, et al. "Protein synthesis, posttranslational modifications, and aging," Ann N Y Acad Sci. Nov. 21, 1992;663:48-62.
Ravetch JV, et al. "IgG Fc receptors," Annu Rev Immunol. 2001;19:275-90.
Rice RH, et al. "Localization of hair shaft protein VSIG8 in the hair follicle, nail unit, and oral cavity," J Invest Dermatol. Sep. 2011;131(9):1936-8.
Rizo J, et al. "Constrained peptides: models of bioactive peptides and protein substructures," Annu Rev Biochem. 1992;61:387-418.
Robben, P. M., et al., Recruitment of Gr-1+ monocytes is essential for control of acute toxoplasmosis. J Exp Med, 2005. 201(11): p. 1761-9.
Roberge JY, et al. "A strategy for a convergent synthesis of N-linked glycopeptides on a solid support," Science. Jul. 14, 1995;269(5221):202-4.
Robertson JM, Jensen PE, Evavold BD. DO11.10 and OT-II T Cells Recognize a C-Terminal Ovalbumin 323-339 Epitope. The Journal of Immunology. 2000;164(9):4706-12. doi: 10.4049/jimmunol.164.9.4706.
Roda G, Jharap B, Neeraj N, Colombel J-F. Loss of Response to Anti-TNFs: Definition, Epidemiology, and Ma nagement. Clin Trans Gastroenterol. 2016;7:e135. doi: 10.1038/ctg.2015.63.
Rose TM, et al. "Consensus-degenerate hybrid oligonucleotide primers for amplification of distantly related sequences," Nucleic Acids Res. Apr. 1, 1998;26(7):1628-35.
Rossolini GM, et al. "Use of deoxyinosine-containing primers vs degenerate primers for polymerase chain reaction based on ambiguous sequence information," Mol Cell Probes. Apr. 1994;8(2):91-8.
Rowe WP, et al. "Plaque assay techniques for murine leukemia viruses," Virology. Dec. 1970;42(4):1136-9.
Saito G, et al. "Drug delivery strategy utilizing conjugation via reversible disulfide linkages: role and site of cellular reducing activities," Adv Drug Deliv Rev. Feb. 10, 2003;55(2):199-215.
Sakaguchi S, et al. "Immunologic self-tolerance maintained by activated T cells expressing IL-2 receptor alpha-chains (CD25). Breakdown of a single mechanism of self-tolerance causes various autoimmune diseases," J Immunol. Aug. 1, 1995;155(3):1151-64.
Sakaguchi S, et al. "Immunologic tolerance maintained by CD25+ CD4+ regulatory T cells: their common role in controlling autoimmunity, tumor immunity, and transplantation tolerance," Immunol Rev. Aug. 2001;182:18-32.
Sakaguchi S, et al. "Organ-specific autoimmune diseases induced in mice by elimination of T cell subset. I. Evidence for the active participation of T cells in natural self-tolerance; deficit of a T cell subset as a possible cause of autoimmune disease," J Exp Med. Jan. 1, 1985;161(1):72-87.
Sakaguchi S, et al. "Regulatory T cells: key controllers of immunologic self-tolerance," Cell. May 26, 2000;101(5):455-8.
Salama AD, et al. "Critical role of the programmed death-1 (PD-1) pathway in regulation of experimental autoimmune encephalomyelitis," J Exp Med. Jul. 7, 2003;198(1):71-8.
Sasikumar P, et al. "Abstact B006: Functional antagonism of VISG8-mediated immune suppression by oral VISTA agents," Abstacts AACR-NCI-EORTC International Conference: Molecular Targets and Cancer Therapeutics; Oct. 2017. 5 pages.
Scaria A, et al. "Antibody to CD40 ligand inhibits both humoral and cellular immune responses to adenoviral vectors and facilitates repeated administration to mouse airway," Gene Ther. Jun. 1997;4(6):611-7.
Scarlett, U. K., et al., In situ stimulation of CD40 and Toll-like receptor 3 transforms ovarian cancerinfiltrating dendritic cells from immunosuppressive to immunostimulatory cells. Cancer Res, 2009. 69(18): p. 7329-37.

(56) References Cited

OTHER PUBLICATIONS

Schreier et al. "Targeting of liposomes to cells expressing CD4 using glycosylphosphatidylinositol-anchored gp120. Influence of liposome composition on intracellular trafficking," J Biol Chem. Mar. 25, 1994;269(12):9090-8.

Schubert R, et al. "Foreign (M13) DNA ingested by mice reaches peripheral leukocytes, spleen, and liver via the intestinal wall mucosa and can be covalently linked to mouse DNA," Proc Natl Acad Sci U S A. Feb. 4, 1997;94(3):961-6.

Schultz LD, et al. "Expression and secretion in yeast of a 400-kDa envelope glycoprotein derived from Epstein-Barr virus," Gene. 1987;54(1):113-23.

Scott JK, et al. "Searching for peptide ligands with an epitope library," Science. Jul. 27, 1990;249(4967):386-90.

Sedy, J. R., "B and T lymphocyte attenuator regulates T cell activation through interaction with herpesvirus entry mediator," Nat Immunol 2005. 6: 90-98.

Seed B. "An LFA-3 cDNA encodes a phospholipid-linked membrane protein homologous to its receptor CD2," Nature. Oct. 29-Nov. 4, 1987;329(6142):840-2.

Seifter S, et al. "Analysis for protein modifications and nonprotein cofactors," Methods Enzymol. 1990;182:626-46.

Senter PD, et al. "Selective activation of anticancer prodrugs by monoclonal antibody-enzyme conjugates, " Adv Drug Deliv Rev. Dec. 31, 2001;53(3):247-64.

Sequence Alignment, 2010, 1 page. U.S. Pat. No. 8,236,304 (U.S. Appl. No. 11/912,397), filed May 14, 2010.

Sequence alignment, 2014, 2 pages. U.S. Pat. No. 9,631,018 (U.S. Appl. No. 13/637,381), filed Oct. 29, 2014.

Sequence alignment, 2015, 3 pages. U.S. Appl. No. 13/925,034, filed Oct. 16, 2015.

Serbina, N. V., et al., TNF/iNOS-producing dendritic cells mediate innate immune defense against bacterial infection. Immunity, 2003. 19(1): p. 59-70.

Seregin SS, et al. "Improving adenovirus based gene transfer: strategies to accomplish immune evasion," Viruses. Sep. 2010;2(9):2013-36.

Sharma, M. D., et al., "Plasmacytoid dendritic cells from mouse tumor-draining lymph nodes directly activate mature Tregs via indoleamine 2,3-dioxygenase," J Clin Invest, 2007. 117(9): p. 2570-82.

Sharma, P. et al., "Novel cancer immunotherapy agents with survival benefit: recent successes and next steps", Nature Reviews Cancer, 2011, vol. 11, pp. 805-812.

Sharpe AH, et al. "The B7-CD28 superfamily," Nat Rev Immunol. Feb. 2002;2(2):116-26.

Shaw DR, et al. "Mouse/human chimeric antibodies to a tumor-associated antigen: biologic activity of the four human IgG subclasses," J Natl Cancer Inst. Dec. 7, 1988;80(19):1553-9.

Sheehan, K, et al. "The relationship between cyclooxygenase-2 expression and colorectal cancer," JAMA, 1999. 282: p. 1254-7.

Shevach EM. "Regulatory T cells in autoimmmunity," Annu Rev Immunol. 2000;18:423-49.

Shevach, E. M., CD4+ CD25+ suppressor T cells: more questions than answers. Nat Rev Immunol, 2002. 2(6): p. 389-400.

Shields RL, et al. "High resolution mapping of the binding site on human IgG1 for Fc gamma RI, Fc gamma RII, Fc gamma RIII, and FcRn and design of IgG1 variants with improved binding to the Fc gamma R," J Biol Chem. Mar. 2, 2001;276(9):6591-604.

Shields RL, et al. "Lack of fucose on human IgG1 N-linked oligosaccharide improves binding to human Fcgamma RIII and antibody-dependent cellular toxicity," J Biol Chem. Jul. 26, 2002;277(30):26733-40.

Shimizu J, et al. "Stimulation of CD25(+)CD4(+) regulatory T cells through GITR breaks immunological self-tolerance," Nat Immunol. Feb. 2002;3(2):135-42.

Shortman, K. et al. "Steady-state and inflammatory dendritic-cell development," Nat Rev Immunol, 2007. 7(1): p. 19-30.

Shulman M, et al. "A better cell line for making hybridomas secreting specific antibodies," Nature. Nov. 16, 1978;276(5685):269-70.

Sica GL, et al. "B7-H4, a molecule of the B7 family, negatively regulates T cell immunity," Immunity. Jun. 2003;18(6):849-61.

Simard C, et al. "Studies of the susceptibility of nude, CD4 knockout, and SCID mutant mice to the disease induced by the murine AIDS defective virus," J Virol. Apr. 1997;71(4):3013-22.

Sizemore DR, et al. "Attenuated Shigella as a DNA delivery vehicle for DNA-mediated immunization," Science. Oct. 13, 1995;270(5234):299-302.

Skehel JJ, et al. "Coiled coils in both intracellular vesicle and viral membrane fusion," Cell. Dec. 23, 1998;95(7):871-4.

Smith DB, et al. "Single-step purification of polypeptides expressed in *Escherichia coli* as fusions with glutathione S-transferase," Gene. Jul. 15, 1988;67(1):31-40.

Smith GE, et al. "Production of human beta interferon in insect cells infected with a baculovirus expression vector," Mol Cell Biol. Dec. 1983;3(12):2156-65.

Smith JH, et al. "Detection of *Mycobacterium tuberculosis* directly from sputum by using a prototype automated Q-beta replicase assay," J Clin Microbiol. Jun. 1997;35(6):1477-83.

Smith JH, et al. "Performance of an automated Q-beta replicase amplification assay for *Mycobacterium tuberculosis* in a clinical trial," J Clin Microbiol. Jun. 1997;35(6):1484-91.

Smith LJ, et al. "Human interleukin 4. The solution structure of a four-helix bundle protein," J Mol Biol. Apr. 20, 1992;224(4):899-904.

Son YI, et al. "A novel bulk-culture method for generating mature dendritic cells from mouse bone marrow cells," J Immunol Methods. Apr. 1, 2002;262(1-2):145-57.

Spatola AF, et al. "Structure-activity relationships of enkephalins containing serially replaced thiomethylene amide bond surrogates," Life Sci. Apr. 7, 1986;38(14):1243-9.

Steinman, R. M. et al. "Tolerogenic dendritic cells," Annu Rev Immunol, 2003. 21: p. 685-711.

Stewart MJ, et al. "Gene transfer in vivo with DNA-liposome complexes: safety and acute toxicity in mice," Hum Gene Ther. Jun. 1992;3(3):267-75.

Studier FW, et al. "Use of T7 RNA polymerase to direct expression of cloned genes," Methods Enzymol. 1990;185:60-89.

Su AI, et al. "Large-scale analysis of the human and mouse transcriptomes," Proc Natl Acad Sci U S A. Apr. 2, 2002;99(7):4465-70.

Suh, W. K., et al. "The B7 family member B7-H3 preferentially down-regulates T helper type 1-mediated immune responses," Nat Immunol 2003. 4: 899-906.

Sun LK, et al. "Chimeric antibody with human constant regions and mouse variable regions directed against carcinoma-associated antigen 17-1A," Proc Natl Acad Sci U S A. Jan. 1987;84(1):214-8.

Sunderkotter, C., et al., "Subpopulations of mouse blood monocytes differ in maturation stage and inflammatory response," J Immunol, 2004. 172(7): p. 4410-7.

Tacke, F. et al. "Migratory fate and differentiation of blood monocyte subsets," Immunobiology, 2006. 211(6-8): p. 609-18.

Tafuri A, et al. "ICOS is essential for effective T-helper-cell responses," Nature. Jan. 4, 2001;409(6816):105-9.

Takamatsu N, et al. "Expression of bacterial chloramphenicol acetyltransferase gene in tobacco plants mediated by TMV-RNA," EMBO J. Feb. 1987;6(2):307-11.

Takamura S, et al. "Premature terminal exhaustion of Friend virus-specific effector CD8+ T cells by rapid induction of multiple inhibitory receptors," J Immunol. May 1, 2010;184(9):4696-707.

Takeda S, et al. "Construction of chimaeric processed immuno-globulin genes containing mouse variable and human constant region sequences," Nature. Apr. 4-10, 1985;314(6010):452-4.

Tarhini, A., E. Lo, and D. R. Minor, Releasing the brake on the immune system: ipilimumab in melanoma and other tumors. Cancer Biother Radiopharm, 2010. 25(6): p. 601-13.

Taylor LD, et al. "A transgenic mouse that expresses a diversity of human sequence heavy and light chain immunoglobulins," Nucleic Acids Res. Dec. 11, 1992;20(23):6287-95.

(56) References Cited

OTHER PUBLICATIONS

Taylor LD, et al. "Human immunoglobulin transgenes undergo rearrangement, somatic mutation and class switching in mice that lack endogenous IgM," Int Immunol. Apr. 1994;6(4):579-91.
Taylor WR. "The classification of amino acid conservation," J Theor Biol. Mar. 21, 1986;119(2):205-18.
Teft WA, et al. "A molecular perspective of CTLA-4 function," Annu Rev Immunol. 2006;24:65-97.
Terawaki, S., "Specific and high-affinity binding of tetramerized PD-LI extracellular domain to PD-I-expressing cells: possible application to enhance T cell function," Int Immunol 2007. 19: 881-890.
Thompson JA, et al. "A phase I trial of CD3/CD28-activated T cells (Xcellerated T cells) and interleukin-2 in patients with metastatic renal cell carcinoma," Clin Cancer Res. Sep. 1, 2003;9(10 Pt 1):3562-70.
Thompson JD, et al. "Clustal W: improving the sensitivity of progressive multiple sequence alignment through sequence weighting, position-specific gap penalties and weight matrix choice," Nucleic Acids Res. Nov. 11, 1994;22(22):4673-80.
Thorpe et al., "The Preparation and Cytotoxic Properties of Antibody-Toxin Conjugates", Immunol. Rev., 62: 119-58 (1982).
Tivol EA, et al. "Loss of CTLA-4 leads to massive lymphoproliferation and fatal multiorgan tissue destruction, revealing a critical negative regulatory role of CTLA-4," Immunity. Nov. 1995;3(5):541-7.
Tomizuka K, et al. "Double trans-chromosomic mice: maintenance of two individual human chromosome fragments containing Ig heavy and kappa loci and expression of fully human antibodies," Proc Natl Acad Sci U S A. Jan. 18, 2000;97(2):722-7.
Tomlinson, et al. (1992) "The Repertoire of Human Germline VH Sequences Reveals about Fifty Groups of VH Segments with Different Hypervariable Loops" J. Mol. Biol. 227: 776-798.
Townsend SE, et al. "Tumor rejection after direct costimulation of CD8+ T cells by B7-transfected melanoma cells," Science. Jan. 15, 1993;259(5093):368-70.
Trail PA, et al. "Monoclonal antibody drug immunoconjugates for targeted treatment of cancer," Cancer Immunol Immunother. May 2003;52(5):328-37.
Transmembrane Region Prediction, "SACS MEMSAT2" 2018, 16 pages.
Traunecker A, et al. "Bispecific single chain molecules (Janusins) target cytotoxic lymphocytes on HIV infected cells," EMBO J. Dec. 1991;10(12):3655-9.
Tuaillon N, et al. "Human immunoglobulin heavy-chain minilocus recombination in transgenic mice: gene-segment use in mu and gamma transcripts," Proc Natl Acad Sci U S A. Apr. 15, 1993;90(8):3720-4.
Tuaillon N, et al. "Biased utilization of DHQ52 and JH4 gene segments in a human Ig transgenic minilocus is independent of antigenic selection," J Immunol. Mar. 15, 1994;152(6):2912-20.
Tuladhar et al., "Role of Co-stimulation in Leishmaniasis." Int J Biol Sci. 2011;7(9):1382-90.
Tutt A, et al. "Trispecific F(ab')3 derivatives that use cooperative signaling via the TCR/CD3 complex and CD2 to activate and redirect resting cytotoxic T cells," J Immunol. Jul. 1, 1991;147(1):60-9.
Umaña P, et al. "Engineered glycoforms of an antineuroblastoma IgG1 with optimized antibody-dependent cellular cytotoxic activity," Nat Biotechnol. Feb. 1999;17(2):176-80.
Umezawa F, et al. "Liposome targeting to mouse brain: mannose as a recognition marker," Biochem Biophys Res Commun. Jun. 30, 1988;153(3):1038-44.
Uy R, et al. "Posttranslational covalent modification of proteins," Science. Dec. 2, 1977;198(4320):890-6.
Vaccaro C, et al. "Engineering the Fc region of immunoglobulin G to modulate in vivo antibody levels," Nature Biotechnology. 2005;23(10):1283-8.
Van Elsas A, et al. "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation," J Exp Med. Aug. 2, 1999;190(3):355-66.
Van Wauwe JP, et al. "OKT3: a monoclonal anti-human T lymphocyte antibody with potent mitogenic properties," The Journal of Immunology. 1980;124(6):2708-13.
Velu V, et al. "Enhancing SIV-specific immunity in vivo by PD-1 blockade," Nature. Mar. 12, 2009;458(7235):206-10.
Verhoeyen M, et al. "Reshaping human antibodies: grafting an antilysozyme activity," Science. Mar. 25, 1988;239(4847):1534-6.
Via CS. "Advances in lupus stemming from the parent-into-FI model". Trends Immunol., Jun. 2010 31(6):236-45).
Wada K, et al. "Codon usage tabulated from the GenBank genetic sequence data," Nucleic Acids Res. May 11, 1992;20 Suppl:2111-8.
Wadia JS, et al. "Protein transduction technology," Curr Opin Biotechnol. Feb. 2002;13(1):52-6.
Walch A, et al. "Microdissection of tissue sections: application to the molecular genetic characterisation of premalignant lesions," Pathobiology. Jan.-Feb. 2000;68(1):9-17.
Walker JD, et al. "Oncolytic herpes simplex virus 1 encoding 15-prostaglandin dehydrogenase mitigates immune suppression and reduces ectopic primary and metastatic breast cancer in mice," J Virol. Jul. 2011;85(14):7363-71.
Wallace DJ, et al. "Long-Term Safety and Efficacy of Epratuzumab in the Treatment of Moderate-to-Severe Systemic Lupus Erythematosus: Results From an Open-Label Extension Study," Arthritis Care Res (Hoboken). Apr. 2016;68(4):534-43.
Wang et al. "Immune checkpoint protein VISTA regulate autoimmunity and anti-tumor immunity" J Immunol (May 2013) vol. 190 (Meeting Abstract Supplement) No. 53.35, abstract. 2 pages.
Wang G, et al. "The effects of PDL-Ig on collagen-induced arthritis," Rheumatol Int. Apr. 2011;31(4):513-9.
Wang HC, et al. "Maximum immunobioactivity of murine small intestinal intraepithelial lymphocytes resides in a subpopulation of CD43+ T cells," J Immunol. Nov. 15, 2004;173(10):6294-302.
Wang H-X, "Immune mechanisms of Concanavalin A model of autoimmune hepatitis," World Journal of Gastroenterology: WJG. 2012;18(2):119-25.
Wang L, et al. "Disruption of the immune-checkpoint VISTA gene imparts a proinflammatory phenotype with predisposition to the development of autoimmunity," Proc Natl Acad Sci U S A. Oct. 14, 2014;111(41):14846-51.
Wang, L., et al., "Programmed death 1 ligand signaling regulates the generation of adaptive Foxp3+CD4+ regulatory T cells," Proc Natl Acad Sci USA, 2008. 105(27): p. 9331-6.
Wang, X., "B7-H4 induces donor-specific tolerance in mouse islet allografts," Cell Transplant 2012. 21: 99-111.
Wang, X., "B7-H4 Treatment of T Cells Inhibits ERK, JN K, p38, and AKT Activation," PLoS One 2012. 7: e28232.
Ward ES, et al. "Binding activities of a repertoire of single immunoglobulin variable domains secreted from *Escherichia coli*," Nature. Oct. 12, 1989;341(6242):544-6.
Warrington et al. Allergy, Asthma & Clinical Immunology 2011, 7(Suppl 1):S1, 8 pages.
Waterhouse P, et al. "Lymphoproliferative disorders with early lethality in mice deficient in Ctla-4," Science. Nov. 10, 1995;270(5238):985-8.
Weber, J., "Immune checkpoint proteins: a new therapeutic paradigm for cancer—preclinical background: CTLA-4 and PD-1 blockade," Semin Oncol, 2010. 37(5): p. 430-9.
Weiner GJ. "Building better monoclonal antibody-based therapeutics," Nat Rev Cancer. 2015;15(6):361-70.
Weintraub H., et al. "Anti-sense RNA as a molecular tool for] genetic analysis," Trends in Genetics, 1985, pp. 22-25.
Weissmuller S, "TGN1412 Induces Lymphopenia and Human Cytokine Release in a Humanized Mouse Model," PloS One. 2016;II(3):e0149093.
Welling GW, et al. "Prediction of sequential antigenic regions in proteins, " FEBS Lett. Sep. 2, 1985;188(2):215-8.
Wetmur JG. "DNA probes: applications of the principles of nucleic acid hybridization," Crit Rev Biochem Mol Biol. 1991;26(3-4):227-59.

(56) References Cited

OTHER PUBLICATIONS

White et al., (2015), "Conformation of the human immunoglobulin G2 hinge imparts superagonistic properties to immunostimulatory anticancer antibodies", Cancer Cell, 27(1), 138-148.
Wilcox, R. A., "Cancer-associated myeloproliferation: old association, new therapeutic target," Mayo Clin Proc, 2010. 85(7): p. 656-63.
Wiley RA, et al. "Peptidomimetics derived from natural products," Med Res Rev. May 1993;13(3):327-84.
Williams G, et al. "Dissection of the extracellular human interferon gamma receptor alpha-chain into two immunoglobulin-like domains. Production in an *Escherichia coli* thioredoxin gene fusion expression system and recognition by neutralizing antibodies," Biochemistry. Feb. 7, 1995;34(5):1787-97.
Willmon C, et al. "Vesicular stomatitis virus-induced immune suppressor cells generate antagonism between intratumoral oncolytic virus and cyclophosphamide," Mol Ther. Jan. 2011;19(1):140-9.
Wilmut I, et al. "Viable offspring derived from fetal and adult mammalian cells," Nature. Feb. 27, 1997;385(6619):810-3.
Wing, K., et al., "CTLA-4 control over Foxp3+ regulatory T cell function," Science, 2008. 322(5899): p. 271-5.
Winoto A, et al. "A novel, inducible and T cell-specific enhancer located at the 3' end of the T cell receptor alpha locus," EMBO J. Mar. 1989;8(3):729-33.
Winter G, et al. "Man-made antibodies," Nature. Jan. 24, 1991;349(6307):293-9.
Wojcik J, et al. "Prediction, assessment and validation of protein interaction maps in bacteria," J Mol Biol. Nov. 1, 2002;323(4):763-70.
Wolchok JD, et al. "Nivolumab plus ipilimumab in advanced melanoma," N Engl J Med. Jul. 11, 2013;369(2):122-33.
Wood CR, et al. "The synthesis and in vivo assembly of functional antibodies in yeast," Nature. Apr. 4-10, 1985;314(6010):446-9.
Wood KJ, et al. "Regulatory T cells in transplantation tolerance," Nat Rev Immunol. Mar. 2003;3(3):199-210.
Wu DY, et al. "The ligation amplification reaction (LAR)—amplification of specific DNA sequences using sequential rounds of template-dependent ligation," Genomics. May 1989;4(4):560-9.
Wu S, et al. "Development and application of 'phosphoflow' as a tool for immunomonitoring," Expert Rev Vaccines. 2010;9(6):631-43.
Xu X, et al. "The genomic sequence of the Chinese hamster ovary (CHO)-K1 cell line," Nat Biotechnol. Jul. 31, 2011;29(8):735-41.
Yamaguchi, T. et al. "Regulatory T cells in immune surveillance and treatment of cancer," Semin Cancer Biol, 2006. 16(2): p. 115-23.
Yamane-Ohnuki N, et al. "Establishment of FUT8 knockout Chinese hamster ovary cells: an ideal host cell line for producing completely defucosylated antibodies with enhanced antibody-dependent cellular cytotoxicity," Biotechnol Bioeng. Sep. 5, 2004;87(5):614-22.
Yamaura, K., "In vivo function of immune inhibitory molecule B7-H4 in alloimmune responses," Am J Transplant 2010. 10: 2355-2362.
Yeh MY, et al. "A cell-surface antigen which is present in the ganglioside fraction and shared by human melanomas," Int J Cancer. Mar. 15, 1982;29(3):269-75.
Yeh MY, et al. "Cell surface antigens of human melanoma identified by monoclonal antibody," Proc Natl Acad Sci U S A. Jun. 1979;76(6):2927-31.
Yetter RA, et al. "CD4+ T cells are required for development of a murine retrovirus-induced immunodeficiency syndrome (Maids)," J Exp Med. Aug. 1, 1988;168(2):623-35.
Yi, K. H., et al. "Fine tuning the immune response through B7-H3 and B7-H4," Immunol Rev, 2009. 229(1): p. 145-51.
Yoon KW, et al. "Control of signaling-mediated clearance of apoptotic cells by the tumor suppressor p53," Science. 2015;349(6247):1261669.
Yoshinaga SK, et al. "T-cell co-stimulation through B7RP-1 and ICOS," Nature. Dec. 16, 1999;402(6763):827-32.
Youle RJ, et al. "Anti-Thy 1.2 monoclonal antibody linked to ricin is a potent cell-type-specific toxin," Proc Natl Acad Sci U S A. Sep. 1980;77(9):5483-6.
Youn JI, et al. "The biology of myeloid-derived suppressor cells: the blessing and the curse of morphological and functional heterogeneity," Eur J Immunol. Nov. 2010;40(11):2969-75.
Youngnak, P., "Differential binding properties of B7-H1 and B7-DC to programmed death-1," Biochem Biophys Res Commun 2003. 307: 672-677.
Zelinskyy G, et al. "The regulatory T-cell response during acute retroviral infection is locally defined and controls the magnitude and duration of the virus-specific cytotoxic T-cell response," Blood. Oct. 8, 2009;114(15):3199-207.
Zenewicz, et al. "CD4 T-cell differentiation and inflammatory bowel disease," Trends Mol Med. May 2009;15(5):199-207.
Zervos AS, et al. "Mxi1, a protein that specifically interacts with Max to bind Myc-Max recognition sites," Cell. Jan. 29, 1993;72(2):223-32.
Zhang X, et al. "Bcr-Abl efficiently induces a myeloproliferative disease and production of excess interleukin-3 and granulocyte-macrophage colony-stimulating factor in mice: a novel model for chronic myelogenous leukemia," Blood. Nov. 15, 1998;92(10):3829-40.
Zhang, A., (2015), "Conformational difference in human IgG2 disulfide isoforms revealed by hydrogen/deuterium exchange mass spectrometry", Biochemistry, 54(10), 1956-1962.
Zheng, S. G., et al., "TGF-beta requires CTLA-4 early after T cell activation to induce FoxP3 and generate adaptive CD4+CD25+ regulatory cells," J Immunol, 2006. 176(6): p. 3321-9.
Zhu N, et al. "Systemic gene expression after intravenous DNA delivery into adult mice," Science. Jul. 9, 1993;261(5118):209-11.
Zhu Y, et al. "B7-H5 costimulates human T cells via CD28H," Nat Commun. 2013;4:2043.
Zhu Z, et al. "High level secretion of a humanized bispecific diabody from *Escherichia coli*," Biotechnology (N Y). Feb. 1996;14(2):192-6.
Zhu, G., "B7-H4-deficient mice display augmented neutrophil-mediated innate immunity," Blood 2009. 113: 1759-1767.
Zon G. "Oligonucleotide analogues as potential chemotherapeutic agents," Pharm Res. Sep. 1988;5(9):539-49.
Zou, W, et al. "Inhibitory B7-family molecules in the tumour microenvironment," Nat Rev Immunol, 2008. 8(6): p. 467-77.
Zou, W., "Regulatory T cells, tumour immunity and immunotherapy," Nat Rev Immunol, 2006. 6(4): p. 295-307.
Zuckermann RN, et al. "Discovery of nanomolar ligands for 7-transmembrane G-protein-coupled receptors from a diverse N-(substituted)glycine peptoid library," J Med Chem. Aug. 19, 1994;37(17):2678-85.
Antonarakis ES. "Combining active immunotherapy with immune checkpoint blockade for the treatment of advanced prostate cancer," Asian J Androl. Jul. 2012;14(4):520-1.
Brahmer JR, et al. "Safety and activity of anti-PD-L1 antibody in patients with advanced cancer," N Engl J Med. Jun. 28, 2012;366(26):2455-65.
Brahmer, et al. Supplementary Appendix, Jun. 28, 2012, 26 pages.
Brahmer, et al. Supplementary Protocol, Jun. 28, 2012, 700 pages.
Curran MA, et al. "PD-1 and CTLA-4 combination blockade expands infiltrating T cells and reduces regulatory T and myeloid cells within B16 melanoma tumors," Proc Natl Acad Sci U S A. Mar. 2, 2010;107(9):4275-80.
Wang, Li PhD—Dartmouth Medical School Presentation at the SITC (Society for Immunotherapy of Cancer) 26th Annual Meeting Dec. 2011.
Martinez Forero I, et al. "Workshop on immunotherapy combinations. Society for Immunotherapy of Cancer annual meeting Bethesda, Nov. 3, 2011," J Transl Med. May 28, 2012;10:108.
Pilon-Thomas S, et al. "Blockade of programmed death ligand 1 enhances the therapeutic efficacy of combination immunotherapy against melanoma," J Immunol. Apr. 1, 2010;184(7):3442-9.
Program of the SITC (Society for Immunotherapy of Cancer) 26th Annual Meeting Nov. 2011.

(56) References Cited

OTHER PUBLICATIONS

Quah BJ, et al. "The use of carboxyfluorescein diacetate succinimidyl ester (CFSE) to monitor lymphocyte proliferation," J Vis Exp. Oct. 12, 2010;(44). pii: 2259.

Topalian SL, et al. "Targeting the PD-1/B7-H1(PD-L1) pathway to activate anti-tumor immunity," Curr Opin Immunol. Apr. 2012;24(2):207-12.

Wang, L. et al. "Immune Checkpoint Protein Vista as a Novel Target for Cancer Immunotherapy," Abstracts for the 27th Annual Scientific Meeting of the Society for Immunotherapy of Cancer (SITC), J Immunother. Nov.-Dec. 2012;35(9):721, 781.

Yu P, et al. "Simultaneous blockade of multiple immune system inhibitory checkpoints enhances antitumor activity mediated by interleukin-15 in a murine metastatic colon carcinoma model," Clin Cancer Res. Dec. 15, 2010;16(24):6019-28.

Yu P, et al. "Simultaneous inhibition of two regulatory T-cell subsets enhanced Interleukin-15 efficacy in a prostate tumor model," Proc Natl Acad Sci U S A. Apr. 17, 2012;109(16):6187-92.

Zitvogel L, et al. "Targeting PD-1/PD-L1 interactions for cancer immunotherapy," Oncoimmunology. Nov. 1, 2012;1(8):1223-1225.

Abdiche, Yasmina Noubia et al. "Assessing kinetic and epitopic diversity across orthogonal monoclonal antibody generation platforms." mAbs vol. 8,2 (2016): 264-77. doi:10.1080/19420862.2015.1118596.

Balducci, Lodovico. "Cancer Prevention in the Older Individual." Seminars in oncology nursing vol. 32,3 (2016): 314-24. doi:10.1016/j.soncn.2016.05.011.

Boyd, Scott D, and James E Crowe Jr. "Deep sequencing and human antibody repertoire analysis." Current opinion in immunology vol. 40 (2016): 103-9. doi:10.1016/j.coi.2016.03.008.

Conroy, Paul J et al. "Antibodies: From novel repertoires to defining and refining the structure of biologically important targets." Methods (San Diego, Calif.) vol. 116 (2017): 12-22. doi:10.1016/j.ymeth.2017.01.003.

Damschroder, Melissa M et al. "Analysis of human and primate CD2 molecules by protein sequence and epitope mapping with anti-human CD2 antibodies." Molecular immunology vol. 41,10 (2004): 985-1000. doi:10.1016/j.molimm.2004.05.004.

Ferrara, Fortunato et al. "Recombinant renewable polyclonal antibodies." mAbs vol. 7,1 (2015): 32-41. doi:10.4161/19420862.2015.989047.

Gupta, S., et al., "Systemic Immunotherapy for Urothelial Cancer: Current Trends and Future Directions," Cancers, vol. 9; No. 2; 14 pages (2017).

Kanyavuz, Alexia et al. "Breaking the law: unconventional strategies for antibody diversification." Nature reviews. Immunology vol. 19,6 (2019): 355-368. doi:10.1038/s41577-019-0126-7.

Khan, Lubina et al. "Cross-neutralizing anti-HIV-1 human single chain variable fragments(scFvs) against CD4 binding site and N332 glycan identified from a recombinant phage library." Scientific reports vol. 7 45163. Mar. 23, 2017, doi:10.1038/srep45163.

Konishi, J., et al., "B7-H1 Expression on Non-Small Cell Lung Cancer Cells and Its Relationship with Tumor-Infiltrating Lymphocytes and Their PD-1 Expression," Clinical Cancer Research; vol. 10; No. 15; 5094-5100 (2004).

Könitzer, Jennifer D et al. "Generation of a highly diverse panel of antagonistic chicken monoclonal antibodies against the GIP receptor." mAbs vol. 9,3 (2017): 536-549. doi:10.1080/19420862.2016.1276683.

Ladjemi, M.Z., et al., "Anti-HER2 vaccines: new prospects for breast cancer therapy," Cancer Immunol. Immunother., vol. 59; 1295-1312 (2010).

Lawrence, M.S., et al., "Mutational heterogeneity in cancer and the search for new cancer-associated genes," Nature, vol. 499; No. 7457; 214-218 (2013).

Lee, Jiwon et al. "Molecular-level analysis of the serum antibody repertoire in young adults before and after seasonal influenza vaccination." Nature medicine vol. 22, 12 (2016): 1456-1464. doi:10.1038/nm.4224.

Linsley PS, et al. "The clinical utility of inhibiting CD28-mediated costimulation," Immunol Rev. May 2009;229(1):307-21.

Parola, Cristina et al. "Integrating high-throughput screening and sequencing for monoclonal antibody discovery and engineering." Immunology vol. 153,1 (2018): 31-41. doi:10.1111/imm.12838.

Pettinello, Rita, and Helen Dooley. "The immunoglobulins of cold-blooded vertebrates." Biomolecules vol. 4,4 1045-69. Nov. 24, 2014, doi:10.3390/biom4041045.

Rizvi, N.A., et al., "Mutational landscape determines sensitivity to PD-1 blockade in non-small cell lung cancer," Science, vol. 348; No. 6230; 124-148 (2015).

Shashidharamurthy, Rangaiah et al. "Analysis of cross-species IgG binding to human and mouse Fcgamma receptors (FcγRs) (138.29)." Journal of Immunology 184 (2010): n. pag. Abstract only.

Shashidharamurthy, Rangaiah et al. "Dynamics of the interaction of human IgG subtype immune complexes with cells expressing R and H allelic forms of a low-affinity Fc gamma receptor CD32A." Journal of immunology (Baltimore, Md. : 1950) vol. 183,12 (2009): 8216-24. doi:10.4049/jimmunol.0902550.

Sheehan, Jared, and Wayne A Marasco. "Phage and Yeast Display." Microbiology spectrum vol. 3,1 (2015): AID-0028-2014. doi:10.1128/microbiolspec.AID-0028-2014.

Van Regenmortel, Marc H V. "Development of a Preventive HIV Vaccine Requires Solving Inverse Problems Which Is Unattainable by Rational Vaccine Design." Frontiers in immunology vol. 8 2009. Jan. 12, 2018, doi:10.3389/fimmu.2017.02009.

Topalian, Suzanne L et al. "Safety, activity, and immune correlates of anti-PD-1 antibody in cancer." The New England journal of medicine vol. 366,26 (2012): 2443-54. doi:10.1056/NEJMoa1200690.

UniProtKB/Swiss-Prot Q9H7M9.3 V-type immunoglobulin domain-containing suppressor of T-cell activation, 2019, 6 pages.

Vafa, Omid et al. "An engineered Fc variant of an IgG eliminates all immune effector functions via structural perturbations." Methods (San Diego, Calif.) vol. 65,1 (2014): 114-26. doi:10.1016/j.ymeth.2013.06.035.

Wang, L. et al., "Vista, a novel mouse Ig superfamily ligand that negatively regulates T cell response," J. Exp. Med. Mar. 7, 2011, vol. 208. No. 3, pp. 577-592.

Wolff, A.C., et al., "American Society of Clinical Oncology/College of American Pathologists Guideline Recommendations for Human Epidermal Growth Factor Receptor 2 Testing in Breast Cancer," Arch Pathol Lab Med, vol. 131; 18-43 (2007).

"MS the Disease," National Multiple Sclerosis Society, Apr. 3, 2019, 5 pages. https://www.nationalmssociety.org/About-the-Society/Press-Room/MS-the-Disease.

"Progress in Autoimmune Disease Research" NIH, The Autoimmune Diseases Coordinating Committee, Mar. 2005, 146 pages.

Allen, Martin J et al. "Interchain disulfide bonding in human IgG2 antibodies probed by site-directed mutagenesis." Biochemistry vol. 48,17 (2009): 3755-66. doi:10.1021/bi8022174.

Beers, Stephen A et al. "Influence of immunoglobulin isotype on therapeutic antibody function." Blood vol. 127,9 (2016): 1097-101. doi:10.1182/blood-2015-09-625343.

Burgers, Wendy A, and Carolyn Williamson. "The challenges of HIV vaccine development and testing." Best practice & research. Clinical obstetrics & gynaecology vol. 19,2 (2005): 277-91. doi:10.1016/j.bpobgyn.2004.11.001.

Chevalier, Mathieu F, and Laurence Weiss. "The split personality of regulatory T cells in HIV infection." Blood vol. 121,1 (2013): 29-37. doi:10.1182/blood-2012-07-409755.

Lapierre, Pascal, and Alain Lamarre. "Regulatory T Cells in Autoimmune and Viral Chronic Hepatitis." Journal of immunology research vol. 2015 (2015): 479703. doi:10.1155/2015/479703.

Lightle, Sandra et al. "Mutations within a human IgG2 antibody form distinct and homogeneous disulfide isomers but do not affect Fc gamma receptor or C1q binding." Protein science : a publication of the Protein Society vol. 19,4 (2010): 753-62. doi:10.1002/pro.352.

Mor, Felix et al. "Identification of aldolase as a target antigen in Alzheimer's disease." Journal of immunology (Baltimore, Md. : 1950) vol. 175,5 (2005): 3439-45. doi:10.4049/jimmunol.175.5.3439.

(56) References Cited

OTHER PUBLICATIONS

Nowak, Elizabeth C et al. "Immunoregulatory functions of VISTA." Immunological reviews vol. 276,1 (2017): 66-79. doi:10.1111/imr.12525.

Overdijk, Marije B et al. "Crosstalk between human IgG isotypes and murine effector cells." Journal of immunology (Baltimore, Md. : 1950) vol. 189,7 (2012): 3430-8. doi:10.4049/jimmunol.1200356.

Papaconstantinou, Harry T, and J Scott Thomas. "Bacterial colitis." Clinics in colon and rectal surgery vol. 20,1 (2007): 18-27. doi:10.1055/s-2007-970196.

Quinn, M A et al. "How do you diagnose rheumatoid arthritis early?." Best practice & research. Clinical rheumatology vol. 15,1 (2001): 49-66. doi:10.1053/berh.2000.0125.

Tecklenborg, J et al. "The role of the immune system in kidney disease." Clinical and experimental immunology vol. 192,2 (2018): 142-150. doi:10.1111/cei.13119.

Wang, Xinhua et al. "IgG Fc engineering to modulate antibody effector functions." Protein & cell vol. 9,1 (2018): 63-73. doi:10.1007/s13238-017-0473-8.

White, Ann L et al. "Conformation of the human immunoglobulin G2 hinge imparts superagonistic properties to immunostimulatory anticancer antibodies." Cancer cell vol. 27,1 (2015): 138-48. doi:10.1016/j.ccell.2014.11.001.

Ben-Zvi, Lior et al. "Diagnosis and Management of Infectious Arthritis in Children." Current infectious disease reports vol. 21,7 23. May 29, 2019, doi:10.1007/s11908-019-0678-5.

Hid Cadena, Rebeca et al. "Decreased Expression of Negative Immune Checkpoint VISTA by CD4+ T Cells Facilitates T Helper 1, T Helper 17, and T Follicular Helper Lineage Differentiation in GCA." Frontiers in immunology vol. 10 1638. Jul. 16, 2019, doi:10.3389/fimmu.2019.01638.

Xu, Wenwen et al. "Immune-Checkpoint Protein VISTA Regulates Antitumor Immunity by Controlling Myeloid Cell-Mediated Inflammation and Immunosuppression." Cancer immunology research vol. 7,9 (2019): 1497-1510. doi:10.1158/2326-6066.CIR-18-0489.

* cited by examiner

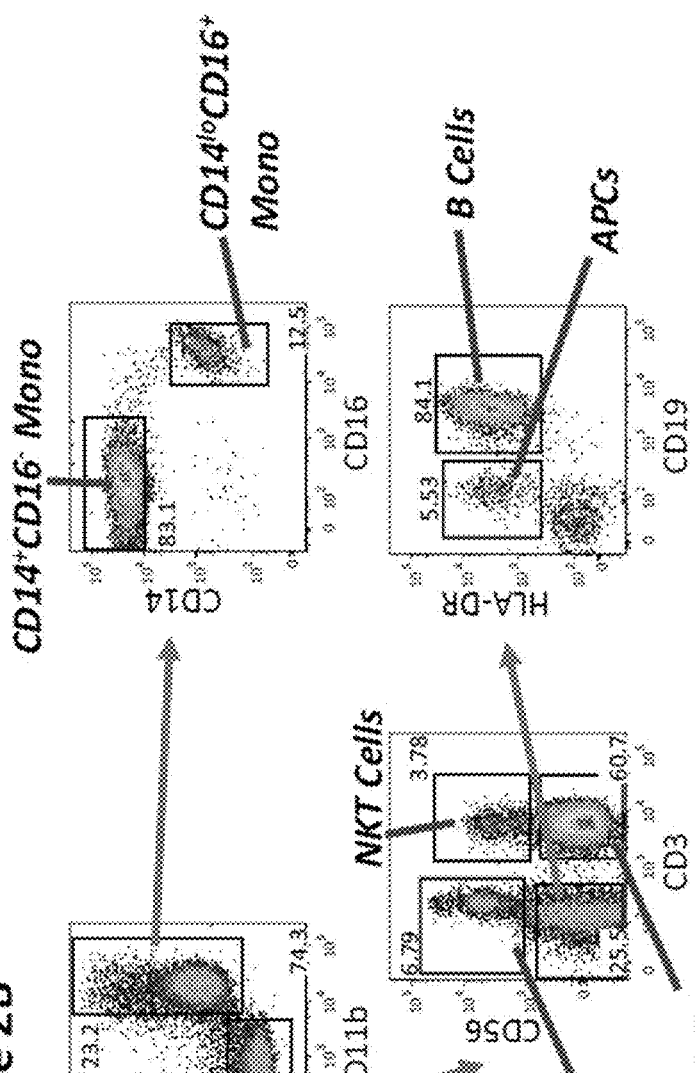

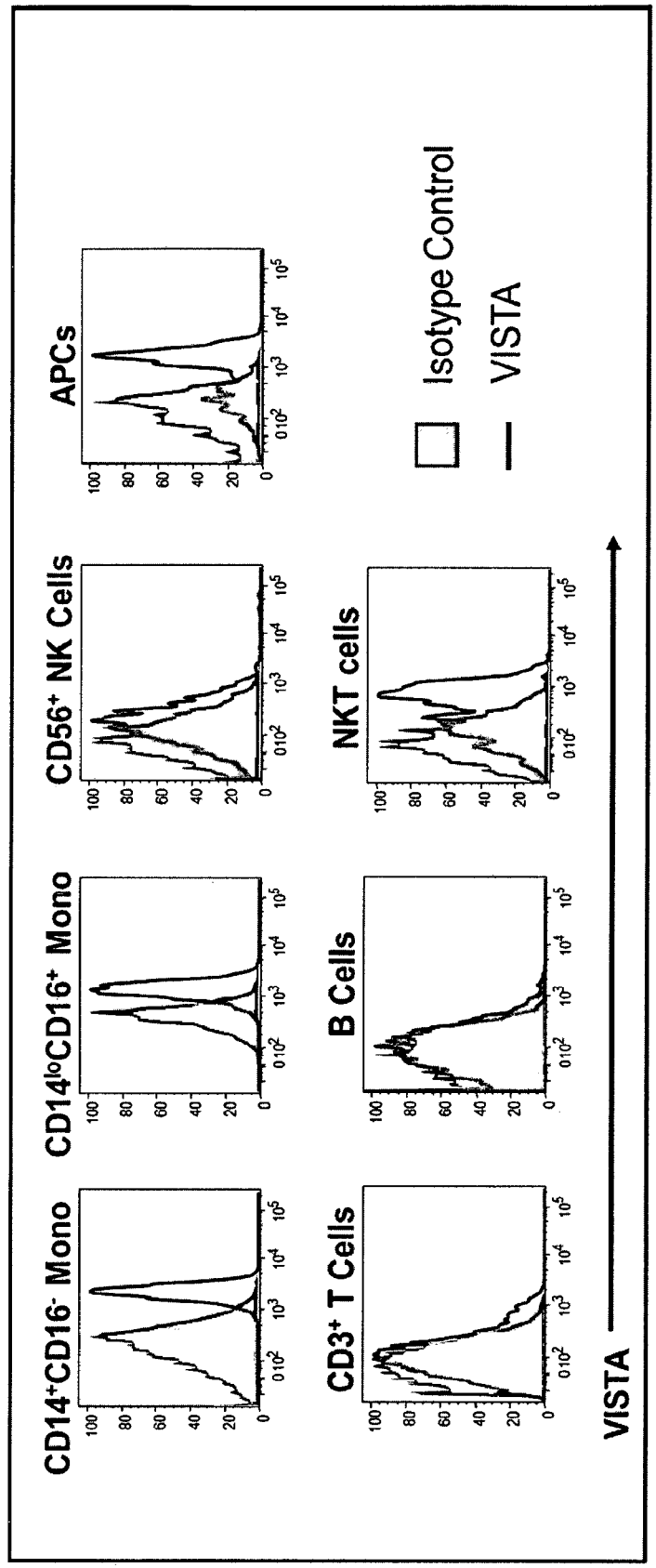

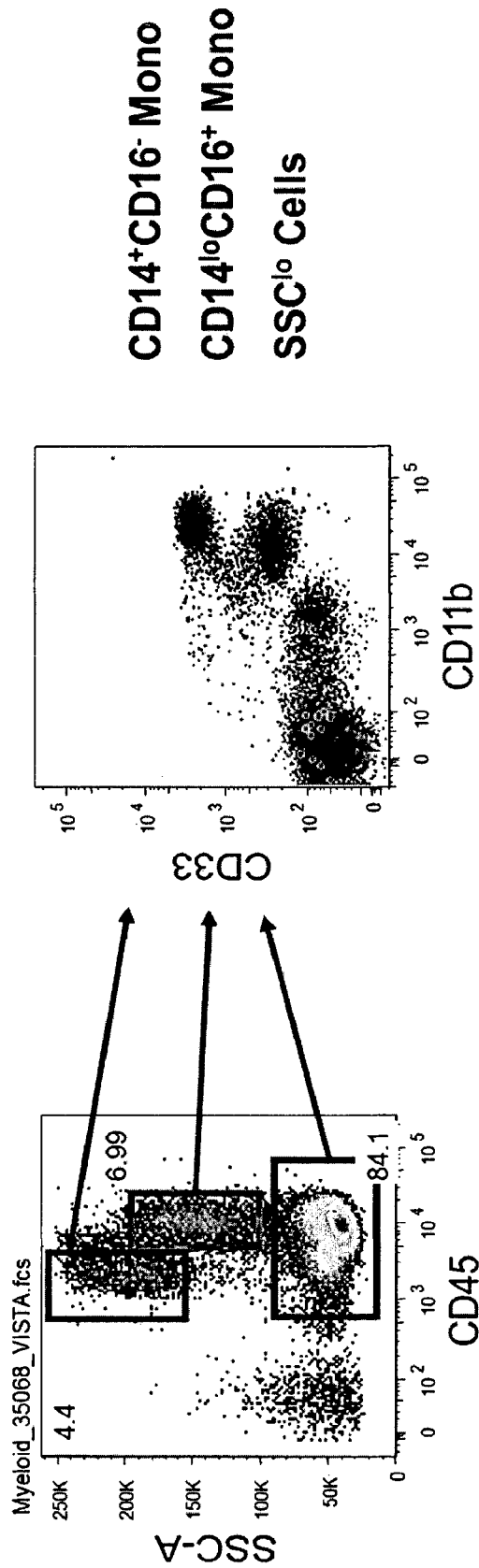

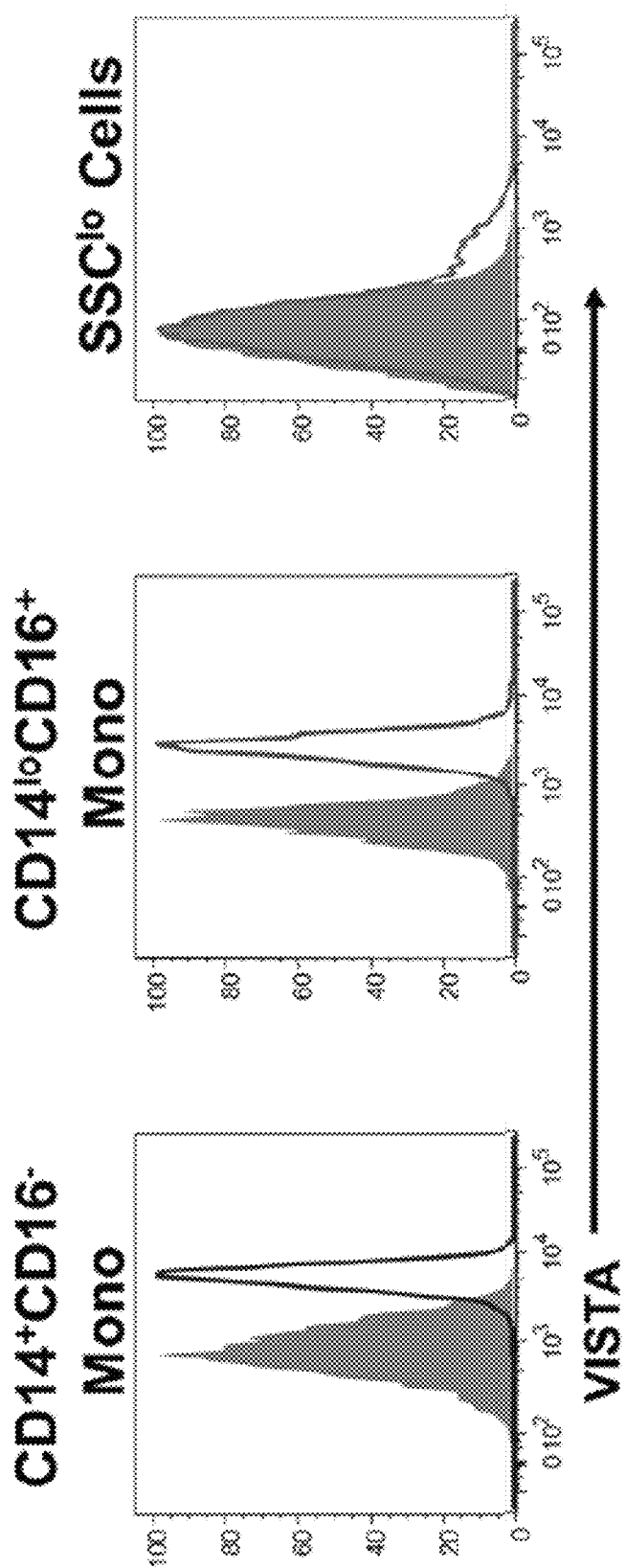

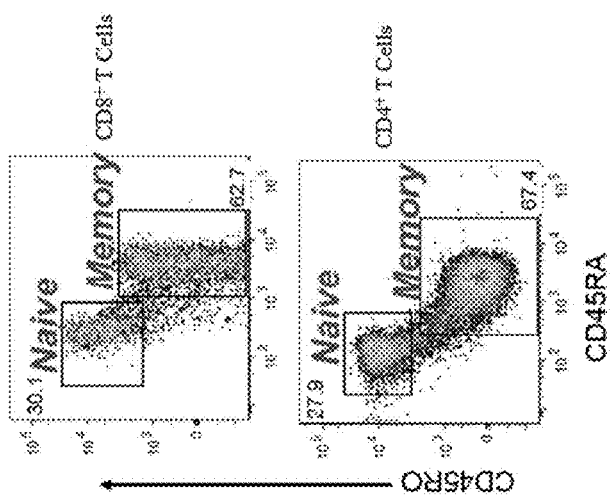
Figure 7D  Figure 7E
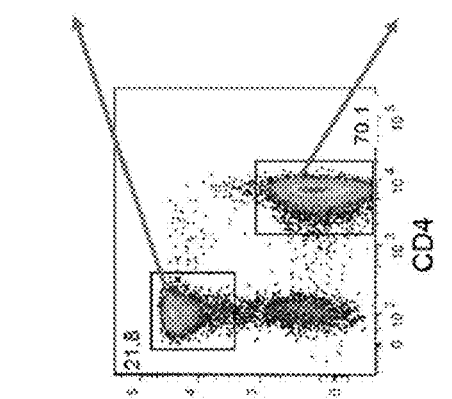
Figure 7C
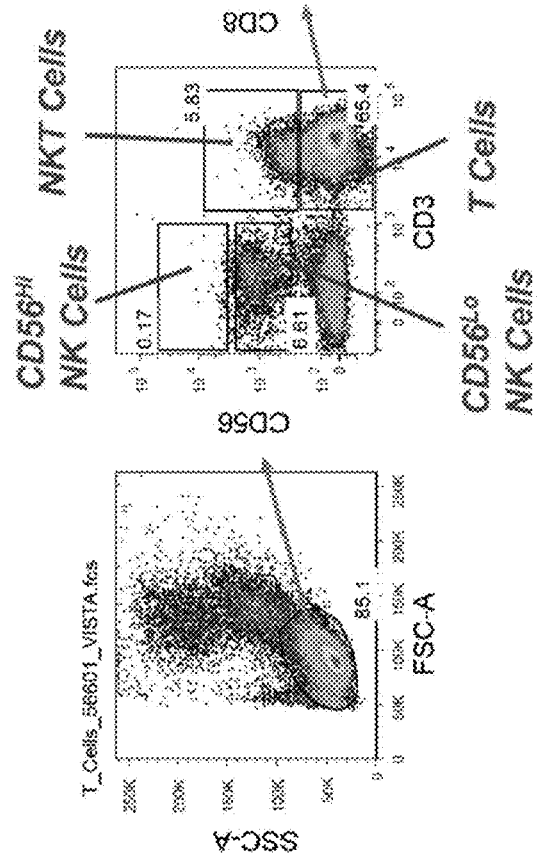
Figure 7B
Figure 7A

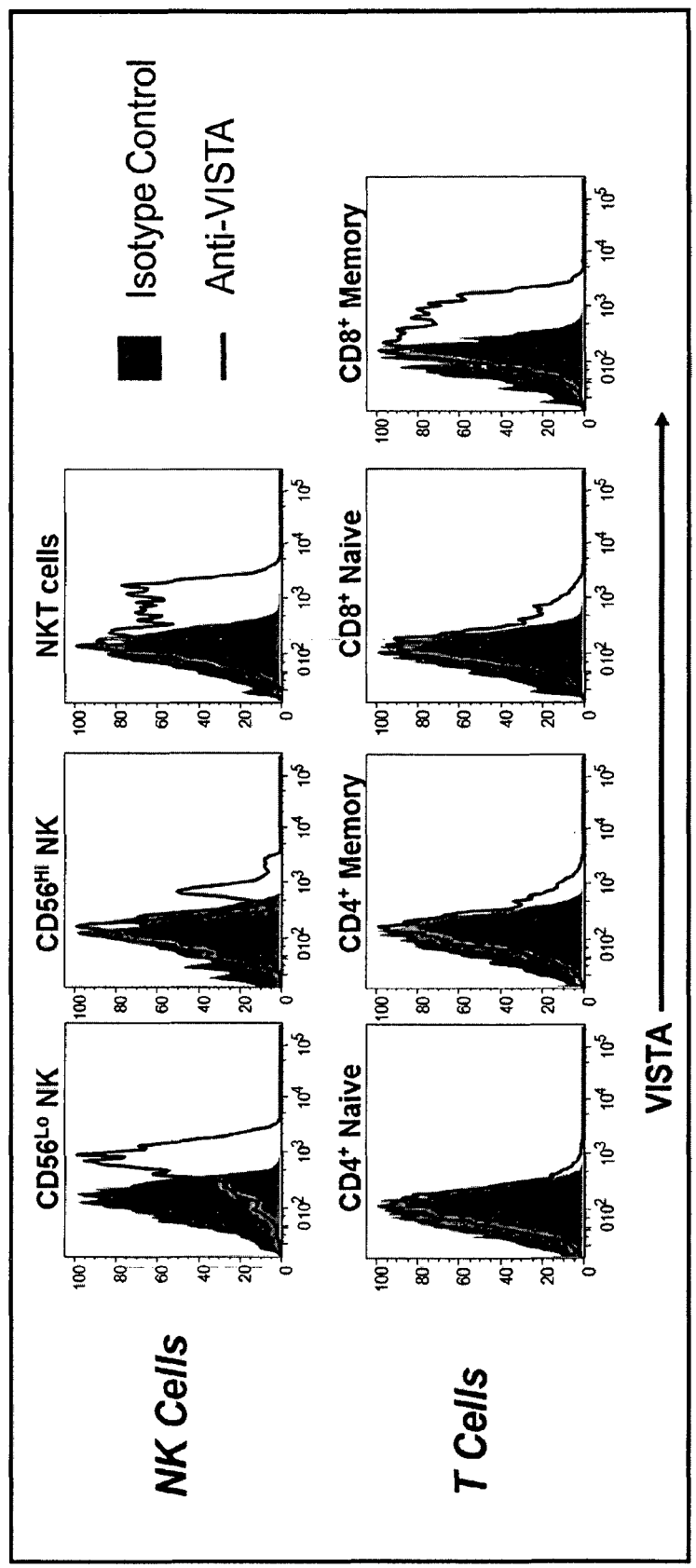

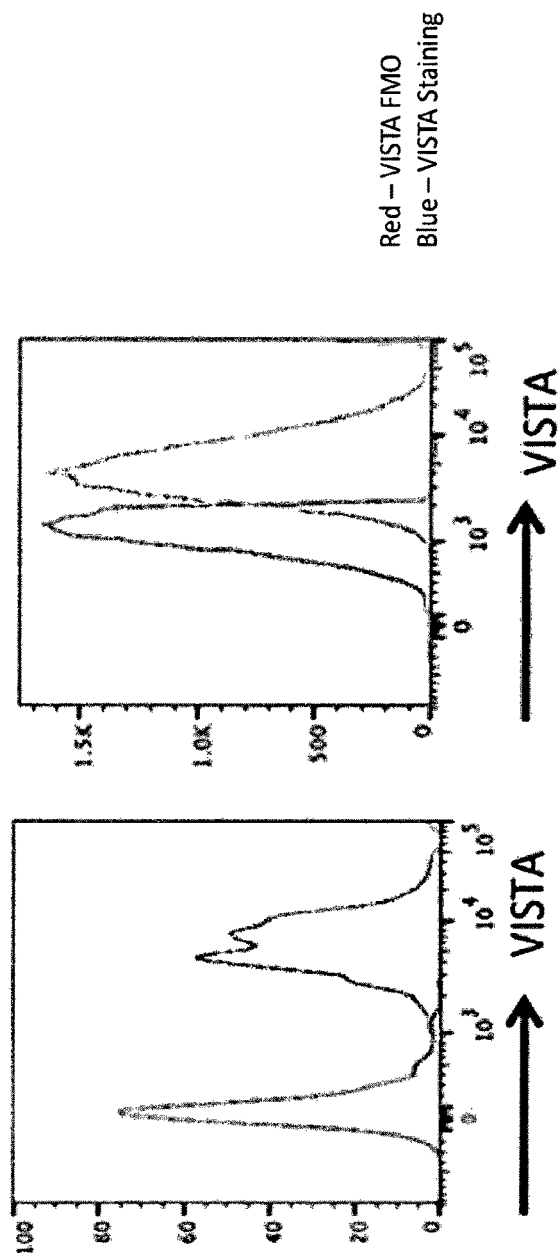
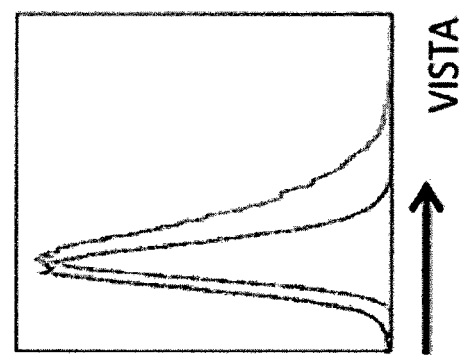
Figure 13A
Figure 13B
Figure 13C
Figure 13D

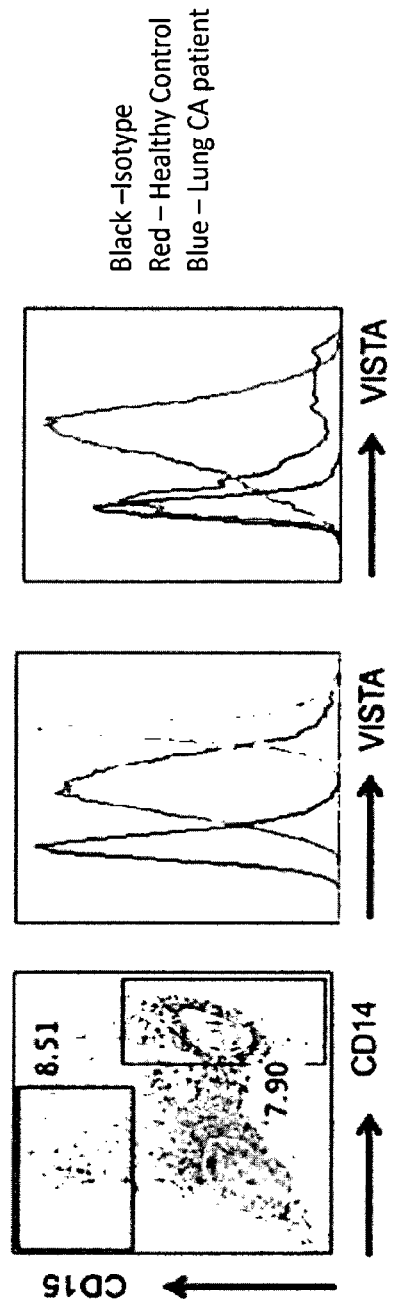

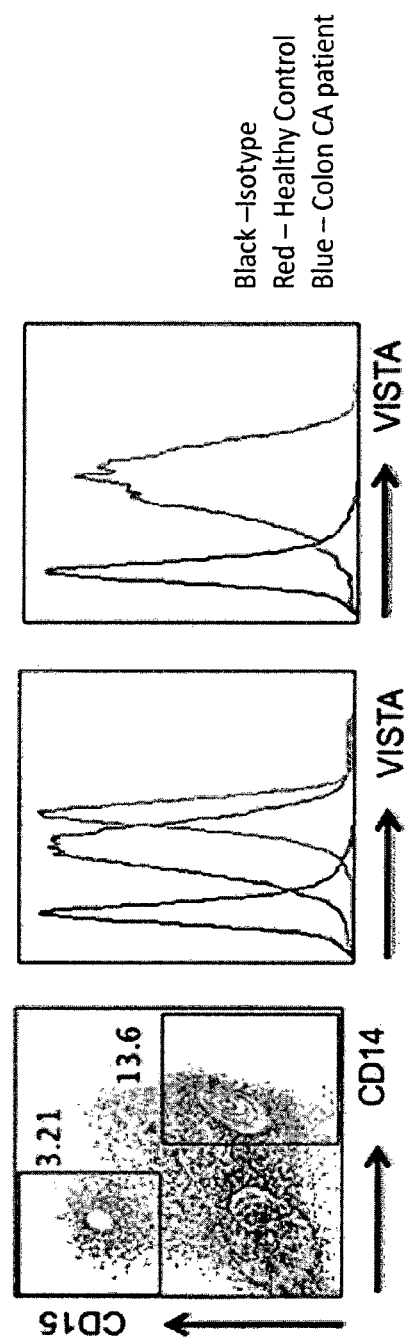

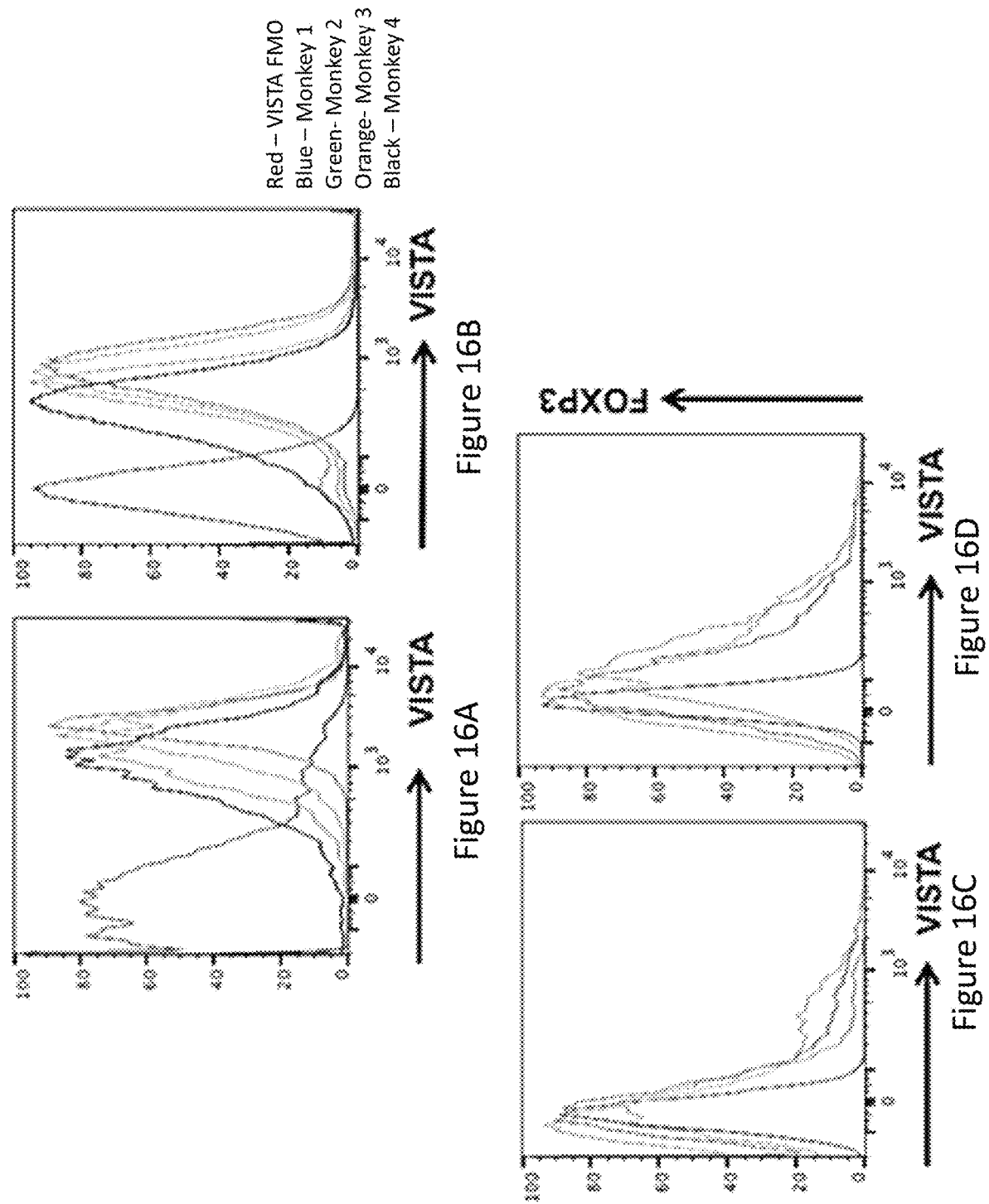

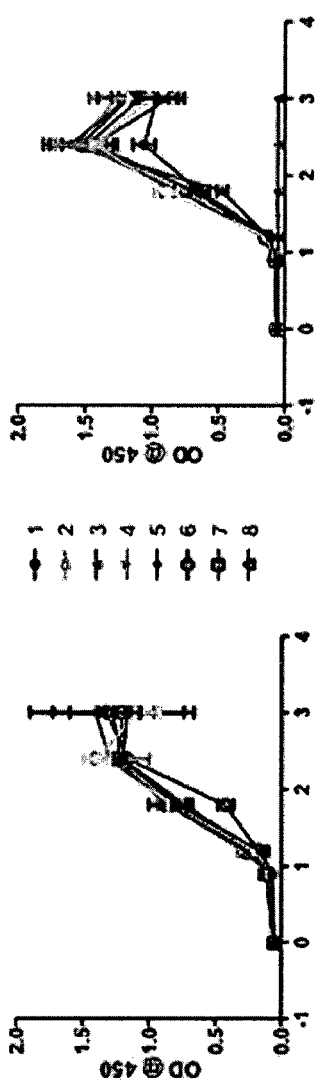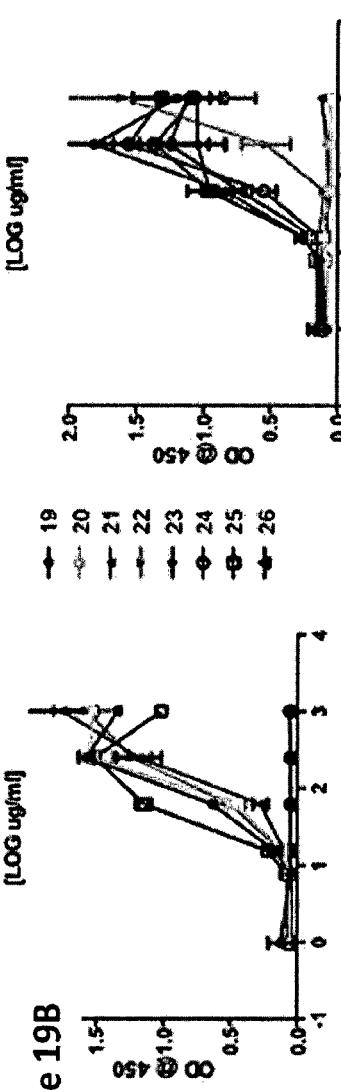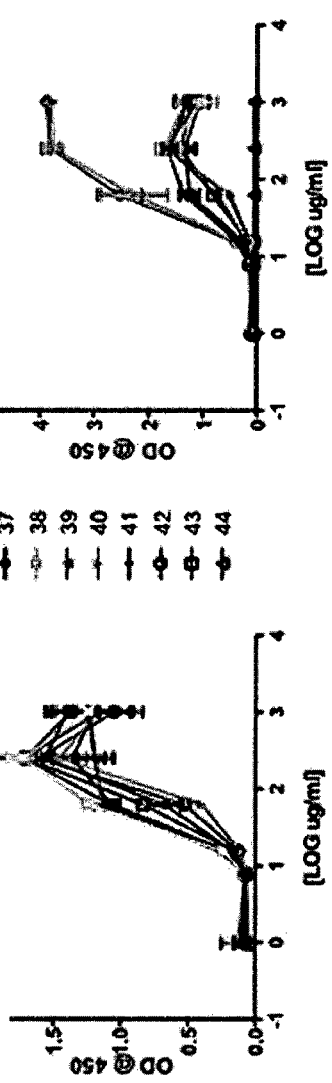

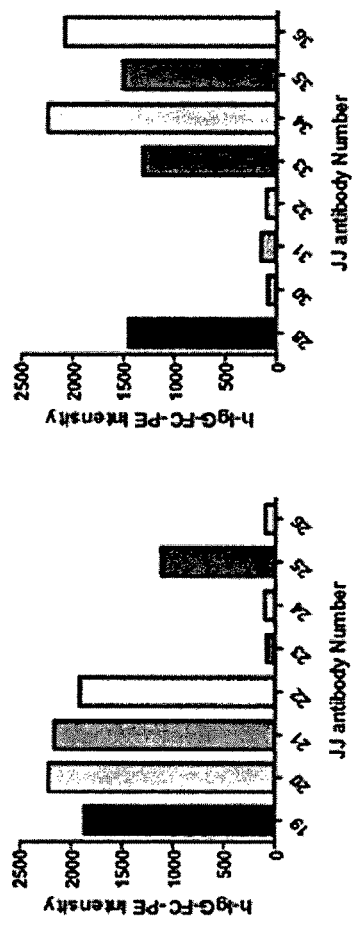
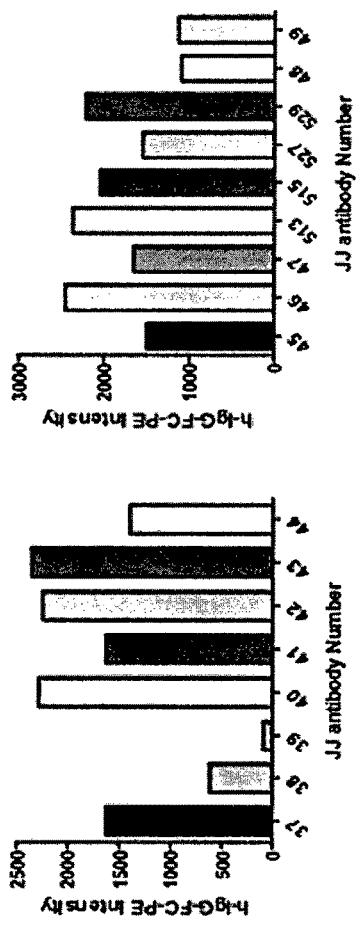

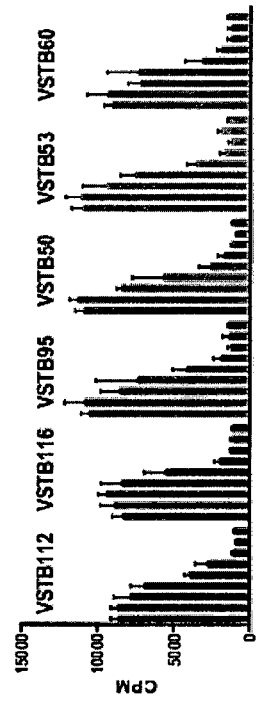
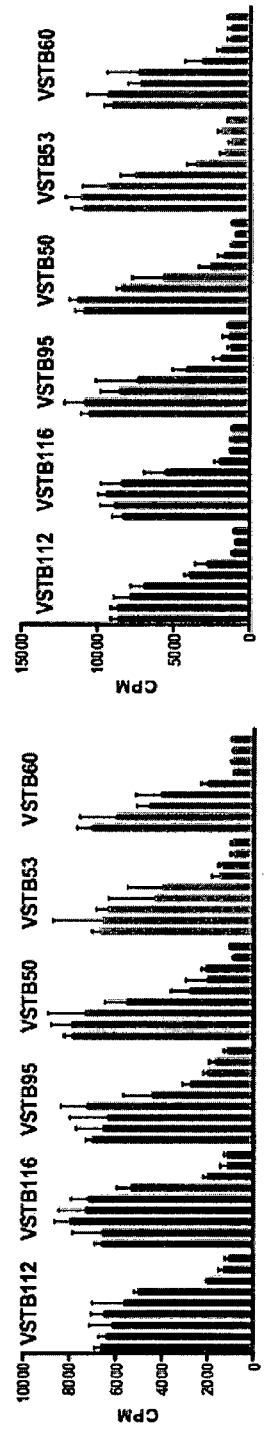
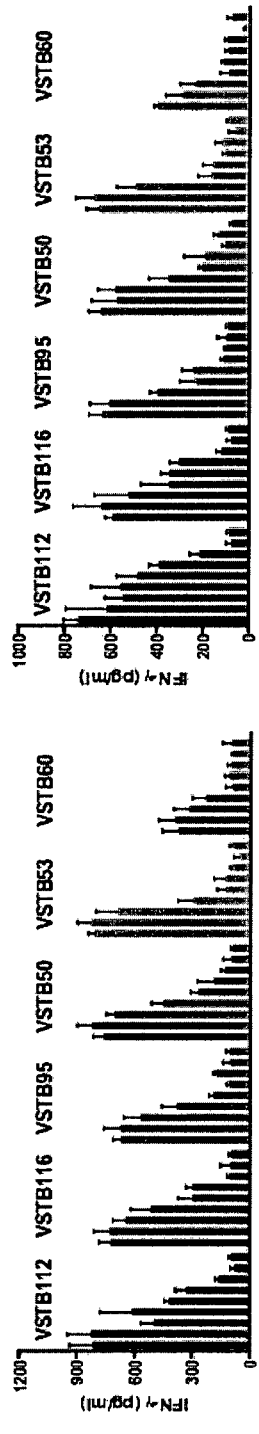
Figure 21A  Figure 21B
Figure 21C  Figure 21D

MGVPTALEAGSWRWGSLLFALFLAASLGPVAAFKVATPYSLYVCP
EGQNVTLTCRLLGPVDKGHDVTFYKTWYRSSRGEVQTCSERRPI
RNLTFQDLHLHHGGHQAANTSHDLAQRHGLESASDHHGNFSIT
MRNLTLLDSGLYCCLVVEIRHHHSEHRVHGAMELQVQTGKDAPS
NCVVYPSSSQESENITAAALATGACIVGILCLPLILLLVYKQ
RQAASNRRAQELVRMDSNIQGIENPGFEASPPAQGIPEAKVRHP
LSYVAQRQPSESGRHLLSEPSTPLSPPGPGDVF (SEQ ID NO:46)

Figure 26

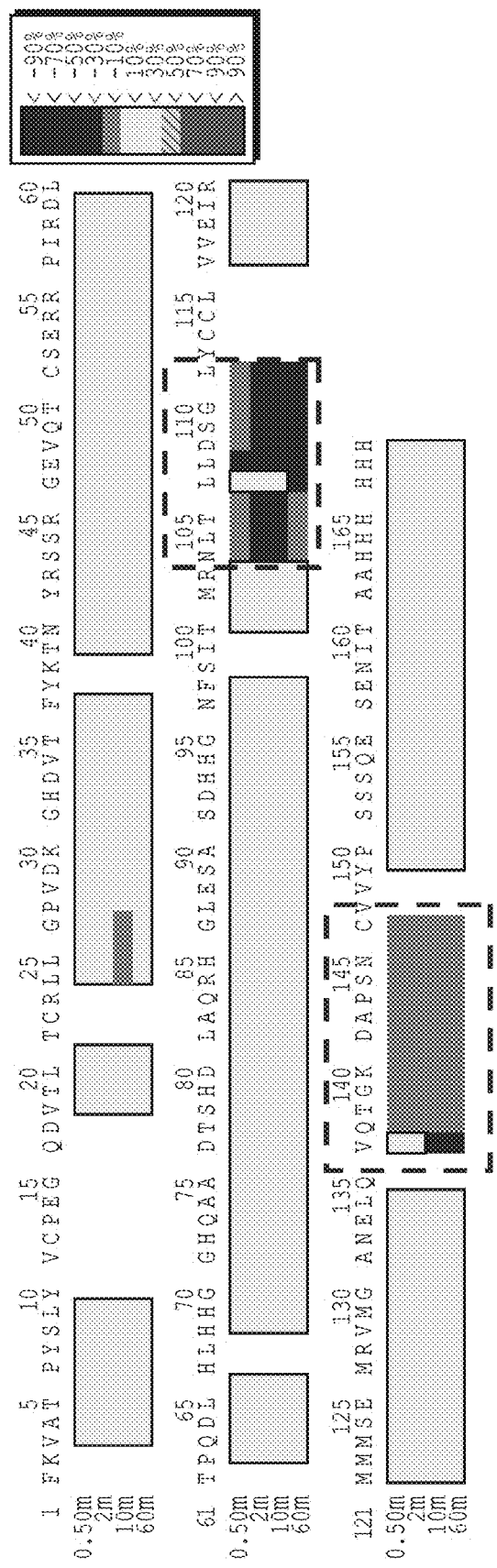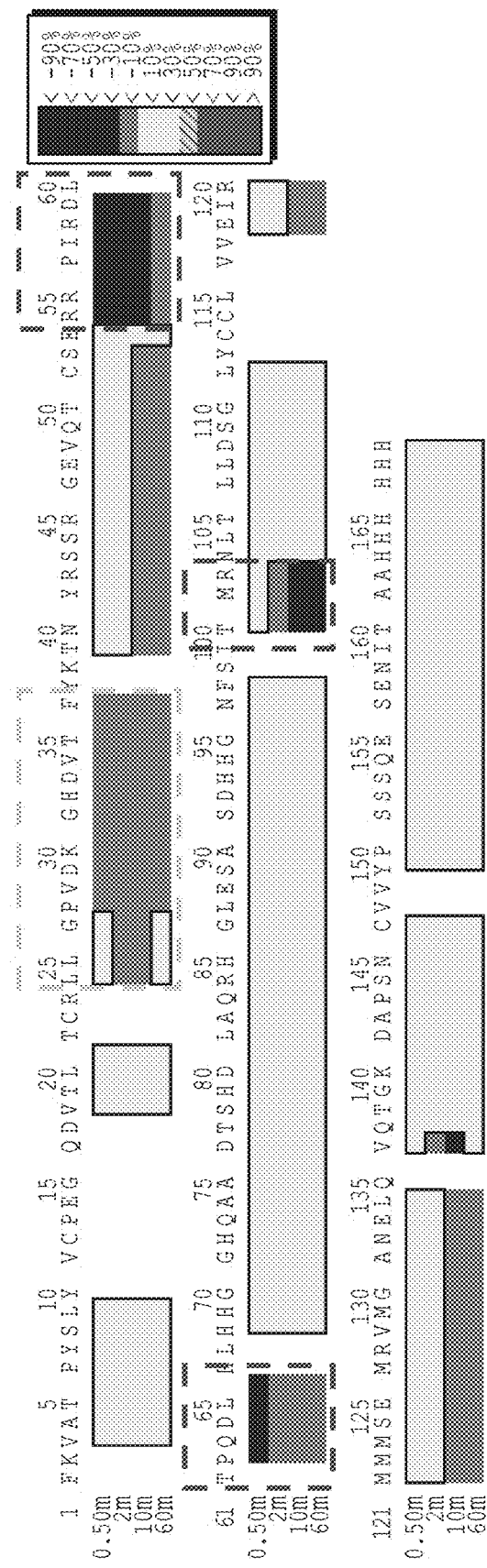
FIG. 28

```
0         10        20        30        40        50
|    *    |    *    |    *    |    *    |    *    |    *
AFKVATPYSLYVCPEGQNVTLTCRLLGPVDKGHDVTFYKTWYRSSRGEVQTCSERRP 60        70        80        90       100       110
|    *    |    *    |    *    |    *    |    *    |
IRQLTFQDLHLHHGGHQAAQTSHDLAQRHGLESASDHHGNFSITMRNLTLLDSGLYC 120       130       140       150       160
*    |    *    |    *    |    *    |    *    |    *
CLVVEIRHHHSEHRVHGAMELQVQTGKDAPSNCVVYPSSSQESEQITAAHHHHHH
```

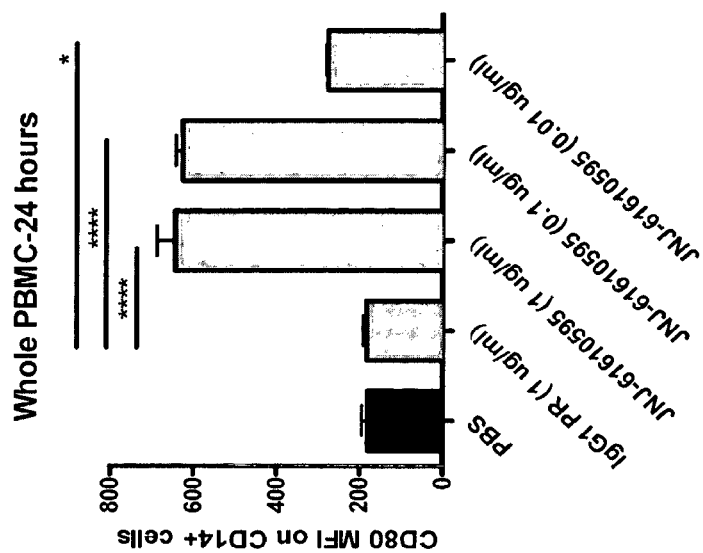
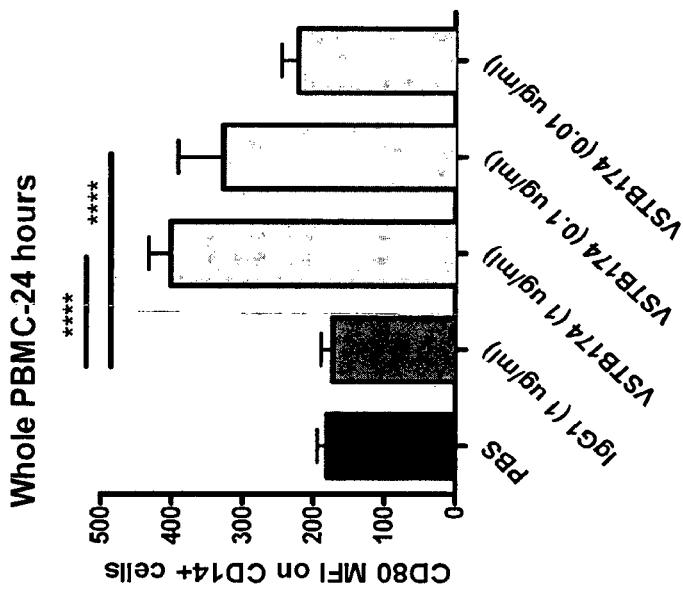
Figure 32

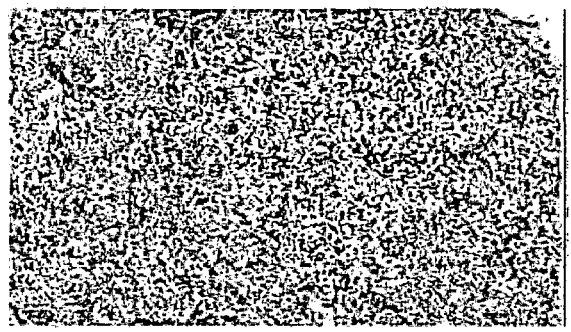
FIG. 41

ANTI-VISTA ANTIBODIES AND FRAGMENTS

CROSS-REFERENCE TO RELATED APPLICATIONS

This application is a divisional of U.S. application Ser. No. 15/738,013, filed Dec. 19, 2017, which is a U.S. National Stage of Int'l Appl. No. PCT/IB2016/000886, filed on Jun. 23, 2016, which claims the benefit of U.S. Provisional Appl. No. 62/184,108, filed on Jun. 24, 2015, and U.S. Provisional Appl. No. 62/187,659, filed on Jul. 1, 2015, each and all of which are hereby incorporated by reference in their entireties.

SEQUENCE DISCLOSURE

This application includes as part of its disclosure an electronic sequence listing text file named "11432600105403.txt", having a size of 89,159 bytes and created on Mar. 18, 2021, which is hereby incorporated by reference in its entirety.

BACKGROUND OF THE INVENTION

The expression of negative immune checkpoint regulators by cancer cells or immune cells in the tumor microenvironment can suppress the host's immune response against the tumor. To effectively combat the cancer, it is desirable to block tumor-mediated suppression of the host immune response. Accordingly, there is a need for new and effective therapeutic agents that inhibit negative immune checkpoint regulators in the tumor microenvironment that suppress anti-tumor immune responses.

SUMMARY OF THE INVENTION

The present invention provides, in one embodiment, an isolated antibody (e.g., a chimeric antibody), or antigen-binding fragment thereof, comprising an antigen-binding region that binds to a mammalian V-domain Ig Suppressor of T cell Activation (VISTA) protein. The antibody comprises an antibody VH domain comprising a VH CDR1 having the amino acid sequence of SEQ ID NO:31, a VH CDR2 having the amino acid sequence of SEQ ID NO:32 and a VH CDR3 having the amino acid sequence of SEQ ID NO:33. The antibody further comprises an antibody VL domain comprising a VL CDR1 having the amino acid sequence of SEQ ID NO:34, a VL CDR2 having the amino acid sequence of SEQ ID NO:35 and a VL CDR3 having the amino acid sequence of SEQ ID NO:36. In addition, the antibody comprises a non-human antibody heavy chain constant region and a non-human antibody light chain constant region.

In one embodiment, the antibody VH domain comprises SEQ ID NO:64. In another embodiment, the antibody VL domain comprises SEQ ID NO:45.

In some embodiments, the antibody comprises a non-human antibody heavy chain constant region that is a murine antibody heavy chain constant region. In a particular embodiment, the murine antibody heavy chain constant region is a murine IgG1 heavy chain constant region. In a specific embodiment, the murine IgG1 heavy chain constant region comprises the heavy chain constant region in SEQ ID NO:76. In another embodiment, the murine antibody heavy chain constant region is a murine IgG2a heavy chain constant region.

In other embodiments, the antibody comprises a non-human antibody light chain constant region that is a murine antibody light chain constant region. In a particular embodiment, the murine antibody light chain constant region is a murine IgG1 light chain constant region. In a specific embodiment, the murine IgG1 light chain constant region comprises the light chain constant region in SEQ ID NO:77. In another embodiment, the murine antibody light chain constant region is a murine IgG2a light chain constant region.

In a certain embodiment, the antibody or antigen-binding fragment binds to a human VISTA protein. In a particular embodiment the antibody or antigen-binding fragment binds to an epitope that is present in a human VISTA protein having the amino acid sequence shown below:

```
                                            (SEQ ID NO: 46)
MGVPTALEAGSWRWGSLLFALFLAASLGPVAAFKVATPYSLYVCPEGQNV

TLTCRLLGPVDKGHDVTFYKTWYRSSRGEVQTCSERRPIRNLTFQDLHLH

HGGHQAANTSHDLAQRHGLESASDHHGNFSITMRNLTLLDSGLYCCLVVE

IRHHHSEHRVHGAMELQVQTGKDAPSNCVVYPSSSQESENITAAALATGA

CIVGILCLPLILLLVYKQRQAASNRRAQELVRMDSNIQGIENPGFEASPP

AQGIPEAKVRHPLSYVAQRQPSESGRHLLSEPSTPLSPPGPGDVF.
```

In one embodiment, the antibody or antigen-binding fragment is a whole antibody.

In another embodiment, the invention provides an isolated antibody, or antigen-binding fragment thereof, comprising an antibody heavy chain comprising SEQ ID NO:77 and an antibody light chain comprising SEQ ID NO:68.

In yet another embodiment, the invention provides a composition comprising an antibody or antigen-binding fragment of the invention.

In an additional embodiment, the invention provides a method for detecting a mammalian VISTA protein in a sample. The method comprises contacting the sample with an antibody or antigen-binding fragment of the invention under conditions in which the antibody or antigen-binding fragment binds to VISTA protein in the sample, and detecting the antibody or antigen-binding fragment that is bound to VISTA protein in the sample.

In one embodiment, the sample comprises cells. The cells can include immune cells (e.g., myeloid cells), stromal cells (e.g., fibroblasts, endothelial cells), and/or cancer (e.g., malignant) cells, such as lung cancer cells, prostate cancer cells, acute myeloid leukemia (AML) cells, melanoma cells, ovarian cancer cells or colon cancer cells, or any combination thereof, among others. In a particular embodiment, the sample comprises a tissue or biological fluid.

In one embodiment, the antibody or antigen-binding fragment employed in the method comprises a detectable label.

In a certain embodiment, the method includes an immunohistochemical (IHC) staining assay. In another embodiment, the method includes a flow cytometry assay.

The present invention provides improved reagents and methods for detecting VISTA protein(s) in biological materials. Such reagents and methods typically have enhanced sensitivity and/or specificity.

BRIEF DESCRIPTION OF THE DRAWINGS

FIGS. 2A-2E: Graphs showing staining and gating strategies for identification of Human Myeloid and Lymphoid Subsets.

FIGS. 3A-3G: Graphs showing expression of VISTA on Human Myeloid and Lymphoid Subsets from one healthy normal donor.

FIGS. 5A-5B: Graph showing staining and gating strategies for identification of expression of VISTA on Human Monocytes and Macrophages.

FIGS. 6A-6C: Graphs showing expression of VISTA on Human Monocytes and Macrophages.

FIGS. 7A-7E: Graphs showing staining and gating strategies for identification of expression of VISTA on Human T and NK Cell Subsets.

FIGS. 8A-8G: Graphs showing expression of VISTA on Human T and NKCell Subsets from one healthy normal donor.

FIGS. 13A-13D: Analysis of VISTA expression on healthy human peripheral blood cells. Profile of VISTA expression on healthy human peripheral blood cells using multicolor flow cytometry analysis: Whole blood samples from 2 different individuals were analyzed for VISTA expression on (FIG. 13A) monocytes $SSC^{lo}$ $CD11b^{hi}CD14^{hu}$ $CD16^{-ve}CD33^{+ve}HLA-DR^{+ve}CD19^{-ve}$) (FIG. 13B) neutrophils ($SSC^{hi}CD177^+CD11b^{hi}CD14^{lo}$ $CD16^{+ve}$ $CD33^{+ve}HLA-DR^{-ve}CD19^{-ve}$). Peripheral blood mononuclear cells were isolated using Ficoll gradient for analysis of (FIG. 13C) CD4+ T cells ($CD3^{+ve}CD4^{+ve}$), and (FIG. 13D) CD8+ T cells ($CD3^{+ve}CD8^{+ve}$).

FIGS. 14A-14C: Analysis of VISTA expression on peripheral blood cells from a lung cancer patient and a healthy control donor. Profile of VISTA expression on lung cancer patient peripheral blood cells using multicolor flow cytometry analysis: Representative FACS plot (FIG. 14A) from one individual is shown. Peripheral blood mononuclear cells were isolated by Ficoll and analyzed for VISTA expression on (FIG. 14B) monocytes (CD14+CD11b+ CD33+ HLADR+ CD15−) and (FIG. 14C) myeloid derived suppressor cells (CD14− CD11b++CD33−HLADR−CD15+ CD16+).

FIGS. 15A-15C: Profile of VISTA expression in peripheral blood cells from a patient with colon cancer, using multicolor flow cytometry analysis: Representative FACS plot (FIG. 15A) from one individual is shown. Peripheral blood mononuclear cells were isolated by Ficoll and analyzed for VISTA expression on (FIG. 15B) monocytes (CD14+CD11b+ CD33+ HLADR+ CD15−) and (FIG. 15C) myeloid derived suppressor cells (CD14− CD11b−CD33− HLADR−CD15+ CD16+).

FIGS. 16A-16D: Profile of VISTA expression on Cynomolgus monkey peripheral blood cells using multicolor flow cytometry analysis: Whole blood from 4 different monkeys was analyzed for VISTA expression on (FIG. 16A) monocytes ($SSC^{lo}$ $CD11b^{hi}CD14^{hi}HLA-DR^{hi}CD16^{-ve}CD19^{-ve}$ and (FIG. 16B) neutrophils $CD11b^{hi}CD14^{lo}$ $HLA-DR^-$ $_{ve}CD16^{-ve}CD19^{-ve}$. Peripheral blood mononuclear cells from three monkeys were isolated using Ficoll gradient for analysis of (FIG. 16C) CD4+ T cells ($TCR\alpha/\beta^{+ve}CD4^{+ve}$) and (FIG. 16D) CD8+ T cells ($TCR\alpha/\beta^{+ve}CD8^{+ve}$).

FIGS. 19A-19F: Graphs showing Human VISTA ELISA results.

FIGS. 20A-20F: Human VISTA FACS results, showing anti-VISTA antibodies binding to cells expressing human VISTA.

FIGS. 21A-21D: Dilution study of 6 anti-VISTA antibody candidates in the mixed lymphocyte reaction from 30 µg/ml to 0.0 µg/ml.

FIG. 26: Amino acid sequence of human VISTA (SEQ ID NO:46).

FIG. 28: Regions of human VISTA bound by VSTB50 and VSTB60 antibodies (top) or VSTB95 and VSTB112 antibodies (bottom), as determined by HDX

FIG. 32: Activation of CD14+ monocytes in whole PBMC by VSTB174 (derived from VSTB112). In each part of the experiment, cells were incubated with PBS, IgG1 control antibody, or VSTB174 at 1, 0.1 or 0.01 ug/ml. Left panel shows CD80 MFI; right panel shows HLA-DR MFI (two donors tested with representative results shown).

FIG. 41: Representative images of VISTA staining using VSTB175 (FIGS. 41A-41C) or negative control sera (FIG. 41D) in lung cancer samples that have been formalin fixed and paraffin embedded. FIG. 41A: small cell lung cancer; FIG. 41B: small cell lung cancer; FIG. 41C: squamous lung cancer; FIG. 41D: small cell lung cancer.

DETAILED DESCRIPTION OF THE INVENTION

Figures 1A, 1B, 1C:
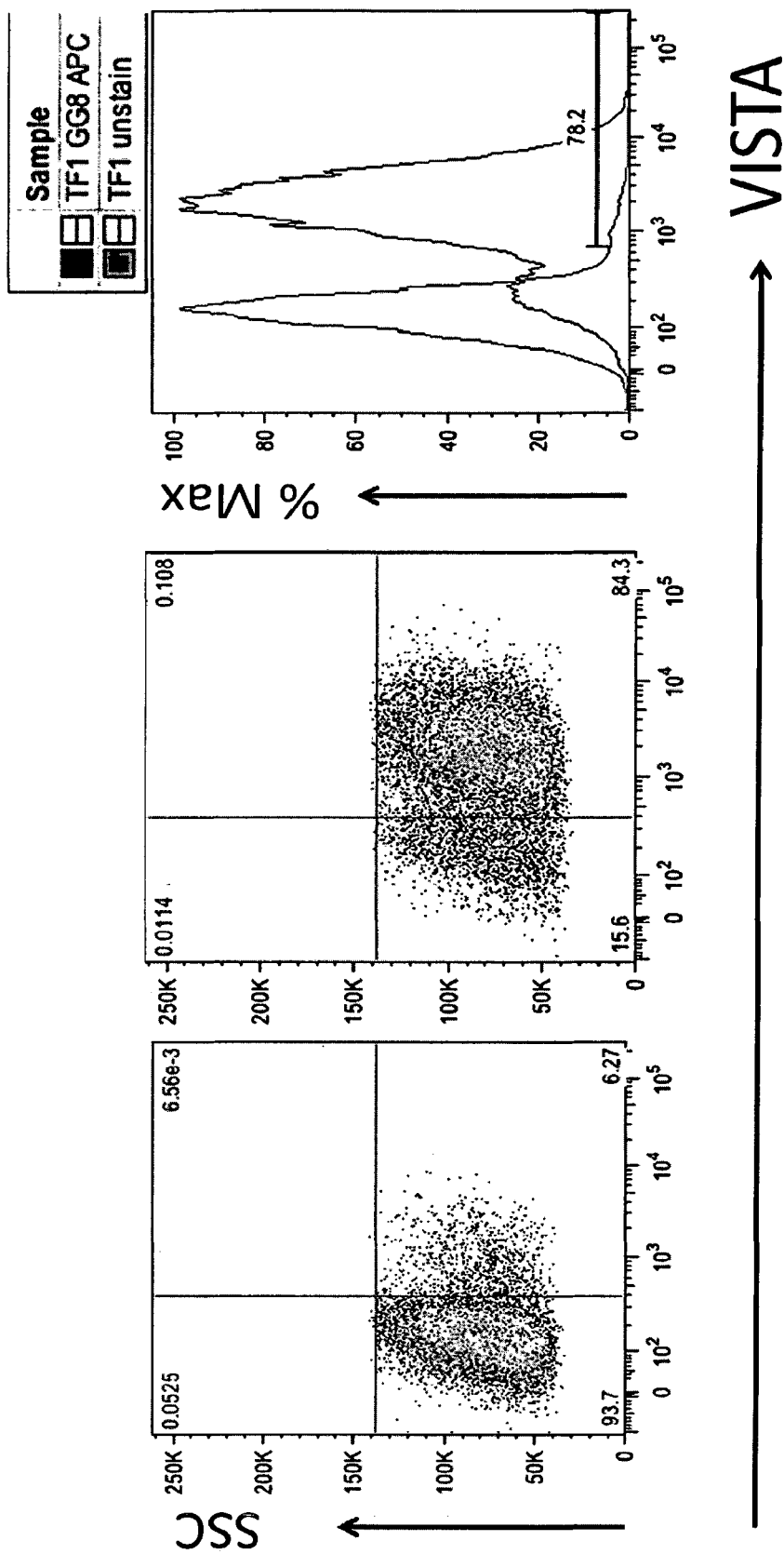
FIGS. 1A-1C: Graphs showing VISTA expression on TF1 AML Cells Expression of VISTA protein by flow cytometry is shown in the TF-1 AML cell line.
Figure 4:
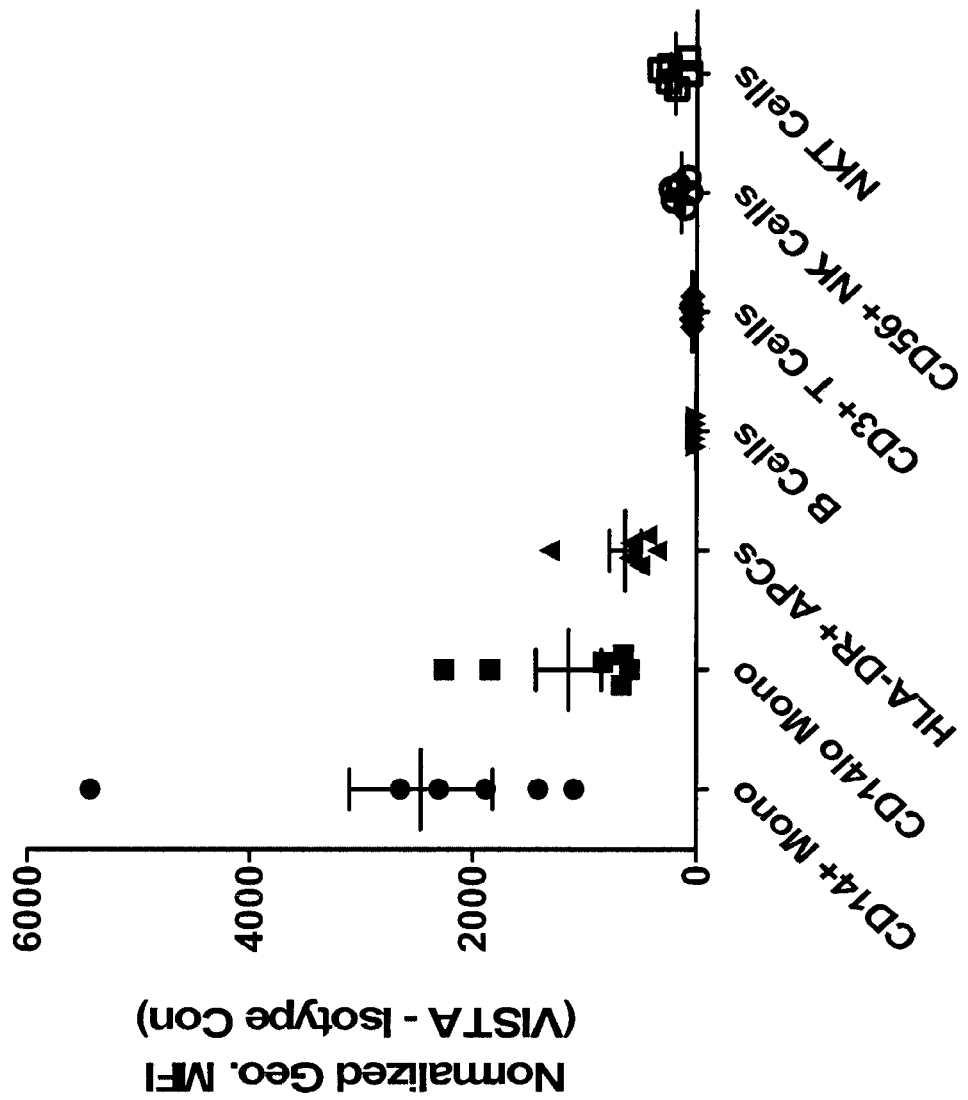
FIG. 4: Graph showing expression of VISTA on Human Myeloid and Lymphoid Subsets across multiple healthy normal donors.
Figure 9:
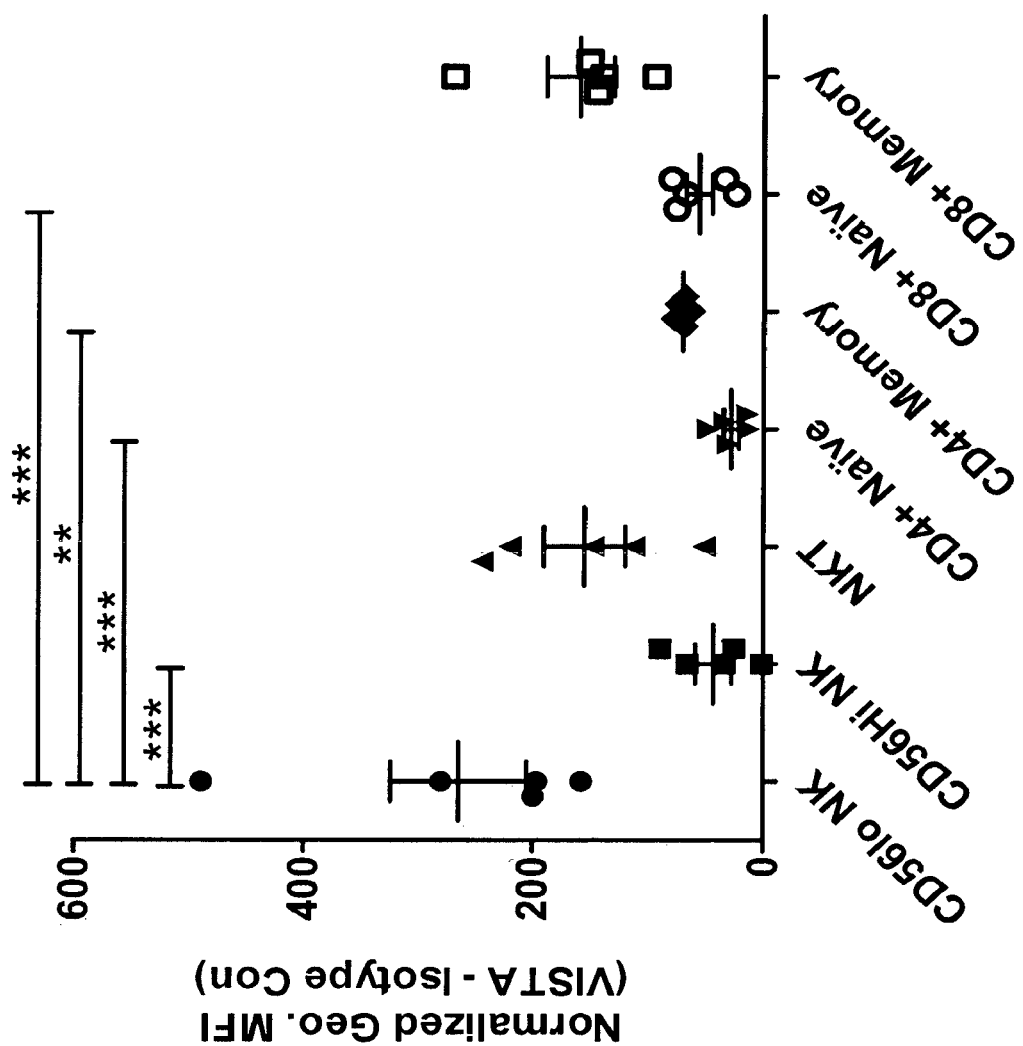
FIG. 9: Graph showing expression of VISTA on Human T and NK Cell Subsets across multiple healthy normal donors.
Figures 10A, 10B, 10C, 10D:
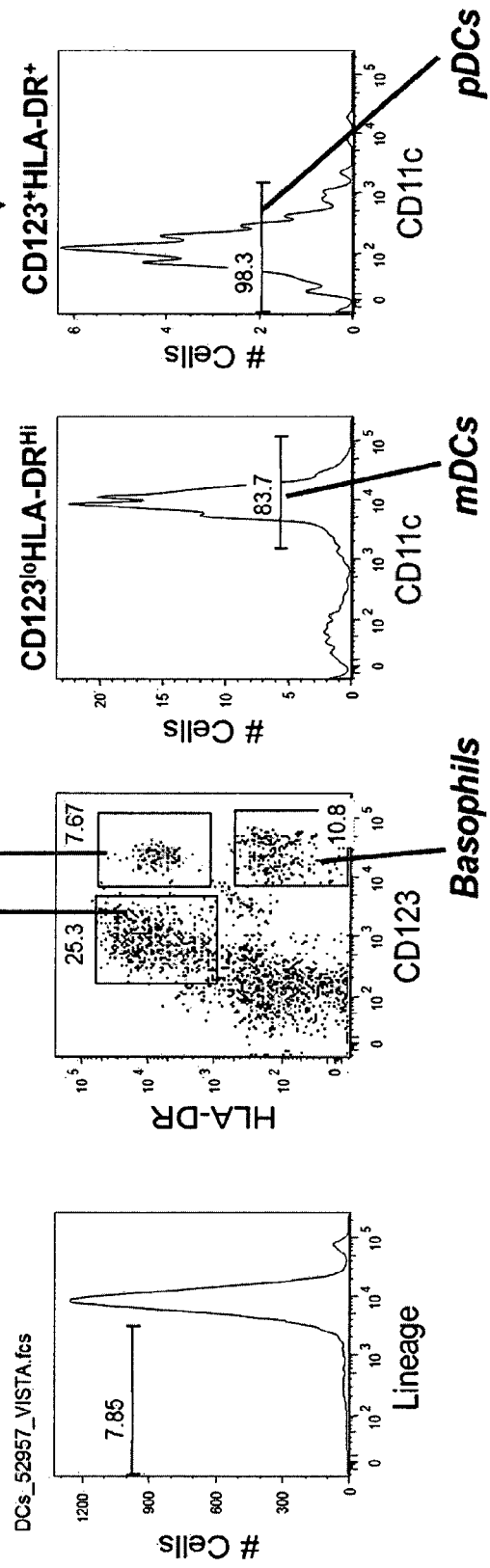
FIGS. 10A-10D: Graphs showing staining and gating strategies for identification of expression of VISTA on Human Dendritic Cell subsets.
Figures 11A, 11B, 11C:
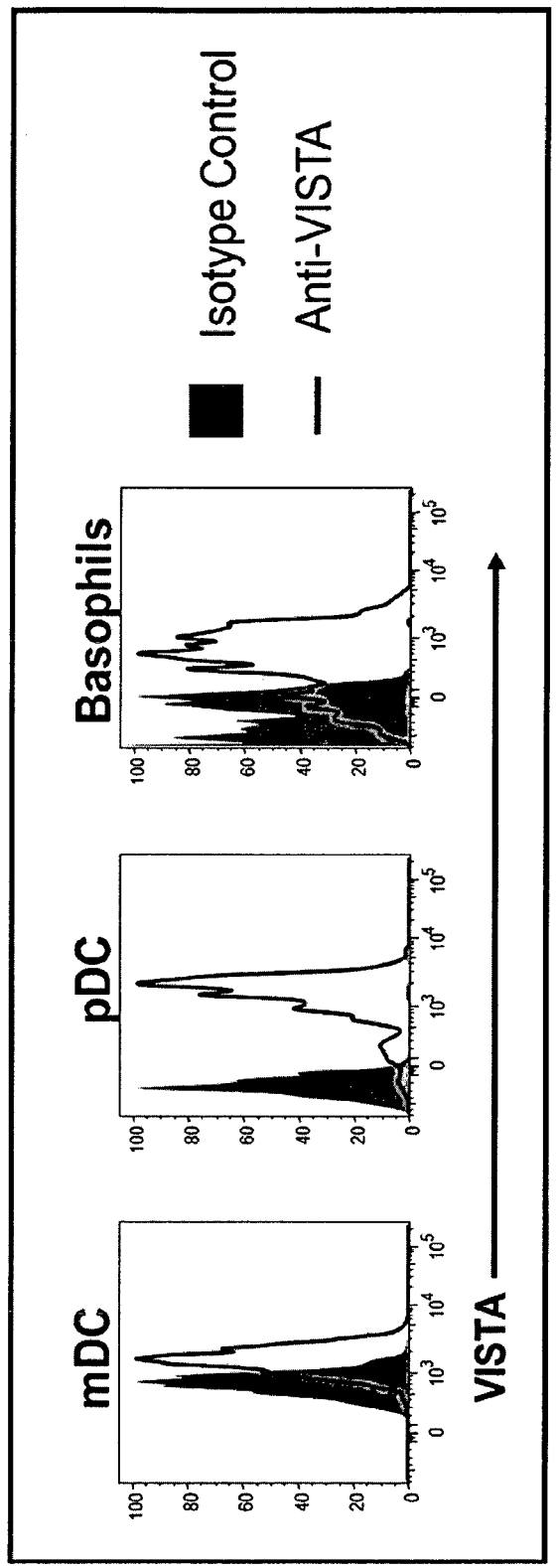
FIGS. 11A-11C: Graphs showing expression of VISTA on Human Dendritic Cell subsets and basophils from one healthy normal donor.
Figure 12:
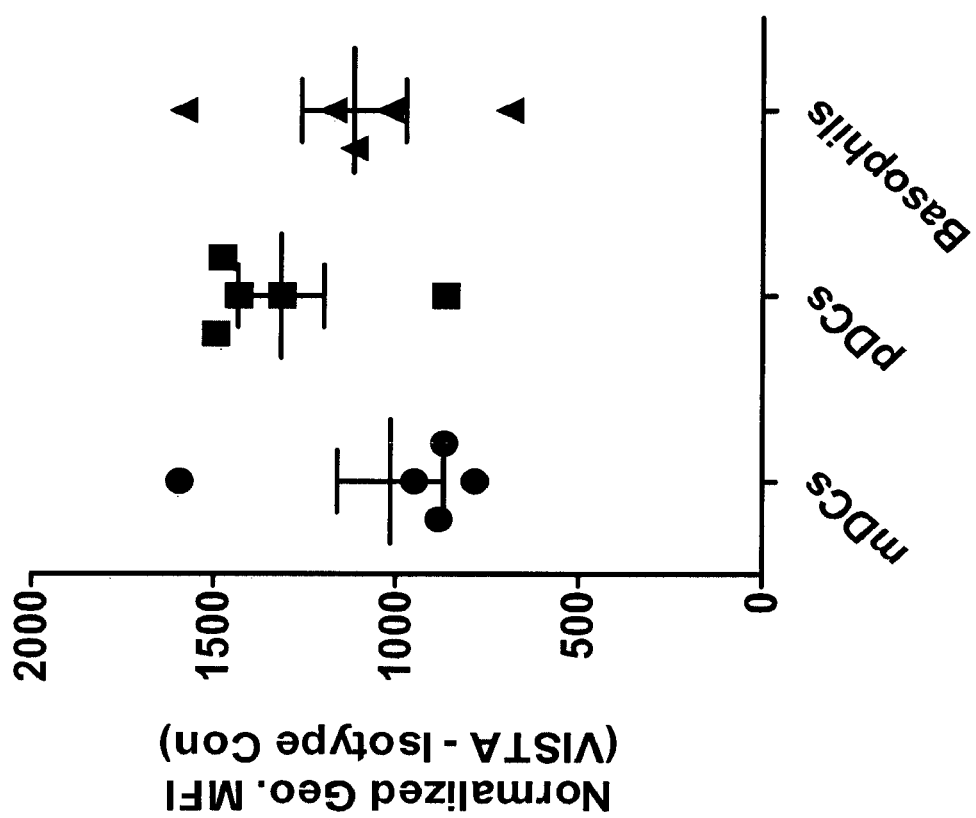
FIG. 12: Graph showing expression of VISTA on Human Dendritic Cell Subsets and basophils across multiple healthy normal donors.

A description of example embodiments of the invention follows.

The present invention relates to antibodies to novel Immunoglobulin family ligand designated V-domain Immunoglobulin Suppressor of T cell Activation (VISTA) (Genbank: JN602184) (Wang et al., 2010, 2011). VISTA bears homology to PD-L1 but displays a unique expression pattern that is restricted to the hematopoietic compartment. Specifically, VISTA is constitutively and highly expressed on CD11b$^{high}$ myeloid cells, and expressed at lower levels on CD4$^+$ and CD8$^+$ T cells. The human homologue shares approximately 85% homology with murine VISTA and has similar expression patterns (Lines et al., Cancer Research 74:1924, 2014). VISTA expressed on antigen presenting cells (APCs) suppresses CD4$^+$ and CD8$^+$ T cell proliferation and cytokine production via a cognate receptor independent of PD-1. In a passive EAE (experimental autoimmune encephalomyelitis) disease model, a VISTA specific monoclonal antibody enhanced T-cell dependent immune responses and exacerbated disease. VISTA over-expression on tumor cells impaired protective anti-tumor immunity in tumor-bearing hosts. Studies of human VISTA confirmed its suppressive function on human T cells (Lines et al Cancer Research 74:1924, 2014. Studies from Flies et al. also identified VISTA (named PD-1H) as a potent immune suppressive molecule (Flies et al., 2011). VISTA is described in further detail in U.S. Published application US 20130177557 A1 and U.S. Pat. Nos. 7,919,585 and 8,236,304, all of which are incorporated herein by reference in their entirety.

As described in Example 12 herein, treatment with a VISTA-specific monoclonal antibody in murine tumor models has been shown to reverse the suppressive character of the tumor immune microenvironment and enhance protective anti-tumor immunity, thus, demonstrating the potential of a VISTA monoclonal antibody as a novel therapeutic for cancer immunotherapy.

Antibodies and Fragments of the Present Invention

The term "antibody" is meant to include polyclonal antibodies, monoclonal antibodies (mAbs), chimeric antibodies, humanized antibodies, human antibodies and anti-idiotypic (anti-Id) antibodies, as well as fragments, regions or derivatives thereof, provided by any known technique, such as, but not limited to, enzymatic cleavage, peptide synthesis or recombinant techniques. Anti-VISTA antibodies of the present invention are capable of binding portions of VISTA that modulate, regulate, or enhance an immune response. In some embodiments, the antibodies competitively inhibit one or more of the anti-VISTA antibodies described herein. Methods for determining whether two or more antibodies compete for binding to the same target are known in the art. For example, a competitive binding assay can be used to determine whether one antibody blocks the binding of another antibody to the target. Typically, a competitive binding assay involves the use of purified target antigen (e.g., PD-1) bound either to a solid substrate or cells, an unlabeled test binding molecule, and a labeled reference binding molecule. Competitive inhibition is measured by determining the amount of label bound to the solid surface or cells in the presence of the test binding molecule. Usually the test binding molecule is present in excess. Typically, when a competing binding molecule is present in excess, it will inhibit specific binding of a reference binding molecule to a common antigen by at least 50-55%, 55-60%, 60-65%, 65-70%, 70-75%, or more. In some embodiments, competitive inhibition is determined using a competitive inhibition ELISA assay.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. Monoclonal antibodies may be obtained by methods known to those skilled in the art. See, for example Kohler and Milstein, *Nature,* 256:495-497 (1975); U.S. Pat. No. 4,376,110; Ausubel et al., eds., Current Protocols in Molecular Biology, Greene Publishing Assoc. and Wiley Interscience, N.Y., (1987, 1992); and Harlow and Lane ANTIBODIES: A Laboratory Manual Cold Spring Harbor Laboratory (1988); Colligan et al., eds., Current Protocols in Immunology, Greene Publishing Assoc. and Wiley Interscience, N.Y., (1992, 1993), the contents of all of which are incorporated entirely herein by reference. Such antibodies may be of any immunoglobulin class including IgG, IgM, IgE, IgA, GILD and any subclass thereof. A hybridoma producing a monoclonal antibody of the present invention may be cultivated in vitro, in situ or in vivo.

The invention also encompasses digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian VISTA protein. For example, antibody fragments capable of binding to VISTA or portions thereof, including, but not limited to Fab (e.g., by papain digestion), Fab' (e.g., by pepsin digestion and partial reduction) and $F(ab')_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra). Antibody fragments of the present invention also include those discussed and described in Aaron L. Nelson, mAbs 2:1, 77-83 (January/February 2010), the contents of which are incorporated by reference in their entirety.

Such fragments can be produced, for example, by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a $F(ab')_2$ heavy chain portion can be designed to include DNA sequences encoding the CH1 domain and/or hinge region of the heavy chain. The various portions of antibodies can be joined together chemically by conventional techniques, or can be prepared as a contiguous protein using genetic engineering techniques.

In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding variable sequence chain described herein. Preferably, 70-100% amino acid identity (e.g., 85, 89, 90, 91, 92, 93, 94, 95, 96, 97, 98, 99, 100 or any range or value therein) is determined using a suitable computer algorithm, as known in the art.

Examples of heavy chain and light chain variable regions sequences are provided herein.

The antibodies of the present invention, or specified variants thereof, can comprise any number of contiguous amino acid residues from an antibody of the present invention, wherein that number is selected from the group of integers consisting of from 10-100% of the number of contiguous residues in an anti-TNF antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%-100% of that of the native (non-synthetic), endogenous or related and known antibody. Methods of assaying and quantifying measures of enzymatic activity and substrate specificity are well known to those of skill in the art.

Substantial similarity refers to a compound having at least 85% (e.g., at least 95%) identity and at least 85% (e.g., at least 95%) of activity of the native (non-synthetic), endogenous or related and known antibody.

As used herein, the term "human antibody" refers to an antibody in which substantially every part of the protein (e.g., CDR, framework, CL, CH domains (e.g., CH1, CH2, CH3), hinge, (VL, VH)) is substantially non-immunogenic in humans, with only minor sequence changes or variations. Similarly, antibodies designated primate (monkey, baboon, chimpanzee, and the like), rodent (mouse, rat, and the like) and other mammals designate such species, sub-genus, genus, sub-family, family specific antibodies. Further, chimeric antibodies can include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably human or humanized, antibodies that have binding specificities for at least two different antigens. In the present case; one of the binding specificities is for at least one VISTA protein, the other one is for any other antigen. Methods for making bispecific antibodies are known in the art. The recombinant production of bispecific antibodies can be based on the co-expression of two immunoglobulin heavy chain-light chain pairs, where the two heavy chains have different specificities (Milstein and Cuello, Nature 305:537 (1983)). See also WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

In one embodiment, the invention relates to a bispecific antibody targeting VISTA and a second target protein (e.g., an immune checkpoint protein). Exemplary bispecific antibodies include a bispecific antibody targeting VISTA and PD-L1 and a bispecific antibody targeting VISTA and PD-L2.

Human antibodies that are specific for human VISTA proteins or fragments thereof can be raised against an appropriate immunogenic antigen, such as VISTA protein or a portion thereof (including synthetic molecules, such as synthetic peptides).

Other specific or general mammalian antibodies can be similarly raised.

Immunogenic antigens preparation and monoclonal antibody production can be performed using any suitable technique.

For example, a hybridoma is produced by fusing a suitable immortal cell line (e.g., a myeloma cell line such as, but not limited to, Sp2/0, Sp2/0-AG14, NSO, NS1, NS2, AE-1, L.5,>243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A, or the like, or heteromylomas, fusion products thereof, or any cell or fusion cell derived therefrom, or any other suitable cell line as known in the art, See, e.g., www.atcc.org, with antibody-producing cells. Antibody-producing cells can include isolated or cloned spleen, peripheral blood, lymph, tonsil, or other immune cells (e.g., B cells), or any other cells expressing heavy or light chain constant or variable or framework or complementarity determining region (CDR) sequences. Such antibody-producing cells can be recombinant or endogenous cells, and can also be prokaryotic or eukaryotic (e.g., mammalian, such as, rodent, equine, ovine, goat, sheep, primate). See, e.g., Ausubel, supra, and Colligan, Immunology, supra, chapter 2, entirely incorporated herein by reference.

Antibody producing cells can also be obtained from the peripheral blood or, preferably the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. Fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., enzyme-linked immunosorbent assay (ELISA)).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; Bioinvent, Lund, Sweden; Dyax Corp., Enzon, Affymax/Biosite; Xoma, Berkeley, Calif.; Ixsys. See, e.g., PCT/GB91/01134; PCT/GB92/01755; PCT/GB92/002240; PCT/GB92/00883; PCT/GB93/00605; PCT/GB94/01422; PCT/GB94/02662; PCT/GB97/01835; WO90/14443; WO90/14424; WO90/14430; PCT/US94/1234; WO92/18619; WO96/07754; EP 614 989; WO95/16027; WO88/06630; WO90/3809; U.S. Pat. No. 4,704,692; PCT/US91/02989; WO89/06283; EP 371 998; EP 550 400; EP 229 046; PCT/US91/07149; or stochastically-generated peptides or proteins—U.S. Pat. Nos. 5,723,323; 5,763,192; 5,814,476; 5,817,483; 5,824,514; 5,976,862; WO 86/05803, EP 590 689, each entirely incorporated herein by reference, or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source which is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., www.ncbi.nlm.nih.gov/entrez/query.fcgi; www.atcc.org/phage/hdb.html, each entirely incorporated herein by reference.

Such imported sequences can be used to reduce immunogenicity or reduce, enhance or modify binding, affinity, avidity, specificity, half-life, or any other suitable characteristic, as known in the art. Generally part or all of the non-human or human CDR sequences are maintained while part or all of the non-human sequences of the framework and/or constant regions are replaced with human or other amino acids. Antibodies can also optionally be humanized with retention of high affinity for the antigen and other favorable biological properties using three-dimensional immunoglobulin models that are known to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, for example, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824514, 5,817483, 5,814476, 5,763,192, 5,723,323, 5,766,886, 5,714,352, 6,204,023, 6,180,370, 5,693,762, 5,530,101, 5,585,089, 5,225,539; 4,816,567, each entirely incorporated herein by reference, included references cited therein.

The anti-VISTA antibody can also be optionally generated by immunization of a transgenic animal (e.g., mouse, rat, rabbit, hamster, non-human primate, and the like) capable of producing a repertoire of human antibodies, as described herein and/or as known in the art. Cells that produce a human anti-VISTA antibody can be isolated from such animals and immortalized using suitable methods, such as the methods described herein.

Transgenic animals that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. Nature 368:856-859 (1994), Taylor et al., Int. Immunol. 6(4)579-591 (1994), Green et al, Nature Genetics 7:13-21 (1994), Mendez et al., Nature Genetics 15:146-156 (1997), Taylor et al., Nucleic Acids Research 20(23):6287-6295 (1992), Tuaillon et al., Proc Natl Acad Sci USA 90(8)3720-3724 (1993), Lonberg et al., Int Rev Immunol 13(1):65-93 (1995) and Fishwald et al., Nat Biotechnol 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278. Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643, 768. Peptide display libraries, vector, and screening kits are commercially available from such suppliers as Invitrogen (Carlsbad, Calif.), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456; 5,223,409, 5,403,484, 5,571,698, 5,837,500, assigned to Dyax, U.S. Pat. Nos. 5,427,908, 5,580,717; 5,885,793, assigned to Cambridge antibody Technologies; U.S. Pat. No. 5,750,373, assigned to Genentech, U.S. Pat. Nos. 5,618,920, 5,595,898, 5,576,195, 5,698,435, 5,693,493, and 5,698,417.

Antibodies of the present invention can also be prepared using at least one anti-VISTA antibody encoding nucleic acid to provide transgenic animals, such as goats, cows, sheep, and the like, that produce such antibodies in their milk. Such animals can be provided using known methods. See, e.g., but not limited to, U.S. Pat. Nos. 5,827,690;

5,849,992; 4,873,316; 5,849,992; 5,994,616; 5,565,362; 5,304,489, and the like, each of which is entirely incorporated herein by reference.

The anti-VISTA antibodies of the present invention can also be produced using transgenic plants, according to known methods. See also, e.g., Fischer et al., Biotechnol. Appl. Biochem. 30:99-108 (October, 1999), Cramer et al., Curr. Top. Microbol. Immunol. 240:95-118 (1999) and references cited therein; Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. Each of the above references is entirely incorporated herein by reference.

The antibodies of the invention can bind human VISTA with a wide range of affinities ($K_D$). In a preferred embodiment, at least one human monoclonal antibody of the present invention can optionally bind human VISTA with high affinity. For example, a human monoclonal antibody can bind human VISTA with a $K_D$ equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein. In some embodiments, the antibody or antibody fragment can binds human VISTA with an affinity of at least $1\times10^{-7}$ liter/mole, for example, at least $1\times10^{-8}$ liter/mole, for example, at least $1\times10^{-9}$ liter/mole liter/mole.

The affinity or avidity of an antibody for an antigen can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W.H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, KO are preferably made with standardized solutions of antibody and antigen, and a standardized buffer.

Nucleic Acid Molecules

Using the information provided herein, such as the nucleotide sequences encoding at least 70-100% of the contiguous amino acids of at least one of specified fragments, variants or consensus sequences thereof, or a deposited vector comprising at least one of these sequences, a nucleic acid molecule of the present invention encoding at least one anti-VISTA antibody comprising all of the heavy chain variable CDR regions of SEQ ID NOS:1, 2 and 3 and/or all of the light chain variable CDR regions of SEQ ID NOS:4, 5 and 6 can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), for example, but not limited to, at least one specified portion of at least one CDR, as CDR1, CDR2 and/or CDR3 of at least one heavy chain or light chain; nucleic acid molecules comprising the coding sequence for an anti-VISTA antibody or fragment, e.g., a fragment comprising a variable region; and nucleic acid molecules which comprise a nucleotide sequence different from those described above but which, due to the degeneracy of the genetic code, still encode at least one anti-VISTA antibody as described herein and/or as known in the art. It would be routine for one skilled in the art to generate such degenerate nucleic acid variants that code for specific anti-VISTA antibodies of the present invention. See, e.g., Ausubel, et al., supra, and such nucleic acid variants are included in the present invention.

As indicated herein, nucleic acid molecules of the present invention which comprise a nucleic acid encoding an anti-VISTA antibody can include, but are not limited to, those encoding the amino acid sequence of an antibody fragment; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example-ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Human genes which encode the constant (C) regions of the antibodies, fragments and regions of the present invention can be derived from a human fetal liver library, by known methods. Human C regions genes can be derived from any human cell including those which express and produce human immunoglobulins. The human $C_H$ region can be derived from any of the known classes or isotypes of human H chains, including γ, μ, α, δ or ε and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC).

Compositions

The pharmaceutical compositions disclosed herein are prepared in accordance with standard procedures and are administered at dosages that are selected to treat, e.g., reduce, prevent, or eliminate, or to slow or halt the progression of, the condition being treated (See, e.g., Remington's Pharmaceutical Sciences, Mack Publishing Company, Easton, PA, and Goodman and Gilman's The Pharmaceutical Basis of Therapeutics, McGraw-Hill, New York, N.Y., the contents of which are incorporated herein by reference, for a general description of the methods for administering various agents for human therapy). The compositions comprising the disclosed antibodies and agents can be delivered using controlled or sustained-release delivery systems (e.g., capsules, biodegradable matrices). Examples of delayed-release delivery systems for drug delivery that would be suitable for administration of the compositions of the disclosed compounds are described in, e.g., U.S. Pat. Nos. 5,990,092; 5,039,660; 4,452,775; and 3,854,480, the entire teachings of which are incorporated herein by reference.

For preparing pharmaceutical compositions from the anti-VISTA antibodies and/or fragments of the present invention, pharmaceutically acceptable carriers can be solid or liquid. Solid form preparations include powders, tablets, pills, capsules, cachets, suppositories, and dispersible granules. For example, the compounds of the present invention can be in powder form for reconstitution at the time of delivery. A solid carrier can be one or more substances which can also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

Liquid form preparations include solutions, suspensions, retention enemas, and emulsions, for example, water or water propylene glycol solutions. For parenteral injection, liquid preparations can be formulated in solution in aqueous polyethylene glycol solution.

The pharmaceutical composition can be in unit dosage form. In such form, the composition is subdivided into unit doses containing appropriate quantities of the active ingredient. The unit dosage form can be a packaged preparation, the package containing discrete quantities of unit doses. The dosages can be varied depending upon the requirements of the patient, the severity of the condition being treated, the compound and the route of administration being employed. Determination of the proper dosage for a particular situation is within the skill in the art.

Also, the pharmaceutical composition can contain, if desired, other compatible agents, e.g., pharmaceutical, therapeutic or prophylactic agents. Therapeutic or prophylactic agents include, but are not limited to, peptides, polypeptides, proteins, fusion proteins, nucleic acid molecules, small molecules, mimetic agents, synthetic drugs, inorganic molecules, and organic molecules. Examples of the classes of such agents (e.g., anti-cancer agents) include, but are not limited to, cytotoxins, angiogenesis inhibitors, immunomodulatory agents, immuno-oncology agents, and agents used to provide relief from pain or to offset the deleterious effects of one or more therapeutic agents (e.g., bisphosphonate use to reduce the hypercalcemic effects of glucocorticoids).

Angiogenesis inhibitors, agents and therapies that are suitable for use in the compositions and methods described herein include, but are not limited to, angiostatin (plasminogen fragment); antiangiogenic antithrombin III; angiozyme. Bisphosphonates include, but are not limited to, alendronate, clodronate, etidronate, ibandronate, pamidronate, risedronate, tiludronate, and zoledronate.

Immunomodulatory agents and therapies that are suitable for use in the compositions and methods described herein include, but are not limited to, anti-T cell receptor antibodies such as anti-CD3 antibodies (e.g. Nuvion (Protein Design Labs), OKT3 (Johnson & Johnson), or anti-CD20 antibodies Rituxan (IDEC)), anti-CD52 antibodies (e.g. CAMPATH 1H (Ilex)), anti-CD11a antibodies (e.g. Xanelim (Genentech)); anti-cytokine or anti-cytokine receptor antibodies and antagonists such as anti-IL-2 receptor antibodies (Zenapax (Protein Design Labs)), anti-IL-6 receptor antibodies (e.g. MRA (Chugai)), and anti-IL-12 antibodies (CNTO1275 (Janssen)), anti-TNFalpha antibodies (Remicade(Janssen)) or TNF receptor antagonist (Enbrel (Immunex)), anti-IL-6 antibodies (BE8 (Diaclone) and siltuximab (CNTO32 (Centocor)), and antibodies that immunospecifically bind to tumor-associated antigens (e.g., trastuzimab (Genentech)).

Immuno-oncology agents that are suitable for use in the compositions and methods described herein include, but are not limited to, ipilimumab (anti-CTLA-4), nivolumab (anti-PD-1), pembrolizumab (anti-PD-1), anti-PD-L1 antibodies, and anti-LAG-3 antibodies.

The composition is preferably made in the form of a dosage unit containing a therapeutically effective amount of the antibody or fragment. Examples of dosage units are tablets and capsules. For therapeutic purposes, the tablets and capsules can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example potato starch, flavoring or coloring agents, or acceptable wetting agents. Oral liquid preparations generally in the form of aqueous or oily solutions, suspensions, emulsions, syrups or elixirs can contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

Other general details regarding methods of making and using the compounds and compositions described herein are well-known in the art. See, e.g., U.S. Pat. No. 7,820,169, the contents of which are incorporated in their entirely.

Methods of Treatment

One of skill in the art, e.g., a clinician, can determine the suitable dosage and route of administration for a particular antibody, fragment or composition for administration to an individual, considering the agents chosen, pharmaceutical formulation and route of administration, various patient factors and other considerations. Preferably, the dosage does not cause or produces minimal or no adverse side effects. In standard multi-dosing regimens, a pharmacological agent may be administered on a dosage schedule that is designed to maintain a pre-determined or optimal plasma concentration in the subject undergoing treatment. The antibodies, fragments and compositions can be added at any appropriate dosage ranges or therapeutically effective amount, for example, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.5 mg/kg, 2.0 mg/kg, 2.5 mg/kg, 3.0 mg/kg, 4.0 mg/kg, 5.0 mg/kg, 6.0 mg/kg, 7.0 mg/kg, 8.0 mg/kg, 9.0 mg/kg, 10.0 mg/kg, 11.0 mg/kg, 12.0 mg/kg, 13.0 mg/kg, 14.0 mg/kg, 15.0 mg/kg, 16.0 mg/kg, 17.0 mg/kg, 18.0 mg/kg, 19.0 mg/kg, 20.0 mg/kg, 30 mg/kg, 40 mg/kg, 50 mg/kg 60 mg/kg, 70 mg/kg, 80 mg/kg, 90 mg/kg and 100 mg/kg. In one embodiment, the dosage of the administered composition, antibody or fragment is 0.1-15 mg/kg per administration.

The antibody or fragment can be administered once, at least once, twice, at least twice, three times, or at least three times per day. The antibody or fragment can be administered once, at least once, twice, at least twice, three times, at least three times, four times, at least four times, five times, at least five times, six times per week, or at least six times per week. The antibody or fragment can be administered once per month, at least once per month, twice per month, at least twice per month, three times per month or at least three times per month. The antibody or antibody fragment can be administered once per year, at least once per year, twice per year, at least twice per year, three times per year, at least three times per year, four times per year, at least four times per year, five times per year, at least five times per year, six times per year or at least six times per year.

The anti-VISTA antibodies, fragments and compositions can, for example, be administered through parenteral or nonparenteral means, including, but not limited to, intravenously, subcutaneously, orally, rectally, intramuscularly, intraperitoneally, transmucosally, transdermally, intrathecally, nasally, or topically. One of ordinary skill in the art will recognize that the following dosage forms can comprise as the active ingredient, either compounds or a corresponding pharmaceutically acceptable salt of a compound of the present invention. In some embodiments, the dosage forms can comprise as the active ingredient, either a compound or a corresponding pharmaceutically acceptable salt of a compound.

The anti-VISTA antibodies of the invention can be administered as part of a combination therapy (e.g., with each other, or with one or more other therapeutic agents). The compounds of the invention can be administered before, after or concurrently with one or more other therapeutic agents. In some embodiments, a compound of the invention and other therapeutic agent can be co-administered simultaneously (e.g., concurrently) as either separate formulations or as a joint formulation. Alternatively, the agents can be administered sequentially, as separate compositions, within an appropriate time frame, as determined by the skilled clinician (e.g., a time sufficient to allow an overlap of the pharmaceutical effects of the therapies). A compound of the invention and one or more other therapeutic agents can be administered in a single dose or in multiple doses, in an order and on a schedule suitable to achieve a desired therapeutic effect.

The present invention also provides a method for modulating or treating at least one malignant disease in a cell, tissue, organ, animal or patient. In some embodiments, the compounds and compositions of the present invention are used to treat or prevent cancer. Cancer can include any malignant or benign tumor of any organ or body system. Examples include, but are not limited to, the following: breast, digestive/gastrointestinal, endocrine, neuroendocrine, eye, genitourinary, germ cell, gynecologic, head and neck, hematologic/blood, musculoskeletal, neurologic, respiratory/thoracic, bladder, colon, rectal, lung, endometrial, kidney, pancreatic, liver, stomach, testicular, esophageal, prostate, brain, cervical, ovarian and thyroid cancers. Other cancers can include leukemias, melanomas, and lymphomas, and any cancer described herein. In some embodiments, the solid tumor is infiltrated with myeloid and/or T-cells. In some embodiments, the cancer is a leukemia, lymphoma, myelodysplastic syndrome and/or myeloma. In some embodiments, the cancer can be any kind or type of leukemia, including a lymphocytic leukemia or a myelogenous leukemia, such as, e.g., acute lymphoblastic leukemia (ALL), chronic lymphocytic leukemia (CLL), acute myeloid (myelogenous) leukemia (AML), chronic myelogenous leukemia (CML), hairy cell leukemia, T-cell prolymphocytic leukemia, large granular lymphocytic leukemia, or adult T-cell leukemia. In some embodiments, the lymphoma is a histocytic lymphoma, follicular lymphoma or Hodgkin lymphoma, and in some embodiments, the cancer is a multiple myeloma. In some embodiments, the cancer is a solid tumor, for example, a melanoma, or bladder cancer. In a particular embodiment, the cancer is a lung cancer, such as a non-small cell lung cancer (NSCLC).

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), hairy cell leukemia, myelodysplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer-related bone pain, and the like. In some embodiments, the solid tumor is infiltrated with myeloid and/or T-cells. In a particular embodiment, the solid tumor is a lung cancer, such as a non-small cell lung cancer (NSCLC).

In some embodiments, the compounds and therapies described herein are co-administered with a vaccine (such as a viral vector vaccine, bacterial vaccine, cell-based vaccine, DNA vaccine, RNA vaccine, peptide vaccine, or protein vaccine). Such vaccines are well known in the art. See, e.g., Jeffrey Schlom, "Therapeutic Cancer Vaccines: Current Status and Moving Forward," *J Natl Cancer Inst;* 104:599-613 (2012), the contents of which are incorporated herein in their entirely.

In some embodiments, the compounds and therapies described herein are co-administered with agents for chemotherapy, hormone therapies and biological therapies, and/or bisphosphonates. In some embodiments, the agent(s) for chemotherapy include one or more of the following: arboplatin (Paraplatin), cisplatin (Platinol, Platinol-AQ), cyclophosphamide (Cytoxan, Neosar), doxorubicin (Adriamycin), etoposide (VePesid), fluorouracil (5-FU), gemcitabine (Gemzar), irinotecan (Camptosar), paclitaxel (Taxol), topotecan (Hycamtin), vincristine (Oncovin, Vincasar PFS), vinblastine (Velban).

In other embodiments, the anti-VISTA compounds and therapies described herein are co-administered with one or more immune checkpoint antibodies, such as, for example, nivolumab, pembrolizumab, tremelimumab, ipilimumab, anti-PD-L1 antibody, anti-PD-L2 antibody, anti-TIM-3 antibody, anti-LAG-3v, anti-OX40 antibody and anti-GITR antibody.

In another embodiment, the anti-VISTA compounds and therapies described herein are co-administered with a small molecule inhibitor of indoleamine 2,3-dioxygenase (IDO).

The anti-VISTA compounds and composition of the invention may be administered to a subject in need thereof to prevent (including preventing the recurrence of cancer) or treat (e.g., manage or ameliorate a cancer or one or more symptoms thereof) cancer. Any agent or therapy (e.g., chemotherapies, radiation therapies, targeted therapies, such as imatinib, sorafenib and vemurafenib, hormonal therapies, and/or biological therapies or immunotherapies) which is known to be useful, or which has been used or is currently being used for the prevention, treatment, management or amelioration of cancer or one or more symptoms thereof can be used in combination with a compound or composition of the invention described herein. Anti-cancer agents, but not limited to: 5-fluoruracil; acivicin; aldesleukin; altretamine; aminoglutethimide; amsacrine; anastrozole; anthramycin; asparaginase; azacitidine; azetepa; azotomycin; batimastat; bicalutamide; bleomycin sulfate; brequinar sodium; bropirimine; busulfan; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; enloplatin; enpromate; epipropidine; epirubicin hydrochloride; erbulozole; esorubicin hydrochloride; estramustine; estramustine phosphate sodium; etanidazole; etoposide; etoposide phosphate; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-m; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; mechlorethamine hydrochloride; megestrol acetate; melengestrol acetate; melphalan; menogaril; mercaptopurine; methotrexate; methotrexate sodium; metoprine; meturedepa; mitomycin; mitosper; mitotane; mitoxantrone hydrochloride; mycophenolic acid; nocodazole; ormaplatin; paclitaxel; pegaspargase; porfromycin; prednimustine; procarbazine hydrochloride; puromycin; rogletimide; safingol hydrochloride; semustine; simtrazene; sparfosate sodium; sparsomycin; spiromustine; spiroplatin; streptonigrin; streptozocin; sulofenur; talisomycin; tegafur; teloxantrone hydrochloride; temoporfin; teniposide; teroxirone; testolactone; thiamiprine; thioguanine; thiotepa; tiazofurin; tirapazamine; topotecan; trimetrexate; trimetrexate glucuronate; triptorelin; uracil mustard; uredepa; vapreotide; verteporfn; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Targeted therapies include, but are not limited to, tyrosine kinase inhibitors (e.g., imatinib, sorafenib, and vemurafenib). The invention also encompasses administration of an anti-VISTA compound of the invention in combination with radiation therapy comprising the use of x-rays, gamma rays and other sources of radiation to destroy the cancer cells. Cancer treatments are known in the art and have been described in such literature as the Physician's Desk Reference (57th ed., 2003).

The anti-VISTA antibodies described herein are also useful, for example, in the treatment of chronic infectious diseases, such as HIV, HBV, HCV, and HSV, among others.
Detection of Vista Protein The antibodies and antigen-binding fragments of the invention described herein are generally useful for, e.g., detecting VISTA protein in a sample (e.g., a biological material). The antibodies of the invention are compatible with many protein detection assays that are known to those of skill in the art, such as, for example, immunological and immunochemical methods including, but not limited to, flow cytometry (e.g., FACS analysis), enzyme-linked immunosorbent assays (ELISA), including chemiluminescence assays, radioimmunoassay, immunoblot (e.g., Western blot), immunohistochemistry (IHC), immunoprecipitation and other antibody-based quantitative methods (e.g., Luminex® beads-based assays). Other suitable methods include, for example, mass spectroscopy.

The VISTA detection methods of the invention generally comprise contacting a sample (e.g., a cell sample) with an anti-VISTA antibody or antigen-binding fragment of the invention described herein under conditions in which the antibody or antigen-binding fragment binds to VISTA protein in the sample. Suitable conditions for binding of an antibody or antigen-binding fragment of the invention to VISTA protein in a sample can be readily determined by those of ordinary skill in the art and include a variety of conditions known in the art. Such conditions include, for example, those described in Example 27 herein.

For example, antibodies to VISTA can be used to determine the presence and/or expression level of VISTA in a sample directly or indirectly using, e.g., immunohistochemistry (IHC). IHC specifically provides a method of detecting targets in a sample or tissue specimen in situ (see Mokry 1996, ACTA MEDICA 39:129). The overall cellular integrity of the sample is maintained in IHC, thus allowing detection of both the presence and location of the targets of interest.

An IHC staining procedure can comprise steps such as: cutting and trimming tissue, fixation, dehydration, paraffin infiltration, cutting in thin sections, mounting onto glass slides, baking, deparaffinization, rehydration, antigen retrieval, blocking steps, applying primary antibody, washing, applying secondary antibody-enzyme conjugate, washing, applying a tertiary antibody conjugated to a polymer and linked with an enzyme, applying a chromogen substrate, washing, counter staining, applying a cover slip and microscopic examination. Washing steps may be performed with any suitable buffer or solvent, e.g., phosphate-buffered saline, TRIS-buffered saline, distilled water. The wash buffer may optionally contain a detergent, e.g., TWEEN®-20 or NP-40.

In one embodiment, an IHC sample is fixed with formalin, embedded in paraffin and cut into sections for staining and subsequent inspection by light microscopy. Current methods of IHC use either direct labeling or secondary antibody-based or hapten-based labeling. Examples of known IHC systems include, for example, EnVision™ (DakoCytomation), Powervision® (Immunovision, Springdale, Ariz.), the NBA® kit (Zymed Laboratories Inc., South San Francisco, Calif.), HistoFine® (Nichirei Corp, Tokyo, Japan).

VISTA protein can be detected in a variety of sample types, including but not limited to, a tissue sample, a biological fluid sample (e.g. mammalian plasma, serum, lymph, whole blood, spinal, amniotic, or other animal-derived fluid), a cell(s) (e.g., a tumor cell, an immune cell) sample, and the like. Samples can include, for instance: (a) preparations comprising un-fixed fresh tissues and/or cells; (b) fixed and embedded tissue specimens, such as archived material; and (c) frozen tissues or cells. Thus, samples can be fresh or preserved, for example, in liquid solution, flash-frozen or lyophilized, smeared or dried, embedded, or fixed on slides or other supports.

In some embodiments, tissue or cell samples are fixed or embedded. Fixatives are used, for example, to preserve cells and tissues in a reproducible and life-like manner. Fixatives also stabilize cells and tissues, thereby protecting them from the rigors of processing and staining techniques. For example, samples comprising tissue blocks, sections, or smears can be immersed in a fixative fluid, or in the case of smears, dried.

Many methods of fixing and embedding tissue specimens are known, for example, alcohol fixation and formalin-fixation and subsequent paraffin embedding (FFPE). Any suitable fixing agent may be used. Examples include ethanol, acetic acid, picric acid, 2-propanol, 3,3'-diaminobenzidine tetrahydrochloride dihydrate, acetoin (mixture of monomer) and dimer, acrolein, crotonaldehyde (cis+trans), formaldehyde, glutaraldehyde, glyoxal, potassium dichromate, potassium permanganate, osmium tetroxide, paraformaldehyde, mercuric chloride, tolylene-2,4-diisocyanate, trichloroacetic acid, tungstic acid. Other examples include formalin (aqueous formaldehyde) and neutral buffered formalin, glutaraldehyde, carbodiimide, imidates, benzoequinone, osmic acid and osmium tetraoxide. Fresh biopsy specimens, cytological preparations (including touch preparations and blood smears), frozen sections, and tissues for IHC analysis may be fixed in organic solvents, including ethanol, acetic acid, methanol and/or acetone.

Any means of sampling from a subject, for example, by blood draw, spinal tap, tissue smear or scrape, or tissue biopsy can be used to obtain a sample. Thus, the sample can be a biopsy specimen (e.g., tumor, polyp, mass (solid, cell)), aspirate, smear or blood sample. The sample can be a tissue that has a tumor (e.g., cancerous growth) and/or tumor cells, or is suspected of having a tumor and/or tumor cells. For example, a tumor biopsy can be obtained in an open biopsy, a procedure in which an entire (excisional biopsy) or partial (incisional biopsy) mass is removed from a target area. Alternatively, a tumor sample can be obtained through a percutaneous biopsy, a procedure performed with a needle-like instrument through a small incision or puncture (with or without the aid of a imaging device) to obtain individual cells or clusters of cells (e.g., a fine needle aspiration (FNA)) or a core or fragment of tissues (core biopsy).

The samples can be examined cytologically (e.g., smear), histologically (e.g., frozen or paraffin section) or using any other suitable method (e.g., molecular diagnostic methods). A tumor sample can also be obtained by in vitro harvest of cultured human cells derived from an individual's tissue. Tumor samples can, if desired, be stored before analysis by suitable storage means that preserve a sample's protein and/or nucleic acid in an analyzable condition, such as quick freezing, or a controlled freezing regime. If desired, freezing can be performed in the presence of a cryoprotectant, for example, dimethyl sulfoxide (DMSO), glycerol, or propane-diol-sucrose. Tumor samples can be pooled, as appropriate, before or after storage for purposes of analysis.

The antibodies of the present invention can include a label, such as, for example, a detectable label that permits detection of the antibody, and proteins bound by the antibody (e.g., VISTA), in a biological sample. A detectable label is particularly suitable for diagnostic applications. For example, a VISTA antibody can be labeled with a radioactive isotope (radioisotope), which can be detected by one of skill in the art using a gamma counter, a scintillation counter or by autoradiography or other suitable means. Isotopes which are useful for the purpose of the present invention include, but are not limited to: $^{3}H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$ and $^{75}Se$.

Antibodies of the invention can also be labeled with a fluorescent compound (e.g., dyes). When the fluorescently-labeled antibody is exposed to light of the proper wave length, its presence can then be detected due to the fluorescence of the compound. Among the most commonly used fluorescent labels are fluorescein isothiocyanate, rhodamine, phycoerytherin, phycocyanin, allophycocyanin, o-phthaldehyde and fluorescamine. The antibodies of the invention can also be labeled using fluorescence emitting metals such as $^{152}Eu$, or others of the lanthanide series. These metals can be attached to the antibody molecule using such metal chelating groups as diethylenetriaminepentaacetic acid (DTPA), tetraaza-cyclododecane-tetraacetic acid (DOTA) or ethylenediaminetetraacetic acid (EDTA).

The antibodies of the present invention also can be coupled to a chemiluminescent compound. Examples of useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Useful bioluminescent compounds for purposes of labeling antibodies are luciferin, luciferase and aequorin.

Detection of the labeled antibodies can be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of the enzymatic reaction of a substrate to similarly prepared standards.

In some embodiments, the approximate amount of VISTA protein in a sample is also determined. For instance, the intensity of the label from the sample can be compared to that of a known standard or control sample. Estimating the amount of a detectable target (e.g., VISTA protein) in a sample is helpful, for instance, in a variety of diagnostic tests, and the estimate may be used to plan a course of treatment for a suspected disease or condition. Several commercial densitometry software programs and related instruments are available to quantitate the intensity of a stained target in a sample, such as those available from Fuji Film, Applied Biosystems, and Molecular Dynamics.

Various properties and sequence information for select anti-VISTA antibodies of the invention are provided in Tables 1A, 1B and 2 herein.

TABLE 1A

CDR Sequences of Select Fully Human or Humanized anti-human VISTA antibodies

| mAb ID | VH family | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) |
|---|---|---|---|---|---|---|---|
| VSTB50 | B | GYTFTNYG (SEQ ID NO: 1) | INPYTGEP (SEQ ID NO: 2) | AREGYGNYIFPY (SEQ ID NO: 3) | ESVDTYANSL (SEQ ID NO: 4) | RAS (SEQ ID NO: 5) | QQTNEDPRT (SEQ ID NO: 6) |
| VSTB53 | | GYTFTHYT (SEQ ID NO: 7) | IIPSSGYS (SEQ ID NO: 8) | ARGAYDDYYDYYAMDY (SEQ ID NO: 9) | QTIVHSNGNTY (SEQ ID NO: 10) | KVS (SEQ ID NO: 11) | FQASHVPWT (SEQ ID NO: 12) |
| VSTB60 | B | GYTFTNYG (SEQ ID NO: 13) | INTYTGES (SEQ ID NO: 14) | ARDYYGIYVSAY (SEQ ID NO: 15) | ESVDNYANSF (SEQ ID NO: 16) | RAS (SEQ ID NO: 17) | QQSHEDPYT (SEQ ID NO: 18) |
| VSTB95 | | GFTFRNYG (SEQ ID NO: 19) | IISGGSYT (SEQ ID NO: 20) | ARIYDHDGDYYAMDY (SEQ ID NO: 21) | QSIVHSNGNTY (SEQ ID NO: 22) | KVS (SEQ ID NO: 23) | FQGSHVPWT (SEQ ID NO: 24) |
| VSTB112 | D | GGTESSYA (SEQ ID NO: 25) | IIPIFGTA (SEQ ID NO: 26) | ARSSYGWSYEFDY (SEQ ID NO: 27) | QSIDTR (SEQ ID NO: 28) | SAS (SEQ ID NO: 29) | QQSAYNPIT (SEQ ID NO: 30) |
| VSTB116 | D | GGTFSSYA (SEQ ID NO: 31) | IIPIFGTA (SEQ ID NO: 32) | ARSSYGWSYEFDY (SEQ ID NO: 33) | QSINTN (SEQ ID NO: 34) | AAS (SEQ ID NO: 35) | QQARDTPIT (SEQ ID NO: 36) |

TABLE 1B

Heavy and Light Chain Sequences of Select Fully Human or Humanized anti-human VISTA antibodies

| Protein ID | Heavy-chain AA CDS | Light-chain AA CDS |
|---|---|---|
| VSTB50 | QVQLVQSGSELKKPGASVKVSCKASGYTFTNYGLNWVRQAPGQGLEWMGWINPYTGEPTYADDFKGRFVFSLDTSVSTAYLQICSLKAEDTAVYYCAREGYGNYIFPYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFELYSKLTVDKSRWQQGNVESCSVMHEALHNHYTQKSLSLSPGK (SEQ ID NO: 47) | DIVMTQTPLSLSVTPGQPASISCRASESVDTYANSLMHWYLQKPGQPPQLLIYRASNLESGVPDRFSGSGSGTDFTLKISRVEAEDVGVYYCQQTNEDPRTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 48) |
| VSTB53 | QVQLVQSGAEVKKPGASVKVSCKASGYTFTHYTIHWVRQAPGQGLEWMGYIIPSSGYSEYNQKFKDRVTMTRDTSTSTVYMELSSLRSEDTAVYYCARGAYDDYYDYYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 49) | DIVMTQSPLSLPVTPGEPASISCRSSQTIVHSNGNTYLEWYLQKPGQSPQLLIYKVSNRFSGVPDRFSGSGSGTDFTLKISRVEAEDVGVYYCFQASHVPWTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 50) |
| VSTB60 | QVQLVQSGSELKKPGASVKVSCKASGYTFTNYGMTWVRQAPGQGLEWMGWINTYTGESTYADDFKGRFVFSLDTSVSTAYLQICSLKAEDTAVYYCARDYYGIYVSAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDILMISRTPEVTCVVVDVSHEDPEVKINWYVDGVEVFINAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 51) | DIVMTQTPLSLSVTPGQPASISCRASESVDNYANSFMHWYLQKPGQSPQLLIYRASNLESGVPDRFSGSGSGTDFTLKISRVEAEDVGVYYCQQSHEDPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 52) |
| VSTB95 | EVQLVESGGGLVQPGGSLRLSCAASGFTFRNYGMSWVRQAPGKGLEWVASIISGGSYTYYPDSVKGRFTISRDNAKNSLYLQMNSLRAEDTAVYYCARIYDHDGDYYAMDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 53) | DIVMTQSPLSLPVTPGEPASISCRSSQSIVHSNGNTYLEWYLQKPGQSPQLLIYKVSNRFSGVPDRFSGSGSGTDFTLKISRVEAEDVGVYYCFQGSHVPWTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 54) |
| VSTB112 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARSSYGWSYEFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 55) | DIQMTQSPSSLSASVGDRVTITCRASQSIDTRLNWYQQKPGKAPKWYSASSLQSGVPSRFSGSGSGTDFTLTISSLQPEDFATYYCQQSAYNPITFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 56) |
| VSTB116 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARSSYGWSYEFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 57) | DIQMTQSPSSLSASVGDRVTITCRASQSINTNLNWYQQKPGKAPKLLIYAASSLQSGVPSRFSGSGSGTDFTLTISSLQPEDFATYYCQQARDTPITFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 58) |

TABLE 1B -continued

Heavy and Light Chain Sequences of Select Fully Human or Humanized anti-human VISTA antibodies

| Protein ID | Heavy-chain AA CDS | Light-chain AA CDS |
|---|---|---|
| VSTB140* | QVQLVQSGAEVKKPGSSVKVSCKASGGTFSSYAISWVRQAPGQGLEW MGGIIPIFGTANYAQKFQGRVTITADESTSTAYMELSSLRSEDTAVYYCAR SSYGWSYEFDYWGQGTLVTVSSASTKGPSVFPLAPCSRSTSESTAALGCL VKDYFPEPVTVSWNSGALTSGVHTFPAVLQSSGLYSLSSVVTVPSSNFGT QTYTCNVDHKPSNTKVDKTVERKCCVECPPCPAPPAAASSVFLFPPKPKD TLMISRTPEVTCVVVDVSAEDPEVQFNWYVDGVEVHNAKTKPREEQFN STFRVVSVLTVLHQDWLNGKEYKCKVSNKGLPSSIEKTISKTKGQPREPQ VYTLPPSREEMTKNQVSLTCLVKGFYPSDIAVEWESNGQPENNYKTTPP MLDSDGSFFLYSKLTVDKSRWQQGNVFSCSVMHEALHNHYTQKSLSLS PGK (SEQ ID NO: 59) | DIQMTQSPSSLSASVGDRVTITCRASQSIDT RLNWYQQKPGKAPKWYSASSLQSGVPSR FSGSGSGTDFTLTISSLQPEDFATYYCQQSA YNPITFGQGTKVEIKRTVAAPSVFIFPPSDE CLLKSGTASVVCLLNNFYPREAKVQWKVDN ALQSGNSQESVTEQDSKDSTYSLSSTLTLSK ADYEKHKVYACEVTHQGLSSPVTKSFNRGE C (SEQ ID NO: 56) |
| VSTB149*Δ | QVQLVQSGAEVKKPGSSVKVSCKASGGTFSSYAISWVRQAPGQGLEW MGGIIPIFGTANYAQKFQGRVTITADESTSTAYMELSSLRSEDTAVYYCAR SSYGWSYEFDYWGQGTLVTVSSASTKGPSVFPLAPSSKSTSGGTAALGCL VKDYFPEPVTVSWNSGALTSGVHTFPAVLQSSGLYSLSSVVTVPSSSLGT QTYICNVNHKPSNTKVDKKVEPKSCDKTHTCPPCPAPPVAGPDVFLFPP KPKDTLMISRTPEVTCVVVDVSHEDPEVKFNWYVDGVEVHNAKTKPREE QYNSTYRVVSVLTVLHQDWLNGKEYKCKVSNAALPAPIAKTISKAKGQP REPQVYTLPPSREEMTKNQVSLTCLVKGFYPSDIAVEWESNGQPENNYK TTPPVLDSDGSFFLYSKLTVDKSRWQQGNVFSCSVMHEALHNHYTQKSL SLSPGK (SEQ ID NO: 60) | DIQMTQSPSSLSASVGDRVTITCRASQSIDT RLNWYQQKPGKAPKLLIYSASSLQSGVPSR FSGSGSGTDFTLTISSLQPEDFATYYCQQSA YNPITFGQGTKVEIKRTVAAPSVFIFPPSDE QLKSGTASVVCLLNNFYPREAKVQWKVDN ALQSGNSQESVTEQDSKDSTYSLSSTLTLSK ADYEKHKVYACEVTHQGLSSPVTKSFNRGE C (SEQ ID NO: 56) |
| VSTB174* | QVQLVQSGAEVKKPGSSVKVSCKASGGTFSSYAISWVRQAPGQGLEW MGGIIPIFGTANYAQKFQGRVTITADESTSTAYMELSSLRSEDTAVYYCAR SSYGWSYEFDYWGQGTLVTVSSASTKGPSVFPLAPSSKSTSGGTAALGCL VKDYFPEPVTVSWNSGALTSGVHTFPAVLQSSGLYSLSSVVTVPSSSLGT QTYICNVNHKPSNTKVDKKVEPKSCDKTHTCPPCPAPELGGPSVFLFPP KPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLS LSPGK (SEQ ID NO: 61) | DIQMTQSPSSLSASVGDRVTITCRASQSIDT RLNWYQQKPGKAPKLLIYSASSLQSGVPSR FSGSGSGTDFTLTISSLQPEDFATYYCQQSA YNPITFGQGTKVEIKRTVAAPSVFIFPPSDE QLKSGTASVVCLLNNFYPREAKVQWKVDN ALQSGNSQESVTEQDSKDSTYSLSSTLTLSK ADYEKHKVYACEVTHQGLSSPVTKSFNRGE C (SEQ. ID NO: 56) |

*Constant region sequences in VSTB140, VSTB149 and VSTB174 are underlined.
ΔAmino acid residues conferring protease resistance in the heavy chain of VSTB14 are indicated in bold.

TABLE 2

Dissociation constant ($K_D$) for select anti-VISTA antibodies

| Sample | KD (M) | ka1 (1/Ms) | kd1 (1/s) | | | |
|---|---|---|---|---|---|---|
| S1 | 1.71E-10 | 1.69E+06 | 2.89E-04 | 1.09E-10 | 1.11E+06 | 1.21E-04 |
| S40 | 5.07E-10 | 1.46E+05 | 7.40E-05 | 6.96E-10 | 1.39E+05 | 9.69E-05 |
| S41 | 6.32E-10 | 4.82E+05 | 3.05E-04 | 3.10E-10 | 7.08E+05 | 2.19E-04 |
| S42 | 1.04E-10 | 1.05E+06 | 1.09E-04 | 2.65E-10 | 5.13E+05 | 1.36E-04 |
| S43 | 2.64E-11 | 1.25E+06 | 3.30E-05 | 5.28E-11 | 1.18E+06 | 6.22E-05 |
| S44 | 2.53E-11 | 1.23E+06 | 3.12E-05 | 6.40E-11 | 9.93E+05 | 6.36E-05 |
| S45 | 2.35E-11 | 1.58E+06 | 3.72E-05 | 2.58E-11 | 1.46E+06 | 3.77E-05 |
| S46 | 1.06E-10 | 1.56E+06 | 1.66E-04 | 2.96E-10 | 1.50E+06 | 4.44E-04 |
| S47 | 3.56E-10 | 5.14E+05 | 1.83E-04 | 2.52E-10 | 5.69E+05 | 1.43E-04 |
| S33 | 8.30E-10 | 1.23E+06 | 1.02E-03 | 1.22E-09 | 8.96E+05 | 1.10E-03 |
| S34 | 1.08E-09 | 5.95E+05 | 6.43E-04 | 2.80E-09 | 5.20E+05 | 1.46E-03 |
| S35 | 8.06E-11 | 2.08E+06 | 1.68E-04 | 1.35E-10 | 1.78E+06 | 2.41E-04 |
| S36 | 6.29E-11 | 1.77E+06 | 1.12E-04 | 2.90E-11 | 1.58E+06 | 4.58E-05 |
| S37 | 2.23E-09 | 5.10E+05 | 1.14E-03 | 4.43E-09 | 3.94E+05 | 1.75E-03 |
| S38 | 2.26E-09 | 5.18E+05 | 1.17E-03 | 2.03E-09 | 5.37E+05 | 1.09E-03 |
| S39 | 5.62E-10 | 3.97E+05 | 2.23E-04 | 3.47E-10 | 4.15E+05 | 1.44E-04 |
| S25 | 1.31E-09 | 6.21E+05 | 8.12E-04 | 1.10E-09 | 5.65E+05 | 6.24E-04 |
| S26 | No Binding | | | 3.53E-09 | 2.38E+05 | 8.41E-04 |
| S27 | 1.13E-09 | 8.86E+05 | 9.97E-04 | 1.61E-09 | 7.12E+05 | 1.15E-03 |
| S48 | 3.12E-10 | 1.24E+06 | 3.87E-04 | 1.21E-09 | 8.78E+05 | 1.06E-03 |

TABLE 2-continued

Dissociation constant ($K_D$) for select anti-VISTA antibodies

| Sample | KD (M) | ka1 (1/Ms) | kd1 (1/s) | | | |
|---|---|---|---|---|---|---|
| S28 | 2.03E−09 | 1.08E+06 | 2.19E−03 | 2.03E−09 | 9.30E+05 | 1.88E−03 |
| S29 | 3.78E−11 | 1.42E+06 | 5.38E−05 | 8.90E−11 | 9.06E+05 | 8.06E−05 |
| S30 | No Binding | | | No Binding | | |
| S31 | Weak Binding | | | Weak Binding | | |
| S32 | Weak Binding | | | Weak Binding | | |
| S15 | 9.34E−11 | 6.46E+05 | 6.04E−05 | 5.13E−10 | 3.50E+05 | 1.80E−04 |
| S16 | 1.26E−10 | 5.54E+05 | 6.99E−05 | 1.92E−10 | 4.43E+05 | 8.53E−05 |
| S17 | 7.68E−10 | 9.88E+05 | 7.59E−04 | 4.10E−10 | 7.09E+05 | 2.91E−04 |
| S18 | 2.28E−09 | 4.90E+05 | 1.12E−03 | 1.05E−09 | 3.13E+05 | 3.29E−04 |
| S19 | 1.54E−09 | 1.02E+06 | 1.58E−03 | 2.86E−10 | 7.03E+05 | 2.01E−04 |
| S20 | 1.48E−09 | 6.67E+05 | 9.85E−04 | 4.57E−10 | 6.36E+05 | 2.91E−04 |
| S21 | 3.18E−09 | 3.16E+05 | 1.00E−03 | 1.34E−09 | 2.70E+05 | 3.60E−04 |
| S22 | 2.98E−09 | 1.09E+06 | 3.25E−03 | 1.27E−09 | 1.25E+06 | 1.59E−03 |
| S6 | 6.36E−10 | 5.28E+05 | 3.36E−04 | 3.02E−10 | 5.98E+05 | 1.80E−04 |
| S7 | 6.75E−10 | 1.31E+06 | 8.87E−04 | 3.27E−10 | 1.15E+06 | 3.75E−04 |
| S8 | 1.15E−10 | 1.89E+06 | 2.18E−04 | 5.97E−11 | 1.25E+06 | 7.48E−05 |
| S9 | 1.67E−10 | 1.87E+06 | 3.11E−04 | 9.31E−11 | 1.27E+06 | 1.18E−04 |
| S10 | 8.90E−11 | 1.55E+06 | 1.38E−04 | 4.30E−11 | 1.22E+06 | 5.27E−05 |
| S12 | 4.94E−10 | 1.57E+06 | 7.76E−04 | 2.39E−10 | 1.19E+06 | 2.86E−04 |
| S13 | 1.02E−10 | 1.42E+06 | 1.44E−04 | 6.46E−11 | 9.55E+05 | 6.17E−05 |
| S14 | 2.02E−10 | 1.26E+06 | 2.55E−04 | 7.55E−11 | 1.12E+06 | 8.43E−05 |
| S1 | 2.06E−10 | 1.60E+06 | 3.29E−04 | 8.35E−11 | 1.21E+06 | 1.01E−04 |
| S2 | 1.56E−10 | 9.74E+05 | 1.52E−04 | 8.66E−11 | 7.25E+05 | 6.28E−05 |
| S3 | 4.33E−11 | 9.07E+05 | 3.93E−05 | 4.89E−11 | 7.41E+05 | 3.63E−05 |
| S4 | 1.52E−10 | 8.98E+05 | 1.36E−04 | 7.54E−11 | 6.93E+05 | 5.23E−05 |
| S49 | 1.45E−10 | 1.01E+06 | 1.46E−04 | 1.04E−10 | 7.28E+05 | 7.60E−05 |
| S5 | 2.13E−10 | 1.25E+06 | 2.67E−04 | 1.37E−10 | 8.51E+05 | 1.17E−04 |

EXAMPLES

Example 1: Analysis of Vista Expression on Human Hematopoietic Cells

Methods:
Preparation and Staining of Fresh Human PBMCs For VISTA Expression

Expression of VISTA was tested on freshly isolated human PBMCs (peripheral blood mononuclear cells) from several donors. Anti-Human VISTA-biotin (GA-1) was used for staining (5 μg/ml). Mouse IgG1, K-biotin (Clone MOPC-21 at 5 μg/ml) was used as an isotype control.

Donor Material

Blood samples were obtained from Biological Specialty Corp. (Colmar, PA) and were collected and analyzed the same day. 10 ml of whole blood containing heparin sulfate were couriered for analysis.

Sample Preparation

Blood was diluted 1:1 in sterile PBS. 22 ml diluted cord blood was layered onto 20 ml sterile Ficoll-Hypaque (GE Healthcare Cat #17-144003) in 50 ml conical tubes. Tubes were centrifuged at 1800 rpm for 20 minutes at room temperature. Mononuclear cells at the interface following centrifugation were harvested using a 1 ml pipettor and combined into two 50 ml conical tubes. Sterile PBS was added to each tube to make the volume up to 50 ml and the cells were centrifuged at 300 g for 10 minutes at 4° C. Supernatant was discarded. Cells were resuspended in 50 ml of sterile PBS and tubes were spun at 300 g for 10 minutes at 4° C. Supernatant was discarded. Cells were combined and resuspended in 50 ml sterile PBS prior to counting.

Staining Protocol: A frozen vial containing 5×10$^7$ PBMCs was used for compensation controls and as a control for staining.

The following reagents and/or consumables were used:
FACS Stain Buffer (BSA) from BD Biosciences (Cat #554657) supplemented with 0.2% EDTA; Phosphate-Buffered saline (PBS) (Gibco cat #14190); 96-well polypropylene round-bottomed plate (BD #3077); 1.2 ml polypropylene cluster tubes (Corning #4451); biotinylated Anti-VISTA clone GA-1 from ImmunoNext Lot #080612B (used at 5 μg/ml); biotinylated mIgG1, K isotype control (Clone MOPC-21); Biolegend cat #400104, Lot #B116649 (used at 5 μg/ml); anti-human antibodies (See staining table below); near-Infrared live/dead dye (Invitrogen, cat #L10119); and streptavidin reagents including STP-APC (BD Biosciences cat #554067, Lot #04251) (used at 1:200 dilution in FACS buffer), STP-PE (Biolegend cat #405203, Lot #B139688) (used at 1:200 dilution in FACS buffer), STP-PE Cy7 (showed non-specific binding in isotype control samples), STP-Q605 (Invitrogen cat #Q10101MP, Lot #53449A) (used at 1:200 dilution in FACS buffer).

Cell Surface Staining Protocol

Prior to staining, 1×10$^6$ cells were transferred into 96-well round-bottomed plates and were washed with 150 μl PBS. Plates were then centrifuged at 1300 rpm at 4° C. for 3 minutes.

Subsequently, cells were washed again in PBS and centrifuged as described above.

Live/dead staining was then performed in 50 μl PBS containing 0.25 μl of near-infrared live/dead dye. After 10 minutes at room temperature the wells were washed with 150 μl FACs staining buffer and centrifuged at 1300 rpm at 4° C. for 3 minutes. Supernatant was discarded.

Cells were blocked with human serum at 1:100 in 50 μl FACS staining buffer. Plates were incubated at 4° C. for 15 minutes. Wells were then washed with 150 μl FACs staining buffer and centrifuged at 1300 rpm at 4° C. for 3 minutes. Supernatant was discarded.

A cocktail containing the following antibodies was then added to each well for surface staining: The cocktails are described in Tables 3-6 below. Each cocktail would be utilized separately from the others depending on the populations of interest.

TABLE 3

Lineage Stain

| Fluoro | Antigen | Target Mouse | Rat | Human | Isotype | Clone | Supplier | Cat No. | Lot No. | Titer (μl/10⁶ Cells) |
|---|---|---|---|---|---|---|---|---|---|---|
| FITC/AF488 | CD19 | | | x | mIgG1 | HIB19 | Biolegend | 302206 | B123019 | 2 |
| PE | CD11b | | | x | mIgG1, K | ICRF44 | BD Bio. | 555388 | 45134 | 2 |
| PerCP-Cy5.5 | HLA-DR | | | x | mIgG2a, K | G46-6 | BD Bio. | 560652 | 25161 | 0.5 |
| PE Cy7 | CD16 | | | x | mIgG1, K | 3G8 | BD Bio. | 557744 | 87825 | 0.2 |
| APC Cy7 | NIR Live/Dead | | | x | | | | | | |
| AF700 | CD56 | | | x | mIgG1, K | B159 | BD Bio. | 557919 | 19470 | 1 |
| APC/AF647 | VISTA-Bio | | | x | | | | | | |
| PB/V450 | CD3 | | | x | mIgG1, K | UCHT1 | BD Bio. | 558117 | 90926 | 0.5 |
| Q605 | CD14 | | | x | mIgG2a, K | TuK4 | Invitrogen | Q10013 | 1049158 | 0.2 |

TABLE 4

T Cell Stain

| Fluoro | Antigen | Target Mouse | Rat | Human | Isotype | Clone | Supplier | Cat No. | Lot No. | Titer (μl/10⁶ Cells) |
|---|---|---|---|---|---|---|---|---|---|---|
| FITC/AF488 | CD4 | | | x | mIgG1, K | RPA-T4 | BD Bio. | 555346 | 38460 | 2 |
| PE | VISTA-Bio | | | x | | | | | | |
| PerCP-Cy5.5 | CD8 | | | x | mIgG1, K | RPA-T8 | BD Bio. | 560662 | 1037 | 0.5 |
| PE Cy7 | CD56 | | | x | mIgG1, K | B159 | BD Bio. | 557747 | 47968 | 0.5 |
| APC Cy7 | NIR | | | x | | | | | | |
| AF700 | CD45RO | | | x | mIgG2a, K | UCHL1 | Biolegend | 304218 | B143062 | 1 |
| APC/AF647 | TCRgd | | | x | mIgG, K | B1 | Biolegend | 331212 | B126473 | 2 |
| PB/V450 | CD45RA | | | x | mIgG2b, K | HI100 | BD Bio. | 560363 | 90928 | 0.5 |
| Q655 | CD3 | | | x | mIgG2a | S4.1 | Invitrogen | Q10012 | 982352 | 0.5 |

TABLE 5

DC Stain

| Fluoro | Antigen | Target Mouse | Rat | Human | Isotype | Clone | Supplier | Cat No. | Lot No. | Titer (μl/10⁶ Cells) |
|---|---|---|---|---|---|---|---|---|---|---|
| FITC/AF488 | Lin1 | | | x | Mix | Mix | BD Bio. | 340546 | 2152758 | 5 |
| PE | CD11c | | | x | mIgG1, K | | BD Bio. | 555392 | 45123 | 2 |
| PerCP-Cy5.5 | HLA-DR | | | x | mIgG2a, K | G46-6 | BD Bio. | 560652 | 25161 | 0.5 |
| APC Cy7 | NIR | | | x | | | | | | |
| APC/AF647 | CD83 | | | x | mIgG1, K | HB15e | BD Bio. | 551073 | 57688 | 2 |
| BV421 | CD123 | | | x | mIgG1, K | 6H6 | Biolegend | 306017 | B148193 | 0.5 |
| Q605 | VISTA-Bio | | | x | | | | | | |

TABLE 6

Myeloid Stain

| Fluoro | Antigen | Target Mouse | Rat | Human | Isotype | Clone | Supplier | Cat No. | Lot No. | Titer (μl/10⁶ Cells) |
|---|---|---|---|---|---|---|---|---|---|---|
| FITC/AF488 | CD33 | | | x | mIgG1 | HM3-4 | Biolegend | 303304 | B100963 | 3 |
| PE | CD11b | | | x | mIgG1, K | ICRF44 | BD Bio. | 555388 | 45134 | 2 |
| APC Cy7 | NIR | | | x | | | | | | |
| APC/AF647 | VISTA-Bio | | | x | | | | | | |
| Q605 | CD45 | | | x | mIgG1, K | HI30 | Invitrogen | Q10051 | 880470 | 1 |

Following the surface staining, cells were washed twice as previously described with FACS staining buffer and centrifuged at 1300 rpm at 4° C. for 5 minutes. Samples were resuspended in 50 µl of FACS staining buffer containing the appropriate fluorescently-labeled streptavidin. Samples were incubated at 4° C. for 30 minutes. Cells were washed with 150 µl FACS staining buffer and centrifuged at 1300 rpm at 4° C. for 5 minutes. This wash step was repeated before samples were resuspended in 250 µl of FACS staining buffer. Samples were analyzed on a BD LSRFortessa™ cell analyzer (BD Biosciences) the same day.

Data Analysis

Flow cytometry data was reanalyzed using FlowJo Version 9 software to gate specific phenotypic populations. Enumeration of geometric mean was used to compare VISTA expression in different cell subsets. Each population was normalized for background by subtracting isotype control values from the mean values of the anti-VISTA treated samples. Graphs were prepared in Prism and statistics were performed using either student's T-test if only two samples were compared, or one-way ANOVA with Bonferroni post-tests.

Results:

Expression of VISTA on Human Myeloid and Lymphoid Subsets:

As shown in FIGS. 2A-2E, 3A-3G, 4, 5A-5B and 6A-6C, VISTA expression on CD14$^+$ monocytes was significantly different from all other populations (p<0.001). No significant differences between other populations were seen. Monocytes expressed the highest levels of VISTA in peripheral blood, with the CD14$^+$CD16$^-$ subset having significantly higher expression than CD14$^{lo}$ CD16$^+$ cells. While APCs showed moderate expression of VISTA, lymphoid subsets showed low expression levels.

Expression of VISTA on Human T and NK Subsets:

As shown in FIGS. 7A-7E, 8A-8G and 9, with NK subsets, CD56$^{lo}$ cells exhibited significantly higher expression levels of VISTA than CD56$^{Hi}$ NK cells. Of T cell subsets, CD8$^+$ memory cells expressed the highest expression levels, although they are not significantly higher than CD8$^+$ naive or CD4$^+$ T cells.

Expression of VISTA on Human Dendritic Cell Subsets:

As shown in FIGS. 10A-10D, 11A-11C and 12, no significant differences in VISTA expression seen; DCs and basophils exhibited low expression of VISTA, with plasmacytoid dendritic cells (pDCs) generally being higher but not to a significant extent.

Conclusion: These results show expression of VISTA on various immune cell subsets, and that VISTA is expressed on monocytes most highly, with some expression on different T cell subsets and NK cells, and little to no expression on B cells.

Example 2: Vista Expression on Peripheral Blood Cells

Methods:

Staining of whole blood: Freshly isolated whole blood (100 µl) was stained with antibody cocktails as indicated below by incubation for 30 minutes at 4° C. Red blood cells (RBCs) were lysed with RBC lysis buffer and the remaining cells were washed 1× with staining buffer. Cells were re-suspended in 200 µl of staining buffer. The data were collected using a MACSQuant flow cytometer and analyzed using FlowJo analysis software.

Staining of peripheral blood mononuclear cells (PBMCs): Peripheral blood mononuclear cells were isolated from whole blood using Ficoll gradient. Freshly isolated 1×10$^6$ PBMCs were stained with antibody cocktails in 100 µl of staining buffer. Samples were incubated for 30 minutes at 4° C. then washed once with staining buffer. Cells were re-suspended in 100 µl of staining buffer. The data were collected using MACSQuant® flow cytometer (Miltenyi Biotec) and analyzed using FlowJo analysis software.

The antibodies used were CD11b, CD33, CD177, CD16, CD15, CD14, CD20, HLADR, CD3, CD4, CD8, CD127, CD69, and FOXP3 antibodies (Biolegend, San Diego, CA). The APC-conjugated mouse anti-human VISTA (clone GG8) was made by ImmuNext (Lebanon, NH).

Conclusions:

Expression of VISTA on Healthy Human Peripheral Blood Cells

Whole blood and peripheral blood mononuclear cells were analyzed for VISTA expression using multicolor flow cytometry. As shown in FIGS. 15A and 15B, the highest level of VISTA expression was detected on monocytes followed by neutrophils. Both the CD4+ and CD8+ T cells expressed low level of VISTA as shown in FIGS. 13C and 13D.

Expression of VISTA on Cancer Patient Peripheral Blood Cells

As shown in FIGS. 14A-C, peripheral blood mononuclear cells (PBMCs) from lung cancer patients were analyzed. FIG. 14A is a representative flow plot showing analysis of CD14$^+$ monocytes and CD15$^+$ myeloid derived suppressive cells (MDSCs). The results suggest that phenotypically CD15$^+$ cells are neutrophil derived MDSCs. Additionally, these cells are absent in healthy blood samples. FIG. 14B is a representative histogram of VISTA expression on healthy and cancer patient derived monocytes, suggesting a higher level of VISTA expression on cancer patient cells compared to healthy controls. Similarly higher level of VISTA was found on MDSCs in cancer patients, as shown in FIG. 14C.

FIG. 15A is a representative FACS plot showing the presence of neutrophil derived MDSCs in the blood of colon cancer patients. FIGS. 15B and 15C are representative histograms showing higher level of VISTA expression on cancer patients' monocytes compare to healthy donor blood samples.

Expression of VISTA on Cynomolgus Monkey Peripheral Blood Cells

As shown in FIGS. 16A and 16B flow cytometry analysis of monkey whole blood revealed the VISTA expression pattern similar to human cells. Both monocytes and neutrophils expressed the highest level of VISTA compared to CD4$^+$ (FIG. 16C) and CD8$^+$ (FIG. 16D) T cells.

Example 3: Vista Expression in Heme Malignancy Cell Lines at the RNA Level and Protein Level Because VISTA is expressed in heme malignancies, an anti-VISTA antibody could potentially target the malignant cells for destruction, as well as block VISTA and promote anti-tumor immune responses.

Figure 17:
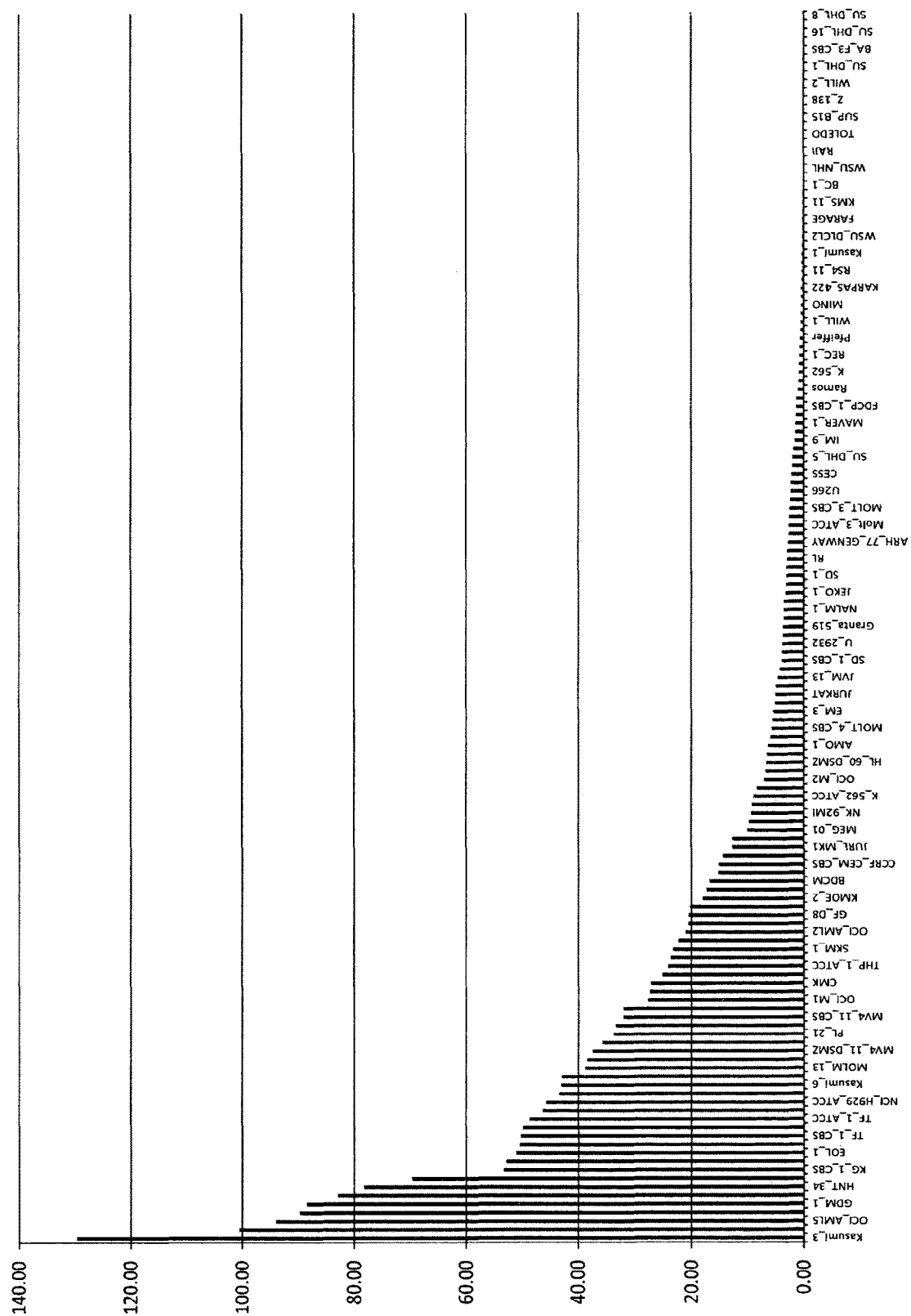
FIG. 17: Graph showing absolute expression values of VISTA RNA in Heme cell lines.

The data includes RNAseq analysis of ~140 heme malignancy cell lines (some cell lines are repeated in the analysis). The data is shown in FIG. 17.

The RNAseq values are listed as FPKM (Fragments Per Kilobase of exon per Million fragments mapped) values.

In essence, this means that all reads falling in the exonic regions of a gene were counted and normalized by both the length of the gene and the total number of reads per sample (to account for inter-sample differences). The cutoff value is 1; above 1 is positive for VISTA expression (at the RNA level), below 1 is negative for VISTA expression.

The results indicated that many cell lines are positive at the RNA level, primarily acute myeloid leukemias and chronic myelogenous leukemias. This may be expected since VISTA is highly expressed in normal myeloid cells, and because its function is believed to dampen immune responses, including anti-tumor immune responses.

Example 4: Generation of Monoclonal Antibodies Against Vista

Phage Panning

Twenty four phage panning experiments were carried out to enrich for phage reactive to Cyno VISTA-His. The cynomolgus VISTA protein was used for these experiments as it showed better biotin conjugation than the human VISTA protein. To determine the success of the phage experiments, phage pools from the individual panning rounds were added to neutravidin plates coated with biotinylated cyno VISTA-His and detected with a HRP-conjugated anti-M13 antibody. Individual colonies were picked from the phage selection rounds and Fabs proteins were produced in 96 well plates. The expressed Fab supernatants were assayed for binding to biotinylated cyno VISTA-His. This resulted in more than 200 hits.

The VH and VL regions from the Fab plates were amplified, submitted for DNA sequencing and were exported as FASTA files. When picking the clones that should be converted and tested as MABs, the clones were chosen based on sequence diversity as well as having limited post-translational modification risks and as few hydrophobic residues as possible.

The VH and VL from the phage clones were sub-cloned into mammalian IgG1/kappa expression vectors and transfected into HEK293 cells. The antibodies were purified on Protein A Sepharose Fast Flow affinity resin. The concentration of the phage MABs was determined by quantitative ELISA using Nanodrop measurements. The antibody panel was expressed at high levels. SDS-PAGE analysis demonstrated the integrity of each expressed antibody variant.

In-line maturation of the phage antibodies was done by amplifying the VH domains from the polyclonal antibody mixes from the last round of panning for cloning into phage vectors that have diversity in the VL. This resulted in an enriched VH pool which was sampled with additional diversity in the VL. The phage were taken through 1-2 rounds of stringent panning with the expectation to identify very high affinity binders to VISTA ECD His protein. A monoclonal Fab ELISA was run to determine the success of the maturation. ELISA and expression data was normalized to a reference clone set to 100% from the original de novo panning experiment and affinity matured clones with higher binding signal to cyno VISTA antigen than the reference clone were identified. This process generated several clones that demonstrated up to 200% binding when screened at low antigen concentration (1 nM), the clones with highest affinity were sequenced and produced as MABs.

Hybridoma Generation

One group of BALB/cAnNCrl mice received one intraperitoneal (IP) injection of 50 μg Hu VISTA-Ig recombinant protein (Sino) emulsified in Complete Freund's Adjuvant followed two weeks later by one IP injection of 50 μg Hu VISTA-Ig recombinant protein emulsified in Incomplete Freund's Adjuvant. Two weeks later the mice received one IP injection of 50 μg cyno VISTA-Fc recombinant protein emulsified in Incomplete Freund's Adjuvant. All mice received a final injection of 25 μg human and 25 μg cyno VISTA at the base of tail in PBS, five days prior to splenic harvest for fusion.

Another group of BALB/cAnNCrl mice received one IP injection of 50 μg Hu VISTA-His recombinant protein emulsified in Complete Freund's Adjuvant. Two weeks later the mice received one IP injection of 50 μg Hu VISTA-His recombinant protein emulsified in Incomplete Freund's Adjuvant. Two weeks later the mice received one IP injection of 50 μg Cyno VISTA-His recombinant protein emulsified in Incomplete Freund's Adjuvant. Two weeks later all mice received a final injection of 25 μg Hu VISTA-His and 25 μg Cyno VISTA-His in PBS, three days prior to splenic harvest for fusion.

On the day of fusion, mice were euthanized by CO2 asphyxiation; the spleens were removed and placed into 10 mL of cold phosphate-buffered saline. A single cell suspension of splenocytes was prepared by grinding spleens through a fine mesh screen with a small pestle and rinsing with PBS at room temperature. Cells were washed once in PBS and subjected to RBC lysis. Briefly, cells were resuspended in 3 mL of RBC lysis buffer (Sigma #R7757) per every spleen and placed on ice for 5 minutes. Cells were again washed once in PBS at room temperature and labeled for magnetic sorting. As per manufacturer's instructions, cells were labeled with anti-murine Thy1.2, anti-murine CD11b and anti-murine IgM magnetic beads (Miltenyi Biotec #130-049-101, 130-049-601 and 130-047-301 respectively) then sorted using a MS column with a Midi MACS. The negative cell fractions (positive cell fractions were discarded) were fused to FO cells. Fusion was carried out at a 1:1 ratio of murine myeloma cells to viable spleen cells. Briefly, spleen and myeloma cells were mixed together, pelleted and washed once in 50 mL of PBS. The pellet was resuspended with 1 mL of polyethylene glycol (PEG) solution (2 g PEG molecular weight 4000, 2 mL DMEM, 0.4 mL DMSO) per 10e8 splenocytes at 37° C. for 30 seconds. The cell/fusion mixture was then immersed in a 37° C. water bath for approximately 60 seconds with gentle agitation. The fusion reaction was stopped by slowly adding 37° C. DMEM over 1 minute. The fused cells were allowed to rest for 5 minutes at room temperature and then centrifuged at 150×g for 5 minutes. Cells were then resuspended in Medium E-HAT (MediumE (StemCell Technologies cat #03805) containing HAT (Sigma cat #H0262) and seeded in 96-well flat bottom polystyrene tissue culture plates (Corning #3997).

A capture EIA was used to screen hybridoma supernatants for antibodies specific for cyno VISTA. Briefly, plates (Nunc-Maxisorp #446612) were coated at 4 μg/ml for at least 60 minutes with goat anti-mouse IgG (Fc) antibody (Jackson #115-006-071) in coating buffer (Thermo 28382). Plates were blocked with 200 μl/well of 0.4% (w/v) bovine serum albumin (BSA) in PBS at for 30 minutes at RT. Plates were washed once and 50 μl/well of hybridoma supernatant was added and incubated at room temperature for at least 30 minutes. Plates were washed once and 50 μl/well of 0.1 μg/mL of cyno VISTA-huIg was added and incubated at RT for 30 minutes. Plates were washed once and 1:40,000 Streptavidin HRP (Jackson 016-030-084) in 0.4% BSA/PBS was added to plates and incubated for 30 minutes at RT. Plates were washed 3× and subsequently developed using 100 μl/well TMB Turbo substrate (Thermo Scientific 34022) incubating approximately 10 minutes at RT. The reaction was stopped using 25 μl/well 4N Sulfuric Acid and absorbance was measured at 450 nm using an automated plate spectrophotometer. Fifteen of the primary hits were selected for subcloning by limiting dilution and were screened in the same primary screen format.

All cyno VISTA reactive hybridoma cell lines were cross screened using human VISTA-Ig to assess cross-reactivity. Briefly, plates (Nunc-Maxisorp #446612) were coated at 4 µg/mL with goat anti-ms Fc (Jackson #115-006-071) in 0.1M sodium carbonate-bicarbonate buffer, pH 9.4 (Pierce 28382 BupH™) 0/N at 4° C. Without washing, the wells were blocked with 200 µl of block (0.4% BSA (Sigma) (w/v) in PBS (Invitrogen)) overnight at 4° C. After removing block solution, undiluted hybridoma supernatants were incubated on coated plates for 30 minutes at RT. Plates were washed once with PBST (0.02% Tween 20 (Sigma) (w/v) in PBS), and then incubated for 30 minutes with Hu VISTA-Ig diluted to 100 ng/ml in block. Plates were washed once with and probed with Goat antihuman-Fc-HRP (Jackson #109-036-098) diluted 1:10,000 in block for 30 minutes at RT. Plates were again washed and subsequently developed using 100 µl/well TMB Turbo substrate (Thermo Scientific 34022) incubating approximately 10 minutes at RT. The reaction was stopped using 25 µl/well 4N Sulfuric Acid and absorbance was measured at 450 nm using an automated plate spectrophotometer.

Hybridomas that were shown to be reactive to both human and cynomolgus VISTA had their V region antibody sequences cloned. Hybridoma cells were prepared prior to the reverse transcriptase (RT) reactions with Invitrogen's SuperScript III cells Direct cDNA System. Briefly, the culture medium was discarded and the plate placed on ice and resuspended in 200 µl cold PBS. Forty microliters was transferred to a MicroAmp fast 96 well Reaction PCR plate and the plate was placed on a cold metal plate base, sealed with plastic film and spun at 700 rpm for 3 minutes. The PBS was discarded and to each well, 10 Resuspension Buffer and 1 µl Lysis Enhancer was added. The plate was sealed and incubated at 75° C. for 10 min and stored at −80° C.

For the RT reaction, each well contained 5 µl water, 1.6 µl 10× DNase Buffer, 1.2 µl 50 mM EDTA, 2 µl Oligo(dT)20 (50 mM) and 1 µl 10 mM dNTP Mix. The plate was incubated at 70° C. for 5 min, followed by incubation on ice for 2 min, then the following reagents were added for each well; 6 µl 5× RT Buffer, 1 µl RNaseOUT™ (40 U/µl), 1 µl SuperScript™ III RT (200 U/µl) and 1 µl of 0.1M DTT. The plate was sealed and placed on a thermal cycler preheated to 50° C. and incubated at 50° C. for 50 minutes, followed by inactivation (5 min incubation at 85° C.). The reaction was chilled on ice and the single-stranded cDNA was stored at −80° C. until further use.

For V region amplifications, 20 µl PCR reactions were set up. Each well contained 16.2 µl water, 2.0 µl 10×PCR Reaction buffer, 0.8 µl MgSO4 (50 mM), 0.4 µl 10 mM dNTP, 0.15 µl 100 uM Forward primer mix 0.05 µl 100 uM Reverse primer, 0.2 µl HiFi Tag enzyme. The cDNA, prepared as described above, was transferred (2 µl/well) to the PCR components mixture, the plate was sealed and an amplification reaction was run; for VH the program was (i) 94° C. for 1 min (ii) 94° C. for 15 sec (iii) 55° C. for 30 sec (iv) 68° C. for 1 min. Steps (ii-iv) were repeated for a total of 35 cycles followed by a final extension at 68° C. for 3 min. for VL the program was (i) 94° C. for 1 min (ii) 94° C. for 15 sec (iii) 55° C. for 30 sec (iv) 65° C. for 30 sec, (v) 68° C. for 1 min. Steps (ii-v) were repeated for a total of 35 cycles followed by a final extension at 68° C. for 3 min.

Forward primers were pre-mixed and such mixture was used in ration 3:1 with the reverse primer. PCR products were verified on an agarose gel. The reactions were prepared for infusion cloning by the addition of Enhancer (In-Fusion HC Cloning Kit, cat #639650, Clontech). Five microliters of the PCR reaction was transferred to a PCR plate followed by the transfer of 2 µl of enhancer/well. The plate was sealed and incubated in a thermal cycler (15 min at 37° C. and 15 min at 80° C.). The destination vector (vDR243 or vDR301) was prepared by Esp3I digestion; (1.5 µg vector was digested in 3 µl Tango Buffer, 2 l Esp3I and water in a 30 µl reaction at 37° C. for 2 hours).

For infusion cloning, 2 µl of enhancer treated PCR product was mixed with 100 ng Esp3I digested vector and 2 µl of 5× infusion enzyme (Clontech). The infusion reaction was done in 96-well PCR plate format. The plate was incubated for 15 mM at 50° C. on a PCR machine and Stella competent cells were transformed by heat shock for 40 seconds at 42° C. without shaking and spread on LB agar plates with select antibiotic and incubated overnight at 37° C. Next day, colonies were picked into 96-well deep well plates containing LB/Carbenicillin media and grown overnight at 37° C. Frozen stocks were made from overnight culture mixing with equal volume of 30% w/v glycerol. The V regions were sequenced using sequencing primer SPF0052. The sequences were analyzed, one positive well per hybridoma vH and vL was chosen, re-arrayed in new plates and grown overnight in rich medium with ampicillin. Clones then had miniprep DNA prepared for small scale transfection in 96-well plate.

Forty eight selected mouse hybridoma sequences for both heavy and light chain were human framework adapted using an internal software program. One human framework was chosen for each one of the mouse vH or vL. V region DNA sequences were obtained through back-translation. Synthetic DNA regions corresponding to the HFA amino acid sequences were ordered from Integrated DNA Technologies (Coralville, IA). Cloning was performed into pre-cut vDR149 and vDR157, human IgG1 and human kappa respectively. Qiagen Endo-free Maxi-prep kits were used to prepare the DNA. Expi293 (100 ml) cultures were used to express this antibody panel.

Example 5: Protocol for Human Vista-Ig T Cell Suppression Assay In Vitro

Figure 18:
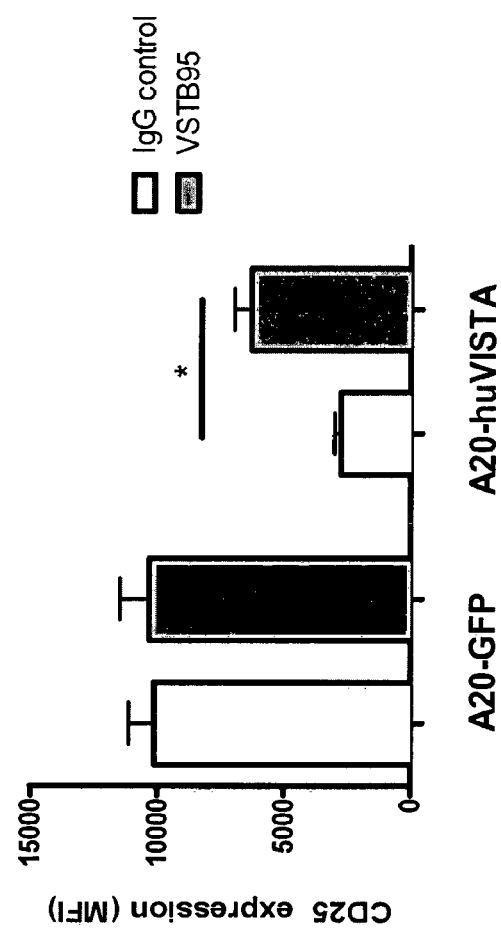
FIG. 18: Mouse A20 cells were stably transfected with either GFP or human VISTA. They were incubated with ova peptide and with DO11.10 T cells. CD25 expression by the T cells was measured 24 hours after incubation began. The A20-huVISTA cells suppress CD25 expression by the T cells, but this readout is significantly restored by incubation with VSTB95.
Figures 22A, 22B:
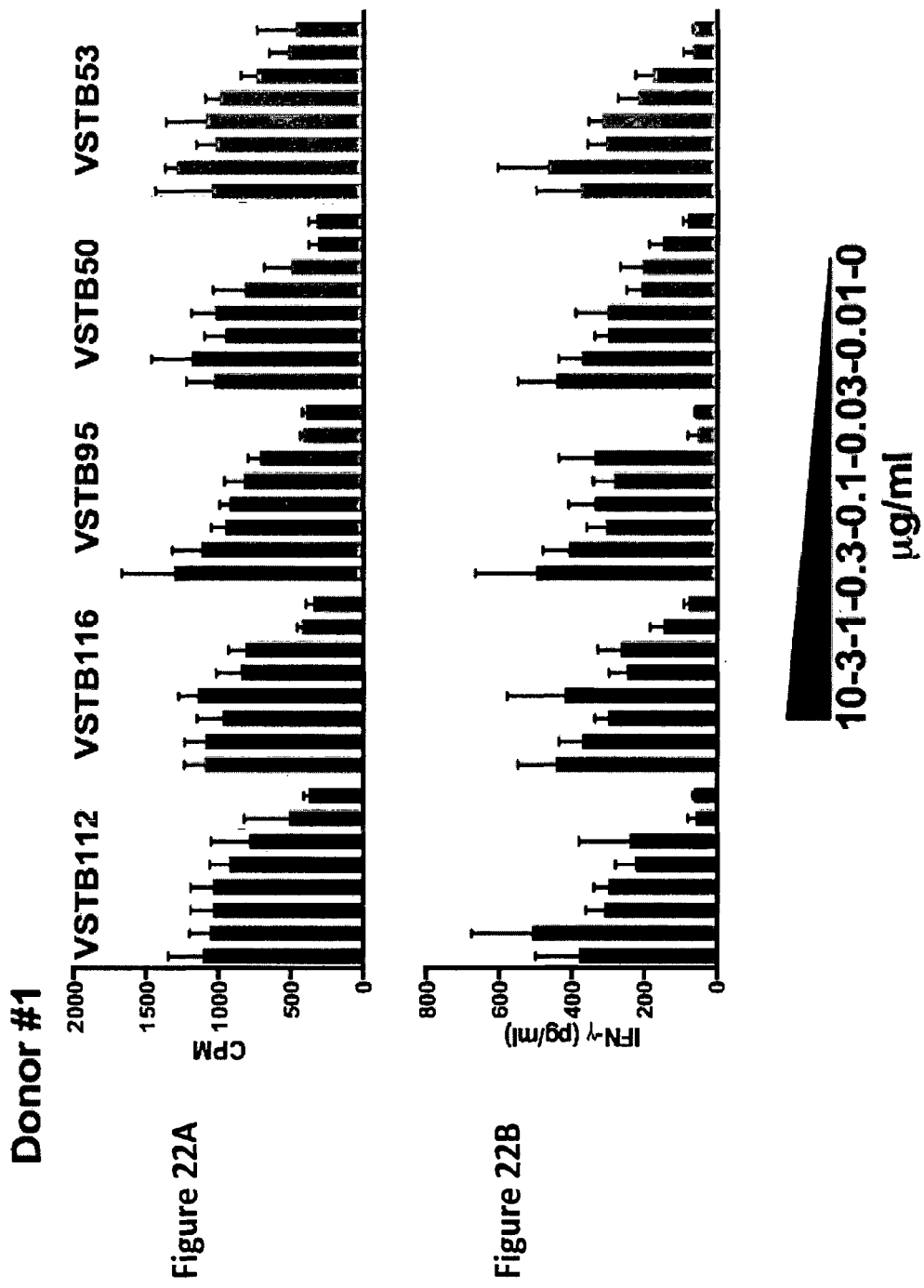
FIGS. 22A-22B: Dilution studies of 6 anti-VISTA antibody candidates in the SEB assay (individual CPM counts and IFN-g concentrations) from 30 µg/ml to 0.0 µg/ml.

Mouse A20 cells were stably transfected with either GFP or human VISTA. They were incubated with ova peptide and with DO11.10 T cells. CD25 expression by the T cells was measured 24 hours after incubation began. The A20-hu-VISTA cells suppress CD25 expression by the T cells, but this readout is significantly restored by incubation with VSTB95 (FIG. 18).

Example 6: Human Framework Regions Adaptation of Anti-Vista Antibodies

Mouse hybridoma sequences for both heavy and light chain were human framework adapted by CDR-grafting (Jones, et al. *Nature,* 321: 522-525 (1986) using an internal software program. The program delineates the complementarity determining regions (CDRs) of the V region sequences according to the Kabat definitions (Wu, T. T. & Kabat, E. A. (1970). *J Exp Med,* 132, 211-50) and compares the framework regions with the human germline genes using Blast. The human germline with the highest sequence identity to the mouse frameworks was chosen as the acceptor gene for human framework adaptation (HFA). In a few cases, closely related human germline genes were chosen instead, based on previous experience with well-expressed human frameworks. DNA sequences for the human frameworks chosen for each one of the mouse vH or vL V regions were obtained through back-translation. Synthetic DNA regions corresponding to the HFA amino acid sequences were ordered from Integrated DNA Technologies (Coralville, IA). Cloning was performed into human IgG1 and human kappa, respectively.

Example 7: Anti-Vista Antibody Constructs

Plasmid and sequence information for the molecules for cell line development: Plasmid constructs were generated for anti-VISTA antibodies having the VSTB112 variable regions and an IgG1κ constant regions (VSTB174, new number due to an allotypic change in the constant region), an IgG2sigma constant region (VSTB140) or an IgG1 protease-resistant constant region (VSTB149).

Lonza Vectors

The pEE6.4 and pEE12.4 Chinese hamster ovary (CHO) expression vector system (Lonza Biologics, PLC) was established in Biologics Research (BR) and Pharmaceutical Development & Manufacturing Sciences (PDMS) as the primary expression system for generation of therapeutic mAbs in mammalian expression cell lines. Each vector contains a human cytomegalovirus (huCMV-MIE) promoter to drive the expression of the heavy chain (HC) or light chain (LC) and contains the ampicillin resistence gene. pEE12.4 vector also includes the gene encoding the glutamine synthetase (GS) enzyme. Growth conditions which require glutamine synthetase activity places selective pressure on the cells to maintain the expression vector (GS Gene Expression System Manual Version 4.0). pEE6.4 was used to clone the HC gene and pEE12.4 to clone the LC gene as single gene vectors. The Lonza double gene plasmid is created from these two Lonza single genes vectors.

```
Amino Acid Sequences of Variable Heavy ChainRegions of Select VISTA
mAbs
>VSTB112 heavy chain
                                                         (SEQ ID NO: 37)
QVQLVQSGAEVKKPGSSVKVSCKASGGTFSSYAISWVRQAPGQGLEWM

GGIIPIFGTANYAQKFQGRVTITADESTSTAYMELSSLRSEDTAVYYCARSSYGWSYE

FDYWGQGTLVTVSS

>VSTB50 heavy chain
                                                         (SEQ ID NO: 38)
QVQLVQSGSELKKPGASVKVSCKASGYTFTNYGLNWVRQAPGQGLEWM

GWINPYTGEPTYADDFKGRFVFSLDTSVSTAYLQICSLKAEDTAVYYCAREGYGNYI

FPYWGQGTLVTVSS

>VSTB53 heavy chain
                                                         (SEQ ID NO: 39)
QVQLVQSGAEVKKPGASVKVSCKASGYTETHYTIHWVRQAPGQGLEWM

GYIIPSSGYSEYNQKFKDRVTMTRDTSTSTVYMELSSLRSEDTAVYYCARGAYDDYY

DYYAMDYWGQGTLVTVSS

>VSTB95 heavy chain
                                                         (SEQ ID NO: 40)
EVQLVESGGGLVQPGGSLRLSCAASGFTFRNYGMSWVRQAPGKGLEWV

ASIISGGSYTYYPDSVKGRFTISRDNAKNSLYLQMNSLRAEDTAVYYCARIYDHDGD

YYAMDYWGQGTTVTVSS

>VSTB116 heavy chain
                                                         (SEQ ID NO: 64)
QVQLVQSGAEVKKPGSSVKVSCKASGGITSSYAISWVRQAPGQGLEWM

GGIIPIEGTANYAQKFQGRVTITADESTSTAYMELSSLRSEDTAVYYCARSSYGWSYE

FDYWGQGTLVTVSS

Amino Acid Sequences of VariableLight ChainRegions of Select VISTA
mAbs
>VSTB50 light chain
                                                         (SEQ ID NO: 41)
DIVMTQTPLSLSVTPGQPASISCRASESVDTYANSLMHWYLQKPGQPPQL

LIYRASNLESGVPDRFSGSGSGTDFTLKISRVEAEDVGVYYCQQTNEDPRTFGQGTKL

EIK
```

```
>VSTB53 light chain
                                                        (SEQ ID NO: 42)
DIVMTQSPLSLPVTPGEPASISCRSSQTIVHSNGNTYLEWYLQKPGQSPQLL

IYKVSNRFSGVPDRFSGSGSGTDFTLKISRVEAEDVGVYYCFQASHVPWITGQGTKL

EIK

>VSTB95 light chain
                                                        (SEQ ID NO: 43)
DIVMTQSPLSLPVTPGEPASISCRSSQSIVHSNGNTYLEWYLQKPGQSPQLL

IYKVSNRFSGVPDRFSGSGSGTDFTLKISRVEAEDVGVYYCFQGSHVPWTFGQGTKL

EIK

>VSTB112 light chain
                                                        (SEQ ID NO: 44)
DIQMTQSPSSLSASVGDRVTITCRASQSIDTRLNWYQQKPGKAPKWYSA

SSLQSGVPSRFSGSGSGTDFTLTISSLQPEDFATYYCQQSAYNPITEGQGTKVEIK

>VSTB116 light chain
                                                        (SEQ ID NO: 45)
DIQMTQSPSSLSASVGDRVTITCRASQSINTNLNWYQQKPGKAPKLLIYAA

SSLQSGVPSRFSGSGSGTDFTLTISSLQPEDFATYYCQQARDTPITFGQGTKVEIK,
```

Example 8: ELISA and FACS Screening of Anti-Vista Antibodies

These experiments were to determine the ability of the produced antibodies to bind human or cynomolgus VISTA protein in an ELISA, as well as to determine, using FACS screening, the ability of the antibodies to bind VISTA protein on the surface of K562 cells (human myelogenous leukemia cell line) expressing human or cynomolgus VISTA proteins.

Methods:

ELISA procedure summary: Plates were coated overnight at 4° C. with 1 µg/ml SB0361 (human) or SB0361 (cyno (cynomolgus)) proteins, which are the extracellular domains of VISTA from the respective species. Antibodies were diluted to 1 µg/ml as a starting concentration with 1:4 step-wise dilutions for a total of 4 concentrations and incubated at room temperature room temperature (RT) for 2 hours. Mouse anti-human IgG 1-HRP (horseradish peroxidase) was used for detection and incubated for 1 hour at RT. All washes were performed using PBS-Tween (0.05%).

FACS procedure summary: 2×10$^5$ K562-G8 (human) or K562-C7 (cyno) cells were stained with 5 µg/ml of each test antibody and incubated for 30 minutes at 4° C. Goat anti-human IgG1-PE (phycoerythrin) antibody was used as a secondary detection antibody at 5 µg/ml. Cells were run on a BD Fortessa and analyzed using FlowJo software (Tree Star, Inc., Ashlang, OR) for MFI (mean fluorescence intensity) of the live population.

Data Analysis/Results: For each antibody, a subjective score (Yes/No) was given relating to whether the antibody bound robustly or not for both the ELISA and FACS analysis for each of the 4 assays. If an antibody gave a "No" result for binding in either assay, it was repeated to confirm that it was negative. The results are shown in Table 7 below and in FIGS. 19A-19F and 20A-20F.

TABLE 7

| INX Code | Hu ELISA | Cyno ELISA | Hu FACS | Cyno FACS |
|---|---|---|---|---|
| 1 | Y | Y | Y | Y |
| 2 | Y | Y | Y | Y |
| 3 | Y | Y | Y | Y |
| 4 | Y | Y | Y | Y |
| 5 | Y | Y | Y | Y |
| 6 | Y | Y | Y | Y |
| 7 | Y | Y | Y | Y |
| 8 | Y | Y | Y | Y |
| 9 | Y | Y | Y | Y |
| 10 | Y | Y | Y | Y |
| 11 | N | N | N | N |
| 12 | Y | Y | Y | Y |
| 14 | Y | Y | Y | Y |
| 16 | Y | Y | Y | Y |
| 17 | Y | Y | Y | Y |
| 18 | Y | Y | Y | Y |
| 19 | Y | Y | Y | Y |
| 20 | Y | Y | Y | Y |
| 21 | Y | Y | Y | Y |
| 22 | Y | Y | Y | Y |
| 23 | N | N | N | N |
| 24 | N | N | N | N |
| 25 | Y | Y | Y | Y |
| 26 | N | Y | N | Y |
| 28 | Y | Y | Y | Y |
| 30 | N | N | N | N |
| 31 | N | N | N | N |
| 32 | N | N | N | N |
| 33 | Y | Y | Y | Y |
| 34 | Y | Y | Y | Y |
| 35 | Y | Y | Y | Y |
| 36 | Y | Y | Y | Y |
| 37 | Y | Y | Y | Y |
| 38 | Y | Y | Y | Y |
| 39 | Y | Y | N | N |
| 40 | Y | Y | Y | Y |
| 41 | Y | Y | Y | Y |
| 42 | Y | Y | Y | Y |
| 43 | Y | Y | Y | Y |
| 44 | Y | Y | Y | Y |
| 45 | Y | Y | Y | Y |
| 46 | Y | Y | Y | Y |
| 47 | Y | Y | Y | Y |
| 48 | Y | Y | Y | Y |
| 49 | Y | Y | Y | Y |

Example 9: Screening Results of Anti-Human Vista Antibodies Using the Mixed Lymphocyte Reaction (MLR) and *Staphylococcus* Enterotoxin B (SEB) Activation Assays The purpose of this study was to present data supporting the identification of multiple functional α-VISTA antibodies that enhance cellular immune responses in the mixed lymphocyte reaction (MLR) assay, as well as the *staphylococcus* enterotoxin B activation (SEB) assay.

The mixed lymphocyte reaction (MLR) is a standard immunological assay that depends upon MHC class I and II mismatching to drive an allogeneic T cell response. Peripheral blood mononuclear cells are isolated from two mismatched individuals, incubated together and as a result of these mismatches, proliferation and cytokine production occurs.

Material and Methods:

10% AB Media was prepared by combining 500 ml of RPMI with 50 ml of human AB serum, 5 ml of Penicillin/Streptomycin (10,000 U/ml), 5 ml of L-glutamine (100×) and 10 ml of HEPES (1M). Media was stored for no longer than 14 days. 1 mCi tritiated thymidine was prepared by diluting 0.2 ml of thymidine stock (1 mCi/ml) in 9.8 ml of RPMI.

Soluble VISTA antibodies were diluted to 20 μg/ml in 10% AB serum media. 100 μl of the appropriate antibody solutions was added to the appropriate wells of a 96 well U-bottom plate (Falcon product #353077 or equivalent). After the various cellular populations were added, the final concentration was 10 μg/ml.

Isolation of white blood cells: Donors were at least 18 years of age, generally healthy and selected randomly from the local population. Transferred donor blood from isolation tubes to 50 ml conicals. Under-laid 15 ml of Ficoll 1077 per 25 ml of blood being careful not to mix with the blood. Centrifuged the cells at 1250 g for 25 minutes at room temperate with no brake. White blood cells were isolated at the interphase of the Ficoll and the serum and diluted the cells into 40 ml of Hanks Balances Salt Solution (HBSS). Centrifuged the cells at 453 g (1500 rpm) for 10 minutes at 4° C. Resuspended the cells in 50 ml of HBSS and counted by transferring 500 μl to a separate tube.

Mixed lymphocyte reaction (MLR) 96 well plate setup: Determined the appropriate number of "stimulator cells" and "responder cells" needed for the assay based on the number of samples to be analyzed. The stimulator population is seeded at $0.5 \times 10^5$ cells/well and the responder population is seeded at $1.0 \times 10^5$ cells/well of a 96 well U-bottom plate. All conditions must be performed in triplicate. The appropriate number of "stimulator cells" were pipetted into a new conical and centrifuged as previously described. Resuspended cells in 10 ml and irradiated with 4000 rads. Centrifuged cells as previously described and resuspended at a concentration of $1 \times 10^6$/ml in 10% AB serum media and added 50 μl to appropriate wells. Isolated the required number of responder cells and centrifuged as previously described and resuspended at a concentration of $2 \times 10^6$/ml in 10% AB serum media and added 50 μl to appropriate wells. Incubated the cells for 5 days at 37° C. and 5% $CO_2$. On the fifth day, removed 30 μl of supernatant for analysis of interferon gamma (IFN-γ) production. On the fifth day, added 25 μl of a 40 μCi/ml tritiated thymidine solution to each well and incubated for 8 hours at 37° C. and 5% $CO_2$. Transferred cells to the 96 well micro scintillation plate per manufacturer's instructions. Counted using the micro scintillation counter per manufacturer's instructions. IFN-γ concentration was determined by ELISA (eBioscience cat #88-7316-88) using manufacturer's protocol.

Data analysis: Calculated the average counts per minute (CPM) or IFN-γ concentration for the non-treated wells. Calculated the average CPM or IFN-γ for each of the test groups. $Log_{10}$ transform the data set. Using 12 MLR fold-scores for each compound, calculated the average for the set of 12 test groups of each compound Average score for 12 experiments=$\Sigma[log_{10}$ (Average CPM of triplicate for test compound))–($log_{10}$ (Average CPM of triplicate for No Treatment))]/12

Acceptance criteria: All test reagents and appropriate controls were tested for endotoxin prior to running the assay and have levels of <0.1 EU/mg. The responder cells alone had CPM counts below 700 CPM on average indicating that the cells were quiescent when incubated alone. The CPM for the MLR group was at least 2 fold higher than the CPM for responder cells incubated alone indicating that a reaction had occurred and that the donors are a mismatch. All MLR assays included a human IgG1 negative control protein. The result of the human IgG1 negative control was not statistically different from the non-treated samples based upon use of a student's t-test.

Screening of anti-VISTA antibodies in the MLR: Initial screen of all compounds. Prior to running the MLR with the anti-VISTA antibodies, antibodies were confirmed to bind both cell bound VISTA via FACS analysis and VISTA protein via ELISA. Antibodies S26 (VSTB77), S30 (VSTB86), S31 (VSTB88), S32 (VSTB90) and S39 (VSTB74) failed this initial screen but were still tested in the assay. For the purpose of initial screening, all antibodies were tested at 10 μg/ml in the MLR with proliferation and IFN-γ being the parameters measured (FIGS. 21A-21D and 22A-22B).

Selection of six lead antibodies. From the initial screen, six candidates were chosen for further analysis: VSTB112 (S2), VSTB116 (S5), VSTB95 (S16), VSTB50 (S41), VSTB53 (S43) and VSTB60 (S47).

Dilution studies of the top six candidates in the MLR: Protocol adjustments. The protocol is identical as previously described with the adjustment that antibodies were diluted to the following concentrations: 30, 10, 3, 1, 0.3, 0.1, 0.03, 0.01 and 0 μg/ml.

Determination of $IC_{50}$ values: Raw CPM counts and IFN-γ concentrations were used to determine the $IC_{50}$ for each of the antibodies. Calculations of $IC_{50}$ were determined through use of the program "EZ-R stats." Six individual responders were used to determine the $IC_{50}$ values. Individual CPM counts and IFN-γ concentrations in the MLR with dose titrations of the lead candidates.

TABLE 8

IC$_{50}$ values for both CPM and IFN-γ in the MLR

| | VSTB112 (S2) | VSTB116 (S5) | VSTB95 (S16) | VSTB50 (S41) | VSTB53 (S43) | VSTB60 (S47) |
|---|---|---|---|---|---|---|
| CPM | −0.67 | −0.78 | −0.54 | −0.12 | −0.33 | 0.02 |
| Gamma | −0.42 | −0.16 | 0.22 | 0.06 | 0.27 | 0.4 |

** Values are in log$_{10}$ of antibody concentrations.

Conclusion: The initial screen indicated that multiple VISTA specific antibodies were capable of enhancing the MLR cellular immune response. Antibodies were then ranked based upon efficacy and variance and based upon these results, VSTB112, VSTB116, VSTB95, VSTB50, VSTB53 and VSTB60 were chosen to evaluate in dose-titration experiments. VSTB60 induced a weaker response than the other five antibodies in the dose-titration experiments.

The *staphylococcus* enterotoxin B (SEB) activation assay: SEB is a bacterial super-antigen that induces activation of specific Vβ+ T cells. Peripheral blood mononuclear cells are isolated and incubated with the SEB antigen in culture, which induces robust cytokine production. This assay was conducted on the five lead candidates.

Preparation of 10% AB Media, preparation of 1 mCi tritiated thymidine, preparation of soluble VISTA antibodies, and isolation of white blood cells were all performed as previous described above in the MLR.

SEB 96 well plate setup: Determined the appropriate number of responder cells needed for the assay based on the number of samples to be analyzed. The responder population is seeded at 2.0×10$^5$ cells/well of a 96 well U-bottom plate. All conditions must were performed in triplicate. Centrifuged cells as previously described and resuspended at a concentration of 4×10$^6$/ml in 10% AB serum media and added 50 μl to the appropriate wells. Added 50 μl of 10% AB serum media containing the SEB antigen at a concentration of 40 ng/ml. In the described experiments, SEB was obtained from Sigma Aldrich (cat #S0812). The final concentration in the well was at 10 ng/ml. Incubated the cells for 3 days at 37° C. and 5% CO$_2$. On the third day, removed 30 μl of supernatant for analysis of IFN-γ production. Added 25 μl of a 1 mCi/ml tritiated thymidine solution to each well and incubated for 8 hours at 37° C. and 5% CO$_2$. Cells were transferred to the 96 well micro scintillation plate per manufacturer's instructions. Counted using the micro scintillation counter per manufacturer's instructions. IFN-γ concentration was determined by ELISA (eBioscience cat #88-7316-88) using manufacturer's protocol.

Protocol: Data analysis. Calculated the average counts per minute (CPM) or IFN-γ concentration for each of antibodies at all concentrations. Acceptance criteria were performed as previously described. Determination of IC$_{50}$ values was performed as described. Individual CPM counts and IFN-γ concentrations in the SEB assay with dose titrations of the lead candidates.

TABLE 9

IC$_{50}$ values for both CPM and IFN-γ in the SEB.

| | VSTB112 (S2) | VSTB116 (S5) | VSTB95 (S16) | VSTB50 (S41) | VSTB53 (S43) | VSTB60 (S47) |
|---|---|---|---|---|---|---|
| CPM | −1.16 | −1.44 | −1.12 | −0.74 | −1.06 | not done |
| Gamma | −1.24 | −0.35 | 0.05 | 1.69 | −1.05 | not done |

**Values are in log$_{10}$ of antibody concentrations.

Conclusions: VISTA specific antibodies enhanced cytokine production and proliferation in a dose dependent manner in the SEB assay. IC$_{50}$ values from the SEB study were generally similar to the results from the MLR dilution studies.

Example 10: Epitope Binning Assay

Methods: ProteOn XPR36 system (BioRad) was used to perform epitope binning. ProteOn GLC chips (BioRad, Cat #176-5011) were coated with two sets of 6 monoclonal antibodies (mAbs) using the manufacturer instructions for amine-coupling chemistry (BioRad, cat #176-2410).

Competing mAbs were pre-incubated in excess (250 nM final concentration) with human VISTA (25 nM final concentration) for 4 hours at room temperature and 6 at a time were run over the chip coated with the panels of coated mAbs with an association time of 4 minutes followed by dissociation for 5 minutes. Following each run, the chips were regenerated with 100 mM phosphoric acid.

The data analysis involved grouping all sensorgrams by ligand and applying an alignment wizard, which automatically performs an X and Y axis alignment, and artifact removal. An Interspot correction was then applied to the data.

A non-competing mAb was defined as having a binding signal the same or >A1 signal (binding to human VISTA only).

A competing mAb was defined as having binding signal <<A1 signal (i.e., binding to human VISTA only).

Figure 23:
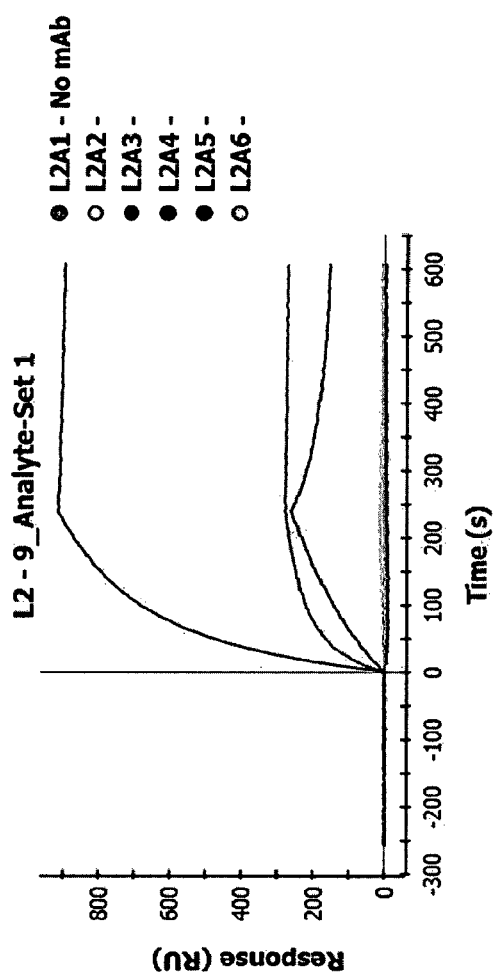
FIG. 23: Sensorgram plot using anti-VISTA antibody VSTB85 coated on a Proteon SPR chip and VISTA protein with the indicated competitors run over the chip (competitors listed in Table 16).

Results: In the example sensorgram shown in FIG. 23, the VSTB85 antibody was coated on the Protean SPR chip and VISTA protein preincubated with the indicated competitors was run over the chip. VSTB50 is an example of a non-competitive antibody, as a positive response was seen when the VISTANSTB50 complex was run. GG8, VSTB49 and VSTB51 complexed with VISTA did not bind to the VSTB85 coated on the chip and were therefore classified as competing for the same binding site on VISTA as VSTB85.

TABLE 10

| Samples | Group | Sample Set #1: coupled to sensor | | | | | | Sample Set #2: coupled to sensor | | | | | |
|---|---|---|---|---|---|---|---|---|---|---|---|---|---|
| | | L1 GG8 | L2 B85 | L3 B95 | L4 B104 | L5 B112 | L6 B113 | L1 B50 | L2 B53 | L3 B66 | L4 B67 | L5 IE8 | L6 B116 |
| GG8 | 1 | Y | Y | Y | Y | Y | Y | N | Y | N | Y | Y | Y |
| VSTB100.001 | 1 | Y | Y | Y | Y | Y | Y | N | Y | N | Y | Y | Y |
| VSTB101.001 | 1 | Y | Y | Y | Y | Y | Y | N | Y | N | Y | Y | Y |
| VSTB102.001 | 1 | Y | Y | Y | Y | Y | Y | N | Y | N | Y | Y | Y |
| VSTB103.001 | 1 | Y | Y | Y | Y | Y | Y | N | Y | N | Y | Y | Y |
| VSTB104.001 | 1 | Y | Y | Y | Y | Y | Y | N | Y | N | Y | Y | Y |
| VSTB105.001 | 1 | Y | Y | Y | Y | Y | Y | N | Y | N | Y | Y | Y |
| VSTB106.001 | 1 | Y | Y | Y | Y | Y | Y | N | Y | N | Y | Y | Y |
| VSTB107.001 | 1 | Y | Y | Y | Y | Y | Y | N | Y | N | Y | Y | Y |
| VSTB108.001 | 1 | Y | Y | Y | Y | Y | Y | N | Y | N | Y | Y | Y |
| VSTB109.001 | 1 | Y | Y | Y | Y | Y | Y | N | Y | N | Y | Y | Y |
| VSTB110.001 | 1 | Y | Y | Y | Y | Y | Y | N | Y | N | Y | Y | Y |
| VSTB111.001 | 1 | Y | Y | Y | Y | Y | Y | N | Y | N | Y | Y | Y |
| VSTB112.001 | 1 | Y | Y | Y | Y | Y | Y | N | Y | N | Y | Y | Y |
| VSTB113.001 | 1 | Y | Y | Y | Y | Y | Y | N | Y | N | Y | Y | Y |
| VSTB114.001 | 1 | Y | Y | Y | Y | Y | Y | N | Y | N | Y | Y | Y |
| VSTB115.001 | 1 | Y | Y | Y | Y | Y | Y | N | Y | N | Y | Y | Y |
| VSTB116.001 | 1 | Y | Y | Y | Y | Y | Y | N | Y | N | Y | Y | Y |
| VSTB49.001 | 1 | Y | Y | Y | Y | Y | Y | N | Y | N | Y | Y | Y |
| VSTB51.001 | 1 | Y | Y | Y | Y | Y | Y | N | Y | N | Y | Y | Y |
| VSTB53.001 | 1 | Y | Y | Y | Y | Y | Y | N | Y | N | Y | Y | Y |
| VSTB59.001 | 1 | Y | Y | Y | Y | Y | Y | N | Y | N | Y | Y | Y |
| VSTB65.001 | 1 | Y | Y | Y | Y | Y | Y | N | Y | N | Y | Y | Y |
| VSTB67.001 | 1 | Y | Y | Y | Y | Y | Y | N | Y | N | Y | Y | Y |
| VSTB70.001 | 1 | Y | Y | Y | Y | Y | Y | N | Y | N | Y | Y | Y |
| VSTB81.001 | 1 | Y | Y | Y | Y | Y | Y | N | Y | N | Y | Y | Y |
| VSTB92.001 | 1 | Y | Y | Y | Y | Y | Y | N | Y | N | Y | Y | Y |
| VSTB95.001 | 1 | Y | Y | Y | Y | Y | Y | N | Y | N | Y | Y | Y |
| VSTB97.001 | 1 | Y | Y | Y | Y | Y | Y | N | Y | N | Y | Y | Y |
| VSTB98.001 | 1 | Y | Y | Y | Y | Y | Y | N | Y | N | Y | Y | Y |
| VSTB99.001 | 1 | Y | Y | Y | Y | Y | Y | N | Y | N | Y | Y | Y |
| VSTB50.001 | 2 | N | N | N | N | N | N | Y | N | Y | N | N | N |
| VSTB54.001 | 2 | N | N | N | N | N | N | Y | N | Y | N | N | N |
| VSTB56.001 | 2 | N | N | N | N | N | N | Y | N | Y | N | N | N |
| VSTB60.001 | 2 | N | N | N | N | N | N | Y | N | Y | N | N | N |
| VSTB63.001 | 2 | N | N | N | N | N | N | Y | N | Y | N | N | N |
| VSTB66.001 | 2 | N | N | N | N | N | N | Y | N | Y | N | N | N |
| VSTB73.001 | 2 | N | N | N | N | N | N | Y | N | Y | N | N | N |
| VSTB76.001 | 2 | N | N | N | N | N | N | Y | N | Y | N | N | N |
| VSTB78.001 | 2 | N | N | N | N | N | N | Y | N | Y | N | N | N |
| VSTB84.001 | 2 | N | N | N | N | N | N | Y | N | Y | N | N | N |
| VSTB85.001 | 3 | Y | Y | Y | Y | Y | Y | N | Y | N | Y | I | Y |
| VSTB74.001 | 4 | N | N | N | N | N | N | N | N | N | N | N | N |
| IE8 | 5 | Y | I | Y | Y | Y | Y | N | Y | N | Y | Y | Y | mAb immobilized on sensor
Y = Yes competed (signal << than A1- human VISTA only)
N = No competed (signal > than A1- human VISTA only)
I = Inconclusive (signal similar to A1-human VISTA only)

Example 11: Proteon Affinity Determination

Antibodies were captured on ProteOn chips using anti-IgG Fc coated surfaces. The antibodies were tested for binding of human and cynomolgus (cyno) VISTA extracellular domains (ECDs) at concentrations of VISTA proteins ranging from 0.39 nM to 100 nM. The antigens were allowed to bind/associate to the antibody-coated chips for 4 minutes after which time dissociation was monitored for 30 minutes. Chips were regenerated with two treatments of 100 mM phosphoric acid for 18 seconds. All experiments were run at 25° C. and data was fit to 1:1 Langmuir binding model.

Example 12: Effects of Anti-Vista Treatment in a Mb49 Murine Bladder Tumor Model Methods:
C57Bl/6 mice were injected with MB49 tumor cells. Once the tumors were established, anti-VISTA treatment was initiated. Tumor growth was then monitored 3 times/week. Mice were euthanized, in accordance with IACUC regulations, once the tumors reached 15 mm in any dimension.

For each experiment, a frozen vial of MB49 cells was thawed and grown in RPMI 1640 (+L-Glut) with 10% serum and penicillin/streptomycin antibiotics. After three days in culture, the cells were harvested using StemPro Accutase and resuspended in RPMI at a concentration of $5\times10^6$ cells/ml and 50 µl injected per mouse.

Female C57Bl/6 mice, aged 6-8 weeks were purchased from the National Cancer Institute. Upon arrival they were allowed to acclimatize for one day prior to having their right flanks shaved and their tails tattooed. They were then injected three-five days later.

Tumor Injection (Intradermal): Mice were injected intradermally (i.d.) on their shaved flank with 50 µl of MB49 cell suspension (~250,000 cells).

Monitoring Tumor Growth: Tumor growth was measured using electronic calipers first across the widest dimension (L) and secondly at a 90° angle to the first measurement (W). Tumor volume derived as follows:

$$\text{Volume} = (L^2 \cdot W^2)/2$$

Tumors were considered established once they reached ~5 mm in diameter (~60 mm³ volume). Once established, treatment was initiated. Tumor growth was measured three times per week over the course of treatment and until the experiment was terminated.

Anti-VISTA Treatment: Chimerized 13F3-mIgG2a monoclonal antibody was injected intraperitoneally at 10 mg/kg. Injection schedules were thrice weekly for four weeks.

Euthanizing Mice: As per IACUC requirements, animals were euthanized once their tumors reached 15 mm in the longest dimension.

Analyzing Efficacy: Mouse tumor volumes were analyzed using Excel for data management, and GraphPad Prism for graphing. Statistical analysis was performed using a macro for R statistical computing software.

Figure 24:
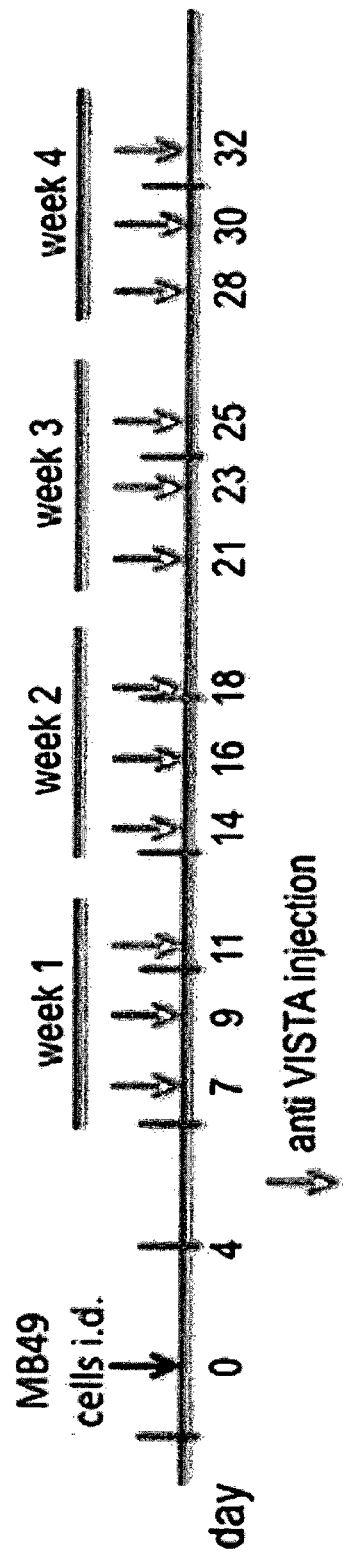
FIG. 24: Experimental design for MB49 murine bladder tumor model

The experimental design is shown in FIG. 24.

Figures 25A, 25B:
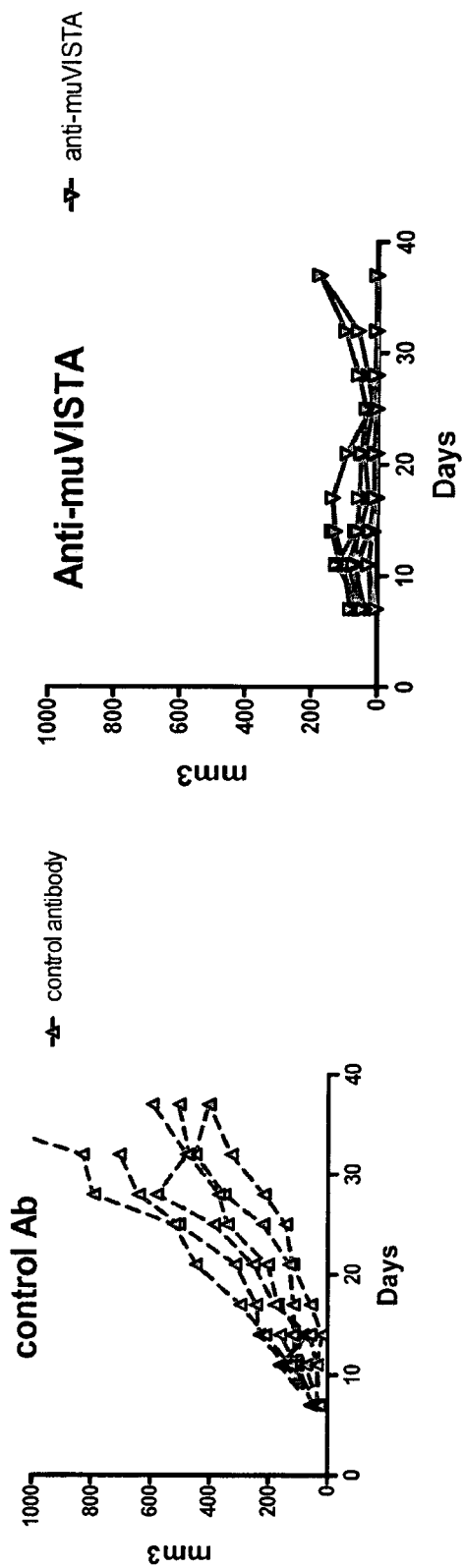
FIGS. 25A-25B: MB49 tumor growth in female C57Bl/6 mice. Graphs illustrate tumor growth in individual mice treated with anti-mouse VISTA antibody (FIG. 25B) or control IgG (FIG. 25A).

Results:

Ch13F3-mIgG2a treatment in female mice led to complete tumor rejection (CR) in 70% of the animals and partial remission (PR) in 30% (n=7) (Table 13 and FIG. 25B). In contrast, all of the control mIgG2a-treated mice showed progressive growth of the tumors (6/6) (FIG. 25A). These data demonstrate that anti-VISTA treatment can have a profound effect on tumor growth.

TABLE 11

Complete remission (CR) versus partial remission (PR)

| | Female 13F3 IgG2a (n = 7) |
|---|---|
| CR | 5 |
| PR | 2 till day 32 |

Figure 27:
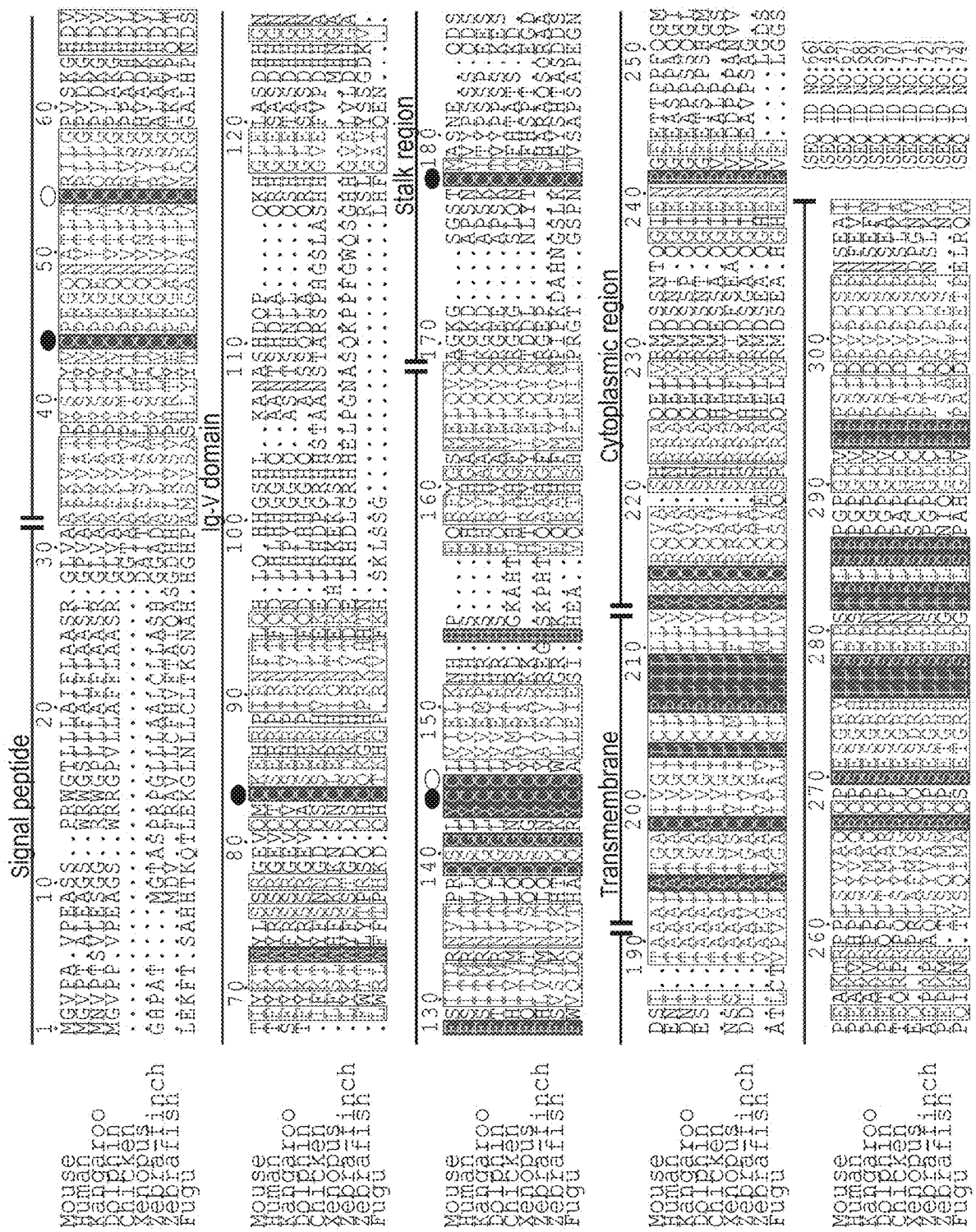
FIG. 27: Multiple sequence alignment of VISTA orthologues

The human VISTA sequence is shown in FIGS. 26 and 27, adapted from Wang et al., 2011, supra, the contents of which are incorporated herein in their entirety.

Example 13: Epitope Mapping of Anti-Vista Antibodies Using Hydrogen/Deuterium (H/D) Exchange Studies To identify the epitopes for VSTB50, 60, 95 and 112 on human VISTA, solution hydrogen/deuterium exchange-mass spectrometry (HDX-MS) was performed using the corresponding Fabs. For H/D exchange, the procedures used to analyze the Fab perturbation were similar to that described previously (Hamuro et al., J. Biomol. Techniques 14:171-182, 2003; Horn et al., Biochemistry 45:8488-8498, 2006) with some modifications. Fabs were prepared from the IgGs with papain digestion and Protein A capture using Pierce Fab Preparation Kit (Thermo Scientific, Cat #44985). The human VISTA protein sequence contains six N-linked glycosylation sites. To improve the sequence coverage, the protein was deglycosylated with PNGase F. The deglycosylated VISTA protein was incubated in a deuterated water solution for predetermined times resulting in deuterium incorporation at exchangeable hydrogen atoms. The deuterated VISTA protein was in complex with either Fab of VSTB50, VSTB60, VSTB95 or VSTB112 in 46 µL deuterium oxide ($D_2O$) at 4° C. for 30 sec, 2 min, 10 min and 60 min. The exchange reaction was quenched by low pH and the proteins were digested with pepsin. The deuterium levels at the identified peptides were monitored from the mass shift on LC-MS. As a reference control, VISTA protein was processed similarly except that it was not in complex with the Fab molecules. Regions bound to the Fab were inferred to be those sites relatively protected from exchange and, thus, containing a higher fraction of deuterium than the reference VISTA protein. About 94% of the protein could be mapped to specific peptides.

The solution HDX-MS perturbation maps of VISTA with VSTB50/VSTB60, and VSTB95/VSTB112 are shown in FIG. 28 top and bottom, respectively. Two epitope groups were identified. Anti-VISTA VSTB50 recognizes the same epitope as VSTB60 does; VSTB95 binds to another epitope region as VSTB112 does on VISTA. Anti-VISTA VSTB50 and 60 share the same epitope which comprises segments, $_{103}$NLTLLDSGL (SEQ ID NO:62), and $_{136}$VQTGKDAPSNC$_{146}$ (SEQ ID NO:63) (FIG. 28 top). Anti-VISTA VSTB95 and 112 appear to target similar epitopes, comprising segments $_{27}$PVDKGHDVTF$_{36}$ (SEQ ID NO:74), and $_{54}$RRPIRNLTFQDL$_{65}$ (SEQ ID NO:65) (FIG. 28 bottom). There are two other segments showing weak perturbation by VSTB95 and 112, including residues 39-52 and 118-134. However, the levels of the reduction are not as strong as the previous regions (27-36 and 54-65) in the differential map. Although one peptide, $_{100}$TMR$_{102}$ showing strong perturbation by VSTB95 and 112, is located on the other face of VISTA surface, it is distant from the epitope regions, 27-36 and 54-65. This perturbation could be due to allosteric effect. These HDX-MS results provide the peptide level epitopes for anti-VISTA antibodies. There were no overlapping epitope regions for these two epitope groups. These results are in agreement with the previous competition binning data in that they do not compete with each other.

Example 14: Structure Determination of the Human Vista ECD:VSTB112 Fab Complex by Protein Crystallography In an effort to determine the VISTA structure and to delineate the epitope and paratope defining the interaction between VISTA extracellular domain (ECD) and the Fab fragment of lead antibody VSTB112, the complex was crystallized and structure determined to 1.85 Å resolution. The structure of the ECD of human VISTA in complex with the Fab fragment of the antibody VSTB112 was determined in an effort both to determine the structure of VISTA ECD itself and to define the epitope/paratope for this interaction. The structure reveals VISTA to adopt an IgV fold with a chain topology similar to the TCR Vα chain. In addition to the canonical disulfide bond bridging B and F strands in the back and front faces of the β-sandwich, the structure reveals the ECD to have two additional disulfide bonds, one tethering the CC' loop to the front sheet and a second between the A' and G' strands. Although crystal contacts between VISTA molecules are present, they are minor and there is no evidence for a dimer of VISTA ECDs based on this structure. The VSTB112 epitope is shown to comprise the portions of the VISTA BC, CC', and FG loops together with residues of the front beta sheet (C'CFG) nearest those loops. The paratope is biased largely toward heavy chain interactions with CDR L3 making minimal contact.

Epitope/Paratope Defining VISTA:VSTB112 Interaction

Figure 29:
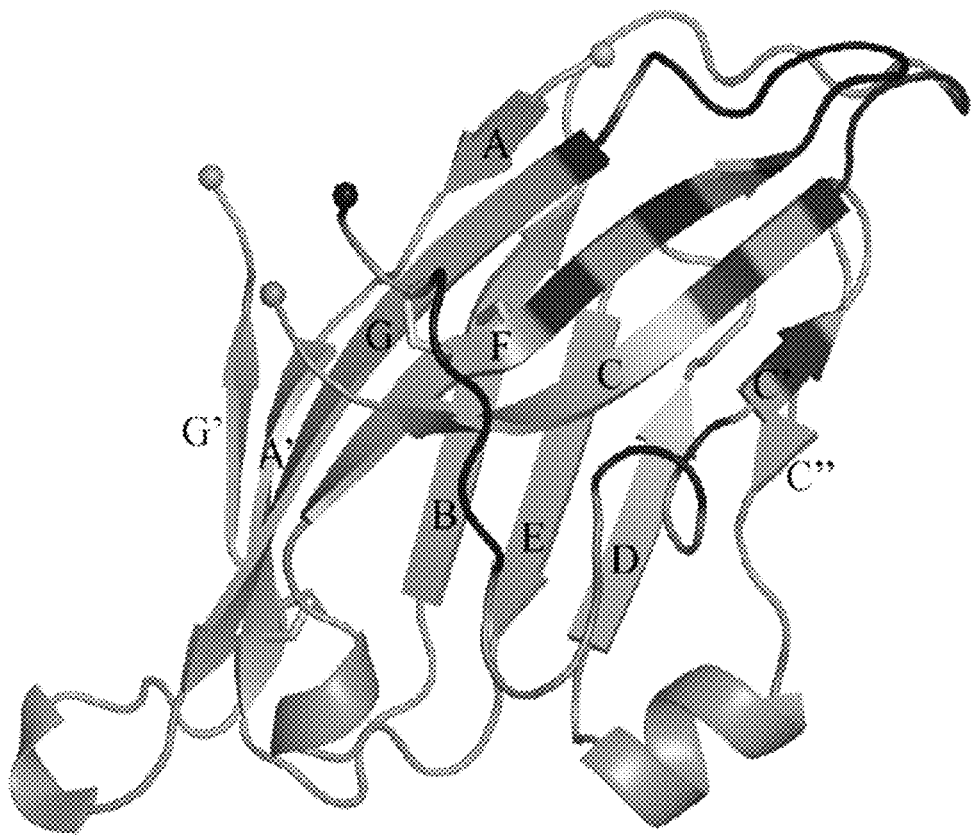
FIG. 29: VISTA Epitope bound by VSTB112. (Top) VISTA is shown in cartoon with strands labeled. Residues having at least one atom within 5 Å of VSTB112 in the complex are colored blue. Blue and orange spheres highlight a chain break, and the cyan and green spheres mark the N- and C-termini of the VISTA structure, respectively. (Bottom) Sequence of VISTA construct used in structure determination. Circles below the sequence are used to indicate residues which make only main chain contacts with VSTB112, triangles indicate a side chain contact, and squares indicate the side chain contact results in either a hydrogen bond or salt bridge interaction as calculated by PISA. Shapes are colored to indicate the CDR having the greatest number of atoms contacted by the given residue with CDR colors defined in FIG. 59. Secondary structural elements are as defined in the program MOE with yellow arrows representing β-strands and red rectangles indicating α-helices.
Figure 30:
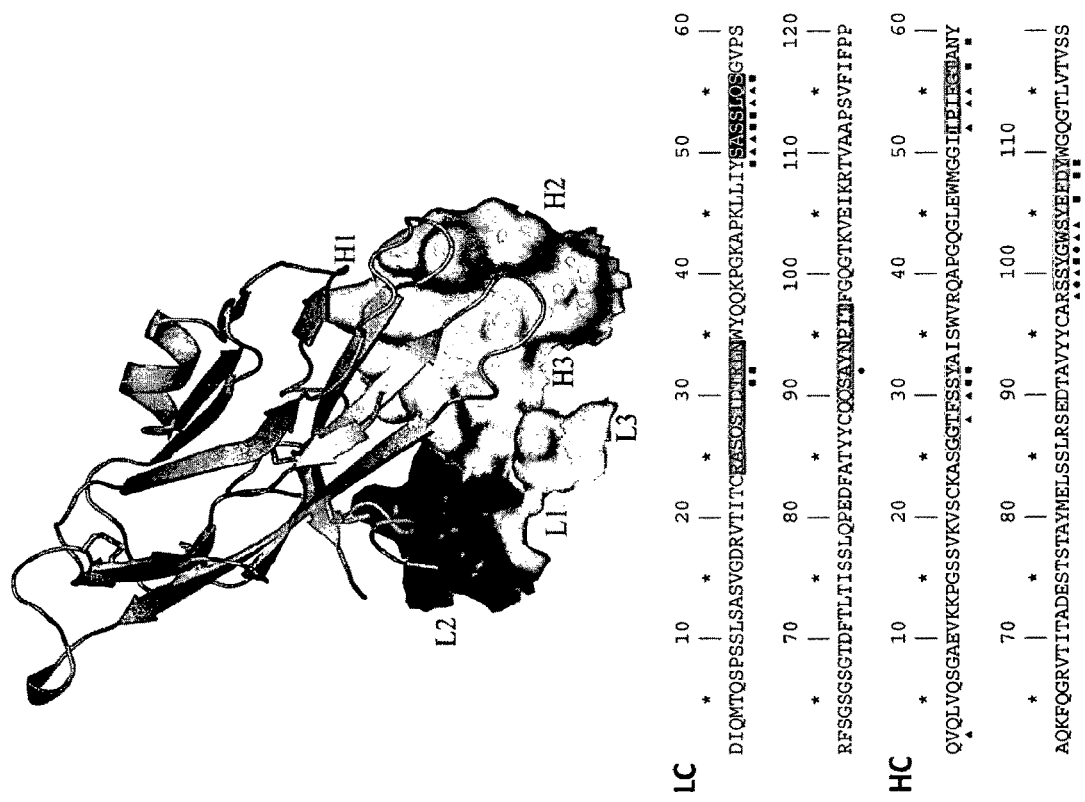
FIG. 30: VSTB112 Paratope. (Top) VISTA antigen is shown in illustration and VSTB112 within 5 angstrom (A) of VISTA is shown in surface with colors used to designate CDR identity as specified in the sequence below. Contacting framework residues adjacent to a CDR are colored similarly to the corresponding CDR (Bottom) Sequence of VSTB112 Fv region. Colored backgrounds specify CDRs according to Kabat definitions. Circles below the sequence are used to indicate residues which make main chain only contacts with VISTA, triangles indicate a side-chain contact, and squares indicate the side chain contact results in either a hydrogen bond or salt bridge interaction as calculated by PISA.

VSTB112 Fab buries a surface area of 1024.3 A2 upon binding VISTA ECD, with burial of the heavy chain surface accounting for 715.3 A2 of this total. Seven hydrogen bonds and 4 salt bridge interactions are formed between VISTA and VSTB112 light chain and 10 hydrogens and 2 salt bridge interactions between VISTA and VSTB112 heavy chain. VSTB112 recognizes residues in the front sheet strands C', C, F, and G on the ends proximal to the FG loop as well as residues in the BC, FG, and CC' loops (FIGS. 29 and 30). Interactions with the CC' loop account for most of the contacts with the Fab light chain with only residues E125 and R127 in the FG loop making additional light chain interactions. Residues 119 to 127 corresponding to the VISTA FG loop account for 38% of the total 1034.8 Å2 of surface area buried upon binding VSTB112. Notably, this loop is highly polar, comprised of the following sequence -IRHHHSEHR- (SEQ ID NO:75). Additionally, W103 in the VSTB112 CDR H3 packs nicely against the backbone of VISTA residues H122 and H123, and VISTA H121 makes an edge on interaction with the aromatic ring of F55 in CDR H2.

Figure 31:
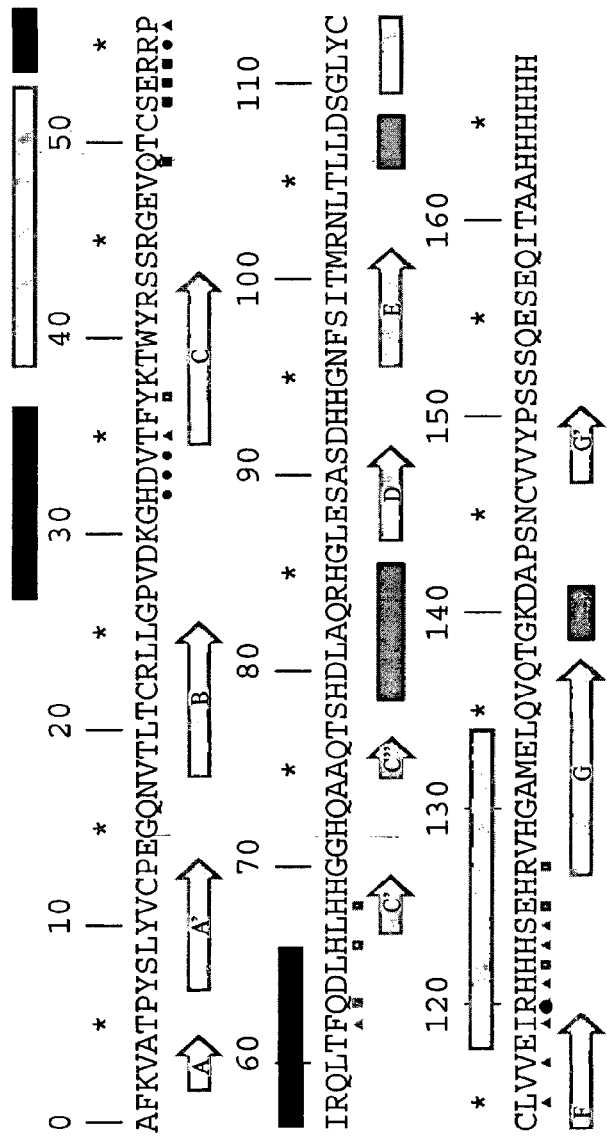
FIG. 31: Comparison of epitope regions identified by crystallography and hydrogen deuterium exchange (HDX). Sequence of VISTA construct used in structure determination. Circles below the sequence are used to indicate residues which make only main chain contacts with VSTB112, triangles indicate a side chain contact, and squares indicate the side chain contact results in either a hydrogen bond or salt bridge interaction as calculated by PISA.

A comparison of epitope regions identified by crystallography and HDX is shown in FIG. 31.

Example 15: Activation of T Cells and Monocytes by Anti-Vista Antibodies

The functional effect of anti-VISTA antibodies was evaluated in two in vitro assays, mixed leukocyte reaction (MLR) and SEB (*Staphylococcus* enterotoxin B). Both assays measure T cell proliferation and cytokine induction as their primary readouts, but these effects are due to different mechanisms. In the MLR, peripheral blood mononuclear cells (PBMCs) from two different human donors are incubated together, and major histocompatibility complex (MHC) mismatch between T.cells of one donor and dendritic cells of the other donor results in T cell proliferation and interferon (IFNγ) production. In the SEB assay, PBMCs from a single donor are incubated with a bacterial superantigen, which directly links MHC Class II protein on the surface of antigen-presenting cells (APC) to the T-cell receptor (TCR) on T cells, causing T cell activation, proliferation, and cytokine secretion. In both assays, VSTB112, which is the parent molecule of VSTB174, demonstrated dose-dependent induction of T cell proliferation and cytokine production, and was most potent among the candidates (FIGS. 21A-21D, Table 12).

TABLE 12

EC50 values for the MLR assay readouts.
VSTB112 (parent of VSTB174) was the most potent molecule.

| Candidate | $EC_{50}$ proliferation (µg/ml) | $EC_{50}$ IFNγ production (µg/ml) |
|---|---|---|
| VSTB112 | 0.21 | 0.38 |
| VSTB116 | 0.17 | 0.69 |
| VSTB95 | 0.29 | 1.67 |
| VSTB50 | 0.77 | 1.14 |
| VSTB53 | 0.47 | 1.88 |
| VSTB60 | 1.04 | 2.48 |

Monocyte Activation Assays

The assay data, shown in Table 12, was generated with VSTB112, the parent molecule of VSTB174. To better understand the activity of VSTB174, monocyte activation assays were conducted. The results showed that incubation of VSTB174 with whole PBMCs induced upregulation of activation markers (CD80 and HLA-DR) on CD14+ monocytes, indicating an effect of antibody binding to an immune cell subset known to express high levels of VISTA (FIG. 32). A further question is whether the effects on monocyte activation in whole PBMC could be facilitated by any antibody that binds VISTA and has an IgG1 Fc. Antibodies VSTB103 and VSTB63 bind to VISTA with high affinity (KD 6.36E-10 and 8.30E-10 respectively) and to cells expressing VISTA protein, similar to VSTB112 and VSTB111. VSTB103 is in the same epitope bin as VSTB112, while VSTB63 is in a different epitope bin; neither antibody facilitated monocyte activation. Taken together, these results show that one mechanism by which VSTB174 may exert its effect on T cell activation/proliferation is via monocyte activation facilitated by NK cells.

Preparation of Media 500 ml of RPMI 1640 (Corning, 10-040-CV) was combined with 50 ml of human AB serum (Valley Biomedical, Inc, Lot #3C0405), 5 ml of Penicillin/Streptomycin (Lonza, 17-602E) 10,000 U/ml, 5 ml of L-glutamine (100×) (Gibco, 25030-081) and 10 ml of HEPES (1M) (Fisher BP299-100, Lot #-1). Media was stored for no longer than 14 days at 4° C.

Preparation of Soluble VISTA and Control Antibodies

Antibodies were diluted to 2× desired concentration in 10% AB serum media: VSTB174: lot VSTB174.003

Added 100 µl of the appropriate antibody solutions to the appropriate wells of a 96 well U-bottom plate (Falcon, 353077). After the various cellular populations were added in 100 µl, the final concentration of each antibody was 1, 0.1 or 0.01 g/ml. IgG1 control antibody CNTO 3930 (Lot 6405, ENDO <0.1 EU/mg) was added at a final concentration of 1 µg/ml.

The PBMCs were isolated

Donors were at least 18 years of age, generally healthy and selected randomly from the local population.

Donor blood was transferred from isolation tube to 50 ml conicals.

15 mls of Ficoll 1077 (SIGMA, 10771) were under-laid being careful not to mix with the blood. This was per 25 mls of blood.

The cells were centrifuged at 1250 g for 25 minutes at room temperature with no brake.

The white blood cells were isolated at the interphase of the Ficoll and the serum and the cells were diluted into 40 ml of Hanks Balanced Salt Solution (HBSS).

The cells were centrifuged at 453 g (1500 rpm) for 10 minutes at 4 C.

The cells were resuspended in 50 mls of HBSS and were counted by transferring 500 l to a separate eppendorf tube.

Additionally, a Pan Monocyte isolation kit from Miltenyi was used per manufacturer's instructions (cat #130-096-537) to isolate CD14+ cells by negative selection in several treatment groups.

In Vitro Culture Setup

The appropriate number of cells needed was determined for the assay based on the number of samples to be analyzed. The responder population was seeded at $2.0 \times 10^5$ cells/well of a 96-well U-bottom plate. For the CD14 negatively selected population, $0.5 \times 10^5$ cells were seeded. All conditions were performed in triplicate.

The cells were centrifuged as described above and resuspended at a concentration of $2\times10^6$/ml for the whole PBMC population and $0.5\times10^6$/ml for the CD14 negatively selected population in 10% AB serum media and added 100 l of test antibody to appropriate wells bringing the total volume in each well to 200 l.

The cells were incubated for 1, 2, or 3 days at 37° C. and 5% $CO_2$.

Antibody Staining and Flow Cytometry

The 96 well U-bottom plate was centrifuged for 5 minutes at 453 g and removed the supernatant.

Cells were washed with 200 µl PBS and centrifuged as in step 5.5.1.

The supernatant was discarded and resuspended in 50 µl of PBS containing the following antibodies:
CD14-APC (clone HCD14) 1:250 (Biolegend cat #325608)
HLA-DR-PE Cy7 (clone L243) 1:250 (Biolegend cat #307616)
CD80-PE (clone 2D10) 1:250 (Biolegend cat #305208)
Hu FcR binding inhibitor (eBioscience cat #14-9161-73)
Was incubated for 20 minutes on wet ice in the dark.

150 µl of PBS was added and centrifuged as in step 5.5.1.

150 l of PBS buffer was added and analyzed via FACS.

Samples were run on a Miltenyi MACSQuant 10-parameter flow cytometer and analyzed using FlowJo 9.7.5 for expression of HLA-DR and CD80 on the CD14+ population. Geometric mean fluorescence intensity (MFI), a statistic that defines the central tendency of a set of numbers, was used as the defining statistic to compare treatments.

Statistical Analysis

All statistics were carried out in Prism GraphPad, version 6. Pair-wise comparisons amongst the groups were made at each of the time-points using One-Way ANOVA with Tukey correction for multiplicity. P-values less than 0.05 for all tests and comparisons were deemed significant. For all graphs and tables, * p<0.05,  p<0.01, * p<0.001, ****p<0.0001.

Example 16: ADCC and ADCP Activities of Anti-Vista Antibodies

Figure 33:
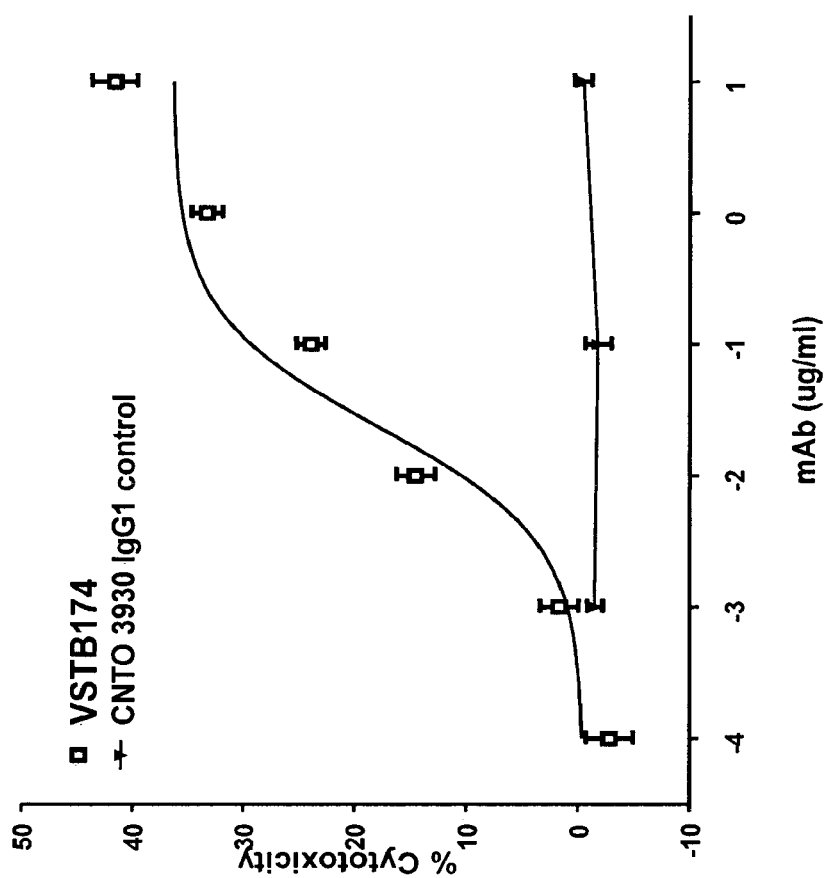
FIG. 33: Graph showing ADCC activity of VSTB174 directed against K562-VISTA cells.
Figure 34:
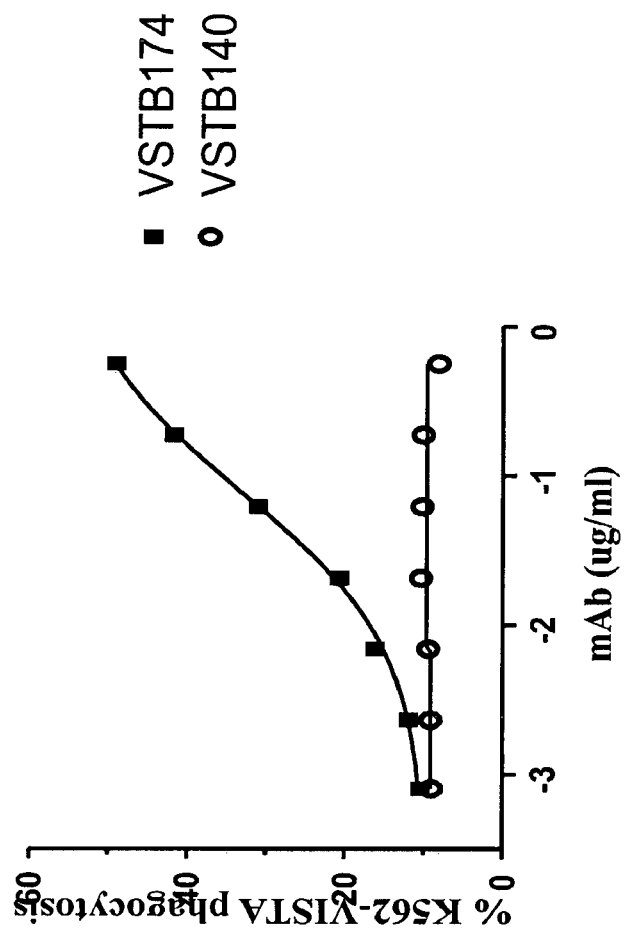
FIG. 34: Graph showing ADCP activity of VSTB174 directed against K562-VISTA cells. Both antibodies depicted have the same Fab, but VSTB174 has an IgG1 Fc and VSTB140 has Fc silent IgG2.

VSTB174 has an IgG1 Fc, which can confer antibody-dependent cell-mediated cytotoxicity (ADCC) and antibody-dependent cell-mediated phagocytosis (ADCP) activity. Both types of assays were conducted and showed that VSTB174 could lyse or phagocytose K562-VISTA cells (FIGS. 33-34), but not K562 myeloma cell line parental cells (data not shown). An additional mechanism of action of VSTB174 to modulate the inhibitory action of VISTA may be the lysis or engulfment of cells expressing high levels of VISTA, thus removing them from the local microenvironment.

Example 17: ADCP Activities of Additional Anti-Vista Antibodies

An in vitro phagocytosis assay was used to study the enhancement of macrophage-mediated phagocytosis of cells ectopically expressing VISTA by anti-human VISTA mAbs (VSTB173 and VSTB174). These mAbs were cloned into different Fc backbones (IgG1 WT (wild type), IgG1 PR (protease resistant), and IgG2σ) and were postulated to potentially have different activities with respect to enhancing phagocytosis. The IgG1 and IgG1 PR backbones are capable of binding to Fc receptors and have the potential to cause ADCP, while the IgG2σ does not bind to Fc receptors and should not mediate ADCP.

Figure 35:
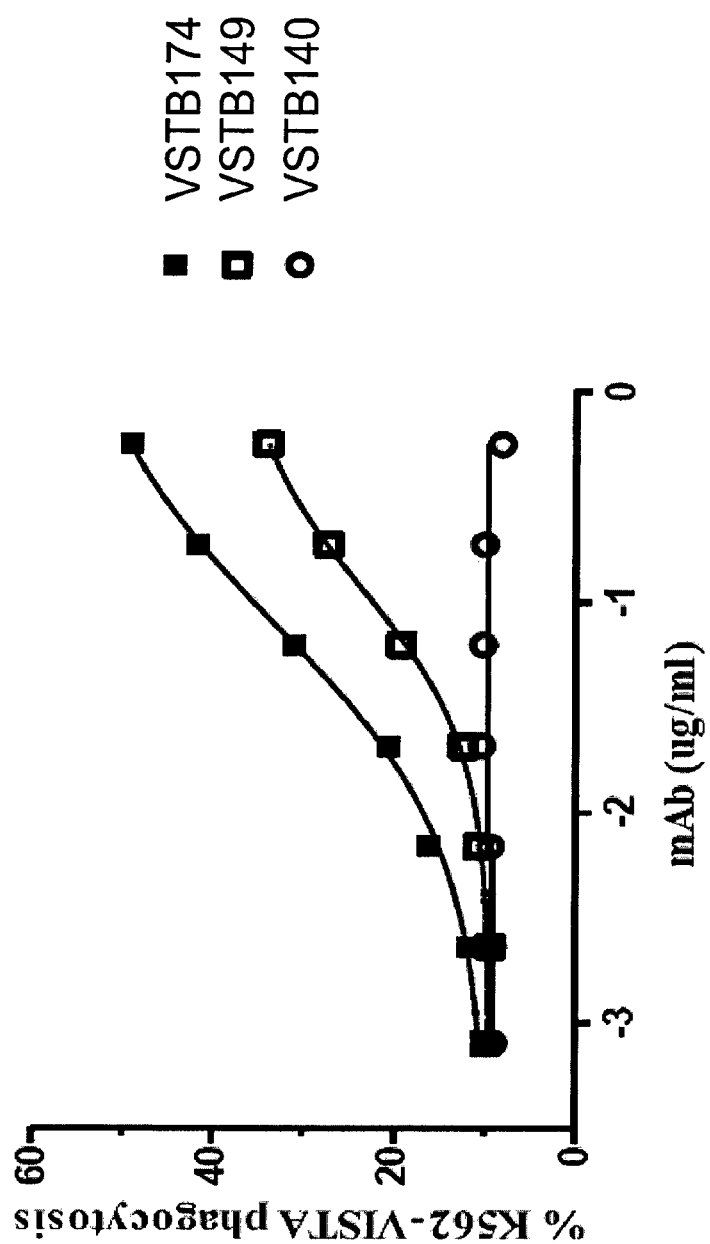
FIG. 35: Graph showing phagocytosis mediated by VSTB174, VSTB149 or VSTB140 mAbs against K562-VISTA. Each mAb was tested with 7 half log doses, ranging from 0.0008 μg/ml to 0.56 ug/ml.
Figure 36:
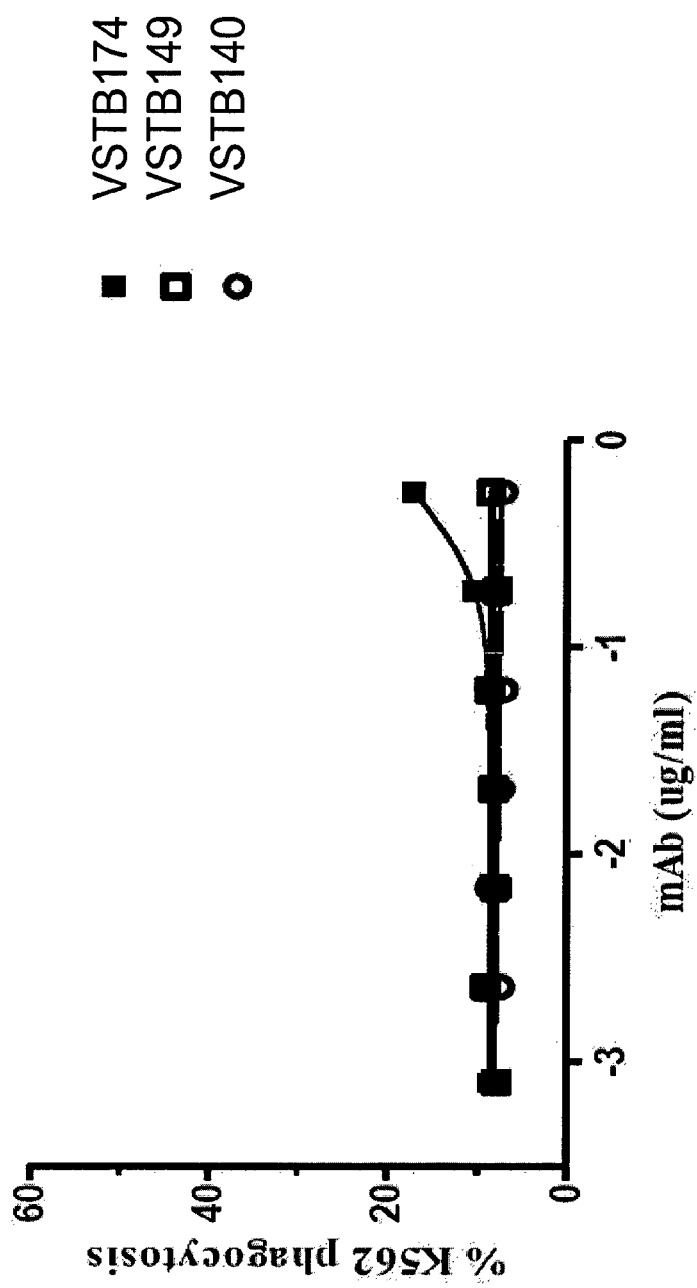
FIG. 36: Graph showing phagocytosis mediated by VSTB174, VSTB149 or VSTB140 mAbs against myeloma cell line K562 cells. Each mAb was tested with 7 half log doses, ranging from 0.0008n/ml to 0.56 ug/ml.

Anti-VISTA antibodies were tested in ADCP assays with K562 parental and K562-VISTA target cells. As shown in FIGS. 35-36, VSTB174, VSTB149, VSTB173 and VSTB145 enhanced hMac phagocytosis of K562-VISTA cells. VISTA antibodies VSTB140 or VSTB132, with the IgG2σ Fc that did not bind Fc receptors, did not enhance phagocytosis as expected. VISTA mAbs VSTB174 and VSTB173 with IgG1 Fc showed more robust phagocytosis than VSTB149 and VSTB145 with the IgG1PR Fc (see Tables 13 and 14 for $EC_{50}$ values).

TABLE 13

Anti-human VISTA mAb $EC_{50}$ values.

| Treatment | VSTB174 | VSTB149 | VSTB140 |
|---|---|---|---|
| $ECs_{50}$ | 0.0782 | 0.1142 | NA |

TABLE 14

Anti-human VISTA mAb $EC_{50}$ values.

| Treatment | VSTB173 | VSTB145 | VSTB132 |
|---|---|---|---|
| $EC_{50}$ | 0.0146 | 0.1075 | NA |

VSTB174 and VSTB173 showed weak enhancement of phagocytosis of K562 parental cells at the highest concentration (FIGS. 35-36), which may be due to low expression of VISTA by the K562 cells. The other anti-VISTA antibodies did not enhance phagocytosis of the K562 cells.

The negative control antibodies were each tested at two different concentrations in the K562-VISTA phagocytosis assay, but did not induce any phagocytosis. This result indicates that the phagocytosis mediated by the anti-VISTA antibodies is specific and due to VISTA antigen expression by the K562-VISTA cells.

Example 18: ADCC Activities of Additional Anti-Vista Antibodies

In order to test their ability to induce ADCC, the following three human anti-VISTA antibodies were tested:
VSTB174 (IgG1)
VSTB149 (IgG1 PR)
VSTB174.LF (IgG1 LF (low fucose)).

Each antibody was tested at six different concentrations within the same plate, in triplicate over two separate experiments for a total of six data points.

VSTB174, VSTB149, and VSTB174.LF each demonstrated measurable ADCC activity at 10, 1, 0.1 and 0.01 µg/mL, while only the LF antibody demonstrated measurable ADCC activity at 0.001 µg/mL; none of the antibodies demonstrated ADCC at 0.0001 µg/mL. As each of these antibodies has an IgG1 or IgG1 variant Fc, this result is expected. The LF antibody demonstrated increased ADCC potency as evidenced by the smaller $EC_{50}$ value for the LF antibody curve (0.002293 µg/mL) as compared to the regular IgG1 antibody curve (0.02381 µg/mL). The IgG1 PR antibody curve had an $EC_{50}$ value similar to the regular IgG1 curve (0.01846 µg/mL).

TABLE 15

EC$_{50}$ values (μg/mL) of three tested anti-VISTA antibodies as determined by ADCC analysis.

| anti-VISTA Antibody | EC$_{50}$ (μg/mL) |
| --- | --- |
| VSTB174 (IgG1) | 0.02381 |
| VSTB149 (IgG1 PR) | 0.01846 |
| VSTB174.LF (IgG1 LF) | 0.002293 |

The human IgG1, human IgG1 PR and human IgG1 LF antibodies all showed measurable ADCC mediated killing at the 10, 1, 0.1 and 0.01 μg/mL antibody concentrations, while only the LF antibody showed killing at the 0.001 μg/mL antibody concentration. None of the anti-VISTA antibodies showed killing at the 0.0001 μg/mL antibody concentration.

The LF antibody showed approximately 10 times more potent ADCC killing than either the regular IgG1 antibody or the IgG1 PR antibody, as seen in the EC50 values.

Example 19: Affinity of VSTB174 for Human and Cynomolgus Vista

The affinity of VSTB174 for human and cynomolgus monkey VISTA extracellular domain (ECD) was determined by surface plasmon resonance (SPR) methods on a ProteOn instrument. VSTB174 displayed very similar KD values for each protein, 1.56E-10 M for human VISTA ECD and 8.66E-11 M for cynomolgus VISTA.

Example 20: Vista Antibodies Exhibit Efficacy in Murine Tumor Models

Mouse Strains, Reagents and Tumor Models

For the in vivo studies, human VISTA knockin (VISTA-KI) mice back-crossed onto a C57Bl/6 background were used.

An anti-human VISTA antibody was generated to enable testing in the VISTA-KI mice, using the VSTB174 variable region grafted onto mouse Fc IgG2a (VSTB123).

The MB49 bladder cancer was evaluated in the VISTA KI mice,

In addition to published studies demonstrating that anti-VISTA antibody therapy inhibits tumor growth in wild type mice (Le Mercier et al., 2014), anti-tumor efficacy has been demonstrated with the surrogate hamster antibody in wt mice using different dosing schedules, and in the VISTA-KI mice treated with VSTB123.

In Vivo Efficacy Studies in the MB49 Tumor Model in VISTA-KI Mice

MB49 efficacy studies were conducted in female VISTA-KI mice, testing VSTB123 at several doses ranging from 1-10 mg/kg. Mice were injected intradermally with 250,000 MB49 tumor cells on day 0. On day 6, dosing began as indicated in FIG. 37 (either 10 mg/kg of the isotype control mIgG2a, or the indicated doses of VSTB123; 10 mice/group).

Figure 37:
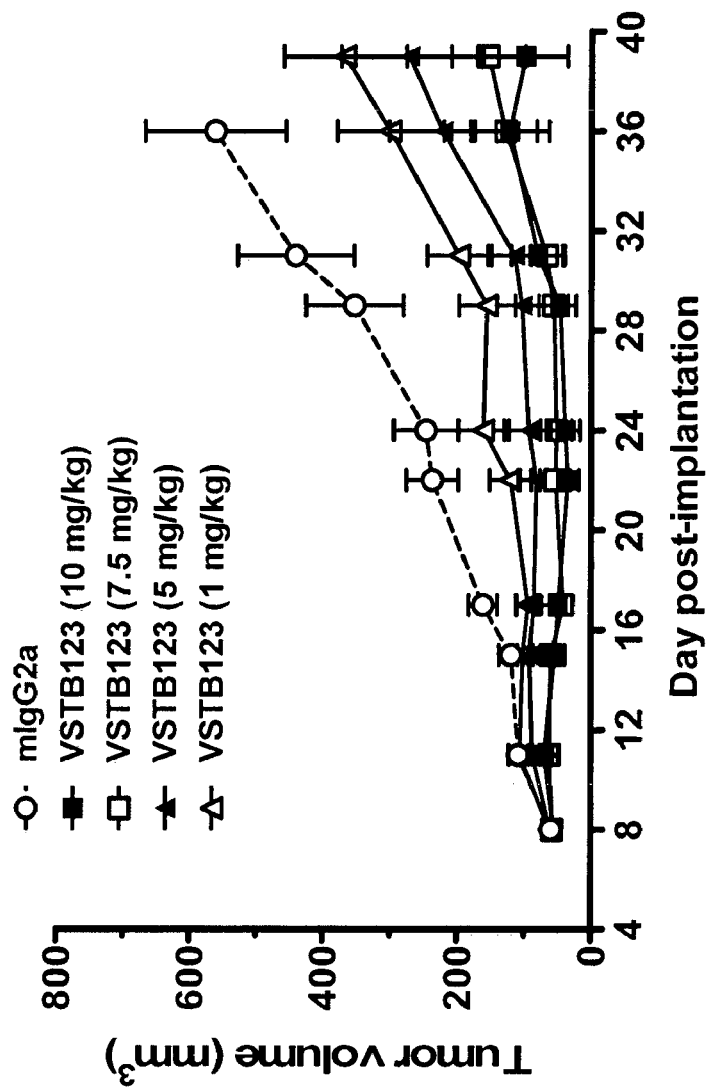
FIG. 37: MB49 tumor efficacy study evaluating VSTB123 1, 5, 7.5, and 10 mg/kg in female VISTA-KI mice. Tumor volumes were approximately 50 mm³ when dosing began at day 6 after implant. VSTB123 is the VSTB112 Fab grafted onto a mouse Fc scaffold and binds to human VISTA in the VISTA-KI mouse.

VSTB123 was more effective at higher vs lower doses, as shown in FIG. 37. Doses of 10 mg/kg and 7.5 mg/kg were equivalent, while tumors grew more quickly in the mice dosed at 5 or 1 mg/kg.

Example 21: Detection of Vista Expression in Human Tumors with Anti-Vista Antibodies FIG. 1 shows VISTA expression by an AML tumor cell line—this and the RNA seq expression data in FIG. 17 support the idea that VISTA is expressed by AML cells and that anti-VISTA drug be efficacious through directly targeting these cells for immune modulation or antibody-mediated killing.

Figure 38:
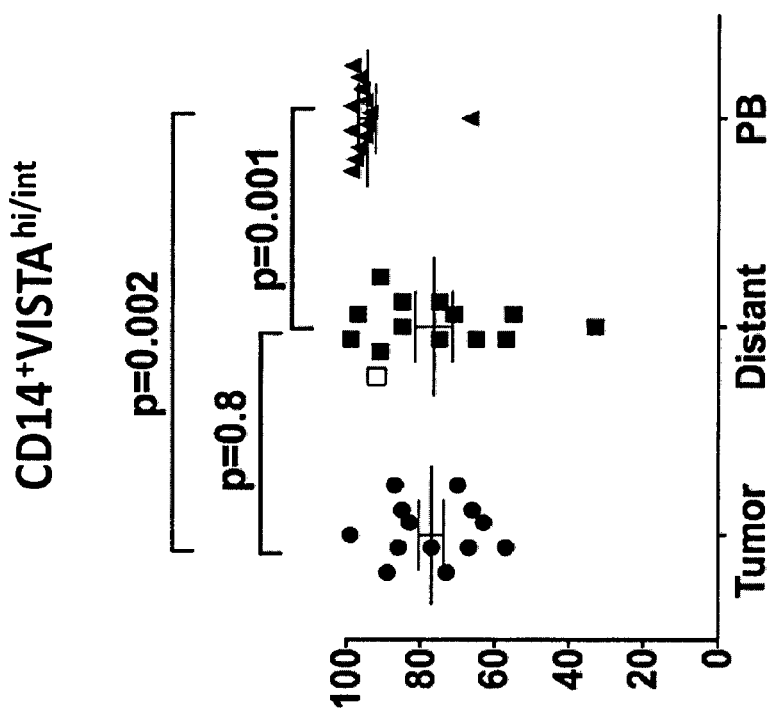
FIG. 38: Graph shows that CD14+ cells expressing high/intermediate levels of VISTA are found in 13/13 lung cancer samples, as well as in distant lung tissue and peripheral blood of patients.

Data to evaluate VISTA expression in lung cancer was obtained from lung tumor samples from surgical resections. Cells were dissociated and characterized for expression of VISTA and many other markers. Results showed that 13/13 lung tumors (squamous or adenocarcinomas) contained CD14+VISTA+ myeloid cells, (FIG. 38).

Example 22: Detection of Vista Expression in Lung Tumors Using Anti-Vista Antibodies An immunohistochemistry assay was optimized using clone GG8, an anti-human VISTA mouse IgG1. This mAb was used to investigate the staining of VISTA in non small cell lung cancer (NSCLC) FFPE tumor sections.

FFPE tumor sections were treated with standard antigen retrieval methods prior to staining. GG8 mouse anti-human VISTA antibody was used at a 1:500 dilution. GG8 binding was detected using a rabbit anti-mouse polyclonal antibody, followed by anti-rabbit polymer HRP. Counterstain with hematoxylin followed, then tumor sections were scored.

Figure 39:
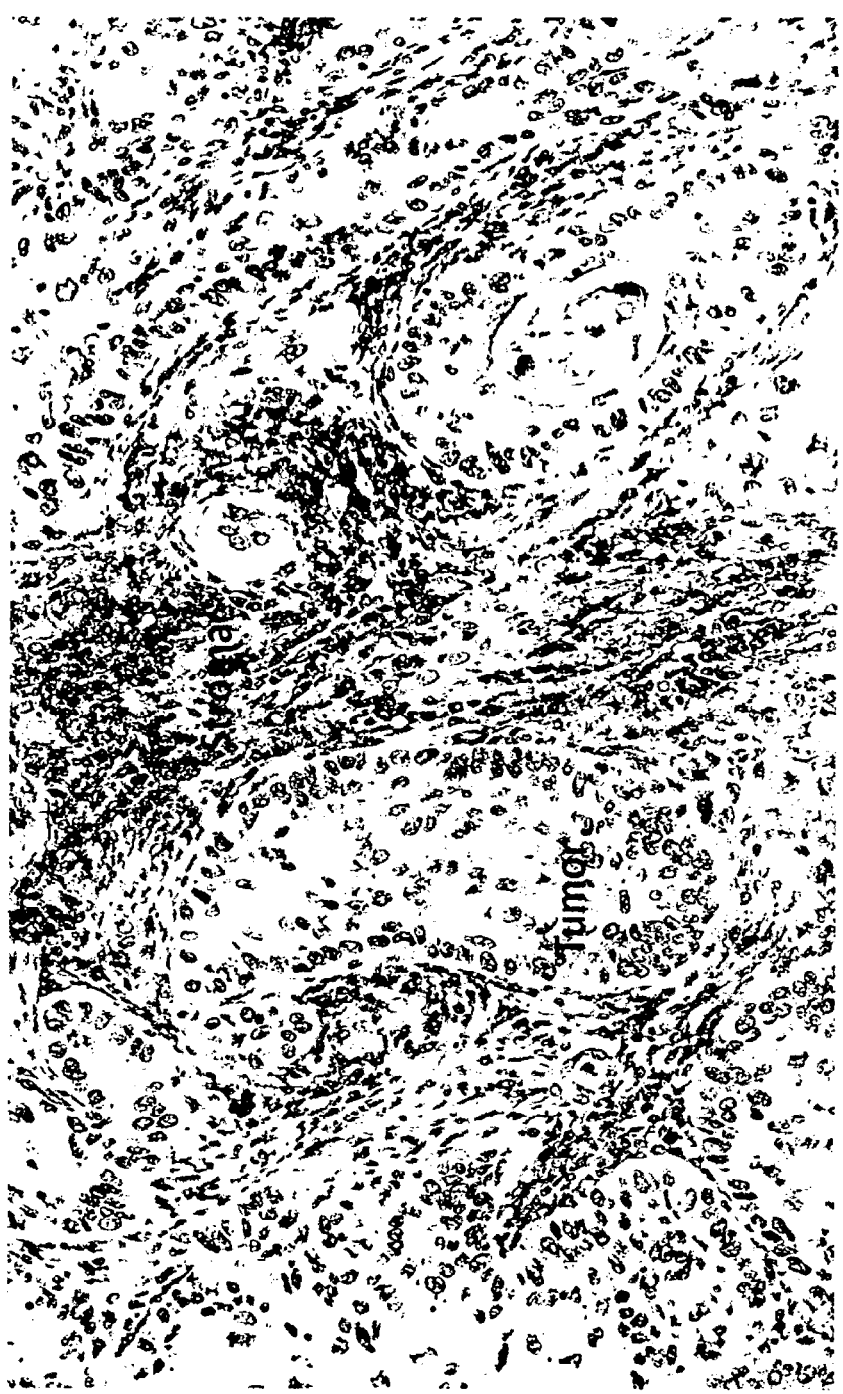
FIG. 39: IHC staining for VISTA in Lung Cancer using GG8.
Figure 40:
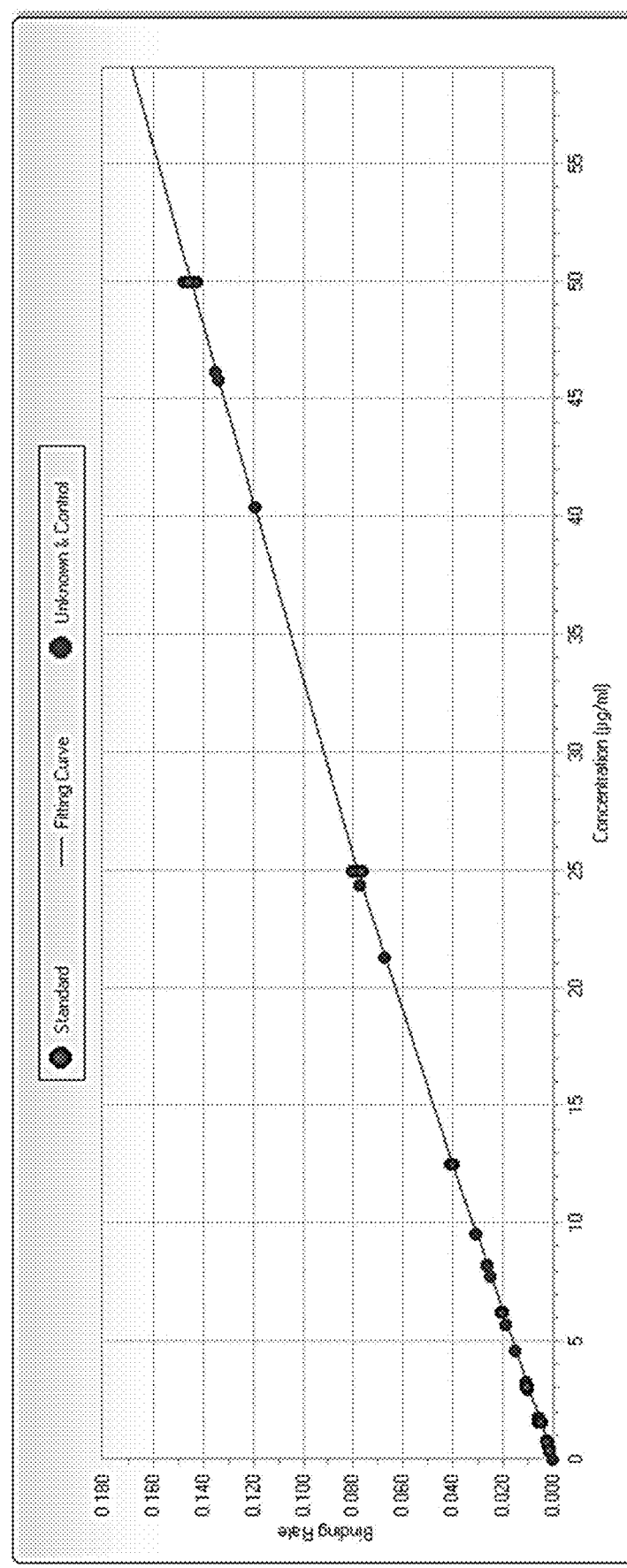
FIG. 40 is a graph of binding rate vs. antibody concentration.

VISTA expression in lung cancer was mostly restricted to the immune infiltrate (example shown in FIG. 39) and high levels of VISTA positive cells were present in many lung cancer samples

Example 23: Structure of the Extracellular Domain (ECD) of Human Vista in Complex with the Fab Fragment of VSTB174

VISTA antigen variants were generated and purified for crystallography. Recombinant his-tagged VSTB174 Fab was internally expressed and purified. Crystals were generated and used to collect higher resolution data for the VISTA ECD:VSTB174 Fab complex using synchrotron radiation and the structural determination was solved using combinations of homology modeling and electron density analyses (FIG. 29(Top)).

The structure of the VISTA ECD:VSTB174 Fab complex was determined by x-ray crystallography to a resolution of 1.85 Å, providing the first structure of the VISTA ECD and delineating the VSTB174 epitope and paratope. The VISTA ECD adopts an IgV fold with a topology similar to CTLA-4 ECD, but possesses a unique G' strand that extends the front sheet of the β-sandwich. A' and G' are further tethered chemically via a disulfide bridge formed between residues C12 in the A' strand and C146 in the G' strand. Six cysteines were found to be engaged in three intramolecular disulfide bonds, and, based on crystal contacts, there is no evidence for a dimeric VISTA.

VSTB174 recognizes residues in the front sheet strands C', C, F, and G on the ends proximal to the FG loop as well as residues in the BC, FG, and CC' loops.

Example 24: Cloning of VSTB116 VH and VL Regions into Mouse IgG1 Backbone

The VSTB116 heavy chain (SEQ ID NO:57) and light chain (SEQ ID NO:58) variable regions were subcloned into a mouse IgG1 backbone to create VSTB175. The VSTB175 heavy chain expression plasmid, pDR23170, was generated using vector vDR000367 (pUnder vector encoding mouse IgG1 Balb C constant regions) and the VSTB116 variable region from pDR17582. Standard synthesis of pDR23170 was performed at Genewiz with HindIII_BamH1 sites and custom cloned into vector vDR000367 (pUnder_mG1 Balb C) at HindIII_BamH1 sites making the final product of pDR23170. The VSTB175 light chain expression plasmid, pDR21003, was generated by standard synthesis of the variable region at GeneArt, with the addition of adapters. vDR000371 (pUnder vector encoding murine kappa constant region) was linearized using Esp3I sites. The synthesized fragment of VSTB175 light chain variable region sequence was then infusion cloned into vDR000371, creating pDR21003. The resultant primary transcripts were sequenced confirmed and large scale DNA preparations were prepared for transfections.

Na+ Acetate pH 3.5. Elution fractions (8-mL) were collected when the OD280 was >25 mAU/2 mm. The elution fractions were neutralized with 2-mL 2.5M Tris HCl pH 7.2 per fraction and were stored at 2-10 C pending further processing. The elution peak fractions were analyzed by OD280 and SE-HPLC to determine protein concentrations and % aggregate. Due to a high amount of aggregate observed in this analysis the sample required SEC polishing. The samples were concentrated and SEC fractionation was done using a Superdex 200 column (26/60 column, 2.5 mL/min 1×DPBS, 4-mL fractions). The sample was analyzed by OD280 (protein concentration), LAL (endotoxin content), SE-HPLC (%

TABLE 16

Complete light chain and heavy chain sequences for VSTB175:

| Protein ID | Heavy chain | Light chain |
|---|---|---|
| VSTB175* | QVQLVQSGAEVKKPGSSVKVSCKASGGTFS*SYAISW*VRQAPGQGLEW MG*IIPIFGTANYAQKFQG*RVTITADESTSTAYMELSSLRSEDTAVYYCAR *SSYGWSYEFDY*WGQGTLVTVSSAKTTPPSVYPLAPGSAAQTNSMVTLG CLVKGYFPEPVTVTWNSGSLSSGVHTFPAVLESDLYTLSSSVTVPSSPRPS ETVTCNVAHPASSTKVDKKIVPRDCGCKPCICTVPE-VSSVFIFPPKPKDVLT ITLTPKVICVVVDISKDDPEVQFSWFVDDVEVHTAQTQPREEQFNSTFRS VSELPIMHQDWLNGKEFKCRVNSAAFPAPIEKTISKTKGRPKAPQVYTIP PPKEQMAKDKVSLTCMITDFFPEDITVEWQWNGQPAENYKNTQPIMN TNGSYFVYSKLNVQKSNWEAGNTFTCSVLHEGLHNHHTEKSLSHSPGK (SEQ ID NO: 76) | DIQMTQSPSSLSASVGDRVTITC*RASQSINT NLNW*YQQKPGKAPKLLIY*AASSLQS*GVPSR FSGSGSGTDFTLTISSLQPEDFATYYC*QQAR DTPITF*GQGTKVEIKRADAAPTVSIFPPSSE QLTSGGASVVCFLNNFYPKDINVKWKIDGS ERQNGVLNSWTDQDSKDSTYSMSSTLTLT KDEYERHNSYTCEATHKTSTSPIVKSFNRNE C (SEQ ID NO: 77) |

*Constant region sequences are underlined; putative CDR sequences are italicized.

Example 25: Expression, Purification and Analysis of VSTB175

Expi293F cells (Life Technologies Corporation Cat #A14527) were grown at 37° C.; 7% CO2; 130 RPM in Expi293 Expression Medium (Life Technologies Corporation Cat #A14351-01). Two days prior to transfection, cells were split at 7e5 cells/ml. At the time of transfection, cells were counted and verified to be at a concentration of at least 30e5 cells/nil and above 95% viable. For each 30-mL transfection; 30 ug of plasmid DNA was mixed with in Opti-MEM I Reduced Serum Medium (Life Technologies Corporation Cat #31985-070) to a total volume of 1.5 mL. (15 ug of pAdvantage DNA and 15 ug of expression vector DNA (for antibodies this is 1:3 ratio of HC:LC expression constructs). 81 uL of ExpiFectamine 293 Reagent (Life Technologies Corporation Cat #A14525). was then diluted in Opti-MEM I medium to a total volume of 1.5 mL. The diluted DNA and ExpiFectamine solutions were then mixed gently and incubated for 5 minutes at room temperature. The diluted DNA was added to the diluted ExpiFectamine 293 Reagent, mixed gently, and incubated for 20 minutes at room temperature. After the incubation the mixture was then added to 25.5 ml of cells in a 125 ml shake flask. Immediately following transfection, 150 uL of ExpiFectamine 293 Transfection Enhancer 1 and 1.5 mL of ExpiFectamine 293 Transfection Enhancer 2 were added to each flask (Life Technologies Corporation Cat #A14525). 5 days post transfection, cells supernatant was harvested by centrifugation and clarified through a 0.2 micron filter.

Two VSTB175 transient 293Expi transfection harvests were pooled and buffered to 1×DPBS+0.5M NaCl. The sample was purified using an AKTApurifier at 2-10 C. The sample was captured to MabSelect SuRe resin (20 mL, 1.6 cm ID×10 cm H). Unbound sample was washed off the resin with 1×DPBS+0.5M NaCl. The mAb was eluted with 0.1M monomeric mAb), and SDS-PAGE. The sample was 98.22% monomeric mAb by SE-HPLC analysis.

1) Soak anti-Human Fc biosensors in transfection media (for example, Freestyle 293 exprsesion medium (Life Technologies) or CHO) for 10 min. before running assay. Add 120 µl media to FIA 96 well plate. Place 96 well plate in biosensor tray and place tips into media in tray. 2) Dilute samples 1:10 in transfection media (or 1:25 for concentrated samples). 3) Transfer 120 µl of each neat and 1:10 diluted sample into a second 96 w black FIA plate. 4) Standard Curve already loaded onto the Octet machine. 5) Add three standard samples (40, 20, and 10 µg/ml of standard control antibody) after all unknown samples have been added. Fill the remaining wells of that column with transfection media as a reference. 6) Run samples in ForteBio Octet according to manufacturer instructions.

Example 26: VSTB175 Molecular Pathology Immunohistochemistry Assay Development

Recommended concentration: 10 µg/ml; Diluent: Dako common antibody

Retrieval method utilized: Freshly prepared Dako low pH retrieval solution in pressurized vessel (Retriever) for 20 minutes @ 121° C. followed by a 40 minute cool down in retriever. Remove and cool down 15 min at RT.

Detection System: Anti Mouse Polymer Envision+system DAB (Dako).

Instrument: Biogenex i6000

Protocol steps: 1) Deparaffinize 4 µm paraffin sections to de-ionized water. 2) Antigen retrieval. 3) Rinse in de-ionized water. 4) Peroxidase Block (3% $H_2O_2$) 15 min. 5) Rinse in Wash Buffer for minimum of 15 min. 6) protein block (Dako, Carpinteria, California) for 60 min RT. 7) Primary antibody 60 min. @ room temperature. 8) Rinse in Wash Buffer five times. 8) Peroxidase labled polymer. anti-mouse 30 min. 9) Rinse in Wash Buffer five times. 10) Working DAB for 5 min. 11) Rinse in de-ionized water three times. 12) Rinse in Wash Buffer five times. 13) Counter stain in Mayers hematoxylin for 5 min. 14) Rinse in Tap water and run up to solvent prior to applying a coverslip.

Results are shown in FIG. 41 and Tables 17-18.

TABLE 17

Tumor Microenvironment Compartment

| Sample | Region | Tissue Area [mm2] | VISTA+ cells/mm2 (0.1 Gate) | VISTA+ cells/mm2 (0.125 Gate) |
| --- | --- | --- | --- | --- |
| 312979A2 | TME | 93.0 | 102.2 | 34.5 |
| 312980A1 | TME | 46.0 | 118.5 | 41.2 |
| 1168370B | TME | 96.8 | 245.8 | 88.2 |
| CNT15G5 | TME | 18.3 | 308.8 | 100.0 |
| 1172984B | TME | 42.9 | 749.9 | 262.5 |
| CNT15EG | TME | 19.8 | 990.7 | 339.1 |
| CNT15D3 | TME | 28.6 | 1719.7 | 652.9 |
| CNT15CD | TME | 27.2 | 1898.6 | 717.4 |
| CNT0RQ1 | AllCells | 39.0 | 3305.9 | 1257.9 |

TABLE 18

Tumor compartment

| Sample | Region | Tissue Area [mm2] | VISTA+ cells/mm2 (0.1 Gate) | VISTA+ cells/mm2 (0.125 Gate) |
| --- | --- | --- | --- | --- |
| 312979A2 | Tumor | 93.0 | 8.3 | 2.4 |
| 312980A1 | Tumor | 46.0 | 22.2 | 7.4 |
| CNT15EG | Tumor | 19.8 | 60.8 | 19.1 |
| CNT15G5 | Tumor | 18.3 | 82.4 | 25.4 |
| CNT15CD | Tumor | 27.2 | 87.8 | 28.2 |
| 1168370B | Tumor | 96.8 | 107.3 | 38.0 |
| CNT15D3 | Tumor | 28.6 | 127.0 | 43.4 |
| 1172984B | Tumor | 42.9 | 545.4 | 175.7 |

Example 27: VSTB175 Antibody Clones in Lung Cancer Tissue

Materials and Methods:

VISTA VSTB175 antibody and NSCLC samples: Frozen aliquots of the VISTA VSTB175 antibody were provided for optimization in human NSCLC tissue samples. Nine formalin-fixed, paraffin-embedded (FFPE) samples were selected for evaluation, and unstained sections on glass slides were provided for immunohistochemical (IHC) staining once an optimized VISTA (VSTB175) IHC assay was identified.

IHC assay optimization: VISTA (VSTB175) IHC assay optimization was performed on tonsil and spleen tissue. Two antigen retrieval times (20 min and 40 min) were evaluated for sodium citrate at pH 6 for a range of antibody dilutions (1:500, 1:1000, and 1:2000). The presentation of staining in tonsil and spleen tissue was evaluated by a board-certified veterinary pathologist, and the optimal assay conditions were identified. The optimal IHC assay used antigen retrieval with sodium citrate at pH 6 for 40 min at 90° C. (this temperature was chosen because of the high altitude location of the laboratory), a VISTA (VSTB175) antibody dilution of 1:500 (6.36 mg/ml starting concentration) for 60 min, and development with DAB for 10 min. The THC assay was performed using a Leica Bond RX Autostainer according to the following protocol:

Detailed protocol (using Leica Bond RX or Max Autostainer):

1. Slides are cut at 4 microns per usual sectioning protocol. Slides are allowed to air dry and are then baked for 60 minutes at 60° C. Slides are generally used for staining within 2 weeks of cutting.

2. Place baked slides on the Leica slide racks, place covertiles on slides, and insert rack into Autostainer.

3. Dilute Primary antibody to 1:500 with Leica Antibody Diluent (#AR9352).

Steps performed on Leica Bond RX/Max Autostainer:

1. Bond Dewax Solution (#AR9222) applied three times at 72° C.

2. 100% Ethanol applied three times

3. Leica Bond Wash 1x Solution (#AR9590) applied three times.

4. Leica ER 1 Epitope Retrieval Solution (#AR9961) incubates for 40 minutes at 90° C.

5. Leica Bond Wash 1x Solution applied five times.

6. Thermo Pierce Protein-Free Blocking Buffer (#37584) incubates for five minutes.

7. No rinse before Antibody Application.

8. Antibody dilution incubates for 60 minutes.

9. Leica Bond Wash 1x Solution applied three times.

10. Post Primary Link (Leica Bond Polymer Refine Kit #DS9800) incubates for 8 minutes.

11. Leica Bond Wash 1x Solution applied for 2 minutes three times.

12. Polymer (Leica Bond Polymer Refine Kit #D59800) incubates for 8 minutes.

13. Leica Bond Wash 1x Solution applied for 2 minutes twice.

14. DI water rinse.

15. Peroxide Block (Leica BPR Kit) incubates for 10 minutes.

16. Leica Bond Wash 1x Solution applied twice.

17. DI water rinse.

18. DAB chromagen/substrate (Leica BPR Kit) incubates for 10 minutes.

19. Leica Bond Wash 1x Solution applied three times.

20. Hematoxylin counterstain (Leica BPR Kit) incubates for 2 minutes.

21. DI water rinse.

22. Leica Bond Wash 1x Solution applied once.

23. DI water rinse.

24. Remove slides from Leica Bond RX/Max

Dehydration and coverslipping performed manually as follows:

23. Two changes of 95% Ethanol (1 minute each)

24. Two changes of 100% Ethanol (1 minute each)

25. Two changes of Xylene (2 minutes each)

26. Coverslip with Cytoseal mounting media.

Slide scanning and annotations: Upon completion of IHC staining, glass slides were digitized using Aperio model CS and XT scanners. Once each glass slide was digitized, annotations were utilized to identify regions of analysis (ROAs). The ROAs captured analyzable tumor tissue within each sample and the surrounding stromal tissue compartment. Unwanted tissue features such as necrosis, large areas of anthracosis (carbon pigment), and lymphoid follicles (such as non-tumor associated pre-existing lymphoid populations) were removed from analysis by annotations. Each ROA identified by the annotations was evaluated and approved by a pathologist prior to performing image analysis.

Image analysis: The number of VISTA positive cells/mm2 was identified as the primary endpoint for this study prior to initiation of the project. Tumor cell nests and associated infiltrating inflammatory cells were analyzed as the tumor tissue compartment. Stromal cell regions, and associated infiltrating inflammatory cells, were analyzed as the tumor microenvironment (TME) tissue compartment. Results:

Results are shown in Tables 17 and 18 above.

Figure 42:
FIG. 42: VISTA (VSTB175) Staining in Human Tonsil. Shown are two regions tonsil tissue block stained with the VISTA (VSTB175) antibody (left and right panels).

IHC Assay Development for VISTA (VSTB175): A matrix of IHC assay conditions was tested to identify an optimal IHC assay for the VISTA VSTB175 antibody reagent. Table 19 outlines the conditions evaluated during optimization. FIG. 42 demonstrates staining of a human tonsil section (positive control tissue) for two independent days of staining. Optimal assay conditions were identified by evaluating the tonsil (positive control) and spleen (negative control) tissue sections. Generally, few positive cells were identified in tonsil follicles. Additionally, VISTA staining was observed in the sub-epithelia regions outside of follicles and was difficult to interpret.

TABLE 19

Assay Conditions Evaluated for Optimization

| | | VISTA Antibody Dilution | | |
|---|---|---|---|---|
| | | 1:500 | 1:1000 | 1:2000 |
| Antigen Retrieval Time (@ pH 6) | 20 minutes | Sub-optimal conditions | Sub-optimal conditions | Sub-optimal conditions |
| | 40 minutes | Optimal conditions | Sub-optimal conditions | Sub-optimal conditions |

Figure 43:
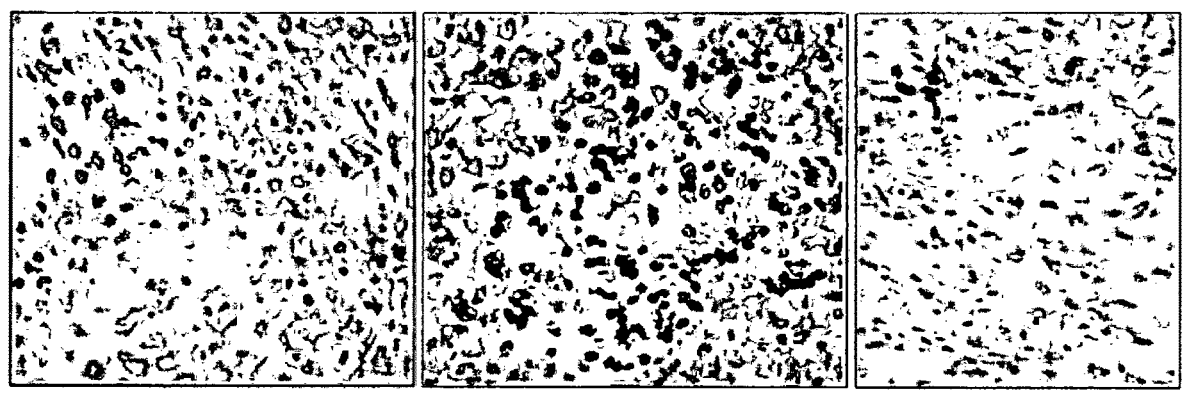
FIG. 43: VISTA (VSTB175) Staining Examples in Human Lung Cancer Tissues. Representative regions of three tissue samples are shown at 20× magnification and demonstrate VISTA staining observed across the study cohort.
Figure 44:
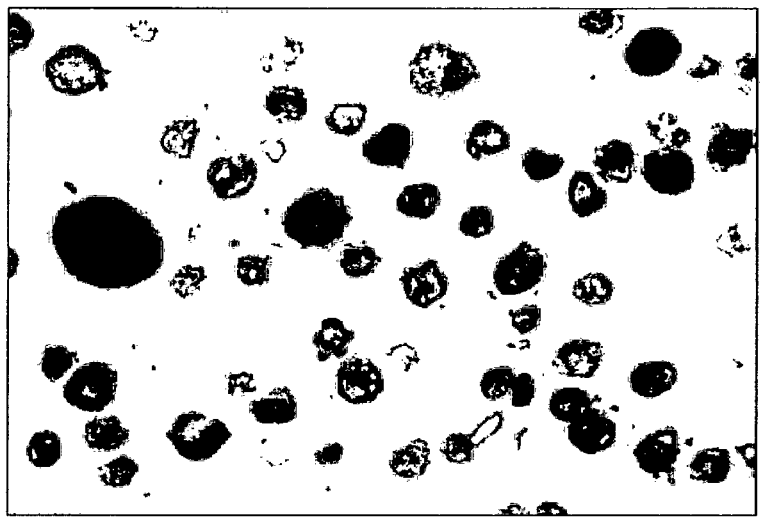
FIG. 44: Cell Line, VISTA-K562. Antibody VSTB175 showed frequent strong staining in VISTA-K562 cells. 40× magnification.
Figure 45:
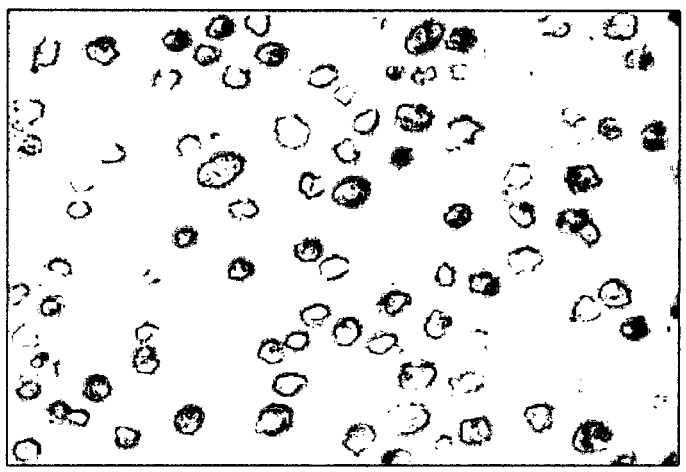
FIG. 45: Cell Line, Raji. Antibody VSTB175 was negative in negative control Raji cells. 40× magnification.
Figure 46:
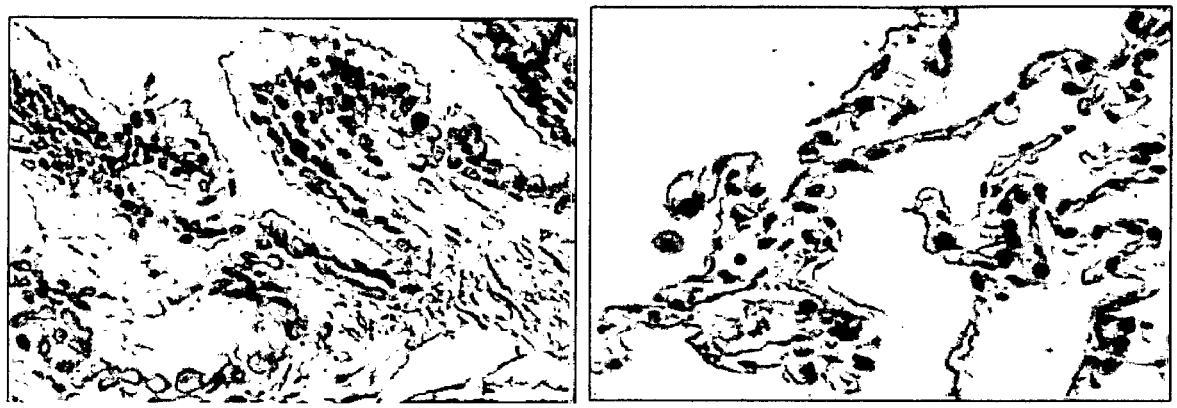
FIG. 46: Lung respiratory epithelium (left panel), alveoli (right panel). This sample of normal lung was obtained at surgery from a 43-year-old female. Antibody VSTB175 shows staining in intravascular leukocytes (mostly neutrophils) and in rare intraepithelial neutrophils within the respiratory epithelium. The epithelium itself and the remaining cell types, including macrophages, were negative. 40× magnification.
Figure 47:
FIG. 47: Lymph Node. This sample of normal lymph node was obtained from a 37-year-old male. Antibody VSTB175 was negative in lymph node tissue of the sinus. 40× magnification.
Figure 48:
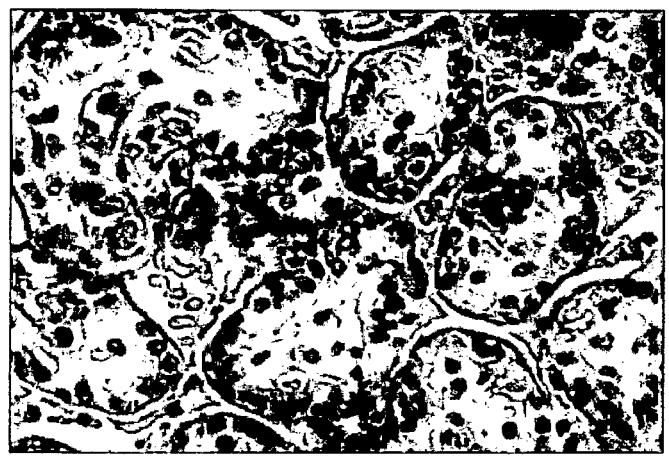
FIG. 48: Placental villi. This sample of normal placenta was obtained at surgery from a 20-year-old female. Antibody VSTB175 showed membranous staining in trophoblasts. 40× magnification.
Figure 49:
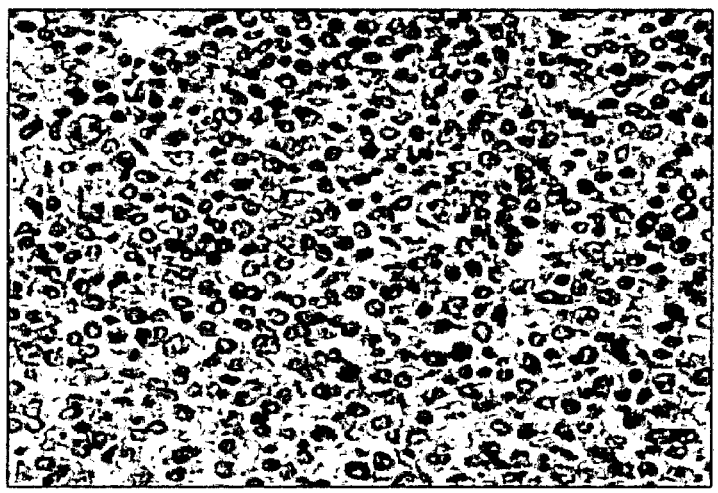
FIG. 49: Spleen. This sample of normal spleen was obtained at autopsy from a 73-year-old female with Alzheimer's disease. Antibody VSTB175 showed focal staining in mononuclear cells, neutrophils, and sinusoidal lining cells in the red pulp. White pulp lymphocytes were mostly negative. 40× magnification.
Figure 50:
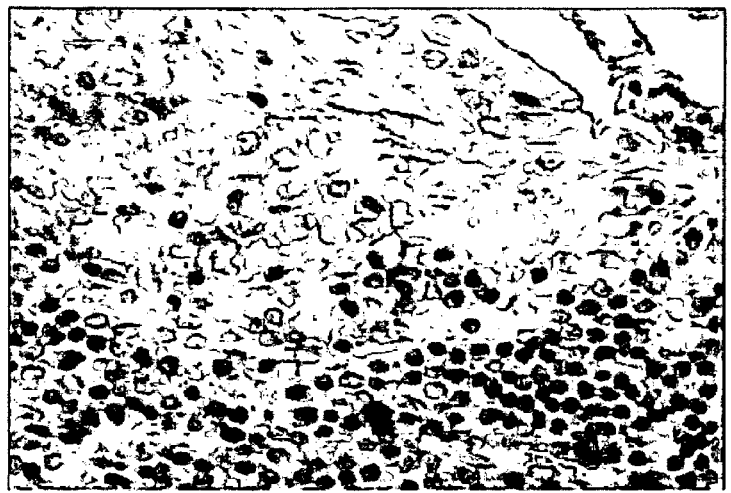
FIG. 50: Tonsil. This sample of normal tonsil was obtained from a 11-year-old female. Antibody VSTB175 showed focal staining in monocytes associated with the surface squamous epithelium, but most lymphocytes were negative. 40× magnification.
Figure 51:
FIG. 51: Colon, Carcinoma. This sample of colon was obtained at surgery from a 57-year-old female. Antibody VSTB175 was negative in this sample, including malignant cells and inflammatory cells (neutrophils). 40× magnification.
Figure 52:
FIG. 52: Melanoma. This sample of melanoma was obtained at surgery from a 54-year-old female. Antibody VSTB175 showed focal staining in benign macrophages but was negative in malignant cells. 40× magnification.
Figure 53:
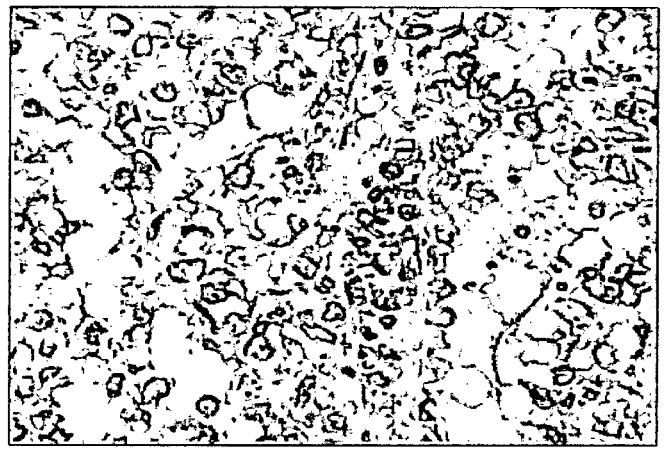
FIG. 53: Ovary, Carcinoma. This sample of ovary was obtained from a 53-year-old female. Antibody VSTB175 showed focal cytoplasmic staining in intravascular leukocytes, including both mononuclear cells and polymorphonuclear neutrophils. Malignant cells were negative, as were rarely identified interspersed inflammatory cells. 40× magnification.

Once optimal assay conditions were identified, the nine human lung cancer samples were stained with the VISTA (VSTB175) IHC assay. FIG. 43 shows three examples of VISTA+(VSTB175) staining observed in the study samples. Initial subjective assessments of each study sample suggested very few, if any, VISTA+ cells. Staining was observed in a number of cells in each study sample.

VISTA Analysis Solution Development: A range of sensitive DAB (i.e. VISTA) positivity gates were assessed to determine the optimal gate for identifying low levels of VISTA staining observed in cells while minimizing false positive cells. The rank-order of samples was poorly preserved between both antibody clones, and suggested each antibody was capturing different phenomena in the tumor tissue compartment. These findings were consistent with the notion that the improved specificity of the VISTA VSTB175 clone led to fewer false positive cell detections in the tumor tissue compartment. Finally, the rank order of samples based on the VSTB175 clone was not dependent on the VISTA positivity gate, and further indicated that both gates were measuring the sample biologic information with different sensitivity.

TABLE 20

Rank-order comparisons of VISTA VSTB175; Rank-order of study samples based on VISTA+ cell density in the TME tissue compartment.
VISTA (VSTB175)

| Sample | Region | VISTA+ cells/mm2 (0.1 Gate) | VISTA+ cells/mm2 (0.125 Gate) |
|---|---|---|---|
| 312979A2 | TME | 102.2 | 34.5 |
| 312980A1 | TME | 118.5 | 41.2 |
| 1168370B | TME | 245.8 | 88.2 |
| CNT15G5 | TME | 308.5 | 100.0 |
| 1172984B | TME | 749.9 | 262.5 |
| CNT15EG | TME | 990.7 | 339.1 |

TABLE 20-continued

Rank-order comparisons of VISTA VSTB175; Rank-order of study samples based on VISTA+ cell density in the TME tissue compartment.
VISTA (VSTB175)

| Sample | Region | VISTA+ cells/mm2 (0.1 Gate) | VISTA+ cells/mm2 (0.125 Gate) |
|---|---|---|---|
| CNT15D3 | TME | 1719.7 | 652.9 |
| CNT15CD | TME | 1898.6 | 717.4 |
| CNT0RQ1 | AllCells | 3305.9 | 1257.9 |

TABLE 21

Rank-order comparison of VISTA VSTB175; Rank-order for VISTA+ cell density in the tumor tissue compartment.
VISTA (VSTB175)

| Sample | Region | VISTA+ cells/mm2 (0.1 Gate) | VISTA+ cells/mm2 (0.125 Gate) |
|---|---|---|---|
| 312979A2 | Tumor | 8.3 | 2.4 |
| 312980A1 | Tumor | 22.2 | 7.4 |
| CNT15EG | Tumor | 60.8 | 19.1 |
| CNT15G5 | Tumor | 82.4 | 25.4 |
| CNT15CD | Tumor | 87.8 | 28.2 |
| 1168370B | Tumor | 107.3 | 38.0 |
| CNT15D3 | Tumor | 127.0 | 43.4 |
| 1172984B | Tumor | 545.4 | 175.7 |

Example 28: Immunohistochemistry

Methods:

Antibody titration experiments were conducted with antibodies provided by Janssen. Immunohistochemical staining was carried out with VSTB175 (chimeric antibody) and one ready-to-use mouse IgG1 isotype control antibody (BioGenex catalog #HK119-7M, referred to as BGX-Ms-IgG1) to establish concentrations that would result in minimal background and maximal detection of signal. Serial dilutions were performed at 20 µg/ml, 10 µg/ml, 5 µg/ml, and 2.5 µg/ml with the two experimental antibodies on formalin-fixed, paraffin-embedded tissues supplied by LifeSpan and positive (Vista K562) and negative (Raji) control cell lines supplied by Janssen. The isotype control antibody was only used at the one ready-to-use concentration. Antibodies VSTB175 and BGX-Ms-IgG1 were used as the primary antibodies, and the principal detection system consisted of a Vector anti-mouse secondary (BA-2000), and a Vector ABC-AP kit (AK-5000) with a Vector Red substrate kit (SK-5100), which was used to produce a fuchsia-colored deposit.

Tissues were also stained with positive control antibodies (CD31 and vimentin) to ensure that the tissue antigens were preserved and accessible for immunohistochemical analysis. Only tissues that were positive for CD31 and vimentin staining were selected for the remainder of this study.

The negative control consisted of performing the entire immunohistochemistry procedure on adjacent sections in the absence of primary antibody, and these slides were appropriately negative.

Slides stained at the reported concentrations were imaged with a DVC 1310C digital camera coupled to a Nikon microscope. Images were stored as TIFF files with Adobe Photoshop. Results are shown in FIGS. 44-53.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed:

1. A nucleic acid which encodes an antibody that binds to human V-domain Ig Suppressor of T cell Activation (VISTA) protein, wherein the antibody comprises:
   a) an antibody VH domain comprising a VH CDR1 having the amino acid sequence of SEQ ID NO: 31, a VH CDR2 having the amino acid sequence of SEQ ID NO:32 and a VH CDR3 having the amino acid sequence of SEQ ID NO:33;
   b) an antibody VL domain comprising a VL CDR1 having the amino acid sequence of SEQ ID NO: 34, a VL CDR2 having the amino acid sequence of SEQ ID NO:35 and a VL CDR3 having the amino acid sequence of SEQ ID NO:36;
   c) a murine antibody heavy chain constant region; and
   d) a murine antibody light chain constant region.

2. The nucleic acid of claim 1, wherein the antibody VH domain comprises SEQ ID NO:64 and/or the antibody VL domain comprises SEQ ID NO:45.

3. The nucleic acid of claim 1, wherein the murine antibody heavy chain constant region is a murine IgG1 heavy chain constant region.

4. The nucleic acid of claim 3, wherein the murine IgG1 antibody heavy chain constant region comprises the murine heavy chain constant region in SEQ ID NO:76.

5. The nucleic acid of claim 1, wherein the murine antibody light chain constant region is a murine IgG1 or murine IgG2a light chain constant region.

6. The nucleic acid of claim 5, wherein the murine IgG1 antibody light chain constant region comprises the light chain constant region in SEQ ID NO:77.

7. The nucleic acid of claim 5, wherein the murine antibody light chain constant region is a murine IgG2a light chain constant region.

8. A nucleic acid encoding an antibody, comprising an antigen-binding region that binds to human V-domain Ig Suppressor of T cell Activation (VISTA) protein and murine heavy and light chain constant regions, wherein the antibody comprises an antibody heavy chain comprising SEQ ID NO:76 and an antibody light chain comprising SEQ ID NO:77.

9. A vector comprising the nucleic acid of claim 1.

10. A method for detecting a human VISTA protein in a sample, comprising contacting the sample with the antibody encoded by the nucleic acid of claim 1 under conditions in which the antibody binds to human VISTA protein in the sample, and detecting the antibody that is bound to VISTA protein in the sample.

11. The method of claim 10, wherein
   (i) the sample comprises human cells;
   (ii) the sample comprises a human tissue;
   (iii) the sample comprises human immune cells or human stromal cells, or a combination thereof;
   (iv) the sample comprises human immune cells including one or more of human myeloid cells, human monocytes or human T cells;
   (v) the sample comprises human cancer cells;
   (vi) the sample comprises human cancer cells selected from the group consisting of human lung cancer cells, human prostate cancer cells, human acute myeloid leukemia (AML) cells, human melanoma cells, human ovarian cancer cells and human colon cancer cells;
   (vii) the antibody comprises a detectable label;
   (viii) the method includes an immunohistochemical (IHC) staining assay;
   (ix) the method includes a flow cytometry assay; or
   (x) a combination of any of the foregoing.

12. A vector comprising the nucleic acid of claim 8.

13. A method for detecting human VISTA protein in a sample, comprising contacting the sample with the antibody encoded by the nucleic acid of claim 8 under conditions in which the antibody binds to human VISTA protein in the sample, and detecting the antibody that is bound to the human VISTA protein in the sample.

14. The method of claim 13, wherein
  (i) the sample comprises human cells;
  (ii) the sample comprises a human tissue;
  (iii) the sample comprises human immune cells or human stromal cells, or a combination thereof;
  (iv) the sample comprises human immune cells including one or more of human myeloid cells, human monocytes or human T cells;
  (v) the sample comprises human cancer cells;
  (vi) the sample comprises human cancer cells selected from the group consisting of human lung cancer cells, human prostate cancer cells, human acute myeloid leukemia (AML) cells, human melanoma cells, human ovarian cancer cells and human colon cancer cells;
  (vii) the antibody comprises a detectable label;
  (viii) the method includes an immunohistochemical (IHC) staining assay;
  (ix) the method includes a flow cytometry assay; or
  (x) a combination of any of the foregoing.

15. An isolated or recombinant cell comprising the nucleic acid of claim 1 or a vector containing said nucleic acid.

16. An isolated or recombinant cell comprising the nucleic acid of claim 8 or a vector containing said nucleic acid.

17. A method of producing an antibody encoded by the nucleic acid of claim 1, comprising culturing a cell which comprises said nucleic acid or a vector containing said nucleic under conditions that permit the expression of the antibody.

18. A method of producing an antibody encoded by the nucleic acid of claim 8, comprising culturing a cell which comprises said nucleic acid or a vector containing said nucleic acid under conditions that permit the expression of the antibody.

\* \* \* \* \*

SEQUENCE LISTING

```
<160> NUMBER OF SEQ ID NOS: 77

<210> SEQ ID NO 1
<211> LENGTH: 8
<212> TYPE: PRT
<213> ORGANISM: Homo sapiens

<400> SEQUENCE: 1

Gly Tyr Thr Phe Thr Asn Tyr Gly
1               5

<210> SEQ ID NO 2
<211> LENGTH: 8
<212> TYPE: PRT
<213> ORGANISM: Homo sapiens

<400> SEQUENCE: 2

Ile Asn Pro Tyr Thr Gly Glu Pro
1               5

<210> SEQ ID NO 3
<211> LENGTH: 12
<212> TYPE: PRT
<213> ORGANISM: Homo sapiens

<400> SEQUENCE: 3

Ala Arg Glu Gly Tyr Gly Asn Tyr Ile Phe Pro Tyr
1               5                   10

<210> SEQ ID NO 4
<211> LENGTH: 10
<212> TYPE: PRT
<213> ORGANISM: Homo sapiens

<400> SEQUENCE: 4

Glu Ser Val Asp Thr Tyr Ala Asn Ser Leu
1               5                   10

<210> SEQ ID NO 5
<211> LENGTH: 3
<212> TYPE: PRT
<213> ORGANISM: Homo sapiens

<400> SEQUENCE: 5

Arg Ala Ser
1

<210> SEQ ID NO 6
<211> LENGTH: 9
<212> TYPE: PRT
<213> ORGANISM: Homo sapiens

<400> SEQUENCE: 6

Gln Gln Thr Asn Glu Asp Pro Arg Thr
1               5

<210> SEQ ID NO 7
<211> LENGTH: 8
<212> TYPE: PRT
<213> ORGANISM: Homo sapiens
```

```
<400> SEQUENCE: 7

Gly Tyr Thr Phe Thr His Tyr Thr
1               5

<210> SEQ ID NO 8
<211> LENGTH: 8
<212> TYPE: PRT
<213> ORGANISM: Homo sapiens

<400> SEQUENCE: 8

Ile Ile Pro Ser Ser Gly Tyr Ser
1               5

<210> SEQ ID NO 9
<211> LENGTH: 16
<212> TYPE: PRT
<213> ORGANISM: Homo sapiens

<400> SEQUENCE: 9

Ala Arg Gly Ala Tyr Asp Asp Tyr Tyr Asp Tyr Ala Met Asp Tyr
1               5                   10                  15

<210> SEQ ID NO 10
<211> LENGTH: 11
<212> TYPE: PRT
<213> ORGANISM: Homo sapiens

<400> SEQUENCE: 10

Gln Thr Ile Val His Ser Asn Gly Asn Thr Tyr
1               5                   10

<210> SEQ ID NO 11
<211> LENGTH: 3
<212> TYPE: PRT
<213> ORGANISM: Homo sapiens

<400> SEQUENCE: 11

Lys Val Ser
1

<210> SEQ ID NO 12
<211> LENGTH: 9
<212> TYPE: PRT
<213> ORGANISM: Homo sapiens

<400> SEQUENCE: 12

Phe Gln Ala Ser His Val Pro Trp Thr
1               5

<210> SEQ ID NO 13
<211> LENGTH: 8
<212> TYPE: PRT
<213> ORGANISM: Homo sapiens

<400> SEQUENCE: 13

Gly Tyr Thr Phe Thr Asn Tyr Gly
1               5

<210> SEQ ID NO 14
<211> LENGTH: 8
<212> TYPE: PRT
<213> ORGANISM: Homo sapiens

<400> SEQUENCE: 14
```

```
Ile Asn Thr Tyr Thr Gly Glu Ser
1               5

<210> SEQ ID NO 15
<211> LENGTH: 12
<212> TYPE: PRT
<213> ORGANISM: Homo sapiens

<400> SEQUENCE: 15

Ala Arg Asp Tyr Tyr Gly Ile Tyr Val Ser Ala Tyr
1               5                   10

<210> SEQ ID NO 16
<211> LENGTH: 10
<212> TYPE: PRT
<213> ORGANISM: Homo sapiens

<400> SEQUENCE: 16

Glu Ser Val Asp Asn Tyr Ala Asn Ser Phe
1               5                   10

<210> SEQ ID NO 17
<211> LENGTH: 3
<212> TYPE: PRT
<213> ORGANISM: Homo sapiens

<400> SEQUENCE: 17

Arg Ala Ser
1

<210> SEQ ID NO 18
<211> LENGTH: 9
<212> TYPE: PRT
<213> ORGANISM: Homo sapiens

<400> SEQUENCE: 18

Gln Gln Ser His Glu Asp Pro Tyr Thr
1               5

<210> SEQ ID NO 19
<211> LENGTH: 8
<212> TYPE: PRT
<213> ORGANISM: Homo sapiens

<400> SEQUENCE: 19

Gly Phe Thr Phe Arg Asn Tyr Gly
1               5

<210> SEQ ID NO 20
<211> LENGTH: 8
<212> TYPE: PRT
<213> ORGANISM: Homo sapiens

<400> SEQUENCE: 20

Ile Ile Ser Gly Gly Ser Tyr Thr
1               5

<210> SEQ ID NO 21
<211> LENGTH: 15
<212> TYPE: PRT
<213> ORGANISM: Homo sapiens

<400> SEQUENCE: 21

Ala Arg Ile Tyr Asp His Asp Gly Asp Tyr Tyr Ala Met Asp Tyr
1               5                   10                  15
```

<210> SEQ ID NO 22
<211> LENGTH: 11
<212> TYPE: PRT
<213> ORGANISM: Homo sapiens

<400> SEQUENCE: 22

Gln Ser Ile Val His Ser Asn Gly Asn Thr Tyr
1               5                   10

<210> SEQ ID NO 23
<211> LENGTH: 3
<212> TYPE: PRT
<213> ORGANISM: Homo sapiens

<400> SEQUENCE: 23

Lys Val Ser
1

<210> SEQ ID NO 24
<211> LENGTH: 9
<212> TYPE: PRT
<213> ORGANISM: Homo sapiens

<400> SEQUENCE: 24

Phe Gln Gly Ser His Val Pro Trp Thr
1               5

<210> SEQ ID NO 25
<211> LENGTH: 8
<212> TYPE: PRT
<213> ORGANISM: Homo sapiens

<400> SEQUENCE: 25

Gly Gly Thr Phe Ser Ser Tyr Ala
1               5

<210> SEQ ID NO 26
<211> LENGTH: 8
<212> TYPE: PRT
<213> ORGANISM: Homo sapiens

<400> SEQUENCE: 26

Ile Ile Pro Ile Phe Gly Thr Ala
1               5

<210> SEQ ID NO 27
<211> LENGTH: 13
<212> TYPE: PRT
<213> ORGANISM: Homo sapiens

<400> SEQUENCE: 27

Ala Arg Ser Ser Tyr Gly Trp Ser Tyr Glu Phe Asp Tyr
1               5                   10

<210> SEQ ID NO 28
<211> LENGTH: 6
<212> TYPE: PRT
<213> ORGANISM: Homo sapiens

<400> SEQUENCE: 28

Gln Ser Ile Asp Thr Arg
1               5

```
<210> SEQ ID NO 29
<211> LENGTH: 3
<212> TYPE: PRT
<213> ORGANISM: Homo sapiens

<400> SEQUENCE: 29

Ser Ala Ser
1

<210> SEQ ID NO 30
<211> LENGTH: 9
<212> TYPE: PRT
<213> ORGANISM: Homo sapiens

<400> SEQUENCE: 30

Gln Gln Ser Ala Tyr Asn Pro Ile Thr
1               5

<210> SEQ ID NO 31
<211> LENGTH: 8
<212> TYPE: PRT
<213> ORGANISM: Homo sapiens

<400> SEQUENCE: 31

Gly Gly Thr Phe Ser Ser Tyr Ala
1               5

<210> SEQ ID NO 32
<211> LENGTH: 8
<212> TYPE: PRT
<213> ORGANISM: Homo sapiens

<400> SEQUENCE: 32

Ile Ile Pro Ile Phe Gly Thr Ala
1               5

<210> SEQ ID NO 33
<211> LENGTH: 13
<212> TYPE: PRT
<213> ORGANISM: Homo sapiens

<400> SEQUENCE: 33

Ala Arg Ser Ser Tyr Gly Trp Ser Tyr Glu Phe Asp Tyr
1               5                   10

<210> SEQ ID NO 34
<211> LENGTH: 6
<212> TYPE: PRT
<213> ORGANISM: Homo sapiens

<400> SEQUENCE: 34

Gln Ser Ile Asn Thr Asn
1               5

<210> SEQ ID NO 35
<211> LENGTH: 3
<212> TYPE: PRT
<213> ORGANISM: Homo sapiens

<400> SEQUENCE: 35

Ala Ala Ser
1

<210> SEQ ID NO 36
<211> LENGTH: 9
```

<212> TYPE: PRT
<213> ORGANISM: Homo sapiens

<400> SEQUENCE: 36

Gln Gln Ala Arg Asp Thr Pro Ile Thr
1               5

<210> SEQ ID NO 37
<211> LENGTH: 120
<212> TYPE: PRT
<213> ORGANISM: Homo sapiens

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Gly Trp Ser Tyr Glu Phe Asp Tyr Trp Gly Gln
            100                 105                 110

Gly Thr Leu Val Thr Val Ser Ser
        115                 120

<210> SEQ ID NO 38
<211> LENGTH: 119
<212> TYPE: PRT
<213> ORGANISM: Homo sapiens

<400> SEQUENCE: 38

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Asn Trp Val Arg Gln Ala Pro Gly Gln Gly Leu Glu Trp Met
        35                  40                  45

Gly Trp Ile Asn Pro Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Glu Gly Tyr Gly Asn Tyr Ile Phe Pro Tyr Trp Gly Gln Gly
            100                 105                 110

Thr Leu Val Thr Val Ser Ser
        115

<210> SEQ ID NO 39
<211> LENGTH: 123
<212> TYPE: PRT
<213> ORGANISM: Homo sapiens

<400> SEQUENCE: 39

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr His Tyr
            20                  25                  30

Thr Ile His Trp Val Arg Gln Ala Pro Gly Gln Gly Leu Glu Trp Met
        35                  40                  45

Gly Tyr Ile Ile Pro Ser Ser Gly Tyr Ser Glu Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Gly Ala Tyr Asp Asp Tyr Tyr Asp Tyr Tyr Ala Met Asp Tyr
        100                 105                 110

Trp Gly Gln Gly Thr Leu Val Thr Val Ser Ser
            115                 120

<210> SEQ ID NO 40
<211> LENGTH: 122
<212> TYPE: PRT
<213> ORGANISM: Homo sapiens

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Gly Met Ser Trp Val Arg Gln Ala Pro Gly Lys Gly Leu Glu Trp Val
        35                  40                  45

Ala Ser Ile Ile Ser Gly Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Ile Tyr Asp His Asp Gly Asp Tyr Tyr Ala Met Asp Tyr Trp
        100                 105                 110

Gly Gln Gly Thr Thr Val Thr Val Ser Ser
            115                 120

<210> SEQ ID NO 41
<211> LENGTH: 111
<212> TYPE: PRT
<213> ORGANISM: Homo sapiens

<400> SEQUENCE: 41

Asp Ile Val Met Thr Gln Thr Pro Leu Ser Leu Ser Val Thr Pro Gly
1               5                   10                  15

Gln Pro Ala Ser Ile Ser Cys Arg Ala Ser Glu Ser Val Asp Thr Tyr
            20                  25                  30

Ala Asn Ser Leu Met His Trp Tyr Leu Gln Lys Pro Gly Gln Pro Pro
        35                  40                  45

Gln Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Thr Asn
                85                  90                  95

Glu Asp Pro Arg Thr Phe Gly Gln Gly Thr Lys Leu Glu Ile Lys
            100                 105                 110

<210> SEQ ID NO 42
<211> LENGTH: 112
<212> TYPE: PRT
<213> ORGANISM: Homo sapiens

<400> SEQUENCE: 42

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Val Pro Trp Thr Phe Gly Gln Gly Thr Lys Leu Glu Ile Lys
            100                 105                 110

<210> SEQ ID NO 43
<211> LENGTH: 112
<212> TYPE: PRT
<213> ORGANISM: Homo sapiens

<400> SEQUENCE: 43

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Leu Glu Ile Lys
            100                 105                 110

<210> SEQ ID NO 44
<211> LENGTH: 107
<212> TYPE: PRT
<213> ORGANISM: Homo sapiens

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Thr Arg
            20                  25                  30

Leu Asn Trp Tyr Gln Gln Lys Pro Gly Lys Ala Pro Lys Leu Leu Ile
                35                  40                  45

Tyr Ser Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ala Tyr Asn Pro Ile
                 85                  90                  95

Thr Phe Gly Gln Gly Thr Lys Val Glu Ile Lys
                100                 105

<210> SEQ ID NO 45
<211> LENGTH: 107
<212> TYPE: PRT
<213> ORGANISM: Homo sapiens

<400> SEQUENCE: 45

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Ser Ile Asn Thr Asn
                 20                  25                  30

Leu Asn Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Arg Asp Thr Pro Ile
                 85                  90                  95

Thr Phe Gly Gln Gly Thr Lys Val Glu Ile Lys
                100                 105

<210> SEQ ID NO 46
<211> LENGTH: 295
<212> TYPE: PRT
<213> ORGANISM: Homo sapiens

<400> SEQUENCE: 46

Met Gly Val Pro Thr Ala Leu Glu Ala Gly Ser Trp Arg Trp Gly Ser
 1               5                   10                  15

Leu Leu Phe Ala Leu Phe Leu Ala Ala Ser Leu Gly Pro Val Ala Ala
                 20                  25                  30

Phe Lys Val Ala Thr Pro Tyr Ser Leu Tyr Val Cys Pro Glu Gly Gln
                35                  40                  45

Asn Val Thr Leu Thr Cys Arg Leu Leu Gly Pro Val Asp Lys Gly His
 50                  55                  60

Asp Val Thr Phe Tyr Lys Thr Trp Tyr Arg Ser Ser Arg Gly Glu Val
 65                  70                  75                  80

Gln Thr Cys Ser Glu Arg Arg Pro Ile Arg Asn Leu Thr Phe Gln Asp
                 85                  90                  95

Leu His Leu His His Gly Gly His Gln Ala Ala Asn Thr Ser His Asp
                100                 105                 110

Leu Ala Gln Arg His Gly Leu Glu Ser Ala Ser Asp His His Gly Asn
                115                 120                 125

Phe Ser Ile Thr Met Arg Asn Leu Thr Leu Leu Asp Ser Gly Leu Tyr
                130                 135                 140

-continued

```
Cys Cys Leu Val Val Glu Ile Arg His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Gln Glu Ser Glu Asn Ile Thr
        180                 185                 190

Ala Ala Ala Leu Ala Thr Gly Ala Cys Ile Val Gly Ile Leu Cys Leu
            195                 200                 205

Pro Leu Ile Leu Leu Val Tyr Lys Gln Arg Gln Ala Ala Ser Asn
        210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
                245                 250                 255

Ala Lys Val Arg His Pro Leu Ser Tyr Val Ala Gln Arg Gln Pro Ser
            260                 265                 270

Glu Ser Gly Arg His Leu Leu Ser Glu Pro Ser Thr Pro Leu Ser Pro
        275                 280                 285

Pro Gly Pro Gly Asp Val Phe
    290                 295

<210> SEQ ID NO 47
<211> LENGTH: 449
<212> TYPE: PRT
<213> ORGANISM: Homo sapiens

<400> SEQUENCE: 47

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Asn Trp Val Arg Gln Ala Pro Gly Gln Gly Leu Glu Trp Met
        35                  40                  45

Gly Trp Ile Asn Pro Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Glu Gly Tyr Gly Asn Tyr Ile Phe Pro Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

-continued

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 48
<211> LENGTH: 218
<212> TYPE: PRT
<213> ORGANISM: Homo sapiens

<400> SEQUENCE: 48

Asp Ile Val Met Thr Gln Thr Pro Leu Ser Leu Ser Val Thr Pro Gly
1               5                   10                  15

Gln Pro Ala Ser Ile Ser Cys Arg Ala Ser Glu Ser Val Asp Thr Tyr
            20                  25                  30

Ala Asn Ser Leu Met His Trp Tyr Leu Gln Lys Pro Gly Gln Pro Pro
        35                  40                  45

Gln Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Thr Asn
                85                  90                  95

Glu Asp Pro Arg Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140
```

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 49
<211> LENGTH: 453
<212> TYPE: PRT
<213> ORGANISM: Homo sapiens

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Tyr
            20                  25                  30

Thr Ile His Trp Val Arg Gln Ala Pro Gly Gln Gly Leu Glu Trp Met
        35                  40                  45

Gly Tyr Ile Ile Pro Ser Ser Gly Tyr Ser Glu Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Asp Asp Tyr Tyr Asp Tyr Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
```

```
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 50
<211> LENGTH: 219
<212> TYPE: PRT
<213> ORGANISM: Homo sapiens

<400> SEQUENCE: 50

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Val Pro Trp Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

```
Pro Val Thr Lys Ser Phe Asn Arg Gly Glu Cys
    210                 215
```

<210> SEQ ID NO 51
<211> LENGTH: 449
<212> TYPE: PRT
<213> ORGANISM: Homo sapiens

<400> SEQUENCE: 51

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Thr Trp Val Arg Gln Ala Pro Gly Gln Gly Leu Glu Trp Met
        35                  40                  45

Gly Trp Ile Asn Thr Tyr Thr Gly Glu Ser Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Asp Tyr Tyr Gly Ile Tyr Val Ser Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

Lys

<210> SEQ ID NO 52
<211> LENGTH: 218
<212> TYPE: PRT
<213> ORGANISM: Homo sapiens

<400> SEQUENCE: 52

Asp Ile Val Met Thr Gln Thr Pro Leu Ser Leu Ser Val Thr Pro Gly
1               5                   10                  15

Gln Pro Ala Ser Ile Ser Cys Arg Ala Ser Glu Ser Val Asp Asn Tyr
            20                  25                  30

Ala Asn Ser Phe Met His Trp Tyr Leu Gln Lys Pro Gly Gln Ser Pro
        35                  40                  45

Gln Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser His
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 53
<211> LENGTH: 452
<212> TYPE: PRT
<213> ORGANISM: Homo sapiens

<400> SEQUENCE: 53

Glu Val Gln Leu Val Glu Ser Gly Gly Gly Leu Val Gln Pro Gly Gly
1               5                   10                  15

-continued

Ser Leu Arg Leu Ser Cys Ala Ala Ser Gly Phe Thr Phe Arg Asn Tyr
            20                  25                  30

Gly Met Ser Trp Val Arg Gln Ala Pro Gly Lys Gly Leu Glu Trp Val
        35                  40                  45

Ala Ser Ile Ile Ser Gly Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ile Tyr Asp His Asp Gly Asp Tyr Tyr Ala Met Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu

-continued

```
                 435                 440                 445

Ser Pro Gly Lys
    450

<210> SEQ ID NO 54
<211> LENGTH: 219
<212> TYPE: PRT
<213> ORGANISM: Homo sapiens

<400> SEQUENCE: 54

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 55
<211> LENGTH: 450
<212> TYPE: PRT
<213> ORGANISM: Homo sapiens

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

85                  90                  95
Ala Arg Ser Ser Tyr Gly Trp Ser Tyr Glu Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 56
<211> LENGTH: 214
<212> TYPE: PRT
<213> ORGANISM: Homo sapiens

<400> SEQUENCE: 56

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Thr Arg
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ala Tyr Asn Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 57
<211> LENGTH: 450
<212> TYPE: PRT
<213> ORGANISM: Homo sapiens

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Gly Trp Ser Tyr Glu Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160
```

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 58
<211> LENGTH: 214
<212> TYPE: PRT
<213> ORGANISM: Homo sapiens

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Thr Asn
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro

-continued

```
               65                  70                  75                  80
Glu Asp Phe Ala Thr Tyr Tyr Cys Gln Gln Ala Arg Asp Thr Pro Ile
                    85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 59
<211> LENGTH: 446
<212> TYPE: PRT
<213> ORGANISM: Homo sapiens

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Gly Trp Ser Tyr Glu Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Asn Phe Gly Thr Gln Thr Tyr Thr Cys Asn Val Asp His Lys
            195                 200                 205

Pro Ser Asn Thr Lys Val Asp Lys Thr Val Glu Arg Lys Cys Cys Val
        210                 215                 220
```

```
Glu Cys Pro Pro Cys Pro Ala Pro Ala Ala Ser Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Ala Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Thr Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
        435                 440                 445

<210> SEQ ID NO 60
<211> LENGTH: 449
<212> TYPE: PRT
<213> ORGANISM: Homo sapiens

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Gly Trp Ser Tyr Glu Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

-continued

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Pro Val Ala Gly Pro
225                 230                 235                 240

Asp Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Ala Ala Leu Pro Ala Pro Ile Ala Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 61
<211> LENGTH: 450
<212> TYPE: PRT
<213> ORGANISM: Homo sapiens

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Ser Ser Tyr Gly Trp Ser Tyr Glu Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 62
<211> LENGTH: 9
<212> TYPE: PRT
<213> ORGANISM: Homo sapiens
```

```
<400> SEQUENCE: 62

Asn Leu Thr Leu Leu Asp Ser Gly Leu
1               5

<210> SEQ ID NO 63
<211> LENGTH: 11
<212> TYPE: PRT
<213> ORGANISM: Homo sapiens

<400> SEQUENCE: 63

Val Gln Thr Gly Lys Asp Ala Pro Ser Asn Cys
1               5                   10

<210> SEQ ID NO 64
<211> LENGTH: 120
<212> TYPE: PRT
<213> ORGANISM: Homo sapiens

<400> SEQUENCE: 64

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Gly Trp Ser Tyr Glu Phe Asp Tyr Trp Gly Gln
            100                 105                 110

Gly Thr Leu Val Thr Val Ser Ser
        115                 120

<210> SEQ ID NO 65
<211> LENGTH: 12
<212> TYPE: PRT
<213> ORGANISM: Homo sapiens

<400> SEQUENCE: 65

Arg Arg Pro Ile Arg Asn Leu Thr Phe Gln Asp Leu
1               5                   10

<210> SEQ ID NO 66
<211> LENGTH: 309
<212> TYPE: PRT
<213> ORGANISM: Mus musculus

<400> SEQUENCE: 66

Met Gly Val Pro Ala Val Pro Glu Ala Ser Ser Pro Arg Trp Gly Thr
1               5                   10                  15

Leu Leu Leu Ala Ile Phe Leu Ala Ala Ser Arg Gly Leu Val Ala Ala
            20                  25                  30

Phe Lys Val Thr Thr Pro Tyr Ser Leu Tyr Val Cys Pro Glu Gly Gln
        35                  40                  45

Asn Ala Thr Leu Thr Cys Arg Ile Leu Gly Pro Val Ser Lys Gly His
    50                  55                  60
```

Asp Val Thr Ile Tyr Lys Thr Trp Tyr Leu Ser Ser Arg Gly Glu Val
65                  70                  75                  80

Gln Met Cys Lys Glu His Arg Pro Ile Arg Asn Phe Thr Leu Gln His
                85                  90                  95

Leu Gln His His Gly Ser His Leu Lys Ala Asn Ala Ser His Asp Gln
            100                 105                 110

Pro Gln Lys His Gly Leu Glu Leu Ala Ser Asp His His Gly Asn Phe
            115                 120                 125

Ser Ile Thr Leu Arg Asn Val Thr Pro Arg Asp Ser Gly Leu Tyr Cys
            130                 135                 140

Cys Leu Val Ile Glu Leu Lys Asn His His Pro Glu Gln Arg Phe Tyr
145                 150                 155                 160

Gly Ser Met Glu Leu Gln Val Gln Ala Gly Lys Gly Ser Gly Ser Thr
                165                 170                 175

Cys Met Ala Ser Asn Glu Gln Asp Ser Asp Ser Ile Thr Ala Ala Ala
                180                 185                 190

Leu Ala Thr Gly Ala Cys Ile Val Gly Ile Leu Cys Leu Pro Leu Ile
            195                 200                 205

Leu Leu Leu Val Tyr Lys Gln Arg Gln Val Ala Ser His Arg Arg Ala
            210                 215                 220

Gln Glu Leu Val Arg Met Asp Ser Ser Asn Thr Gln Gly Ile Glu Asn
225                 230                 235                 240

Pro Gly Phe Glu Thr Thr Pro Pro Phe Gln Gly Met Pro Glu Ala Lys
                245                 250                 255

Thr Arg Pro Pro Leu Ser Tyr Val Ala Gln Arg Gln Pro Ser Glu Ser
                260                 265                 270

Gly Arg Tyr Leu Leu Ser Asp Pro Ser Thr Pro Leu Ser Pro Pro Gly
            275                 280                 285

Pro Gly Asp Val Phe Phe Pro Ser Leu Asp Pro Val Pro Asp Ser Pro
            290                 295                 300

Asn Ser Glu Ala Ile
305

<210> SEQ ID NO 67
<211> LENGTH: 312
<212> TYPE: PRT
<213> ORGANISM: Macropus rufus

<400> SEQUENCE: 67

Met Asn Val Pro Thr Ser Val Leu Glu Ser Gly Gly Arg Arg Trp Gly
1               5                   10                  15

Pro Leu Leu Leu Ala Phe Phe Leu Ala Ala Ser Arg Gly Leu Val Ala
                20                  25                  30

Ala Phe Lys Val Ala Thr Pro Tyr Ser Leu Tyr Val Cys Pro Glu Gly
            35                  40                  45

Glu Asn Ile Thr Leu Ala Cys Gln Leu Leu Gly Pro Val Pro Lys Gly
        50                  55                  60

His Asp Val Ser Phe Tyr Lys Thr Trp Phe Arg Ser Ser Arg Gly Glu
65                  70                  75                  80

Val Gln Val Cys Ser Glu His Arg Pro Ile Arg Asn Val Thr Leu Gln
                85                  90                  95

Asn Leu His Pro Tyr His Gly Gly His Gln Ala Ser Asn Thr Ser His
            100                 105                 110

Asn Leu Leu Gln Ser His Gly Leu Glu Thr Ala Ser Asp His His Gly
            115                 120                 125

```
Asn Phe Ser Ile Thr Met Arg Asn Leu Thr Val Gln Asp Gly Gly Leu
        130                 135                 140

Tyr Cys Cys Leu Val Val Glu Met Arg His Arg His Ser Glu His Arg
145                 150                 155                 160

Val His Ala Ala Met Glu Leu Gln Val Gln Lys Gly Lys Asp Ala Pro
                165                 170                 175

Ser Lys Cys Ile Thr Tyr Pro Ser Ser Pro Glu Glu Ser Asp Asn Ile
                180                 185                 190

Thr Ala Ala Ala Leu Ala Thr Gly Ala Cys Ile Val Gly Ile Leu Cys
            195                 200                 205

Leu Pro Leu Ile Leu Leu Val Tyr Lys Gln Arg Gln Val Ala Ser
        210                 215                 220

His Arg Arg Ala Gln Glu Leu Val Arg Met Asp Ser Ser Pro Gln Gly
225                 230                 235                 240

Ile Glu Asn Pro Gly Phe Glu Ala Pro Pro Ser Ser Gln Gly Leu Pro
                245                 250                 255

Glu Ala Lys Val Arg Pro Pro Leu Ser Tyr Met Ala Gln Arg Gln Pro
                260                 265                 270

Ser Glu Ser Gly Arg His Leu Leu Ser Glu Pro Asn Thr Pro Leu Ser
            275                 280                 285

Pro Pro Gly Pro Gly Asp Val Phe Phe Pro Ser Leu Asp Pro Val Pro
290                 295                 300

Asp Ser Pro Asn Ser Glu Phe Asn
305                 310
```

<210> SEQ ID NO 68
<211> LENGTH: 310
<212> TYPE: PRT
<213> ORGANISM: Delphinus delphis

<400> SEQUENCE: 68

```
Met Gly Val Pro Pro Val Pro Glu Ala Gly Ser Trp Arg Arg Gly Pro
1               5                   10                  15

Val Leu Leu Ala Phe Phe Leu Ala Ala Ser Arg Gly Leu Val Ala Ala
                20                  25                  30

Phe Lys Val Ala Thr Pro Tyr Ser Leu Tyr Val Cys Pro Glu Gly Gln
            35                  40                  45

Asn Val Thr Leu Thr Cys Arg Leu Leu Gly Pro Leu Ala Lys Gly His
        50                  55                  60

Asp Val Thr Phe Tyr Lys Thr Trp Tyr Arg Ser Ser Arg Gly Glu Val
65                  70                  75                  80

Gln Ala Cys Ser Glu Arg Arg Pro Ile Arg Asn Leu Thr Phe Gln Asp
                85                  90                  95

Leu His Leu His His Gly Gly His Gln Ala Asn Ser Ser Gln Asp Leu
            100                 105                 110

Ala Gln Arg His Gly Leu Glu Ser Ala Ser His His Gly Asn Phe
        115                 120                 125

Thr Ile Thr Met Arg Asn Leu Thr Leu Leu Asp Gly Gly Leu Tyr Cys
        130                 135                 140

Cys Leu Val Val Glu Ile Arg His Arg His Ser Glu Gln Arg Leu Tyr
145                 150                 155                 160

Gly Ala Met Glu Leu Gln Val Gln Arg Gly Glu Glu Ala Pro Ser Lys
                165                 170                 175

Cys Thr Val Tyr Pro Pro Ser Ser Lys Glu Ser Glu Ser Ile Thr Ala
```

```
                180                 185                 190
Ala Ala Leu Ala Thr Ser Ala Cys Ile Val Gly Ile Leu Cys Leu Pro
            195                 200                 205

Leu Ile Leu Leu Leu Val Tyr Lys Gln Arg Gln Val Ala Ser Asn Arg
210                 215                 220

Arg Ala Gln Glu Leu Val Arg Met Asp Ser Asn Thr Gln Gly Ile Glu
225                 230                 235                 240

Asn Pro Gly Phe Glu Thr Ser Pro Pro Ser His Gly Met Pro Glu Thr
                245                 250                 255

Lys Pro Arg Gln Pro Leu Thr Tyr Met Ala Arg Arg Gln Pro Ser Glu
            260                 265                 270

Ser Gly Arg His Leu Leu Ser Glu Pro Asn Thr Pro Leu Ser Pro Pro
        275                 280                 285

Gly Pro Gly Asp Val Phe Phe Pro Ser Leu Asp Pro Val Pro Asp Ser
290                 295                 300

Pro Asn Ser Glu Ala Ile
305                 310

<210> SEQ ID NO 69
<211> LENGTH: 288
<212> TYPE: PRT
<213> ORGANISM: Gallus gallus

<400> SEQUENCE: 69

Gly Gly Thr Ala Ala Phe Leu Val Thr Val Pro Tyr Thr Leu Cys Ile
1               5                   10                  15

Cys Pro Glu Gly Gln Asn Val Thr Leu Ser Cys Arg Val Ser Gly Pro
            20                  25                  30

Pro Ala Asp His His Asp Leu Ile Phe Lys Thr Trp Tyr Phe Ser Asn
        35                  40                  45

Asn Gly Asp Gln Ser Cys Ser Glu Lys Arg His Val Arg Asn Leu Thr
    50                  55                  60

Glu Lys Glu Leu Arg His Asp Pro Gly Arg His His Ser Thr Ala Ala
65                  70                  75                  80

Asn Ser Thr Ala Arg Ser Pro His Gly Ser Leu Ala Ser His His Gly
                85                  90                  95

Val Glu Phe Val Pro Asp His His Gly Ala Phe His Ile Val Val Met
            100                 105                 110

Asn Leu Thr Leu Gln Asp Ser Gly Asn Tyr Cys Cys Tyr Ala Met Glu
        115                 120                 125

Thr Arg Arg Asp His Gly Lys Ala His Thr Leu His Ile Ala His Gly
    130                 135                 140

Phe Val Glu Leu Gln Ile Gln Arg Gly Arg Gly Ser Leu Gln Asn Cys
145                 150                 155                 160

Thr Phe His Thr Ala Thr Ser Lys Asp Ile Thr Ala Ala Ala Leu Ala
                165                 170                 175

Thr Gly Ala Cys Ile Val Gly Ile Leu Cys Leu Pro Leu Ile Leu Leu
            180                 185                 190

Leu Ile Tyr Lys Gln Arg Gln Ala Val Ser His Arg Arg Ala His Glu
        195                 200                 205

Leu Val Arg Met Glu Ser Ser Ala Gln Gly Ile Glu Asn Pro Val Phe
    210                 215                 220

Glu Ala Leu Pro Ala Gly Ser Thr Glu Gln Arg Pro Arg Pro Gln Leu
225                 230                 235                 240
```

```
Ser Tyr Leu Gly Gly Arg Gln Leu Ser Glu Ser Gly Arg His Leu Leu
            245                 250                 255

Ser Glu Pro Asn Thr Pro Leu Ser Pro Pro Ala Pro Gly Glu Cys Phe
            260                 265                 270

Phe Pro Thr Leu Asp Pro Val Pro Asp Ser Pro Asn Ser Leu Lys Ala
            275                 280                 285

<210> SEQ ID NO 70
<211> LENGTH: 260
<212> TYPE: PRT
<213> ORGANISM: Xenopus laevis

<400> SEQUENCE: 70

Asp Ala Ile Thr Ala Phe Ser Val Ser Ala Leu Tyr Ser His Ile Thr
1               5                   10                  15

Cys Pro Glu Gly Gln Asn Val Asn Leu Thr Cys Thr Val Ser Gly His
            20                  25                  30

Val Ala Asp Lys His Asp Val Leu Phe Ser Leu Trp His Phe Ser Lys
        35                  40                  45

Asp Lys Asn Ser Asn Cys Leu Glu Arg Arg His Ile Gln Asn Thr Thr
    50                  55                  60

Glu Arg Asp His Leu His Lys Glu His Leu Ser His Ser Met His Asn
65                  70                  75                  80

Gly Ala Phe Gln Ile Thr Leu Thr Asn Val Ser Gln Gln Asp Ser Gly
                85                  90                  95

Gly Tyr Cys Cys Tyr Val Ile Glu Ala Ser Lys Lys His His Thr Arg
            100                 105                 110

His Tyr Ser Tyr Ile Glu Phe Gln Val Lys Thr Asp Asp Leu Asn Leu
        115                 120                 125

Tyr Thr Cys Met Phe His Ser Pro Thr Glu Gly Asp Asn Ser Ser Thr
    130                 135                 140

Ala Ala Ala Leu Ala Ile Val Ser Cys Val Ile Gly Ile Leu Cys Met
145                 150                 155                 160

Pro Leu Ile Leu Phe Leu Val Tyr Lys Gln Arg Arg Ala Ile Ser His
                165                 170                 175

Arg Arg Ser Tyr His Phe Val Phe Ile Asp Phe Ser Glu Ala Gln Gly
            180                 185                 190

Ile Glu Asn Pro Val Phe Asp Asp Pro Pro Ala Asn Val Val Glu
        195                 200                 205

Gln Arg Pro Arg Leu Ala Phe Met Ala Ser Arg Gln Gln Ser Glu Ser
    210                 215                 220

Asp Arg His Leu Leu Ser Glu Pro Asn Thr Pro Leu Ser Pro Ser Cys
225                 230                 235                 240

Pro Asn Glu Cys Phe Phe Pro Ser Leu Pro Val Pro Asp Ser Pro Asp
                245                 250                 255

Pro Gly Asn Val
            260

<210> SEQ ID NO 71
<211> LENGTH: 315
<212> TYPE: PRT
<213> ORGANISM: Taeniopygia guttata

<400> SEQUENCE: 71

Gly His Pro Ala Thr Met Gly Thr Ala Ser Pro Arg Pro Gly Leu Leu
1               5                   10                  15
```

```
Leu Ala Ala Leu Cys Leu Leu Ala Ser His Gly Gly Ala Asp Ala Phe
             20                  25                  30

Leu Ile Ser Thr Pro Tyr Ser Leu Cys Val Cys Pro Glu Gly Gln Asn
             35                  40                  45

Val Thr Leu Ser Cys Arg Ile Ser Gly Ala Leu Ala Glu Arg His Asp
 50                  55                  60

Leu Leu Tyr Lys Thr Trp Tyr Phe Ser Ser Thr Gly Asp Gln Ser Cys
 65                  70                  75                  80

Ser Asp Lys Arg His Ile Arg Asn Val Thr Asp Lys Glu Leu Arg His
                 85                  90                  95

Asp Leu Gly Arg His His Glu Leu Pro Gly Asn Ala Ser Gln Lys Pro
                100                 105                 110

Pro Phe Gly Trp Gln Ser Gly His His Gly Val Glu Leu Val Leu Asp
            115                 120                 125

His His Gly Ala Phe His Leu Val Val Met Asn Leu Thr Leu Gln Asp
        130                 135                 140

Ser Gly Asn Tyr Cys Cys Tyr Ala Val Glu Val Arg Arg Glu Gly His
145                 150                 155                 160

Ser Lys Pro His Thr Val Gln Ala Ala His Gly Phe Val Glu Leu Gln
                165                 170                 175

Ile Gln Arg Gly Glu Pro Cys Ser His Ala Arg Ala Gln Ser Gln Arg
            180                 185                 190

Ala Ala Asp Asp Ile Thr Ala Ala Val Leu Ala Thr Gly Ala Cys Ile
        195                 200                 205

Val Gly Ile Leu Cys Leu Pro Leu Ile Leu Leu Ile Tyr Lys Gln
    210                 215                 220

Arg Gln Ala Ala Ser Arg Arg Ala His Glu Leu Val Arg Met Asp
225                 230                 235                 240

Ser Gly Ala Gln Gly Ile Glu Asn Pro Val Phe Glu Ala Val Pro Ser
                245                 250                 255

Ala Gly Ala Glu Pro Arg Pro Arg Ala Gln Leu Ser Tyr Val Ala Ser
                260                 265                 270

Arg Leu Pro Ser Glu Ser Gly Arg His Leu Leu Ser Glu Pro Ser Thr
                275                 280                 285

Pro Leu Ser Pro Pro Gly Pro Gly Asp Cys Phe Phe Pro Thr Leu Asp
            290                 295                 300

Pro Val Pro Asp Ser Pro Asn Ser Leu Lys Ala
305                 310                 315

<210> SEQ ID NO 72
<211> LENGTH: 275
<212> TYPE: PRT
<213> ORGANISM: Danio rerio

<400> SEQUENCE: 72

Met Asp Val Phe Arg Ala Val Leu Leu Cys Phe His Val Phe Thr Ala
 1                5                  10                  15

Ile Gln Ala Ser Gly Asp His His Ser Leu Arg Val Ser Val Pro His
             20                  25                  30

Arg Thr Tyr Glu Cys Pro Glu Gly Ala Asp Val Ile Leu Lys Cys Val
             35                  40                  45

Pro Ser Gly Thr Lys Ala Tyr Pro Gln Asp Thr Phe Trp Thr Thr Trp
 50                  55                  60

Leu Tyr Thr Pro Arg Ser Gln Asp His Cys Gln Lys Gly Ala His Pro
 65                  70                  75                  80
```

-continued

```
Arg Lys Ala Asn His Thr Asn Arg Ser Leu Gly Val Val Tyr Ser Ser
                85                  90                  95

Gly Asp Lys Val Phe Ser Val Ser Leu Lys Asn Val Lys His Thr Asp
            100                 105                 110

Gln Gly Lys Tyr Cys Cys Trp Leu Leu Asp Leu His Gly Arg His Lys
        115                 120                 125

Glu Gln Glu Ala His Asp Phe Met Tyr Leu Ser Val Met Pro Thr Pro
    130                 135                 140

Lys Asp Ala His Asn Gly Ser Leu Lys Cys Leu Glu Tyr Ser His Thr
145                 150                 155                 160

Ala Ser Asp Asp Ser Val Ala Glu Gly Leu Ala Ile Ala Ala Cys Val
                165                 170                 175

Ala Phe Val Leu Cys Leu Pro Leu Ile Leu Met Leu Val Tyr Arg Gln
            180                 185                 190

Arg Gln Thr Val Glu Arg His Arg Ala His Glu Leu Val Arg Met
        195                 200                 205

Asp Ser Glu Ala Gln Gly His Glu Asn Pro Val Phe Leu Gly Asp Ser
    210                 215                 220

Pro Glu Pro Lys Met Arg Thr Val Ser Gln Ile Met Met Arg Gln Pro
225                 230                 235                 240

Ser Glu Thr Gly His His Leu Leu Ser Glu Pro Gly Thr Pro Phe Ser
                245                 250                 255

Pro Asn Ile Gln Gly Glu Leu Phe Phe Ser Ala Gln Gly Leu Pro Glu
            260                 265                 270

Ser Asn Ile
        275

<210> SEQ ID NO 73
<211> LENGTH: 293
<212> TYPE: PRT
<213> ORGANISM: Fugu rubripes

<400> SEQUENCE: 73

Leu Glu Lys Phe Thr Ser Ala His His Thr Lys Gln Thr Leu Glu Lys
1               5                   10                  15

Gly Leu Asn Leu Leu Cys Leu Thr Lys Ser Asn Ala His His Gly His
            20                  25                  30

Pro Ala Met Ser Val Ser Ala Ser His Leu Tyr Tyr Thr Cys Pro Glu
        35                  40                  45

Gly Ala Asn Ala Thr Leu Val Cys Asn Gln Arg Gly Gly Ala Leu His
    50                  55                  60

Pro Asn Asp Ser Leu Trp Arg Leu Trp Phe Phe Thr Pro His Lys Asp
65                  70                  75                  80

Gln His Cys Thr Lys His Gly Pro Arg Asn Val Thr Phe Lys His Ser
                85                  90                  95

Lys Leu Ser Ser Gly Leu His Phe Gly Ala Thr Gln Glu Asn Phe Trp
            100                 105                 110

Val Gln Leu Gln Asn Val Thr His Ala Asp Gln Gly Arg Tyr Cys Cys
        115                 120                 125

Ala Ala Leu Glu Ile Glu Ser Ile His His Glu Ala Val Gln Arg Thr
    130                 135                 140

His Ser His Met Phe Leu Asn Ile Ile Pro Arg Gly Thr Gly Ser Pro
145                 150                 155                 160

Asn Cys Thr Val Ser Ala Pro Ser Ala Pro Glu Gly Asn Ala Thr Leu
```

```
                165                 170                 175
Cys Thr Val Pro Val Ala Leu Ala Met Gly Ala Cys Ile Leu Ala Leu
            180                 185                 190

Leu Ser Leu Pro Leu Ile Leu Leu Val Tyr Arg Gln Arg Gln Ser
        195                 200                 205

Ala Gln Ser Arg Arg Ala Gln Glu Leu Val Arg Met Asp Ser Glu
    210                 215                 220

Ala His Gly His Glu Asn Pro Val Phe Leu Gly Gly Ser Pro Gln Ile
225                 230                 235                 240

Lys Asn Arg Thr Val Ser Gln Ile Met Ala Arg Gln Ser Ser Glu Thr
                245                 250                 255

Gly Arg His Leu Leu Ser Glu Pro Gly Thr Pro Leu Ser Pro Pro Ala
            260                 265                 270

His Gly Asp Val Phe Phe Pro Ala Glu Asp Thr Ile Phe Glu Thr Pro
        275                 280                 285

Glu Leu Arg Gln Val
        290

<210> SEQ ID NO 74
<211> LENGTH: 10
<212> TYPE: PRT
<213> ORGANISM: Homo sapiens

<400> SEQUENCE: 74

Pro Val Asp Lys Gly His Asp Val Thr Phe
1               5                   10

<210> SEQ ID NO 75
<211> LENGTH: 9
<212> TYPE: PRT
<213> ORGANISM: Homo sapiens

<400> SEQUENCE: 75

Ile Arg His His His Ser Glu His Arg
1               5

<210> SEQ ID NO 76
<211> LENGTH: 444
<212> TYPE: PRT
<213> ORGANISM: Artificial Sequence
<220> FEATURE:
<223> OTHER INFORMATION: Chimeric antibody heavy chain

<400> SEQUENCE: 76

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Gly Trp Ser Tyr Glu Phe Asp Tyr Trp Gly Gln
            100                 105                 110
```

Gly Thr Leu Val Thr Val Ser Ser Ala Lys Thr Thr Pro Ser Val
            115                 120                 125

Tyr Pro Leu Ala Pro Gly Ser Ala Ala Gln Thr Asn Ser Met Val Thr
130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Glu Ser Asp Leu Tyr Thr Leu Ser Ser Val Val Thr Val Pro Ser
            180                 185                 190

Ser Pro Arg Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asn Thr Asn Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440

<210> SEQ ID NO 77
<211> LENGTH: 215
<212> TYPE: PRT
<213> ORGANISM: Artificial Sequence
<220> FEATURE:
<223> OTHER INFORMATION: Chimeric antibody light chain

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Thr Asn
            20                  25                  30

-continued

```
Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65              70                  75                  80

Glu Asp Phe Ala Thr Tyr Tyr Cys Gln Gln Ala Arg Asp Thr Pro Ile
                 85                  90                  95

Thr Phe Gly Gln Gly Thr Lys Val Glu Ile Lys Arg Ala Asp Ala Ala
             100                 105                 110

Pro Thr Val Ser Ile Phe Pro Pro Ser Ser Glu Gln Leu Thr Ser Gly
         115                 120                 125

Gly Ala Ser Val Val Cys Phe Leu Asn Asn Phe Tyr Pro Lys Asp Ile
     130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                 165                 170                 175

Ser Thr Leu Thr Leu Thr Lys Asp Glu Tyr Glu Arg His Asn Ser Tyr
             180                 185                 190

Thr Cys Glu Ala Thr His Lys Thr Ser Thr Ser Pro Ile Val Lys Ser
         195                 200                 205

Phe Asn Arg Asn Glu Cys Val
210                 215
```